(12) United States Patent
Shelton, IV et al.

(10) Patent No.: US 10,485,542 B2
(45) Date of Patent: Nov. 26, 2019

(54) SURGICAL STAPLING INSTRUMENT COMPRISING MULTIPLE LOCKOUTS

(71) Applicant: Ethicon Endo-Surgery, LLC, Guaynabo, PR (US)

(72) Inventors: Frederick E. Shelton, IV, Hillsboro, OH (US); Anil K. Nalagatla, Mason, OH (US); Sudhir B. Patel, Mason, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 734 days.

(21) Appl. No.: 15/089,335

(22) Filed: Apr. 1, 2016

(65) Prior Publication Data

US 2017/0281155 A1    Oct. 5, 2017

(51) Int. Cl.
*A61B 17/072* (2006.01)
*A61B 17/064* (2006.01)
(Continued)

(52) U.S. Cl.
CPC ...... *A61B 17/07207* (2013.01); *A61B 17/068* (2013.01); *A61B 17/0644* (2013.01); *A61B 17/072* (2013.01); *A61B 17/105* (2013.01); *A61B 17/1155* (2013.01); *A61B 17/07292* (2013.01); *A61B 2017/00017* (2013.01); *A61B 2017/00115* (2013.01); *A61B 2017/00398* (2013.01); *A61B 2017/00407* (2013.01); *A61B 2017/00464* (2013.01); *A61B 2017/00734* (2013.01); *A61B 2017/07221* (2013.01); *A61B 2017/07228* (2013.01);
(Continued)

(58) Field of Classification Search
CPC ............ A61B 2017/07214; A61B 2017/07271
USPC ...................................................... 227/175.2
See application file for complete search history.

(56) References Cited

U.S. PATENT DOCUMENTS

| 2,224,882 A | 12/1940 | Peck |
| 2,742,955 A | 4/1956 | Dominguez |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Gloria R Weeks

(57) ABSTRACT

A surgical stapling attachment is disclosed. The surgical stapling attachment comprises an attachment portion, a shaft assembly, an articulation joint, and an end effector assembly. The end effector assembly comprises a drive system comprising a main drive and a lockout drive driven by a single rotary input. The main drive is configured to capture, clamp, and staple tissue. The lockout drive is configured to prevent the main drive from being driven in the event a staple cartridge is not installed within the end effector assembly. Another lockout is provided to prevent the drive system from being actuated when a spent staple cartridge is installed within the end effector assembly.

20 Claims, 88 Drawing Sheets

(51) Int. Cl.
*A61B 17/115* (2006.01)
*A61B 17/068* (2006.01)
*A61B 17/10* (2006.01)
A61B 90/00 (2016.01)
A61B 17/00 (2006.01)
A61B 17/29 (2006.01)

(52) U.S. Cl.
CPC .............. *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/07285* (2013.01); *A61B 2017/291* (2013.01); *A61B 2017/2903* (2013.01); *A61B 2017/2908* (2013.01); *A61B 2017/2923* (2013.01); *A61B 2017/2927* (2013.01); *A61B 2090/0808* (2016.02); *A61B 2090/0811* (2016.02)

(56) References Cited

U.S. PATENT DOCUMENTS

| | | |
|---|---|---|
| 2,853,074 A | 9/1958 | Olson |
| 3,080,564 A | 3/1963 | Strekopitov et al. |
| 3,166,072 A | 1/1965 | Sullivan, Jr. |
| 3,266,494 A | 8/1966 | Brownrigg et al. |
| 3,359,978 A | 12/1967 | Smith, Jr. |
| 3,490,675 A | 1/1970 | Green et al. |
| 3,494,533 A | 2/1970 | Green et al. |
| 3,551,987 A | 1/1971 | Wilkinson |
| 3,643,851 A | 2/1972 | Green et al. |
| 3,662,939 A * | 5/1972 | Bryan ............... A61B 17/0684 227/109 |
| 3,717,294 A | 2/1973 | Green |
| 3,744,495 A | 7/1973 | Johnson |
| 3,746,002 A | 7/1973 | Haller |
| 3,819,100 A * | 6/1974 | Noiles ............... A61B 17/0684 227/121 |
| 3,863,639 A | 2/1975 | Kleaveland |
| RE28,932 E | 8/1976 | Noiles et al. |
| 4,111,206 A | 9/1978 | Vishnevsky et al. |
| 4,190,042 A | 2/1980 | Sinnreich |
| 4,198,982 A | 4/1980 | Fortner et al. |
| 4,207,898 A | 6/1980 | Becht |
| 4,272,002 A | 6/1981 | Moshofsky |
| 4,274,398 A | 6/1981 | Scott, Jr. |
| 4,289,133 A | 9/1981 | Rothfuss |
| 4,304,236 A | 12/1981 | Conta et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,408,692 A | 10/1983 | Sigel et al. |
| 4,415,112 A | 11/1983 | Green |
| 4,417,890 A | 11/1983 | Dennehey et al. |
| 4,429,695 A | 2/1984 | Green |
| 4,473,077 A | 9/1984 | Noiles et al. |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |
| 4,573,468 A | 3/1986 | Conta et al. |
| 4,573,622 A | 3/1986 | Green et al. |
| 4,580,712 A | 4/1986 | Green |
| 4,585,153 A | 4/1986 | Failla et al. |
| 4,605,004 A | 8/1986 | Di Giovanni et al. |
| 4,610,383 A | 9/1986 | Rothfuss et al. |
| 4,619,262 A | 10/1986 | Taylor |
| 4,619,391 A | 10/1986 | Sharkany et al. |
| 4,629,107 A | 12/1986 | Fedotov et al. |
| 4,632,290 A | 12/1986 | Green et al. |
| 4,654,028 A | 3/1987 | Suma |
| 4,655,222 A | 4/1987 | Florez et al. |
| 4,662,555 A | 5/1987 | Thornton |
| 4,664,305 A | 5/1987 | Blake, III et al. |
| 4,669,647 A | 6/1987 | Storace |
| 4,671,445 A | 6/1987 | Barker et al. |
| 4,684,051 A | 8/1987 | Akopov et al. |
| 4,700,703 A | 10/1987 | Resnick et al. |
| 4,715,520 A | 12/1987 | Roehr, Jr. et al. |
| 4,728,020 A | 3/1988 | Green et al. |
| 4,744,363 A | 5/1988 | Hasson |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,848,637 A | 7/1989 | Pruitt |
| 4,869,414 A | 9/1989 | Green et al. |
| 4,869,415 A * | 9/1989 | Fox .................. A61B 17/07207 227/19 |
| 4,873,977 A | 10/1989 | Avant et al. |
| 4,892,244 A * | 1/1990 | Fox .................... A61B 17/068 227/120 |
| 4,893,622 A | 1/1990 | Green et al. |
| 4,903,697 A | 2/1990 | Resnick et al. |
| 4,909,789 A | 3/1990 | Taguchi et al. |
| 4,921,479 A | 5/1990 | Grayzel |
| 4,930,674 A | 6/1990 | Barak |
| 4,941,623 A | 7/1990 | Pruitt |
| 4,944,443 A | 7/1990 | Oddsen et al. |
| 4,973,302 A | 11/1990 | Armour et al. |
| 4,984,564 A | 1/1991 | Yuen |
| 5,002,553 A | 3/1991 | Shiber |
| 5,014,899 A | 5/1991 | Presty et al. |
| 5,027,834 A | 7/1991 | Pruitt |
| 5,065,929 A | 11/1991 | Schulze et al. |
| 5,071,430 A | 12/1991 | de Salis et al. |
| 5,074,454 A | 12/1991 | Peters |
| 5,080,088 A | 1/1992 | LeVahn |
| 5,082,005 A | 1/1992 | Kaldany |
| 5,084,057 A | 1/1992 | Green et al. |
| 5,104,025 A | 4/1992 | Main et al. |
| 5,104,397 A | 4/1992 | Vasconcelos et al. |
| 5,108,368 A | 4/1992 | Hammerslag et al. |
| 5,116,349 A | 5/1992 | Aranyi |
| 5,119,983 A | 6/1992 | Green et al. |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,609 A | 10/1992 | Nakao et al. |
| 5,158,567 A | 10/1992 | Green |
| 5,171,247 A | 12/1992 | Hughett et al. |
| 5,171,249 A | 12/1992 | Stefanchik et al. |
| 5,195,505 A | 3/1993 | Josefsen |
| 5,197,649 A | 3/1993 | Bessler et al. |
| 5,205,459 A | 4/1993 | Brinkerhoff et al. |
| 5,211,649 A | 5/1993 | Kohler et al. |
| 5,211,655 A | 5/1993 | Hasson |
| 5,221,036 A | 6/1993 | Takase |
| 5,222,945 A | 6/1993 | Basnight |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,239,981 A | 8/1993 | Anapliotis |
| 5,258,009 A | 11/1993 | Conners |
| 5,263,937 A | 11/1993 | Shipp |
| 5,271,543 A | 12/1993 | Grant et al. |
| 5,275,322 A | 1/1994 | Brinkerhoff et al. |

(56) References Cited

U.S. PATENT DOCUMENTS

| | | | |
|---|---|---|---|
| 5,282,806 A | 2/1994 | Haber et al. | |
| 5,282,829 A | 2/1994 | Hermes | |
| 5,285,945 A | 2/1994 | Brinkerhoff et al. | |
| 5,304,204 A | 4/1994 | Bregen | |
| 5,307,976 A * | 5/1994 | Olson | A61B 17/07207 |
| | | | 227/175.3 |
| 5,309,896 A | 5/1994 | Moll et al. | |
| 5,309,927 A | 5/1994 | Welch | |
| 5,312,023 A | 5/1994 | Green et al. | |
| 5,314,445 A | 5/1994 | Heidmueller et al. | |
| 5,330,502 A | 7/1994 | Hassler et al. | |
| 5,333,772 A | 8/1994 | Rothfuss et al. | |
| 5,333,773 A | 8/1994 | Main et al. | |
| 5,336,232 A | 8/1994 | Green et al. | |
| 5,342,385 A | 8/1994 | Norelli et al. | |
| 5,342,395 A | 8/1994 | Jarrett et al. | |
| 5,342,396 A | 8/1994 | Cook | |
| 5,346,115 A | 9/1994 | Perouse et al. | |
| 5,350,104 A | 9/1994 | Main et al. | |
| 5,350,400 A | 9/1994 | Esposito et al. | |
| 5,354,250 A | 10/1994 | Christensen | |
| 5,354,303 A | 10/1994 | Spaeth et al. | |
| 5,358,506 A | 10/1994 | Green et al. | |
| 5,366,479 A | 11/1994 | McGarry et al. | |
| 5,374,277 A | 12/1994 | Hassler | |
| 5,375,588 A | 12/1994 | Yoon | |
| 5,383,880 A | 1/1995 | Hooven | |
| 5,383,888 A | 1/1995 | Zvenyatsky et al. | |
| 5,383,895 A | 1/1995 | Holmes et al. | |
| 5,391,180 A | 2/1995 | Tovey et al. | |
| 5,395,030 A | 3/1995 | Kuramoto et al. | |
| 5,395,033 A | 3/1995 | Byrne et al. | |
| 5,395,384 A | 3/1995 | Duthoit et al. | |
| 5,397,324 A | 3/1995 | Carroll et al. | |
| 5,403,312 A | 4/1995 | Yates et al. | |
| 5,404,870 A | 4/1995 | Brinkerhoff et al. | |
| 5,405,072 A | 4/1995 | Zlock et al. | |
| 5,405,073 A | 4/1995 | Porter | |
| 5,405,344 A | 4/1995 | Williamson et al. | |
| 5,405,360 A | 4/1995 | Tovey | |
| 5,411,508 A | 5/1995 | Bessler et al. | |
| 5,413,267 A * | 5/1995 | Solyntjes | A61B 17/072 |
| | | | 227/175.4 |
| 5,413,272 A | 5/1995 | Green et al. | |
| 5,413,573 A | 5/1995 | Koivukangas | |
| 5,415,334 A | 5/1995 | Williamson et al. | |
| 5,417,361 A | 5/1995 | Williamson, IV | |
| 5,419,766 A | 5/1995 | Chang et al. | |
| 5,425,745 A | 6/1995 | Green et al. | |
| 5,433,721 A | 7/1995 | Hooven et al. | |
| 5,441,494 A | 8/1995 | Ortiz | |
| 5,445,644 A | 8/1995 | Pietrafitta et al. | |
| 5,449,365 A | 9/1995 | Green et al. | |
| 5,452,836 A * | 9/1995 | Huitema | A61B 17/072 |
| | | | 227/176.1 |
| 5,452,837 A | 9/1995 | Williamson, IV et al. | |
| 5,458,279 A * | 10/1995 | Plyley | A61B 17/072 |
| | | | 227/176.1 |
| 5,462,215 A * | 10/1995 | Viola | A61B 17/072 |
| | | | 227/176.1 |
| 5,465,894 A | 11/1995 | Clark et al. | |
| 5,470,006 A * | 11/1995 | Rodak | A61B 17/072 |
| | | | 227/176.1 |
| 5,470,009 A * | 11/1995 | Rodak | A61B 17/072 |
| | | | 227/176.1 |
| 5,474,057 A | 12/1995 | Makower et al. | |
| 5,474,566 A | 12/1995 | Alesi et al. | |
| 5,476,479 A | 12/1995 | Green et al. | |
| 5,478,354 A | 12/1995 | Tovey et al. | |
| 5,480,089 A | 1/1996 | Blewett | |
| 5,480,409 A | 1/1996 | Riza | |
| 5,482,197 A | 1/1996 | Green et al. | |
| 5,483,952 A | 1/1996 | Aranyi | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,819 A | 2/1996 | Nicholas et al. | |
| 5,497,933 A | 3/1996 | DeFonzo et al. | |
| 5,503,320 A | 4/1996 | Webster et al. | |
| 5,503,635 A | 4/1996 | Sauer et al. | |
| 5,505,363 A | 4/1996 | Green et al. | |
| 5,507,426 A | 4/1996 | Young et al. | |
| 5,509,596 A | 4/1996 | Green et al. | |
| 5,511,564 A | 4/1996 | Wilk | |
| 5,514,157 A | 5/1996 | Nicholas et al. | |
| 5,518,163 A | 5/1996 | Hooven | |
| 5,518,164 A | 5/1996 | Hooven | |
| 5,520,609 A | 5/1996 | Moll et al. | |
| 5,520,678 A | 5/1996 | Heckele et al. | |
| 5,520,700 A | 5/1996 | Beyar et al. | |
| 5,527,264 A | 6/1996 | Moll et al. | |
| 5,529,235 A * | 6/1996 | Boiarski | A61B 17/07207 |
| | | | 227/175.1 |
| 5,531,856 A | 7/1996 | Moll et al. | |
| 5,533,661 A | 7/1996 | Main et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,547,117 A | 8/1996 | Hamblin et al. | |
| 5,549,621 A | 8/1996 | Bessler et al. | |
| 5,549,637 A | 8/1996 | Crainich | |
| 5,551,622 A | 9/1996 | Yoon | |
| 5,553,765 A | 9/1996 | Knodel et al. | |
| 5,554,169 A | 9/1996 | Green et al. | |
| 5,556,416 A | 9/1996 | Clark et al. | |
| 5,556,918 A | 9/1996 | Brodt et al. | |
| 5,558,665 A | 9/1996 | Kieturakis | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,690 A | 10/1996 | Green et al. | |
| 5,562,701 A | 10/1996 | Huitema et al. | |
| 5,562,702 A | 10/1996 | Huitema et al. | |
| 5,564,615 A | 10/1996 | Bishop et al. | |
| 5,571,116 A | 11/1996 | Bolanos et al. | |
| 5,571,285 A | 11/1996 | Chow et al. | |
| 5,575,799 A | 11/1996 | Bolanos et al. | |
| 5,575,803 A | 11/1996 | Cooper et al. | |
| 5,575,805 A | 11/1996 | Li | |
| 5,577,654 A | 11/1996 | Bishop | |
| 5,579,978 A | 12/1996 | Green et al. | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,607,450 A | 3/1997 | Zvenyatsky et al. | |
| 5,609,285 A | 3/1997 | Grant et al. | |
| 5,613,937 A | 3/1997 | Garrison et al. | |
| 5,615,820 A | 4/1997 | Viola | |
| 5,618,303 A | 4/1997 | Marlow et al. | |
| 5,618,307 A | 4/1997 | Donlon et al. | |
| 5,620,452 A | 4/1997 | Yoon | |
| 5,624,452 A | 4/1997 | Yates | |
| 5,628,446 A | 5/1997 | Geiste et al. | |
| 5,628,743 A | 5/1997 | Cimino | |
| 5,630,539 A | 5/1997 | Plyley et al. | |

(56) References Cited

U.S. PATENT DOCUMENTS

| | | |
|---|---|---|
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,651,762 A | 7/1997 | Bridges |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,685,826 A | 11/1997 | Bonutti |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,408 A | 12/1997 | Wales et al. |
| 5,702,409 A | 12/1997 | Rayburn et al. |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,359 A | 2/1998 | Palmer et al. |
| 5,718,360 A | 2/1998 | Green et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,874 A | 4/1998 | Measamer et al. |
| 5,738,629 A | 4/1998 | Moll et al. |
| 5,741,271 A | 4/1998 | Nakao et al. |
| 5,743,456 A | 4/1998 | Jones et al. |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,752,970 A | 5/1998 | Yoon |
| 5,758,814 A * | 6/1998 | Gallagher .......... A61B 17/115 227/176.1 |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,859 A | 7/1998 | Nicholas et al. |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,797,959 A | 8/1998 | Castro et al. |
| 5,799,857 A | 9/1998 | Robertson et al. |
| 5,807,376 A | 9/1998 | Viola et al. |
| 5,807,378 A | 9/1998 | Jensen et al. |
| 5,810,721 A | 9/1998 | Mueller et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,817,084 A | 10/1998 | Jensen |
| 5,817,093 A | 10/1998 | Williamson, IV et al. |
| 5,820,009 A | 10/1998 | Melling et al. |
| 5,826,776 A | 10/1998 | Schulze et al. |
| 5,827,298 A | 10/1998 | Hart et al. |
| 5,829,662 A | 11/1998 | Allen et al. |
| 5,833,695 A | 11/1998 | Yoon |
| 5,836,503 A | 11/1998 | Ehrenfels et al. |
| 5,839,369 A | 11/1998 | Chatterjee et al. |
| 5,839,639 A | 11/1998 | Sauer et al. |
| 5,843,096 A | 12/1998 | Igaki et al. |
| 5,855,311 A | 1/1999 | Hamblin et al. |
| 5,855,583 A | 1/1999 | Wang et al. |
| 5,860,581 A | 1/1999 | Robertson et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,876,401 A | 3/1999 | Schulze et al. |
| 5,878,937 A | 3/1999 | Green et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,902,312 A | 5/1999 | Frater et al. |
| 5,906,577 A | 5/1999 | Beane et al. |
| 5,906,625 A | 5/1999 | Bito et al. |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,947,984 A | 9/1999 | Whipple |
| 5,951,576 A | 9/1999 | Wakabayashi |
| 5,954,259 A | 9/1999 | Viola et al. |
| 5,964,774 A | 10/1999 | McKean et al. |
| 5,997,528 A | 12/1999 | Bisch et al. |
| 5,997,552 A | 12/1999 | Person et al. |
| 6,003,517 A | 12/1999 | Sheffield et al. |
| 6,010,054 A | 1/2000 | Johnson et al. |
| 6,017,356 A | 1/2000 | Frederick et al. |
| 6,024,741 A | 2/2000 | Williamson, IV et al. |
| 6,024,748 A | 2/2000 | Manzo et al. |
| 6,032,849 A | 3/2000 | Mastri et al. |
| 6,045,560 A | 4/2000 | McKean et al. |
| 6,050,472 A | 4/2000 | Shibata |
| 6,053,390 A | 4/2000 | Green et al. |
| RE36,720 E | 5/2000 | Green et al. |
| 6,056,735 A | 5/2000 | Okada et al. |

(56) References Cited

U.S. PATENT DOCUMENTS

| | | |
|---|---|---|
| 6,063,025 A | 5/2000 | Bridges et al. |
| 6,063,097 A | 5/2000 | Oi et al. |
| 6,066,132 A | 5/2000 | Chen et al. |
| 6,074,401 A | 6/2000 | Gardiner et al. |
| 6,079,606 A | 6/2000 | Milliman et al. |
| 6,083,234 A | 7/2000 | Nicholas et al. |
| 6,083,241 A | 7/2000 | Longo et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| H1904 H | 10/2000 | Yates et al. |
| 6,126,058 A | 10/2000 | Adams et al. |
| 6,131,790 A | 10/2000 | Piraka |
| 6,142,933 A | 11/2000 | Longo et al. |
| 6,155,473 A | 12/2000 | Tompkins et al. |
| 6,159,146 A | 12/2000 | El Gazayerli |
| 6,159,200 A | 12/2000 | Verdura et al. |
| 6,162,208 A | 12/2000 | Hipps |
| 6,165,188 A | 12/2000 | Saadat et al. |
| 6,171,330 B1 | 1/2001 | Benchetrit |
| 6,174,318 B1 | 1/2001 | Bates et al. |
| 6,179,195 B1 | 1/2001 | Adams et al. |
| 6,193,129 B1 | 2/2001 | Bittner et al. |
| 6,202,914 B1 | 3/2001 | Geiste et al. |
| 6,214,020 B1 | 4/2001 | Mulhauser et al. |
| 6,214,028 B1 | 4/2001 | Yoon et al. |
| 6,216,698 B1 | 4/2001 | Regula |
| 6,221,007 B1 | 4/2001 | Green |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,248,117 B1 | 6/2001 | Blatter |
| 6,250,532 B1 | 6/2001 | Green et al. |
| 6,254,534 B1 | 7/2001 | Butler et al. |
| 6,258,107 B1 | 7/2001 | Balazs et al. |
| 6,264,086 B1 | 7/2001 | McGuckin, Jr. |
| 6,264,087 B1 | 7/2001 | Whitman |
| 6,267,772 B1 | 7/2001 | Mulhauser et al. |
| 6,273,897 B1 | 8/2001 | Dalessandro et al. |
| 6,293,927 B1 | 9/2001 | McGuckin, Jr. |
| 6,302,311 B1 | 10/2001 | Adams et al. |
| 6,309,403 B1 | 10/2001 | Minor et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,364,888 B1 | 4/2002 | Niemeyer et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| RE37,814 E | 8/2002 | Allgeyer |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,523 B1 | 9/2002 | Middleman et al. |
| 6,450,391 B1 | 9/2002 | Kayan et al. |
| 6,458,077 B1 | 10/2002 | Boebel et al. |
| 6,478,210 B2 | 11/2002 | Adams et al. |
| 6,488,196 B1 * | 12/2002 | Fenton, Jr. ......... A61B 17/068 227/175.1 |
| 6,488,197 B1 | 12/2002 | Whitman |
| 6,491,201 B1 | 12/2002 | Whitman |
| 6,491,701 B2 | 12/2002 | Tierney et al. |
| 6,494,885 B1 | 12/2002 | Dhindsa |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,540,737 B2 | 4/2003 | Bacher et al. |
| 6,543,456 B1 | 4/2003 | Freeman |
| 6,551,333 B2 | 4/2003 | Kuhns et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,585,144 B2 | 7/2003 | Adams et al. |
| 6,588,643 B2 | 7/2003 | Bolduc et al. |
| 6,592,597 B2 | 7/2003 | Grant et al. |
| 6,601,749 B2 | 8/2003 | Sullivan et al. |
| 6,605,078 B2 | 8/2003 | Adams |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,285 B2 | 10/2003 | Gabbay |
| 6,638,297 B1 | 10/2003 | Huitema |
| 6,644,532 B2 | 11/2003 | Green et al. |
| 6,645,201 B1 | 11/2003 | Utley et al. |
| 6,648,901 B2 | 11/2003 | Fleischman et al. |
| 6,656,193 B2 | 12/2003 | Grant et al. |
| 6,666,854 B1 | 12/2003 | Lange |
| 6,669,073 B2 | 12/2003 | Milliman et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,726,697 B2 | 4/2004 | Nicholas et al. |
| 6,736,825 B2 | 5/2004 | Blatter et al. |
| 6,749,600 B1 | 6/2004 | Levy |
| 6,752,816 B2 | 6/2004 | Culp et al. |
| 6,755,338 B2 | 6/2004 | Hahnen et al. |
| 6,769,590 B2 | 8/2004 | Vresh et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,820,791 B2 | 11/2004 | Adams |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,830,174 B2 | 12/2004 | Hillstead et al. |
| 6,835,199 B2 | 12/2004 | McGuckin, Jr. et al. |
| 6,840,423 B2 | 1/2005 | Adams et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,866,178 B2 | 3/2005 | Adams et al. |
| 6,866,671 B2 | 3/2005 | Tierney et al. |

(56) References Cited

U.S. PATENT DOCUMENTS

| | | |
|---|---|---|
| 6,872,214 B2 | 3/2005 | Sonnenschein et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,913,608 B2 | 7/2005 | Liddicoat et al. |
| 6,913,613 B2 | 7/2005 | Schwarz et al. |
| 6,936,042 B2 | 8/2005 | Wallace et al. |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,220 B2 | 11/2005 | Marino et al. |
| 6,964,363 B2 | 11/2005 | Wales et al. |
| 6,971,988 B2 | 12/2005 | Orban, III |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,032,798 B2 | 4/2006 | Whitman et al. |
| 7,032,799 B2 | 4/2006 | Viola et al. |
| 7,037,314 B2 | 5/2006 | Armstrong |
| 7,044,352 B2 | 5/2006 | Shelton, IV et al. |
| 7,044,353 B2 | 5/2006 | Mastri et al. |
| 7,052,454 B2 | 5/2006 | Taylor |
| 7,055,731 B2 | 6/2006 | Shelton, IV et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,083,626 B2 | 8/2006 | Hart et al. |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,247 B2 | 8/2006 | Monassevitch et al. |
| 7,097,089 B2 | 8/2006 | Marczyk |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,134,587 B2 | 11/2006 | Schwemberger et al. |
| 7,140,527 B2 | 11/2006 | Ehrenfels et al. |
| 7,140,528 B2 * | 11/2006 | Shelton, IV ..... A61B 17/07207 227/175.4 |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,650 B2 | 12/2006 | Lee |
| 7,156,863 B2 | 1/2007 | Sonnenschein et al. |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,229,408 B2 | 6/2007 | Douglas et al. |
| 7,234,624 B2 | 6/2007 | Gresham et al. |
| 7,235,089 B1 | 6/2007 | McGuckin, Jr. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,252,660 B2 | 8/2007 | Kunz |
| 7,258,262 B2 | 8/2007 | Mastri et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,334,718 B2 | 2/2008 | McAlister et al. |
| 7,338,505 B2 | 3/2008 | Belson |
| 7,338,513 B2 | 3/2008 | Lee et al. |
| 7,343,920 B2 | 3/2008 | Toby et al. |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 * | 6/2008 | Doll ................ A61B 17/07207 227/175.1 |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |

(56) References Cited

U.S. PATENT DOCUMENTS

| | | | |
|---|---|---|---|
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,641,091 B2 | 1/2010 | Olson et al. |
| 7,641,092 B2 | 1/2010 | Kruszynski et al. |
| 7,641,095 B2 | 1/2010 | Viola |
| 7,644,848 B2 | 1/2010 | Swayze et al. |
| 7,648,519 B2 | 1/2010 | Lee et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,686 B2 | 3/2010 | Curro et al. |
| 7,686,201 B2 | 3/2010 | Csiky |
| 7,686,826 B2 | 3/2010 | Lee et al. |
| 7,691,098 B2 | 4/2010 | Wallace et al. |
| 7,694,864 B2 | 4/2010 | Okada et al. |
| 7,694,865 B2 | 4/2010 | Scirica |
| 7,699,204 B2 | 4/2010 | Viola |
| 7,699,844 B2 | 4/2010 | Utley et al. |
| 7,699,859 B2 | 4/2010 | Bombard et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,873 B2 | 5/2010 | Swick |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,736,306 B2 | 6/2010 | Brustad et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 * | 10/2010 | Hall .............. A61B 17/07207 227/175.2 |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,823,760 B2 | 11/2010 | Zemlok et al. |

(56) References Cited

U.S. PATENT DOCUMENTS

| | | |
|---|---|---|
| 7,824,426 B2 | 11/2010 | Racenet et al. |
| 7,828,189 B2 | 11/2010 | Holsten et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,862,502 B2 | 1/2011 | Pool et al. |
| 7,866,525 B2 | 1/2011 | Scirica |
| 7,866,527 B2 | 1/2011 | Hall et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,461 B2 | 2/2011 | Albrecht et al. |
| 7,886,952 B2 | 2/2011 | Scirica et al. |
| 7,886,953 B2 * | 2/2011 | Schwemberger .... A61B 17/072 227/178.1 |
| 7,891,531 B1 | 2/2011 | Ward |
| 7,891,532 B2 | 2/2011 | Mastri et al. |
| 7,896,214 B2 | 3/2011 | Farascioni |
| 7,896,215 B2 | 3/2011 | Adams et al. |
| 7,896,897 B2 | 3/2011 | Gresham et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,963,433 B2 | 6/2011 | Whitman et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,791 B2 | 6/2011 | Franer et al. |
| 7,980,443 B2 | 7/2011 | Scheib et al. |
| 7,981,132 B2 | 7/2011 | Dubrul et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,469 B2 | 8/2011 | Olson et al. |
| 8,002,696 B2 | 8/2011 | Suzuki |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,021,389 B2 | 9/2011 | Molz, IV |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,043,207 B2 | 10/2011 | Adams |
| 8,043,328 B2 | 10/2011 | Hahnen et al. |
| 8,056,787 B2 | 11/2011 | Boudreaux et al. |
| 8,056,788 B2 | 11/2011 | Mastri et al. |
| 8,061,558 B2 | 11/2011 | Jordan et al. |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,074,858 B2 | 12/2011 | Marczyk |
| 8,075,476 B2 | 12/2011 | Vargas |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,096,457 B1 | 1/2012 | Manoux et al. |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,767 B2 | 2/2012 | Bauman et al. |
| 8,127,975 B2 | 3/2012 | Olson et al. |
| 8,128,559 B2 | 3/2012 | Minnelli |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,141,762 B2 | 3/2012 | Bedi et al. |
| 8,141,763 B2 | 3/2012 | Milliman |
| 8,146,790 B2 | 4/2012 | Milliman |
| 8,147,456 B2 | 4/2012 | Fisher et al. |
| 8,152,041 B2 | 4/2012 | Kostrzewski |
| 8,152,773 B2 | 4/2012 | Albrecht et al. |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |

(56) References Cited

U.S. PATENT DOCUMENTS

| | | |
|---|---|---|
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,226,553 B2 | 7/2012 | Shelton, IV et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,189 B2 | 10/2012 | Fisher et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,638 B2 | 11/2012 | Hart |
| 8,313,496 B2 | 11/2012 | Sauer et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,333,691 B2 | 12/2012 | Schaaf |
| 8,336,753 B2 | 12/2012 | Olson et al. |
| 8,337,517 B2 | 12/2012 | Van Dalen |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,669 B2 | 3/2013 | Kim |
| 8,403,198 B2 | 3/2013 | Sorrentino et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,740 B2 | 4/2013 | Shelton, IV et al. |
| 8,424,741 B2 | 4/2013 | McGuckin, Jr. et al. |
| 8,439,246 B1 | 5/2013 | Knodel |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,515 B2 | 6/2013 | Drew et al. |
| 8,474,677 B2 | 7/2013 | Woodard, Jr. et al. |
| 8,475,457 B2 | 7/2013 | Shano |
| 8,479,967 B2 | 7/2013 | Marczyk |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,485,414 B2 | 7/2013 | Criscuolo et al. |
| 8,485,970 B2 | 7/2013 | Widenhouse et al. |
| 8,490,853 B2 | 7/2013 | Criscuolo et al. |
| 8,491,603 B2 | 7/2013 | Yeung et al. |
| 8,496,156 B2 | 7/2013 | Sniffin et al. |
| 8,499,993 B2 | 8/2013 | Shelton, IV et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,931 B2 | 8/2013 | Minnelli et al. |
| 8,523,043 B2 | 9/2013 | Ullrich et al. |
| 8,523,881 B2 | 9/2013 | Cabiri et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,655 B2 | 10/2013 | Nalagatla et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,464 B2 | 11/2013 | Nalagatla et al. |
| 8,573,465 B2 | 11/2013 | Shelton, IV |

(56) References Cited

U.S. PATENT DOCUMENTS

| | | |
|---|---|---|
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,603,089 B2 | 12/2013 | Viola |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,640,788 B2 | 2/2014 | Dachs, II et al. |
| 8,640,940 B2 | 2/2014 | Ohdaira |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,839 B2 | 3/2014 | Ewers et al. |
| 8,672,951 B2 | 3/2014 | Smith et al. |
| 8,679,154 B2 | 3/2014 | Smith et al. |
| 8,679,156 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,213 B2 | 4/2014 | Shelton, IV et al. |
| 8,714,429 B2 | 5/2014 | Demmy |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,961 B2 | 5/2014 | Ziv |
| 8,733,612 B2 | 5/2014 | Ma |
| 8,733,613 B2 | 5/2014 | Huitema et al. |
| 8,734,336 B2 | 5/2014 | Bonadio et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,773 B2 | 7/2014 | Harari et al. |
| 8,770,458 B2 | 7/2014 | Scirica |
| 8,770,459 B2 | 7/2014 | Racenet et al. |
| 8,770,460 B2 | 7/2014 | Belzer |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,808,311 B2 * | 8/2014 | Heinrich ............ A61B 17/0469 606/142 |
| 8,808,325 B2 | 8/2014 | Hess et al. |
| 8,814,024 B2 | 8/2014 | Woodard, Jr. et al. |
| 8,814,788 B2 | 8/2014 | Gan |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,834,464 B2 | 9/2014 | Stewart et al. |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,911 B2 | 10/2014 | Williams et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,888,695 B2 | 11/2014 | Piskun et al. |
| 8,893,946 B2 | 11/2014 | Boudreaux et al. |
| 8,893,949 B2 | 11/2014 | Shelton, IV et al. |
| 8,899,462 B2 * | 12/2014 | Kostrzewski .... A61B 17/07207 227/175.1 |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,910,847 B2 | 12/2014 | Nalagatla et al. |
| 8,911,471 B2 | 12/2014 | Spivey et al. |
| 8,920,435 B2 | 12/2014 | Smith et al. |
| 8,925,782 B2 | 1/2015 | Shelton, IV |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,682 B2 | 1/2015 | Timm et al. |
| 8,955,732 B2 * | 2/2015 | Zemlok ................ A61B 17/072 227/176.1 |
| 8,956,390 B2 | 2/2015 | Shah et al. |
| 8,960,519 B2 | 2/2015 | Whitman et al. |
| 8,967,448 B2 | 3/2015 | Carter et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,005,243 B2 | 4/2015 | Stopek et al. |

(56) References Cited

U.S. PATENT DOCUMENTS

| | | |
|---|---|---|
| 9,016,541 B2 | 4/2015 | Viola et al. |
| 9,016,542 B2 | 4/2015 | Shelton, IV et al. |
| 9,028,494 B2 | 5/2015 | Shelton, IV et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,120 B2 | 6/2015 | Swarup et al. |
| 9,055,941 B2 | 6/2015 | Schmid et al. |
| 9,055,942 B2 | 6/2015 | Balbierz et al. |
| 9,055,945 B2 | 6/2015 | Miksza et al. |
| 9,060,770 B2 | 6/2015 | Shelton, IV et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,095,339 B2 | 8/2015 | Moore et al. |
| 9,095,340 B2 | 8/2015 | Felder et al. |
| 9,095,362 B2 | 8/2015 | Dachs, II et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,957 B2 | 9/2015 | Gantz et al. |
| 9,125,654 B2 | 9/2015 | Aronhalt et al. |
| 9,125,662 B2 | 9/2015 | Shelton, IV |
| 9,131,835 B2 | 9/2015 | Widenhouse et al. |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,173,978 B2 | 11/2015 | Kelly et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,186,148 B2 | 11/2015 | Felder et al. |
| 9,198,661 B2 | 12/2015 | Swensgard |
| 9,198,662 B2 | 12/2015 | Barton et al. |
| 9,204,830 B2 | 12/2015 | Zand et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,265,581 B2 | 2/2016 | Navve et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,289,210 B2 | 3/2016 | Baxter, III et al. |
| 9,289,211 B2 * | 3/2016 | Williams ......... A61B 17/07207 |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,463 B2 | 3/2016 | Viola et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,763 B2 | 4/2016 | Qiao et al. |
| 9,307,965 B2 | 4/2016 | Ming et al. |
| 9,307,986 B2 | 4/2016 | Hall et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,812 B2 | 5/2016 | Waaler et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,082 B2 | 5/2016 | Wei et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,351,734 B2 | 5/2016 | Prior |
| 9,358,003 B2 | 6/2016 | Hall et al. |
| 9,358,005 B2 | 6/2016 | Shelton, IV et al. |
| 9,364,217 B2 | 6/2016 | Kostrzewski et al. |
| 9,364,219 B2 | 6/2016 | Olson et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,371,226 B2 | 6/2016 | Fox et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,427,223 B2 | 8/2016 | Park et al. |
| 9,433,419 B2 | 9/2016 | Gonzalez et al. |
| 9,439,649 B2 | 9/2016 | Shelton, IV et al. |
| 9,439,651 B2 | 9/2016 | Smith et al. |
| 9,451,958 B2 | 9/2016 | Shelton, IV et al. |
| 9,451,980 B2 | 9/2016 | Alfieri |
| 9,463,260 B2 | 10/2016 | Stopek |
| 9,468,438 B2 | 10/2016 | Baber et al. |
| 9,474,519 B2 | 10/2016 | Brustad et al. |
| 9,480,476 B2 | 11/2016 | Aldridge et al. |
| 9,486,132 B2 | 11/2016 | Green |
| 9,486,200 B2 | 11/2016 | Melsheimer et al. |
| 9,486,213 B2 | 11/2016 | Altman et al. |
| 9,486,214 B2 | 11/2016 | Shelton, IV |
| 9,492,154 B2 | 11/2016 | Melsheimer et al. |
| 9,492,167 B2 | 11/2016 | Shelton, IV et al. |
| 9,492,170 B2 | 11/2016 | Bear et al. |
| 9,498,219 B2 | 11/2016 | Moore et al. |
| 9,517,063 B2 | 12/2016 | Swayze et al. |
| 9,517,068 B2 | 12/2016 | Shelton, IV et al. |

(56) References Cited

U.S. PATENT DOCUMENTS

| | | |
|---|---|---|
| 9,517,070 B2 | 12/2016 | Mulreed |
| 9,521,996 B2 | 12/2016 | Armstrong |
| 9,522,029 B2 | 12/2016 | Yates et al. |
| 9,549,732 B2 | 1/2017 | Yates et al. |
| 9,549,738 B2 | 1/2017 | Mandakolathur Vasudevan et al. |
| 9,554,794 B2 | 1/2017 | Baber et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,572,573 B2 | 2/2017 | Scheib et al. |
| 9,572,574 B2 | 2/2017 | Shelton, IV et al. |
| 9,572,577 B2 | 2/2017 | Lloyd et al. |
| 9,585,550 B2 | 3/2017 | Abel et al. |
| 9,585,657 B2 | 3/2017 | Shelton, IV et al. |
| 9,585,660 B2 | 3/2017 | Laurent et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| 9,615,826 B2 | 4/2017 | Shelton, IV et al. |
| 9,615,892 B2 | 4/2017 | Piferi et al. |
| 9,629,623 B2 | 4/2017 | Lytle, IV et al. |
| 9,629,626 B2 | 4/2017 | Soltz et al. |
| 9,629,628 B2 * | 4/2017 | Aranyi ............. A61B 17/07207 |
| 9,629,629 B2 | 4/2017 | Leimbach et al. |
| 9,629,631 B2 | 4/2017 | Nicholas et al. |
| 9,629,814 B2 | 4/2017 | Widenhouse et al. |
| 9,636,112 B2 | 5/2017 | Penna et al. |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,662,131 B2 | 5/2017 | Omori et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,870 B2 * | 6/2017 | Baxter, III ....... A61B 17/07207 |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,236 B2 | 6/2017 | Leimbach et al. |
| 9,690,362 B2 | 6/2017 | Leimbach et al. |
| 9,693,777 B2 | 7/2017 | Schellin et al. |
| 9,700,309 B2 | 7/2017 | Jaworek et al. |
| 9,700,317 B2 | 7/2017 | Aronhalt et al. |
| 9,700,321 B2 | 7/2017 | Shelton, IV et al. |
| 9,700,326 B2 | 7/2017 | Morriss et al. |
| 9,706,991 B2 | 7/2017 | Hess et al. |
| 9,724,091 B2 | 8/2017 | Shelton, IV et al. |
| 9,724,094 B2 | 8/2017 | Baber et al. |
| 9,724,100 B2 | 8/2017 | Scheib et al. |
| 9,730,692 B2 | 8/2017 | Shelton, IV et al. |
| 9,733,663 B2 | 8/2017 | Leimbach et al. |
| 9,737,301 B2 | 8/2017 | Baber et al. |
| 9,737,335 B2 | 8/2017 | Butler et al. |
| 9,743,928 B2 | 8/2017 | Shelton, IV et al. |
| 9,743,929 B2 | 8/2017 | Leimbach et al. |
| 9,750,499 B2 | 9/2017 | Leimbach et al. |
| 9,750,502 B2 | 9/2017 | Scirica et al. |
| 9,750,503 B2 | 9/2017 | Milliman |
| 9,757,123 B2 | 9/2017 | Giordano et al. |
| 9,757,124 B2 | 9/2017 | Schellin et al. |
| 9,757,128 B2 | 9/2017 | Baber et al. |
| 9,757,130 B2 | 9/2017 | Shelton, IV |
| 9,757,133 B2 | 9/2017 | Latimer et al. |
| 9,770,245 B2 | 9/2017 | Swayze et al. |
| 9,775,608 B2 | 10/2017 | Aronhalt et al. |
| 9,775,613 B2 | 10/2017 | Shelton, IV et al. |
| 9,782,169 B2 | 10/2017 | Kimsey et al. |
| 9,788,834 B2 | 10/2017 | Schmid et al. |
| 9,788,836 B2 | 10/2017 | Overmyer et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,814,460 B2 | 11/2017 | Kimsey et al. |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,833,236 B2 | 12/2017 | Shelton, IV et al. |
| 9,833,241 B2 | 12/2017 | Huitema et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,848,873 B2 | 12/2017 | Shelton, IV |
| 9,848,875 B2 | 12/2017 | Aronhalt et al. |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,872,684 B2 | 1/2018 | Hall et al. |
| 9,877,721 B2 | 1/2018 | Schellin et al. |
| 9,877,722 B2 | 1/2018 | Schellin et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,895,148 B2 | 2/2018 | Shelton, IV et al. |
| 9,901,342 B2 | 2/2018 | Shelton, IV et al. |
| 9,907,600 B2 | 3/2018 | Stulen et al. |
| 9,913,642 B2 | 3/2018 | Leimbach et al. |
| 9,913,646 B2 | 3/2018 | Shelton, IV |
| 9,918,704 B2 | 3/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,974,529 B2 | 5/2018 | Shelton, IV et al. |
| 9,980,713 B2 | 5/2018 | Aronhalt et al. |
| 9,987,000 B2 | 6/2018 | Shelton, IV et al. |
| 9,987,001 B2 | 6/2018 | Williams |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 10,004,497 B2 | 6/2018 | Overmyer et al. |
| 10,004,498 B2 | 6/2018 | Morgan et al. |
| 10,004,501 B2 | 6/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| 10,039,529 B2 | 8/2018 | Kerr et al. |
| 10,045,769 B2 | 8/2018 | Aronhalt et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,058,963 B2 | 8/2018 | Shelton, IV et al. |
| 10,064,621 B2 | 9/2018 | Kerr et al. |
| 10,071,452 B2 | 9/2018 | Shelton, IV et al. |
| 10,085,748 B2 | 10/2018 | Morgan et al. |

(56) References Cited

U.S. PATENT DOCUMENTS

| | | |
|---|---|---|
| 10,092,292 B2 | 10/2018 | Boudreaux et al. |
| 10,111,679 B2 | 10/2018 | Baber et al. |
| 10,117,649 B2 | 11/2018 | Baxter, III et al. |
| 10,123,798 B2 | 11/2018 | Baxter, III et al. |
| 10,130,352 B2 | 11/2018 | Widenhouse et al. |
| 10,130,359 B2 | 11/2018 | Hess et al. |
| 10,130,363 B2 | 11/2018 | Huitema et al. |
| 10,130,366 B2 | 11/2018 | Shelton, IV et al. |
| 10,135,242 B2 | 11/2018 | Baber et al. |
| 10,136,887 B2 | 11/2018 | Shelton, IV et al. |
| 10,136,890 B2 | 11/2018 | Shelton, IV et al. |
| 10,136,891 B2 | 11/2018 | Shelton, IV et al. |
| 10,149,680 B2 | 12/2018 | Parihar et al. |
| 10,149,682 B2 | 12/2018 | Shelton, IV et al. |
| 10,159,482 B2 | 12/2018 | Swayze et al. |
| 10,159,483 B2 | 12/2018 | Beckman et al. |
| 10,166,025 B2 | 1/2019 | Leimbach et al. |
| 10,172,611 B2 | 1/2019 | Shelton, IV et al. |
| 10,172,617 B2 | 1/2019 | Shelton, IV et al. |
| 10,178,992 B2 | 1/2019 | Wise et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,393 B2 | 1/2019 | Smith et al. |
| 10,194,913 B2 | 2/2019 | Nalagatla et al. |
| 10,201,364 B2 | 2/2019 | Leimbach et al. |
| 10,206,678 B2 | 2/2019 | Shelton, IV et al. |
| 10,213,198 B2 | 2/2019 | Aronhalt et al. |
| 10,226,250 B2 | 3/2019 | Beckman et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,058 B2 | 4/2019 | Omori et al. |
| 2001/0025183 A1 | 9/2001 | Shahidi |
| 2001/0044656 A1* | 11/2001 | Williamson, IV ............... A61B 17/0469 623/2.11 |
| 2002/0095175 A1 | 7/2002 | Brock et al. |
| 2002/0103494 A1 | 8/2002 | Pacey |
| 2002/0117534 A1 | 8/2002 | Green et al. |
| 2003/0190584 A1 | 10/2003 | Heasley |
| 2004/0054353 A1 | 3/2004 | Taylor |
| 2004/0098040 A1 | 5/2004 | Taniguchi et al. |
| 2004/0108357 A1 | 6/2004 | Milliman et al. |
| 2004/0147909 A1 | 7/2004 | Johnston et al. |
| 2004/0158230 A1 | 8/2004 | Hunn et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0254566 A1 | 12/2004 | Plicchi et al. |
| 2004/0260315 A1 | 12/2004 | Dell et al. |
| 2004/0267310 A1 | 12/2004 | Racenet et al. |
| 2005/0033226 A1 | 2/2005 | Kim |
| 2005/0051163 A1 | 3/2005 | Deem et al. |
| 2005/0059997 A1 | 3/2005 | Bauman et al. |
| 2005/0070929 A1 | 3/2005 | Dalessandro et al. |
| 2005/0085693 A1 | 4/2005 | Belson et al. |
| 2005/0131390 A1 | 6/2005 | Heinrich et al. |
| 2005/0131457 A1 | 6/2005 | Douglas et al. |
| 2005/0143756 A1 | 6/2005 | Jankowski |
| 2005/0143759 A1 | 6/2005 | Kelly |
| 2005/0154406 A1 | 7/2005 | Bombard et al. |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0203550 A1 | 9/2005 | Laufer et al. |
| 2005/0216055 A1 | 9/2005 | Scirica et al. |
| 2005/0236459 A1 | 10/2005 | Gresham |
| 2005/0245965 A1 | 11/2005 | Orban, III et al. |
| 2005/0246881 A1 | 11/2005 | Kelly et al. |
| 2005/0256452 A1 | 11/2005 | DeMarchi et al. |
| 2005/0263563 A1 | 12/2005 | Racenet et al. |
| 2005/0283188 A1 | 12/2005 | Loshakove et al. |
| 2006/0020258 A1 | 1/2006 | Strauss et al. |
| 2006/0025812 A1 | 2/2006 | Shelton |
| 2006/0041188 A1 | 2/2006 | Dirusso et al. |
| 2006/0049229 A1 | 3/2006 | Milliman et al. |
| 2006/0052669 A1 | 3/2006 | Hart |
| 2006/0052825 A1 | 3/2006 | Ransick et al. |
| 2006/0100643 A1 | 5/2006 | Laufer et al. |
| 2006/0149306 A1 | 7/2006 | Hart et al. |
| 2006/0161050 A1 | 7/2006 | Butler et al. |
| 2006/0161185 A1 | 7/2006 | Saadat et al. |
| 2006/0173470 A1 | 8/2006 | Oray et al. |
| 2006/0180634 A1 | 8/2006 | Shelton et al. |
| 2006/0185682 A1 | 8/2006 | Marczyk |
| 2006/0201989 A1 | 9/2006 | Ojeda |
| 2006/0211919 A1 | 9/2006 | Wilk |
| 2006/0235368 A1 | 10/2006 | Oz |
| 2006/0241651 A1 | 10/2006 | Wilk |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2006/0289602 A1 | 12/2006 | Wales et al. |
| 2007/0027468 A1 | 2/2007 | Wales et al. |
| 2007/0043387 A1 | 2/2007 | Vargas et al. |
| 2007/0073341 A1 | 3/2007 | Smith et al. |
| 2007/0078484 A1 | 4/2007 | Talarico et al. |
| 2007/0080188 A1* | 4/2007 | Spence ............... A61B 17/0401 227/175.1 |
| 2007/0080814 A1 | 4/2007 | Ellsworth et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0135803 A1 | 6/2007 | Belson |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0208359 A1 | 9/2007 | Hoffman |
| 2007/0225562 A1 | 9/2007 | Spivey et al. |
| 2007/0244471 A1 | 10/2007 | Malackowski |
| 2007/0246505 A1 | 10/2007 | Pace-Floridia et al. |
| 2007/0276409 A1 | 11/2007 | Ortiz et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0197167 A1 | 8/2008 | Viola et al. |
| 2008/0200933 A1 | 8/2008 | Bakos et al. |
| 2008/0242939 A1 | 10/2008 | Johnston |
| 2008/0255413 A1 | 10/2008 | Zemlok et al. |
| 2008/0262654 A1 | 10/2008 | Omori et al. |
| 2008/0294179 A1 | 11/2008 | Balbierz et al. |
| 2008/0296346 A1 | 12/2008 | Shelton, IV et al. |

(56) References Cited

U.S. PATENT DOCUMENTS

| | | |
|---|---|---|
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0012534 A1 | 1/2009 | Madhani et al. |
| 2009/0078736 A1 | 3/2009 | Van Lue |
| 2009/0090763 A1 | 4/2009 | Zemlok et al. |
| 2009/0149871 A9 | 6/2009 | Kagan et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0292283 A1 | 11/2009 | Odom |
| 2009/0308907 A1 | 12/2009 | Nalagatla et al. |
| 2010/0069942 A1 | 3/2010 | Shelton, IV |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2010/0292540 A1 | 11/2010 | Hess et al. |
| 2010/0312261 A1 | 12/2010 | Suzuki et al. |
| 2011/0006101 A1 | 1/2011 | Hall et al. |
| 2011/0011916 A1 | 1/2011 | Levine |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0060363 A1 | 3/2011 | Hess et al. |
| 2011/0071356 A1 | 3/2011 | Edwards |
| 2011/0087276 A1 | 4/2011 | Bedi et al. |
| 2011/0114697 A1 | 5/2011 | Baxter, III et al. |
| 2011/0118706 A1 | 5/2011 | Gingras et al. |
| 2011/0125176 A1 | 5/2011 | Yates et al. |
| 2011/0147433 A1 | 6/2011 | Shelton, IV et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0295295 A1 | 12/2011 | Shelton, IV et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0175398 A1 | 7/2012 | Sandborn et al. |
| 2012/0199602 A1 | 8/2012 | Jordan et al. |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026209 A1 | 1/2013 | Mozdzierz et al. |
| 2013/0026210 A1 | 1/2013 | Shelton, IV et al. |
| 2013/0030253 A1 | 1/2013 | Titus |
| 2013/0085339 A1 | 4/2013 | Jaworek et al. |
| 2013/0087597 A1 | 4/2013 | Shelton, IV et al. |
| 2013/0098970 A1 | 4/2013 | Racenet et al. |
| 2013/0116669 A1 | 5/2013 | Shelton, IV et al. |
| 2013/0153636 A1 | 6/2013 | Shelton, IV et al. |
| 2013/0153641 A1 | 6/2013 | Shelton, IV et al. |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0231667 A1 | 9/2013 | Taylor et al. |
| 2013/0233906 A1 | 9/2013 | Hess et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0270322 A1 | 10/2013 | Scheib et al. |
| 2013/0324982 A1 | 12/2013 | Smith et al. |
| 2013/0331867 A1 | 12/2013 | Reeser et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014704 A1 | 1/2014 | Onukuri et al. |
| 2014/0014705 A1 | 1/2014 | Baxter, III |
| 2014/0021239 A1* | 1/2014 | Kostrzewski .... A61B 17/07207 227/175.3 |
| 2014/0107640 A1 | 4/2014 | Yates et al. |
| 2014/0151433 A1 | 6/2014 | Shelton, IV et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0200561 A1 | 7/2014 | Ingmanson et al. |
| 2014/0224857 A1 | 8/2014 | Schmid |
| 2014/0243865 A1 | 8/2014 | Swayze et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0284371 A1 | 9/2014 | Morgan et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0309666 A1 | 10/2014 | Shelton, IV et al. |
| 2015/0053737 A1 | 2/2015 | Leimbach et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0282810 A1 | 10/2015 | Shelton, IV et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0313594 A1 | 11/2015 | Shelton, IV et al. |
| 2016/0066913 A1 | 3/2016 | Swayze et al. |
| 2016/0089146 A1 | 3/2016 | Harris et al. |
| 2016/0113653 A1 | 4/2016 | Zingman |
| 2016/0120544 A1 | 5/2016 | Shelton, IV et al. |
| 2016/0135796 A1 | 5/2016 | Hundertmark et al. |
| 2016/0143637 A1 | 5/2016 | Nering et al. |
| 2016/0249910 A1 | 9/2016 | Shelton, IV et al. |
| 2016/0249916 A1 | 9/2016 | Shelton, IV et al. |
| 2016/0256071 A1 | 9/2016 | Shelton, IV et al. |
| 2016/0256154 A1 | 9/2016 | Shelton, IV et al. |

(56) References Cited

U.S. PATENT DOCUMENTS

| | | |
|---|---|---|
| 2016/0256160 A1 | 9/2016 | Shelton, IV et al. |
| 2016/0256185 A1 | 9/2016 | Shelton, IV et al. |
| 2016/0367246 A1 | 12/2016 | Baxter, III et al. |
| 2016/0367254 A1 | 12/2016 | Baxter, III et al. |
| 2016/0367255 A1 | 12/2016 | Wise et al. |
| 2016/0374672 A1 | 12/2016 | Bear et al. |
| 2017/0007229 A1 | 1/2017 | Widenhouse et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055986 A1 | 3/2017 | Harris et al. |
| 2017/0056000 A1 | 3/2017 | Nalagatla et al. |
| 2017/0056008 A1 | 3/2017 | Shelton, IV et al. |
| 2017/0119386 A1 | 5/2017 | Scheib et al. |
| 2017/0119387 A1 | 5/2017 | Dalessandro et al. |
| 2017/0119388 A1 | 5/2017 | Kostrzewski |
| 2017/0119389 A1 | 5/2017 | Turner et al. |
| 2017/0119390 A1 | 5/2017 | Schellin et al. |
| 2017/0119392 A1 | 5/2017 | Shelton, IV et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196566 A1 | 7/2017 | Sgroi |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0258540 A1 | 9/2017 | Blatt |
| 2017/0281161 A1 | 10/2017 | Shelton, IV et al. |
| 2017/0281162 A1 | 10/2017 | Shelton, IV et al. |
| 2017/0281163 A1 | 10/2017 | Shelton, IV et al. |
| 2017/0281164 A1 | 10/2017 | Harris et al. |
| 2017/0281165 A1 | 10/2017 | Harris et al. |
| 2017/0281166 A1 | 10/2017 | Morgan et al. |
| 2017/0281167 A1 | 10/2017 | Shelton, IV et al. |
| 2017/0281168 A1 | 10/2017 | Shelton, IV et al. |
| 2017/0281169 A1 | 10/2017 | Harris et al. |
| 2017/0281170 A1 | 10/2017 | Shelton, IV et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281178 A1 | 10/2017 | Shelton, IV et al. |
| 2017/0281179 A1 | 10/2017 | Shelton, IV et al. |
| 2017/0281180 A1 | 10/2017 | Morgan et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281188 A1 | 10/2017 | Shelton, IV et al. |
| 2017/0281189 A1 | 10/2017 | Nalagatla et al. |
| 2018/0325508 A1 | 11/2018 | Aronhalt et al. |
| 2019/0021718 A1 | 1/2019 | Aronhalt et al. |
| 2019/0029661 A1 | 1/2019 | Widenhouse et al. |
| 2019/0059934 A1 | 2/2019 | Williams |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 2686539 Y | 3/2005 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101675898 A | 3/2010 |
| CN | 101683280 A | 3/2010 |
| CN | 102188270 A | 9/2011 |
| CN | 101534723 B | 1/2012 |
| CN | 202313540 U | 7/2012 |
| CN | 101541251 A | 11/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U1 | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 4/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |

(56) References Cited

FOREIGN PATENT DOCUMENTS

| | | |
|---|---|---|
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1486172 A1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |

(56) References Cited

FOREIGN PATENT DOCUMENTS

| | | |
|---|---|---|
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110083 A2 | 10/2009 |
| EP | 2110084 A2 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |

(56) References Cited

FOREIGN PATENT DOCUMENTS

| | | |
|---|---|---|
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 1962711 B1 | 2/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 1884206 B1 | 3/2013 |
| EP | 2090238 B1 | 4/2013 |
| EP | 1806103 B1 | 5/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2759267 A2 | 7/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | H02279149 A | 11/1990 |
| JP | H0312126 A | 1/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H067357 A | 1/1994 |
| JP | H0630945 A | 2/1994 |
| JP | H0654857 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H0731623 A | 2/1995 |
| JP | H0747070 A | 2/1995 |
| JP | H0751273 A | 2/1995 |
| JP | H07124166 A | 5/1995 |
| JP | H07163574 A | 6/1995 |
| JP | H07171163 A | 7/1995 |
| JP | H07255735 A | 10/1995 |
| JP | H07285089 A | 10/1995 |
| JP | H0833641 A | 2/1996 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H10113352 A | 5/1998 |
| JP | H10118090 A | 5/1998 |
| JP | H10151137 A | 6/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003523251 A | 8/2003 |

(56) References Cited

FOREIGN PATENT DOCUMENTS

| | | |
|---|---|---|
| JP | 2003523254 A | 8/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006506106 A | 2/2006 |
| JP | 2006510879 A | 3/2006 |
| JP | 2006187649 A | 7/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 3934161 B2 | 6/2007 |
| JP | 2007203049 A | 8/2007 |
| JP | 2007203051 A | 8/2007 |
| JP | 2007203057 A | 8/2007 |
| JP | 2007209751 A | 8/2007 |
| JP | 2007524435 A | 8/2007 |
| JP | 2007222615 A | 9/2007 |
| JP | 2007229448 A | 9/2007 |
| JP | 4001860 B2 | 10/2007 |
| JP | 2007325922 A | 12/2007 |
| JP | 2008068073 A | 3/2008 |
| JP | 2008206967 A | 9/2008 |
| JP | 2008212637 A | 9/2008 |
| JP | 2008212638 A | 9/2008 |
| JP | 2008220956 A | 9/2008 |
| JP | 2008259860 A | 10/2008 |
| JP | 2008264535 A | 11/2008 |
| JP | 2008283459 A | 11/2008 |
| JP | 2009502351 A | 1/2009 |
| JP | 2009506799 A | 2/2009 |
| JP | 2009507526 A | 2/2009 |
| JP | 2009072599 A | 4/2009 |
| JP | 2009090113 A | 4/2009 |
| JP | 2009106752 A | 5/2009 |
| JP | 2009189836 A | 8/2009 |
| JP | 2009189837 A | 8/2009 |
| JP | 2009189838 A | 8/2009 |
| JP | 2009536082 A | 10/2009 |
| JP | 2009261944 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504846 A | 2/2010 |
| JP | 2010505524 A | 2/2010 |
| JP | 2010069310 A | 4/2010 |
| JP | 2010088876 A | 4/2010 |
| JP | 2010098844 A | 4/2010 |
| JP | 4461008 B2 | 5/2010 |
| JP | 4549018 B2 | 9/2010 |
| JP | 2010540192 A | 12/2010 |
| JP | 4783373 B2 | 9/2011 |
| JP | 5140421 B2 | 2/2013 |
| JP | 5162595 B2 | 3/2013 |
| JP | 2013128791 A | 7/2013 |
| JP | 5333899 B2 | 11/2013 |
| KR | 20110003229 A | 1/2011 |
| RU | 1814161 A1 | 5/1993 |
| RU | 1814161 C | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-9412108 A1 | 6/1994 |
| WO | WO-9418893 A1 | 9/1994 |
| WO | WO-9420030 A1 | 9/1994 |
| WO | WO-9422378 A1 | 10/1994 |

(56) References Cited

FOREIGN PATENT DOCUMENTS

| | | |
|---|---|---|
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024322 A1 | 5/2000 |
| WO | WO-0024330 A1 | 5/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A2 | 1/2003 |
| WO | WO-03001986 A2 | 1/2003 |
| WO | WO-03013363 A1 | 2/2003 |
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |

(56) References Cited

FOREIGN PATENT DOCUMENTS

| | | |
|---|---|---|
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005055846 A1 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006051252 A1 | 5/2006 |
| WO | WO-2006059067 A1 | 6/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007016290 A2 | 2/2007 |
| WO | WO-2007018898 A2 | 2/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021969 A2 | 2/2008 |
| WO | WO-2008039249 A1 | 4/2008 |
| WO | WO-2008039270 A1 | 4/2008 |
| WO | WO-2008045383 A2 | 4/2008 |
| WO | WO-2008057281 A2 | 5/2008 |
| WO | WO-2008070763 A1 | 6/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109125 A1 | 9/2008 |
| WO | WO-2008124748 A1 | 10/2008 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2010028332 A2 | 3/2010 |
| WO | WO-2010030434 A1 | 3/2010 |
| WO | WO-2010050771 A2 | 5/2010 |
| WO | WO-2010054404 A1 | 5/2010 |
| WO | WO-2010063795 A1 | 6/2010 |
| WO | WO-2010093333 A1 | 8/2010 |
| WO | WO-2010098871 A2 | 9/2010 |
| WO | WO-2011008672 A2 | 1/2011 |
| WO | WO-2011013103 A1 | 2/2011 |
| WO | WO-2011044343 A2 | 4/2011 |
| WO | WO-2011060311 A2 | 5/2011 |
| WO | WO-2012006306 A2 | 1/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012058213 A2 | 5/2012 |
| WO | WO-2012068156 A2 | 5/2012 |
| WO | WO-2012127462 A1 | 9/2012 |
| WO | WO-2012143913 A2 | 10/2012 |
| WO | WO-2012148667 A2 | 11/2012 |
| WO | WO-2012148703 A2 | 11/2012 |
| WO | WO-2012160163 A1 | 11/2012 |
| WO | WO-2013009699 A2 | 1/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013/087092 A1 | 6/2013 |
| WO | WO-2013148762 A2 | 10/2013 |
| WO | WO-2013167427 A1 | 11/2013 |
| WO | WO-2014004199 A1 | 1/2014 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

"Biomedical Coatings," Fort Wayne Metals, Research Products Corporation, obtained online at www.fwmetals.com on Jun. 21, 2010 (1 page).

(56) References Cited

OTHER PUBLICATIONS

Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get The Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
The Sodem Aseptic Battery Transfer Kit, Sodem Systems, 2000, 3 pages.
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
"Indian Standard: Automotive Vehicles—Brakes and Braking Systems (IS 11852-1:2001)", Mar. 1, 2001.
Zhang et al.; "Viscoelastic Properties of Wood Materials Characterized by Nanoindentation Experiments"; Dec. 20, 2011 (Year: 2011).
Batista et al.; "Evaluation of Weather Influence on Mechanical and Viscoelastic Properties of Polyetherimide/Carbon Fiber Composites"; Apr. 30, 2013 (Year: 2013).
L. Edward Parkman, III; "Viscoelastic Effects on a Polyetherimide Cylinder with Constant Radial Deformation"; May 2015; (Year: 2015).

\* cited by examiner

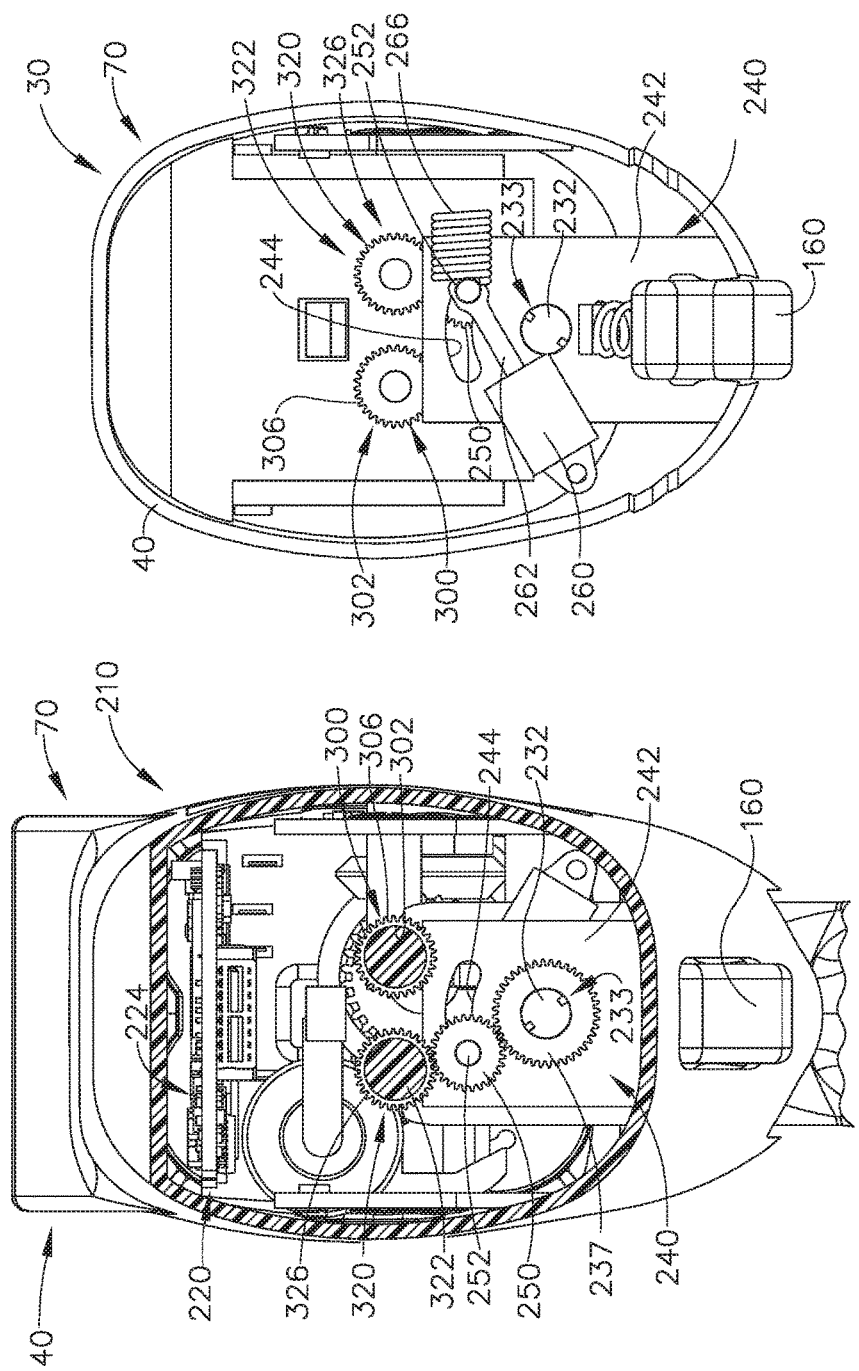

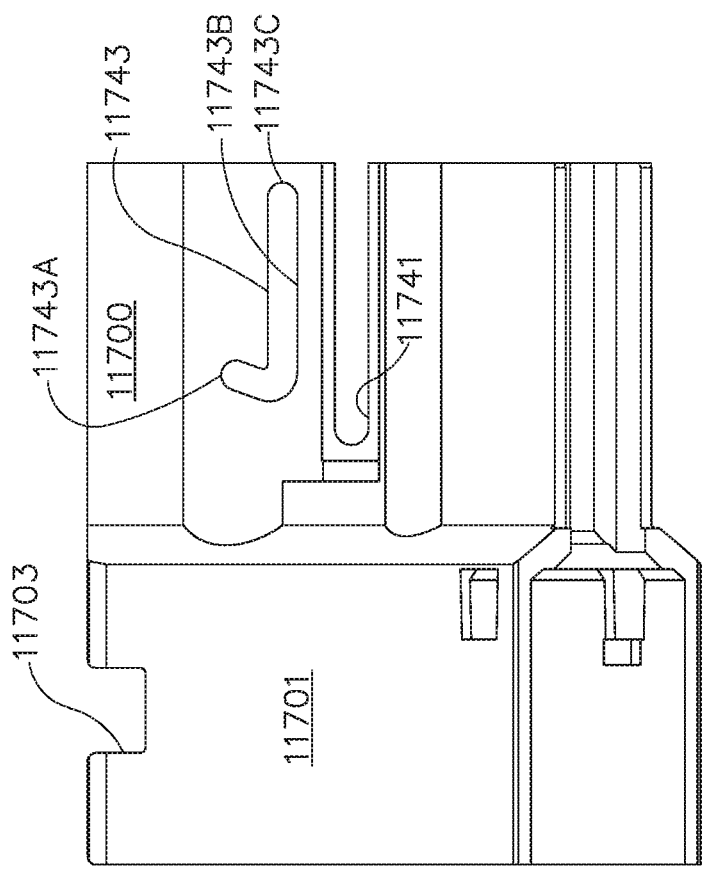
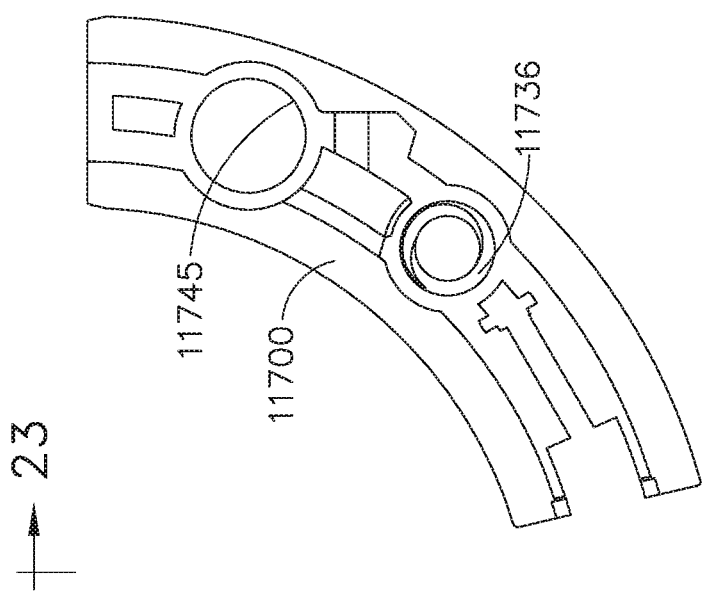
FIG. 23
FIG. 22

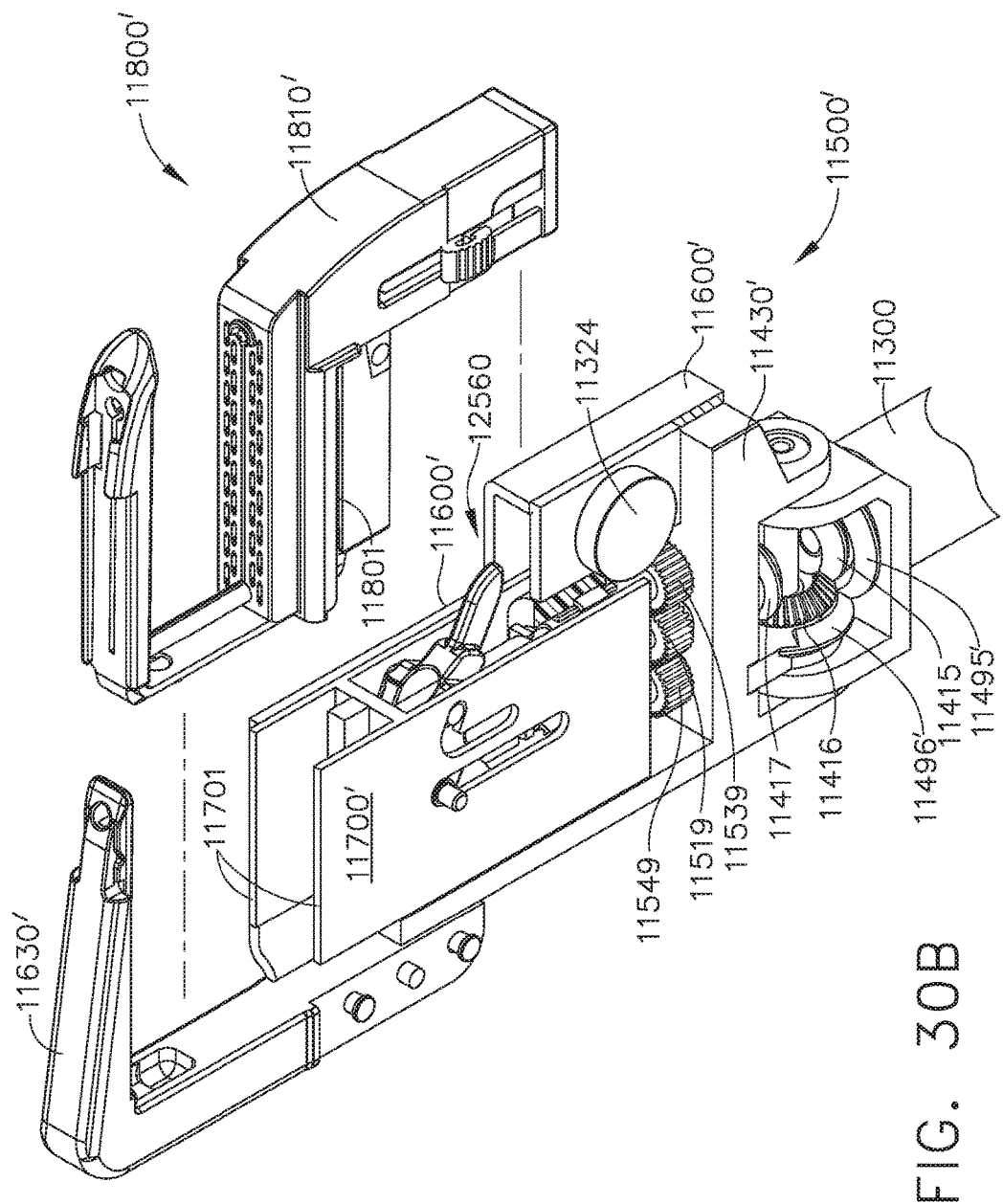

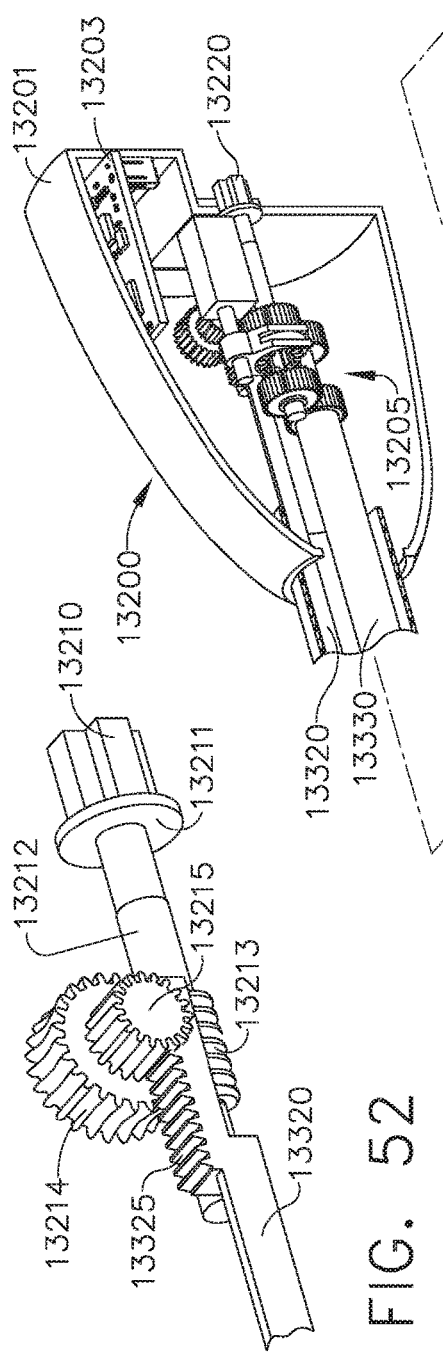
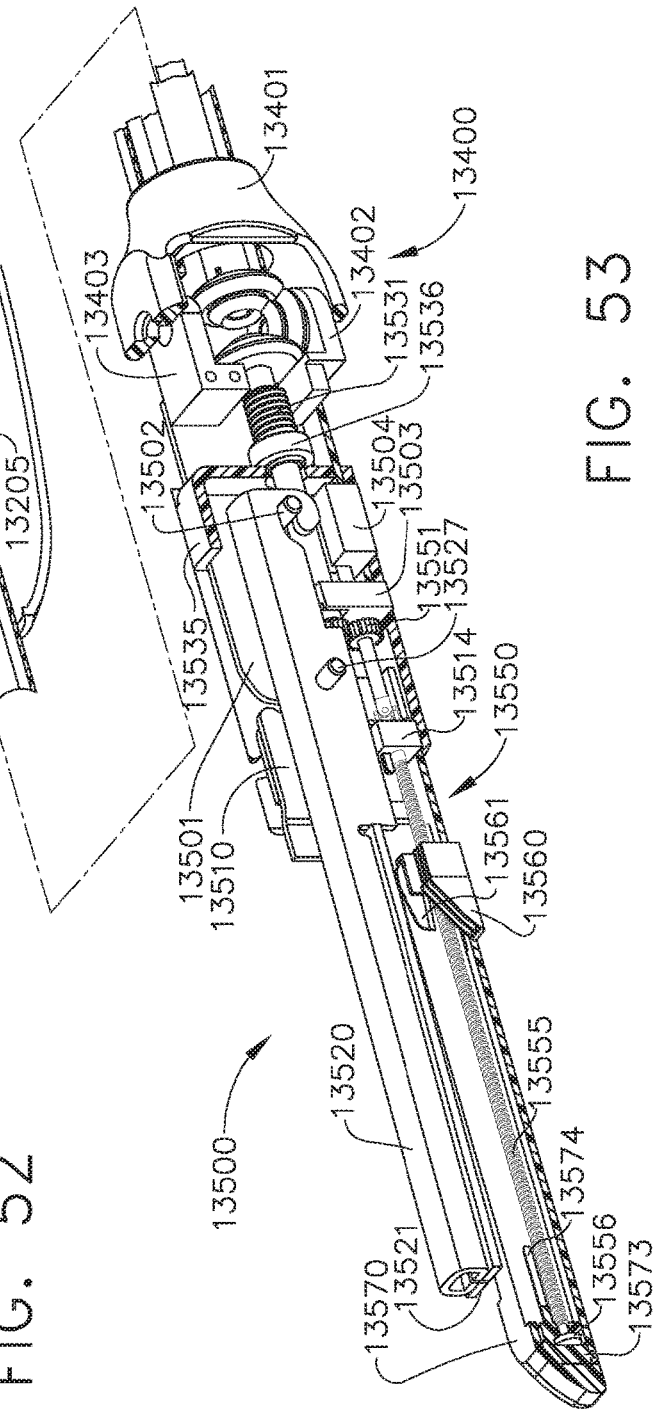
FIG. 52
FIG. 53

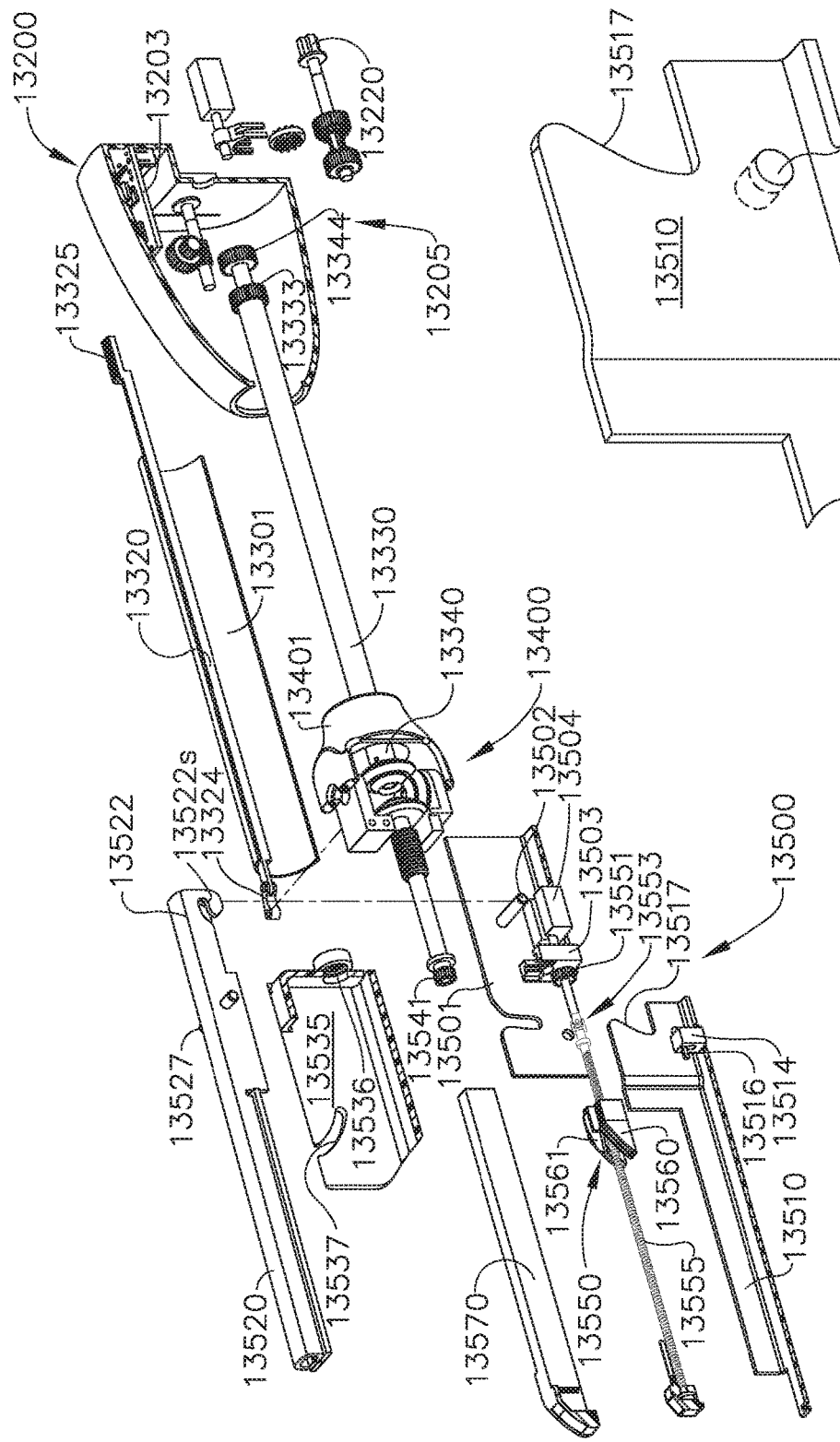
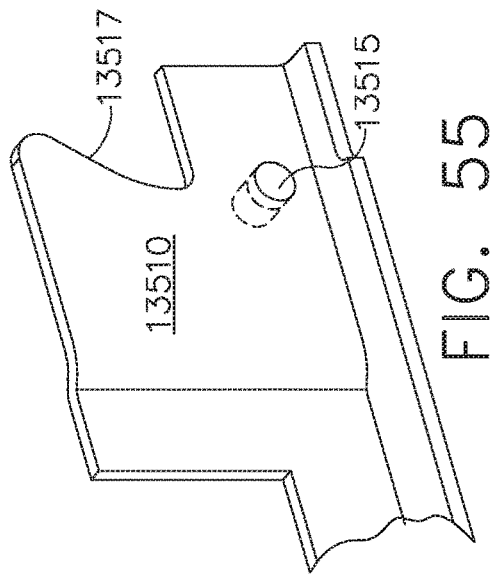
FIG. 54
FIG. 55

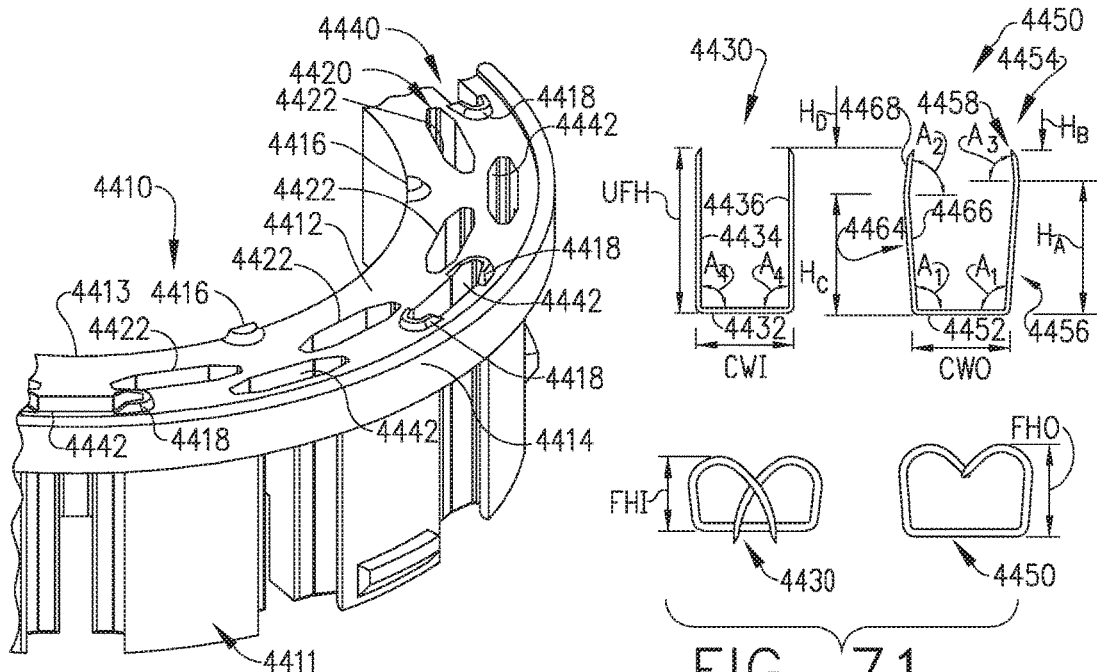
FIG. 70
FIG. 71
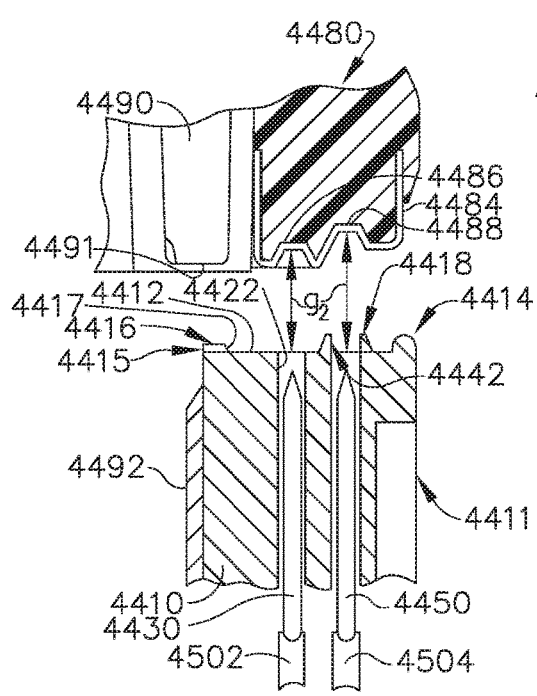
FIG. 72
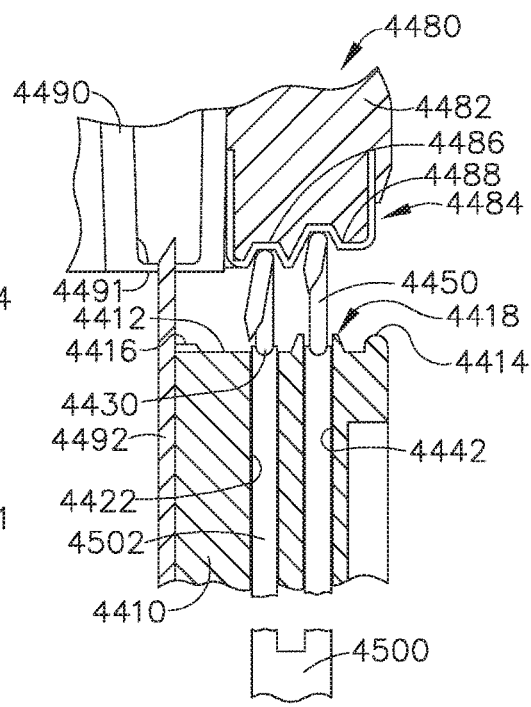
FIG. 73

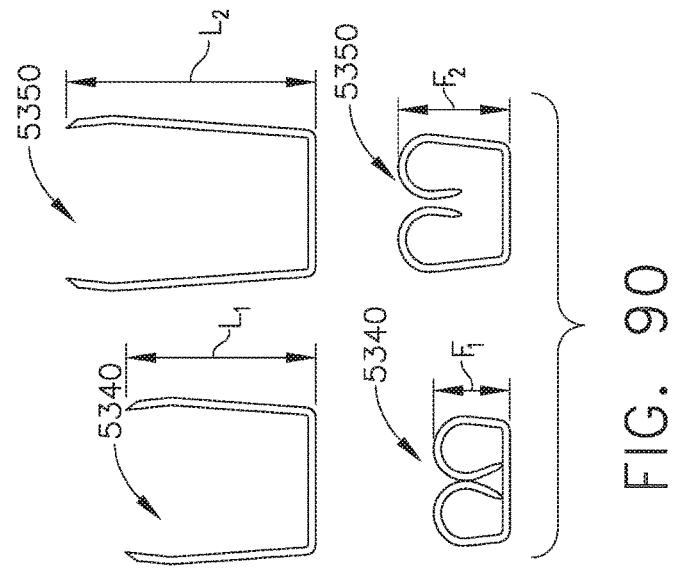
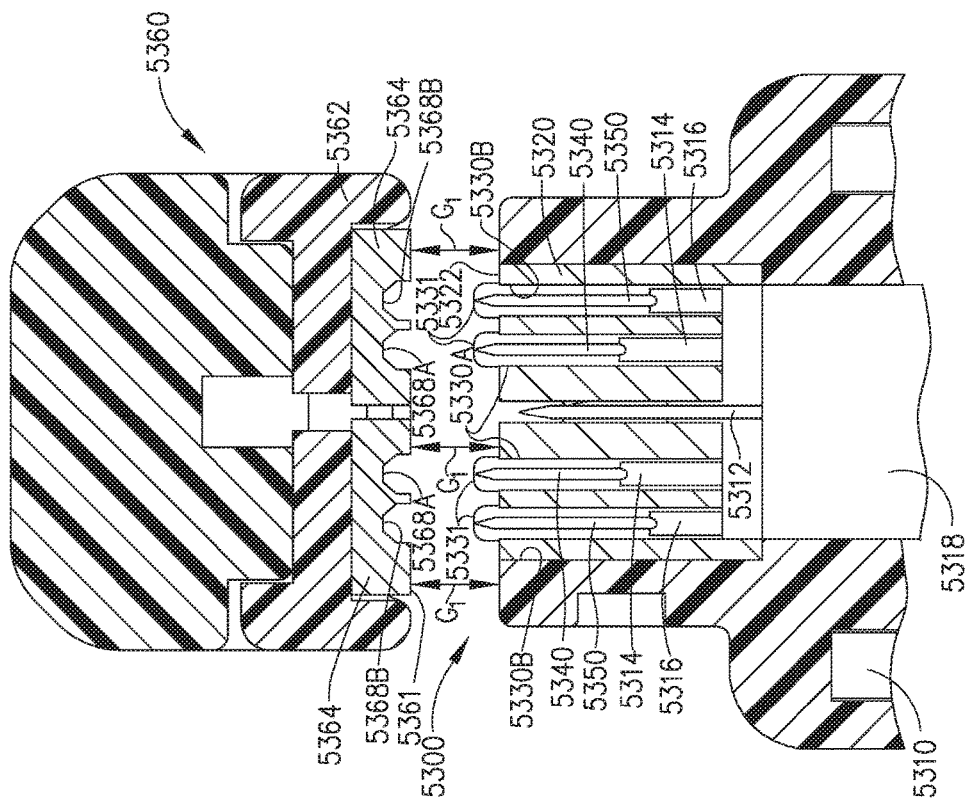

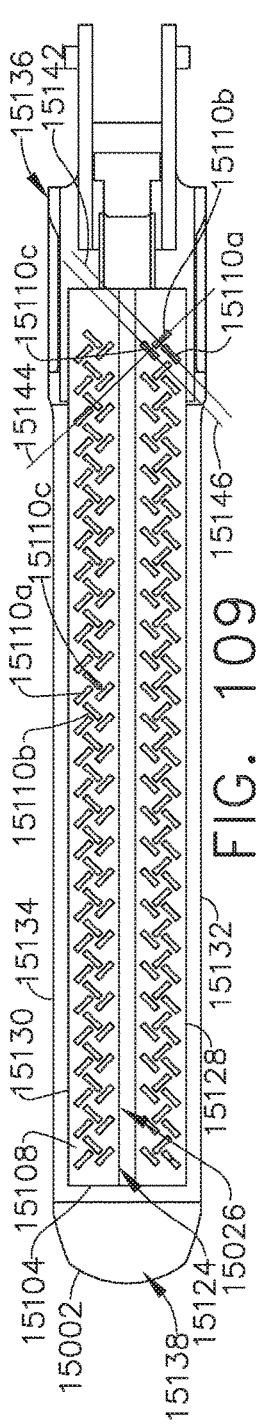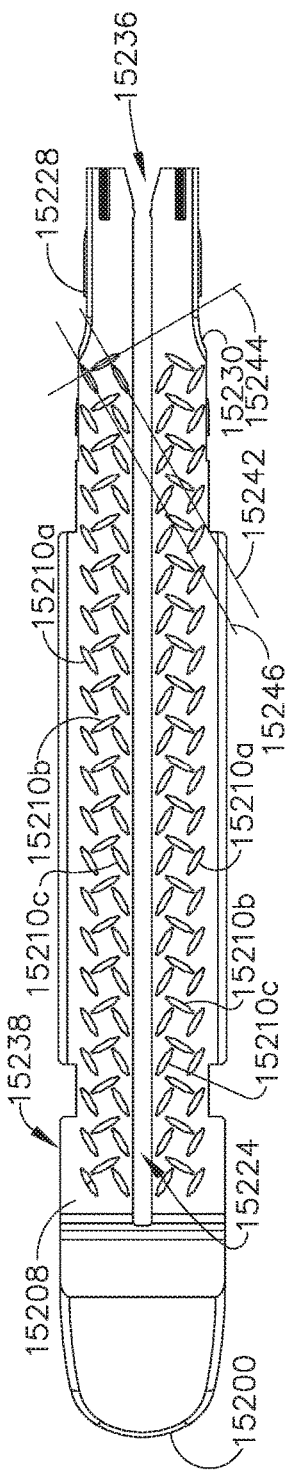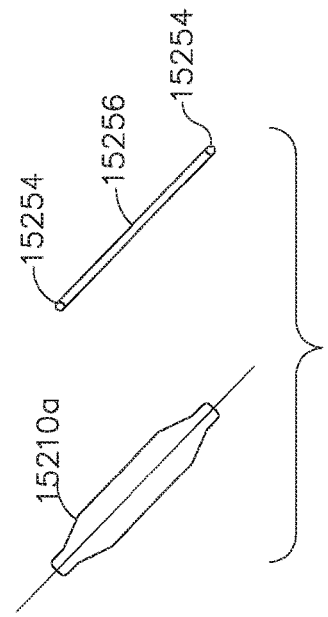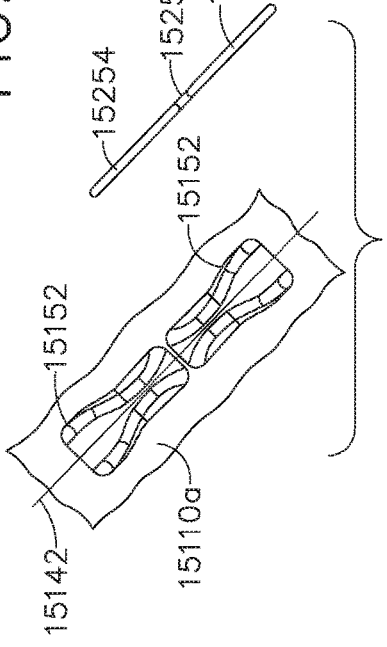

SURGICAL STAPLING INSTRUMENT COMPRISING MULTIPLE LOCKOUTS

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 8 is another end cross-sectional view of the handle assembly of FIGS. 2-7 showing a shifter gear in meshing engagement with a drive gear on a rotary drive socket;

FIG. 9 is another end cross-sectional view of the handle assembly of FIGS. 2-8 showing the position of a shifter solenoid when the shifter gear is in meshing engagement with the drive gear on the rotary drive socket;

FIG. 22 is a bottom view of the closure frame shown in FIG. 21;

FIG. 23 is a side view of the closure frame shown in FIG. 21;

FIG. 30B is a partial perspective view of the shaft assembly of FIG. 30A illustrating the staple cartridge detached from the shaft assembly;

FIG. 52 is a partial perspective view of an articulation transmission of the attachment portion of the instrument of FIG. 51;

FIG. 53 is a perspective cross-sectioned view of the end effector assembly of the instrument of FIG. 51, wherein some portions of the instrument are removed to expose inner portions of the instrument;

FIG. 54 is a partial exploded view of the instrument of FIG. 51;

FIG. 55 is a partial perspective view of a cartridge support jaw of the instrument of FIG. 51 comprising a pivot pin defining a pivot axis about which the cartridge support jaw is rotatable;

FIG. 70 is a perspective view of a portion of a surgical staple cartridge for use with a circular surgical stapling instrument in accordance with at least one embodiment;

FIG. 71 depicts a pair of staples in accordance with at least one embodiment in unformed and formed configurations;

FIG. 72 is a cross-sectional view of a portion of an anvil in relation to a portion of the surgical staple cartridge of FIG. 70 prior to actuation of the staple forming process;

FIG. 73 is another cross-sectional view of the anvil of FIG. 72 and the staple cartridge of FIG. 70 after the staples have been formed;

FIG. 89 is a side elevational cross-sectional view of a portion of a surgical stapling device according to at least one embodiment;

FIG. 90 depicts staples in accordance with at least one embodiment in unformed and formed configurations;

FIG. 109 is a top view of an anvil assembly of a surgical stapler in accordance with at least one embodiment;

FIG. 110 is a top view of a staple cartridge of the surgical stapler of FIG. 109;

FIG. 111 illustrates a forming pocket of an anvil modification member and a staple formed by the forming pocket;

FIG. 112 illustrates a staple cavity of the surgical stapler of FIG. 109 and an unformed staple;

FIG. 113 is a perspective of a staple driver supporting three staples of the surgical stapler of FIG. 109;

FIG. 114 is a top view of the staple driver of FIG. 113;

FIG. 115 illustrates a cross-sectional view of an end effector including a staple cartridge, an anvil, and an anvil modification member in accordance with at least one alternative embodiment; and FIG. 116 illustrates three staples in unformed configurations and formed configurations in accordance with at least one embodiment.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
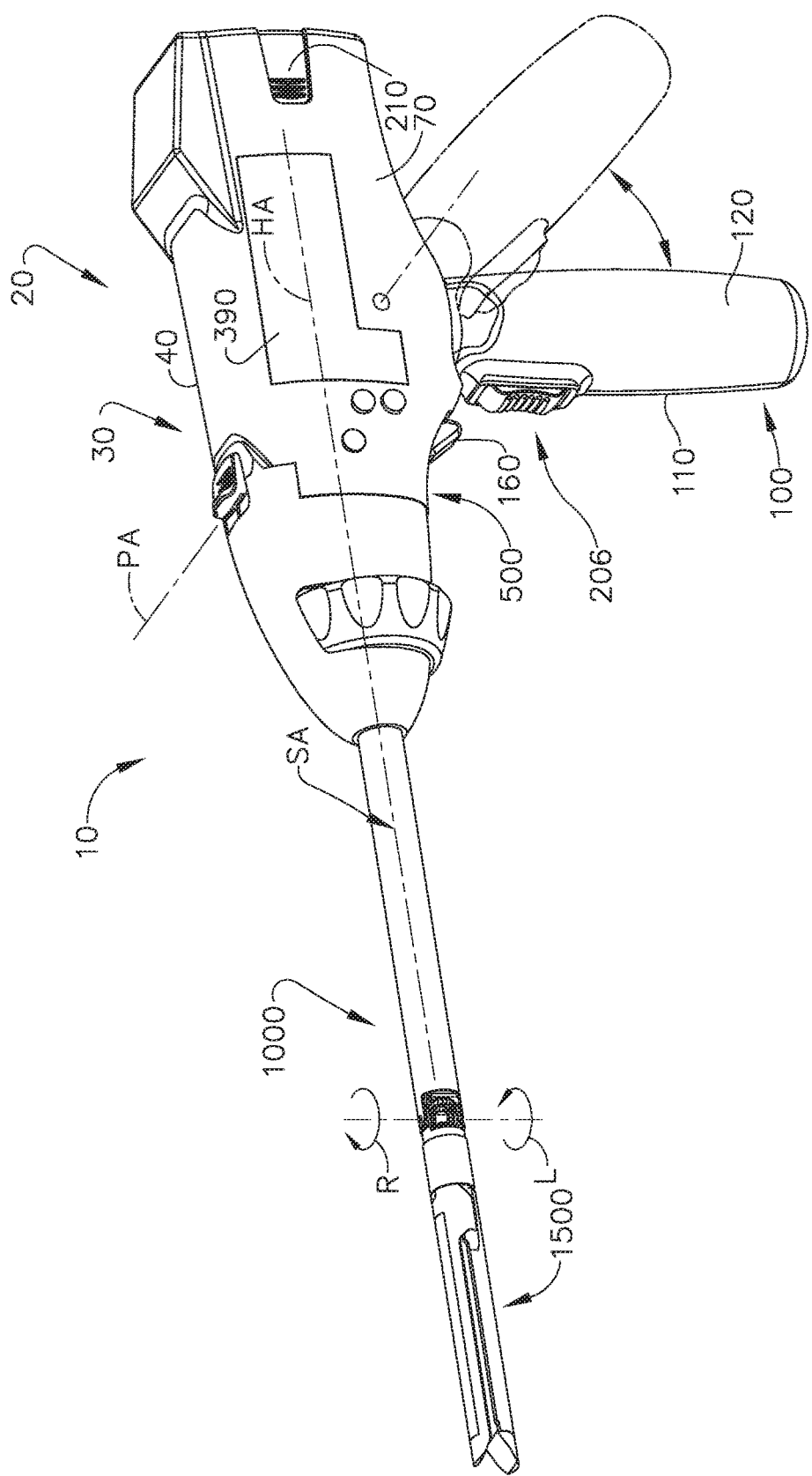
FIG. 1 is a perspective view of a surgical instrument including an interchangeable surgical tool assembly in accordance with at least one embodiment.

Applicant of the present application owns the following patent applications that were filed on Apr. 1, 2016 and which are each herein incorporated by reference in their respective entireties:
- U.S. patent application Ser. No. 15/089,325, entitled METHOD FOR OPERATING A SURGICAL STAPLING SYSTEM;
- U.S. patent application Ser. No. 15/089,321, entitled MODULAR SURGICAL STAPLING SYSTEM COMPRISING A DISPLAY;
- U.S. patent application Ser. No. 15/089,326, entitled SURGICAL STAPLING SYSTEM COMPRISING A DISPLAY INCLUDING A RE-ORIENTABLE DISPLAY FIELD;
- U.S. patent application Ser. No. 15/089,263, entitled SURGICAL INSTRUMENT HANDLE ASSEMBLY WITH RECONFIGURABLE GRIP PORTION;
- U.S. patent application Ser. No. 15/089,262, entitled ROTARY POWERED SURGICAL INSTRUMENT WITH MANUALLY ACTUATABLE BAILOUT SYSTEM;
- U.S. patent application Ser. No. 15/089,277, entitled SURGICAL CUTTING AND STAPLING END EFFECTOR WITH ANVIL CONCENTRIC DRIVE MEMBER;
- U.S. patent application Ser. No. 15/089,283, entitled CLOSURE SYSTEM ARRANGEMENTS FOR SURGICAL CUTTING AND STAPLING DEVICES WITH SEPARATE AND DISTINCT FIRING SHAFTS;
- U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;
- U.S. patent application Ser. No. 15/089,258, entitled SURGICAL STAPLING SYSTEM COMPRISING A SHIFTABLE TRANSMISSION;
- U.S. patent application Ser. No. 15/089,278, entitled SURGICAL STAPLING SYSTEM CONFIGURED TO PROVIDE SELECTIVE CUTTING OF TISSUE;
- U.S. patent application Ser. No. 15/089,284, entitled SURGICAL STAPLING SYSTEM COMPRISING A CONTOURABLE SHAFT;
- U.S. patent application Ser. No. 15/089,295, entitled SURGICAL STAPLING SYSTEM COMPRISING A TISSUE COMPRESSION LOCKOUT;
- U.S. patent application Ser. No. 15/089,300, entitled SURGICAL STAPLING SYSTEM COMPRISING AN UNCLAMPING LOCKOUT;
- U.S. patent application Ser. No. 15/089,196, entitled SURGICAL STAPLING SYSTEM COMPRISING A JAW CLOSURE LOCKOUT;
- U.S. patent application Ser. No. 15/089,203, entitled SURGICAL STAPLING SYSTEM COMPRISING A JAW ATTACHMENT LOCKOUT;
- U.S. patent application Ser. No. 15/089,210, entitled SURGICAL STAPLING SYSTEM COMPRISING A SPENT CARTRIDGE LOCKOUT;
- U.S. patent application Ser. No. 15/089,324, entitled SURGICAL INSTRUMENT COMPRISING A SHIFTING MECHANISM;
- U.S. patent application Ser. No. 15/089,339, entitled SURGICAL STAPLING INSTRUMENT;
- U.S. patent application Ser. No. 15/089,253, entitled SURGICAL STAPLING SYSTEM CONFIGURED TO APPLY ANNULAR ROWS OF STAPLES HAVING DIFFERENT HEIGHTS;
- U.S. patent application Ser. No. 15/089,304, entitled SURGICAL STAPLING SYSTEM COMPRISING A GROOVED FORMING POCKET;
- U.S. patent application Ser. No. 15/089,331, entitled ANVIL MODIFICATION MEMBERS FOR SURGICAL STAPLERS;
- U.S. patent application Ser. No. 15/089,336, entitled STAPLE CARTRIDGES WITH ATRAUMATIC FEATURES;
- U.S. patent application Ser. No. 15/089,312, entitled CIRCULAR STAPLING SYSTEM COMPRISING AN INCISABLE TISSUE SUPPORT;
- U.S. patent application Ser. No. 15/089,309, entitled CIRCULAR STAPLING SYSTEM COMPRISING ROTARY FIRING SYSTEM;
- U.S. patent application Ser. No. 15/089,349, entitled CIRCULAR STAPLING SYSTEM COMPRISING LOAD CONTROL.

The Applicant of the present application also owns the U.S. Patent Applications identified below which were filed on Dec. 31, 2015 which are each herein incorporated by reference in their respective entirety:
- U.S. patent application Ser. No. 14/984,488, entitled MECHANISMS FOR COMPENSATING FOR BATTERY PACK FAILURE IN POWERED SURGICAL INSTRUMENTS;
- U.S. patent application Ser. No. 14/984,525, entitled MECHANISMS FOR COMPENSATING FOR DRIVETRAIN FAILURE IN POWERED SURGICAL INSTRUMENTS; and
- U.S. patent application Ser. No. 14/984,552, entitled SURGICAL INSTRUMENTS WITH SEPARABLE MOTORS AND MOTOR CONTROL CIRCUITS.

The Applicant of the present application also owns the U.S. Patent Applications identified below which were filed on Feb. 9, 2016 which are each herein incorporated by reference in their respective entirety:
- U.S. patent application Ser. No. 15/019,220, entitled SURGICAL INSTRUMENT WITH ARTICULATING AND AXIALLY TRANSLATABLE END EFFECTOR;
- U.S. patent application Ser. No. 15/019,228, entitled SURGICAL INSTRUMENTS WITH MULTIPLE LINK ARTICULATION ARRANGEMENTS;
- U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

The Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entireties:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT;

U.S. patent application Ser. No. 14/640,795, entitled MULTIPLE LEVEL THRESHOLDS TO MODIFY OPERATION OF POWERED SURGICAL INSTRUMENTS;

U.S. patent application Ser. No. 14/640,832, entitled ADAPTIVE TISSUE COMPRESSION TECHNIQUES TO ADJUST CLOSURE RAPES FOR MULTIPLE TISSUE TYPES;

U.S. patent application Ser. No. 14/640,935, entitled OVERLAID MULTI SENSOR RADIO FREQUENCY (RF) ELECTRODE SYSTEM TO MEASURE TISSUE COMPRESSION;

U.S. patent application Ser. No. 14/640,831, entitled MONITORING SPEED CONTROL AND PRECISION INCREMENTING OF MOTOR FOR POWERED SURGICAL INSTRUMENTS;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES;

U.S. patent application Ser. No. 14/640,817, entitled INTERACTIVE FEEDBACK SYSTEM FOR POWERED SURGICAL INSTRUMENTS;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE;

U.S. patent application Ser. No. 14/640,837, entitled SMART SENSORS WITH LOCAL SIGNAL PROCESSING;

U.S. patent application Ser. No. 14/640,765, entitled SYSTEM FOR DETECTING THE MIS-INSERTION OF A STAPLE CARTRIDGE INTO A SURGICAL STAPLER;

U.S. patent application Ser. No. 14/640,799, entitled SIGNAL AND POWER COMMUNICATION SYSTEM POSITIONED ON A ROTATABLE SHAFT; and U.S. patent application Ser. No. 14/640,780, entitled SURGICAL INSTRUMENT COMPRISING A LOCKABLE BATTERY HOUSING.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND;

U.S. patent application Ser. No. 14/633,560, entitled SURGICAL CHARGING SYSTEM THAT CHARGES AND/OR CONDITIONS ONE OR MORE BATTERIES;

U.S. patent application Ser. No. 14/633,566, entitled CHARGING SYSTEM THAT ENABLES EMERGENCY RESOLUTIONS FOR CHARGING A BATTERY;

U.S. patent application Ser. No. 14/633,555, entitled SYSTEM FOR MONITORING WHETHER A SURGICAL INSTRUMENT NEEDS TO BE SERVICED;

U.S. patent application Ser. No. 14/633,542, entitled REINFORCED BATTERY FOR A SURGICAL INSTRUMENT;

U.S. patent application Ser. No. 14/633,548, entitled POWER ADAPTER FOR A SURGICAL INSTRUMENT;

U.S. patent application Ser. No. 14/633,526, entitled ADAPTABLE SURGICAL INSTRUMENT HANDLE;

U.S. patent application Ser. No. 14/633,541, entitled MODULAR STAPLING ASSEMBLY; and U.S. patent application Ser. No. 14/633,562, entitled SURGICAL APPARATUS CONFIGURED TO TRACK AN END-OF-LIFE PARAMETER.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING;

U.S. patent application Ser. No. 14/574,483, entitled SURGICAL INSTRUMENT ASSEMBLY COMPRISING LOCKABLE SYSTEMS;

U.S. patent application Ser. No. 14/575,139, entitled DRIVE ARRANGEMENTS FOR ARTICULATABLE SURGICAL INSTRUMENTS;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE;

U.S. patent application Ser. No. 14/575,143, entitled SURGICAL INSTRUMENTS WITH IMPROVED CLOSURE ARRANGEMENTS;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS;

U.S. patent application Ser. No. 14/574,493, entitled SURGICAL INSTRUMENT ASSEMBLY COMPRISING A FLEXIBLE ARTICULATION SYSTEM; and U.S. patent application Ser. No. 14/574,500, entitled SURGICAL INSTRUMENT ASSEMBLY COMPRISING A LOCKABLE ARTICULATION SYSTEM.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Patent Application Publication No. 2014/0246474;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Patent Application Publication No. 2014/0246477;

U.S. patent application Ser. No. 13/782,481, entitled SENSOR STRAIGHTENED END EFFECTOR DURING REMOVAL THROUGH TROCAR, now U.S. Patent Application Publication No. 2014/0246479;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Patent Application Publication No. 2014/0246473; and U.S. patent application Ser. No. 13/782,536, entitled SURGICAL INSTRUMENT SOFT STOP, now U.S. Patent Application Publication No. 2014/0246476.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Patent Application Publication No. 2014/0263537;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Patent Application Publication No. 2014/0263553;

U.S. patent application Ser. No. 13/803,130, entitled DRIVE TRAIN CONTROL ARRANGEMENTS FOR MODULAR SURGICAL INSTRUMENTS, now U.S. Patent Application Publication No. 2014/0263543; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled USE OF POLARITY OF HALL MAGNET DEJECTION TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis;

however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven surgical system 10 that may be used to perform a variety of different surgical procedures. In the illustrated embodiment, the motor driven surgical system 10 comprises a selectively reconfigurable housing or handle assembly 20 that is attached to one form of an interchangeable surgical tool assembly 1000. For example, the system 10 that is depicted in FIG. 1 includes an interchangeable surgical tool assembly 1000 that comprises a surgical cutting and fastening instrument which may be referred to as an endocutter. As will be discussed in further detail below, the interchangeable surgical tool assemblies may include end effectors that are adapted to support different sizes and types of staple cartridges and, have different shaft lengths, sizes, and types, etc. Such arrangements, for example, may utilize any suitable fastener, or fasteners, to fasten tissue. For instance, a fastener cartridge comprising a plurality of fasteners removably stored therein can be removably inserted into and/or attached to the end effector of a surgical tool assembly. Other surgical tool assemblies may be interchangeably employed with the handle assembly 20. For example, the interchangeable surgical tool assembly 1000 may be detached from the handle assembly 20 and replaced with a different surgical tool assembly that is configured to perform other surgical procedures. In other arrangements, the surgical tool assembly may not be interchangeable with other surgical tool assemblies and essentially comprise a dedicated shaft that is non-removably affixed or coupled to the handle assembly 20, for example. The surgical tool assemblies may also be referred to as elongate shaft assemblies. The surgical tool assemblies may be reusable or, in other configurations, the surgical tool assemblies may be designed to be disposed of after a single use.

As the present Detailed Description proceeds, it will be understood that the various forms of interchangeable surgical tool assemblies disclosed herein may also be effectively employed in connection with robotically-controlled surgical systems. Thus, the terms "housing" and "housing assembly" may also encompass a housing or similar portion of a robotic system that houses or otherwise operably supports at least one drive system that is configured to generate and apply at least one control motion which could be used to actuate the elongate shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the surgical tool assemblies disclosed herein may be employed with various robotic systems, instruments, components and methods such as, but not limited to, those disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719 which is hereby incorporated by reference herein in its entirety.

Figure 2:
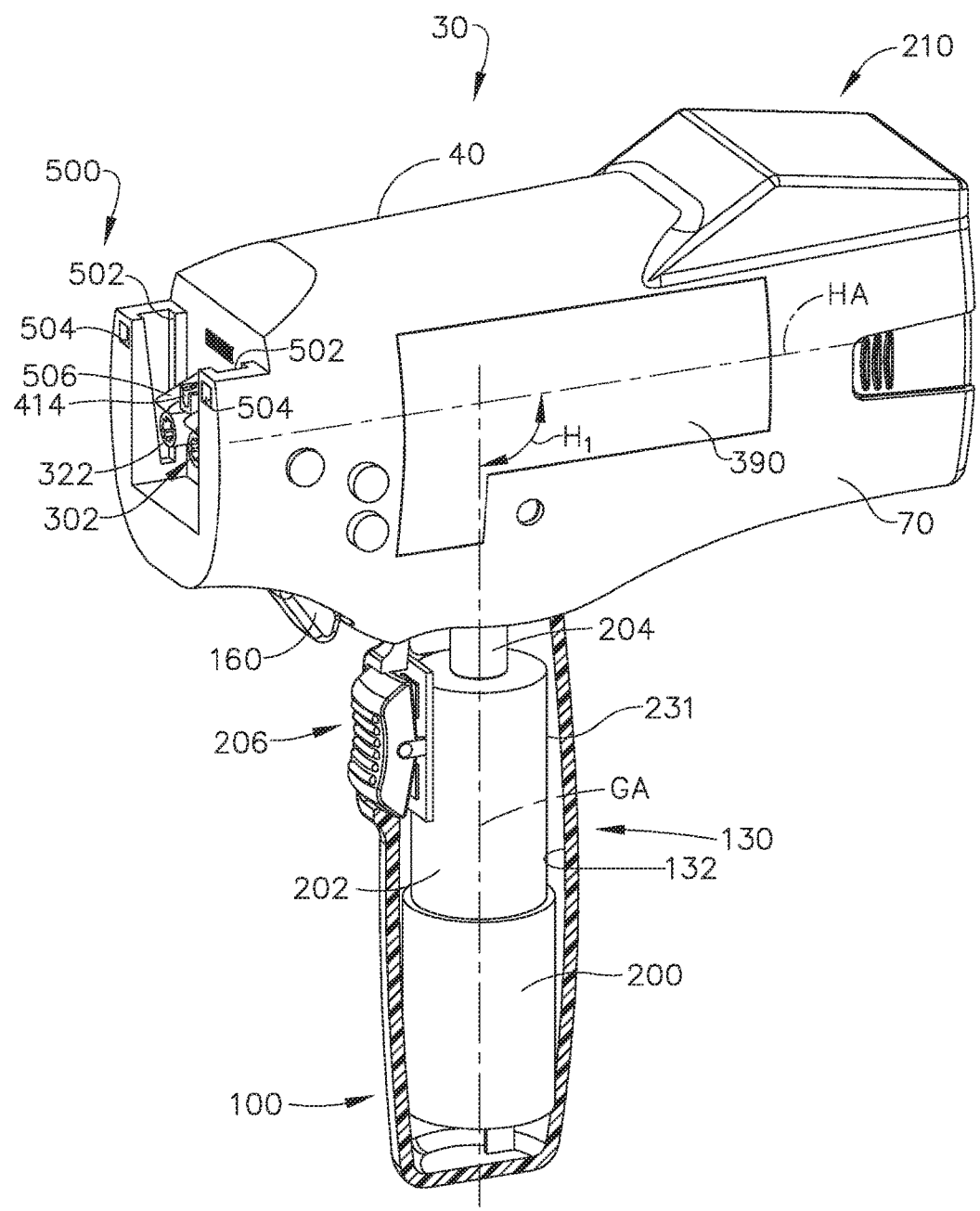
FIG. 2 is another perspective view of a handle assembly of the surgical instrument of FIG. 1, with a portion of the handle housing omitted to expose components housed therein.

Referring now to FIGS. 1 and 2, the housing assembly or handle assembly 20 comprises a primary housing portion 30 that may be formed from a pair of housing segments 40, 70 that may be fabricated from plastic, polymer materials, metal, etc. and be joined together by an appropriate fastener arrangement such as, for example, adhesive, screws, press-fit features, snap-fit features, latches, etc. As will be discussed in further detail below, the primary housing portion 30 operably supports a plurality of drive systems therein that are configured to generate and apply various control motions to corresponding portions of the interchangeable surgical tool assembly that is operably attached thereto. The handle assembly 20 further comprises a grip portion 100 that is movably coupled to the primary housing portion 30 and is configured to be gripped and manipulated by the clinician in various positions relative to the primary housing portion 30. The grip portion 100 may be fabricated from a pair of grip segments 110, 120 that may be fabricated from plastic, polymer materials, metal, etc. and are joined together by an appropriate fastener arrangement such as, for example, adhesive, screws, press-fit features, snap-fit features, latches, etc. for assembly and maintenance purposes.

Figure 5:
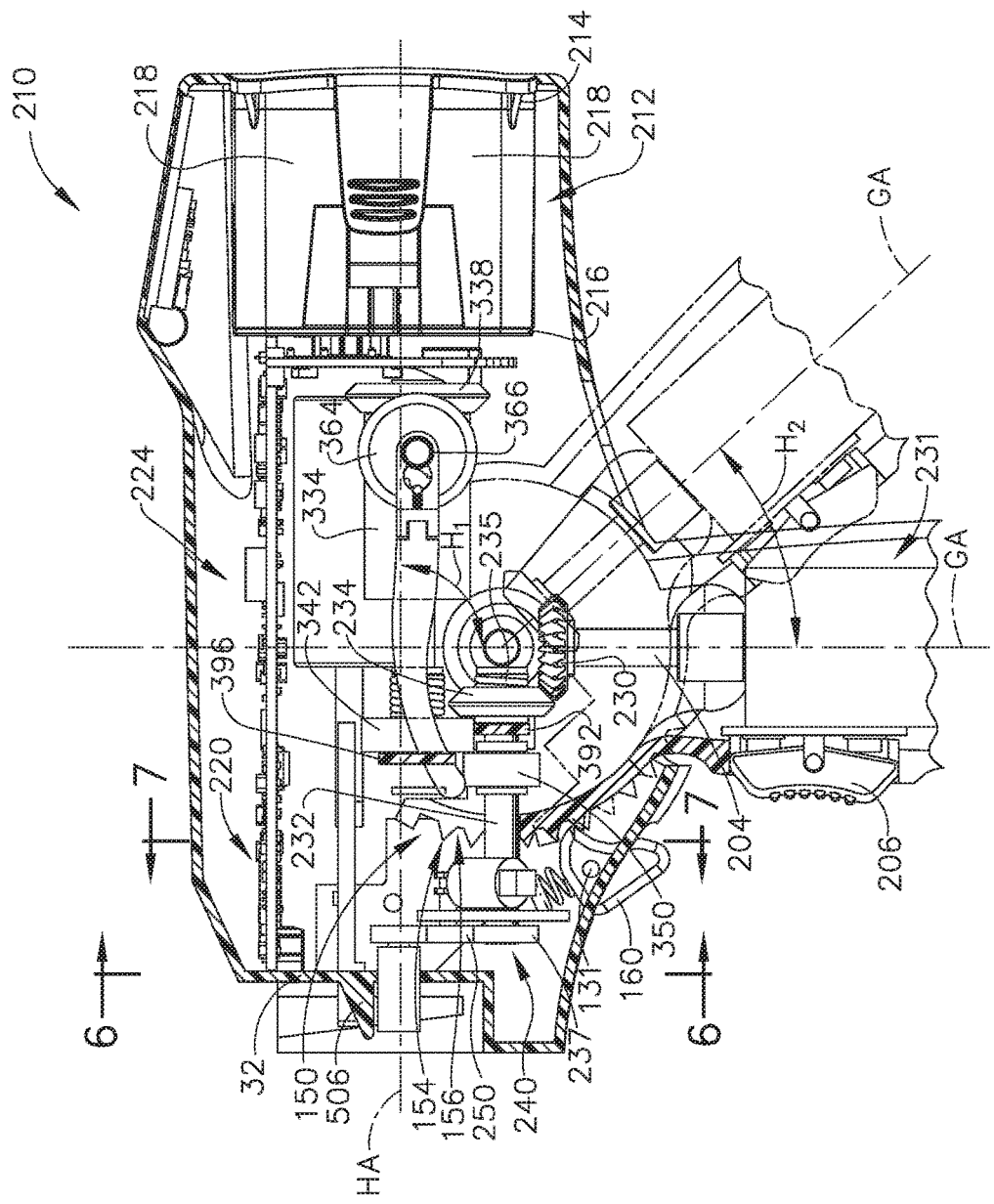
FIG. 5 is a partial cross-sectional side view of the handle assembly of FIGS. 2-4 with a grip portion of the handle assembly shown in solid lines in one position relative to a primary housing portion and in phantom lines in another position relative to the primary housing portion of the handle assembly.

As can be seen in FIG. 2, the grip portion 100 comprises a grip housing 130 that defines a hollow cavity 132 that is configured to operably support a drive motor and gearbox which will be discussed in further detail below. The upper portion 134 of the grip housing 130 is configured to extend through an opening 80 in the primary housing portion 30 and be pivotally journaled on a pivot shaft 180. The pivot shaft 180 defines a pivot axis designated as "PA". See FIG. 3. For reference purposes, the handle assembly 20 defines a handle axis designated as "HA" that may be parallel to the shaft axis "SA" of the elongate shaft assembly of the interchangeable surgical tool that is operably attached to the handle assembly 20. The pivot axis PA is transverse to the handle axis HA. See FIG. 1. Such arrangement enables the grip portion 100 to be pivoted relative to the primary housing portion 30 about the pivot axis PA to a position that is best suited for the type of interchangeable surgical tool assembly that is coupled to the handle assembly 20. The grip housing 130 defines a grip axis, generally designated as "GA". See FIG. 2. When the interchangeable surgical tool assembly that is coupled to the handle assembly 20 comprises an endocutter for example, the clinician might want to position the grip portion 100 relative to the primary housing portion 30 such that the grip axis GA is perpendicular or approximately perpendicular (angle "H1") to the handle axis HA (referred to herein as a "first grip position"). See FIG. 5. However, if the handle assembly 20 is being used to control an interchangeable surgical tool assembly that comprises a circular stapler for example, the clinician may wish to pivot the grip portion 100 relative to the primary housing portion 30 to a position wherein the grip axis GA is at a forty-five degree or approximately forty-five degree angle or other suitable acute angle (angle "H2") relative to the handle axis HA. This position is referred to herein as a "second grip position". FIG. 5 illustrates the grip portion 100 in phantom lines in the second grip position.

Figure 3:
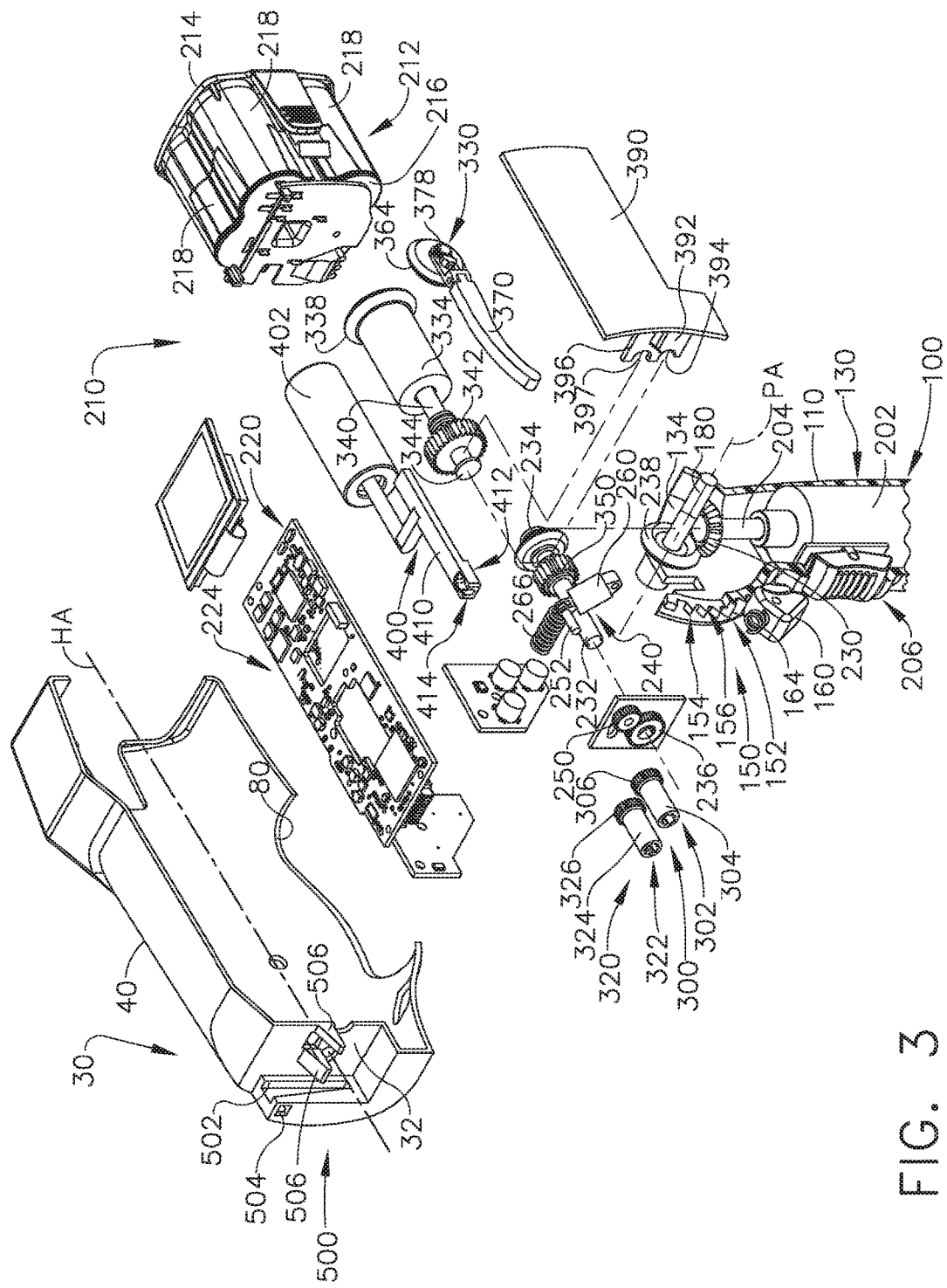
FIG. 3 is an exploded assembly view of portions of the handle assembly of the surgical instrument of FIGS. 1 and 2.
Figure 4:
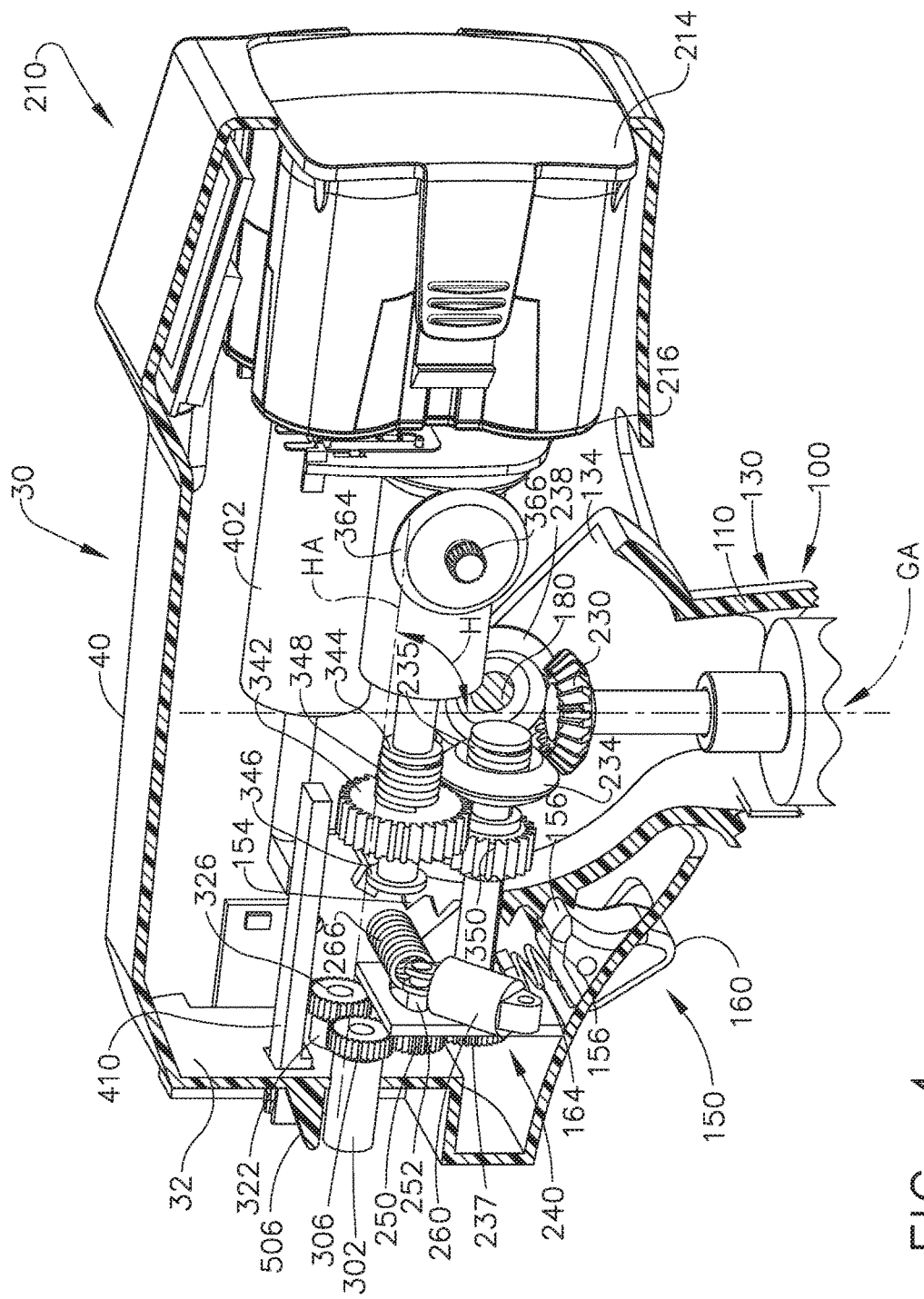
FIG. 4 is a cross-sectional perspective view of the handle assembly of FIGS. 2 and 3.

Referring now to FIGS. 3-5, the handle assembly 20 also includes a grip locking system, generally designated as 150, for selectively locking the grip portion 100 in the desired orientation relative to the primary housing portion 30. In one arrangement, the grip locking system 150 comprises an arcuate series 152 of pointed teeth 154. The teeth 154 are spaced from each other and form a locking groove 156 therebetween. Each locking groove 156 corresponds to a particular angular locking position for the grip portion 100. For example, in at least one arrangement, the teeth 154 and locking grooves or "locking locations" 156 are arranged to permit the grip portion 100 to be locked at 10-15 degree intervals between the first grip position and the second grip position. The arrangement may employ two stop positions which are tailored to the type of instrument (shaft arrangement) employed. For example, for an endocutter shaft arrangement, it may be approximately around ninety degrees to the shaft and for a circular stapler arrangement, the angle may be approximately forty-five degrees to the shaft while being swept forward towards the surgeon. The grip locking system 150 further includes a locking button 160 that has a locking portion 162 that is configured to lockingly engage the locking grooves 156. For example, the locking button 160 is pivotally mounted in the primary handle portion 30 on a pivot pin 131 to permit the locking button 160 to pivot into engagement with a corresponding locking groove 156. A locking spring 164 serves to bias the locking button 160 into an engaged or locked position with the corresponding locking groove 156. The locking portion 162 and the teeth configurations serve to enable the teeth 154 to slide past the locking portion 162 when the clinician depresses the locking button 160. Thus, to adjust the angular position of the grip portion 100 relative to the primary housing portion 30, the clinician depresses the locking button 160 and then pivots the grip portion 100 to the desired angular position. Once the grip portion 100 has been moved to the desired position, the clinician releases the locking button 160. The locking spring 164 will then bias the locking button 160 toward the series of teeth 154 so that the locking portion 162 enters the corresponding locking groove 156 to retain the grip portion 100 in that position during use.

The handle assembly 20 operably supports a first rotary drive system 300, a second rotary drive system 320 and a third axial drive system 400. The rotary drive systems 300, 320 are each powered by a motor 200 that is operably supported in the grip portion 100. As can be seen in FIG. 2, for example, the motor 200 is supported within the cavity 132 in the grip portion 100 and has a gear box assembly 202 that has an output drive shaft 204 protruding therefrom. In various forms, the motor 200 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 200 may be powered by a power source 210 that, in one form, may comprise a removable power pack 212. The power source 210 may comprise, for example, anyone of the various power source arrangements disclosed in further detail in U.S. Patent Application Publication No. 2015/0272575 and entitled SURGICAL INSTRUMENT COMPRISING A SENSOR SYSTEM, the entire disclosure of which is hereby incorporated by reference herein. In the illustrated arrangement, for example, the power pack 212 may comprise a proximal housing portion 214 that is configured for attachment to a distal housing portion 216. The proximal housing portion 214 and the distal housing portion 216 are configured to operably support a plurality of batteries 218 therein. Batteries 218 may each comprise, for example, a Lithium Ion ("LI") or other suitable battery. The distal housing portion 216 is configured for removable operable attachment to a handle circuit board assembly 220 which is also operably coupled to the motor 200. The handle circuit board assembly 220 may also be generally referred to herein as the "control system or CPU 224". A number of batteries 218 may be connected in series may be used as the power source for the handle assembly 20. In addition, the power source 210 may be replaceable and/or rechargeable. In other embodiments, the surgical instrument 10 may be powered by alternating current (AC) for example. The motor 200 may be controlled by a rocker switch 206 that is mounted to the grip portion 100.

Figure 14:
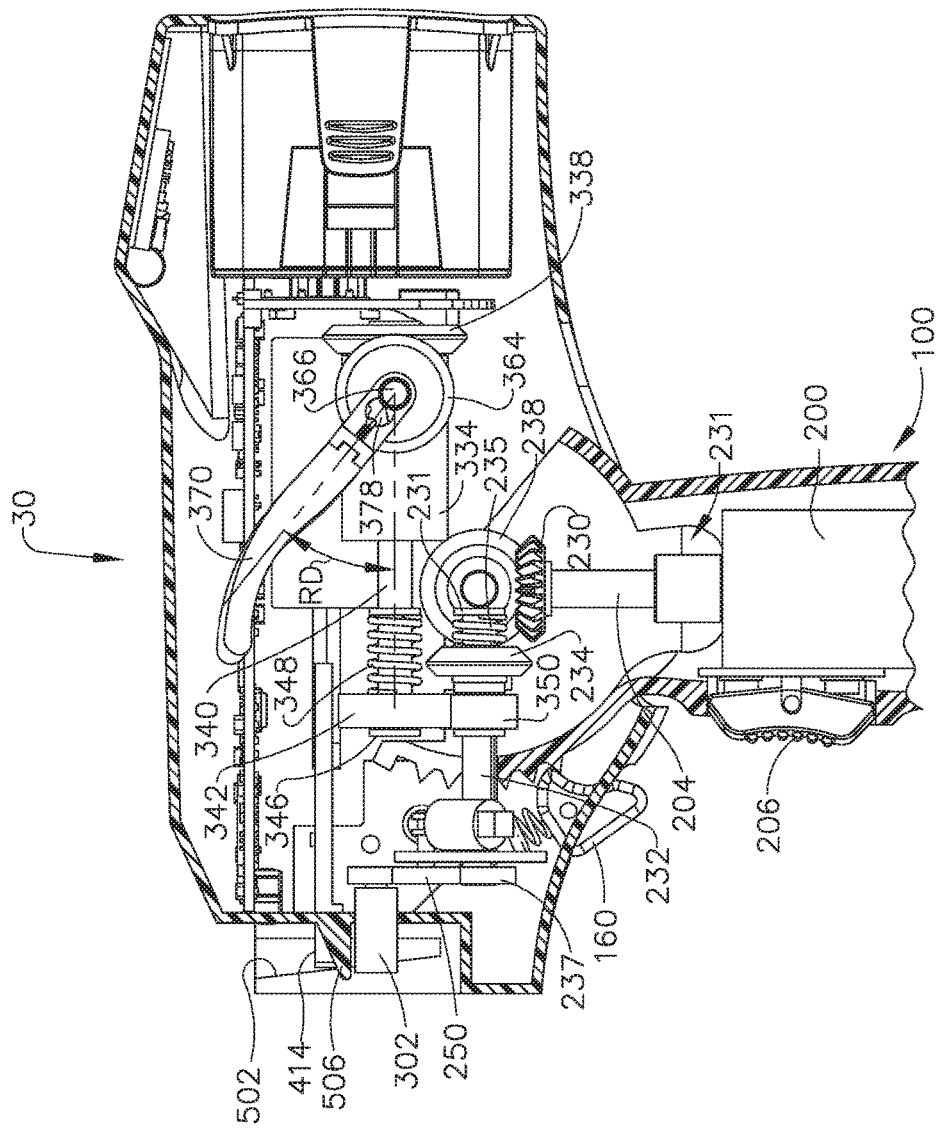
FIG. 14 is a cross-sectional elevation view of the handle assembly of FIG. 11.

As outlined above, the motor 200 is operably coupled to a gear box assembly 202 that includes an output drive shaft 204. Attached to the output drive shaft 204 is a driver bevel gear 230. The motor 200, the gear box assembly 202, the output drive shaft 204 and the driver bevel gear 230 may also be collectively referred to herein as a "motor assembly 231". The driver bevel gear 230 interfaces with a driven bevel gear 234 that is attached to a system drive shaft 232 as well as a pivot bevel gear 238 that is journaled on the pivot shaft 180. The driven bevel gear 234 is axially movable on the system drive shaft 232 between an engaged position wherein the driven bevel gear 234 is in meshing engagement with the driver bevel gear 230 (FIG. 5) and a disengaged position wherein the driven bevel gear 234 is out of meshing engagement with the drive bevel gear 230 (FIG. 14). A drive system spring 235 is journaled between the driven bevel gear 234 and a proximal end flange 236 that is formed on a proximal portion of the system drive shaft 232. See FIGS. 4 and 14. The drive system spring 235 serves to bias the driven bevel gear 234 out of meshing engagement with the driver bevel gear 230 as will be discussed in further detail below. The pivot bevel gear 238 facilitates pivotal travel of the output drive shaft 204 and driver bevel gear 230 with the grip portion 100 relative to the primary handle portion 30.

In the illustrated example, the system drive shaft 232 interfaces with a rotary drive selector system, generally designated as 240. In at least one form, for example, the rotary drive selector system 240 comprises a shifter gear 250 that is selectively movable between the first rotary drive system 300 and the second rotary drive system 320. As can be seen in FIGS. 6-9, for example, the drive selector system 240 comprises a shifter mounting plate 242 that is non-movably mounted within primary handle portion 30. For example, the shifter mounting plate 242 may be frictionally retained between mounting lugs (not shown) formed in the housing segments 40, 70 or be otherwise retained therein by screws, adhesive, etc. Still referring to FIGS. 6-9, the system drive shaft 232 extends through a hole in the shifter mounting plate 242 and has the central, or system, drive gear 237 non-rotatably attached thereto. For example the central drive gear 237 may be attached to the system drive shaft 232 by a keyway arrangement 233. See FIGS. 6-9. In other arrangements, the system drive shaft 232 may be rotatably supported in the shifter mounting plate 242 by a corresponding bearing (not shown) that is mounted thereto. In any event, rotation of the system drive shaft 232 will result in rotation of the central drive gear 234.

As can be seen in FIG. 3, the first drive system 300 includes a first drive socket 302 that is rotatably supported in a distal wall 32 formed in the primary handle portion 30. The first drive socket 302 may comprise a first body portion 304 that has a splined socket formed therein. A first driven gear 306 is formed on or is non-movably attached to the first body portion 304. The first body portion 304 may be rotatably supported in a corresponding hole or passage provided the distal wall 32 or it may be rotatably supported in a corresponding bearing (not shown) that is mounted in the distal wall 32. Similarly, the second rotary drive system 320 includes a second drive socket 322 that is also rotatably supported in the distal wall 32 of the primary handle portion 30. The second drive socket 322 may comprise a second body portion 324 that has a splined socket formed therein. A second driven gear 326 is formed on or is non-rotatably mounted to the second body portion 324. The second body portion 324 may be rotatably supported in a corresponding hole or passage provided the distal wall 32 or it may be rotatably supported in a corresponding bearing (not shown) that is mounted in the distal wall 32. The first and second drive sockets 302, 322 are spaced from each other on each lateral side of the handle axis HA. See FIG. 4, for example.

Figures 6, 7:
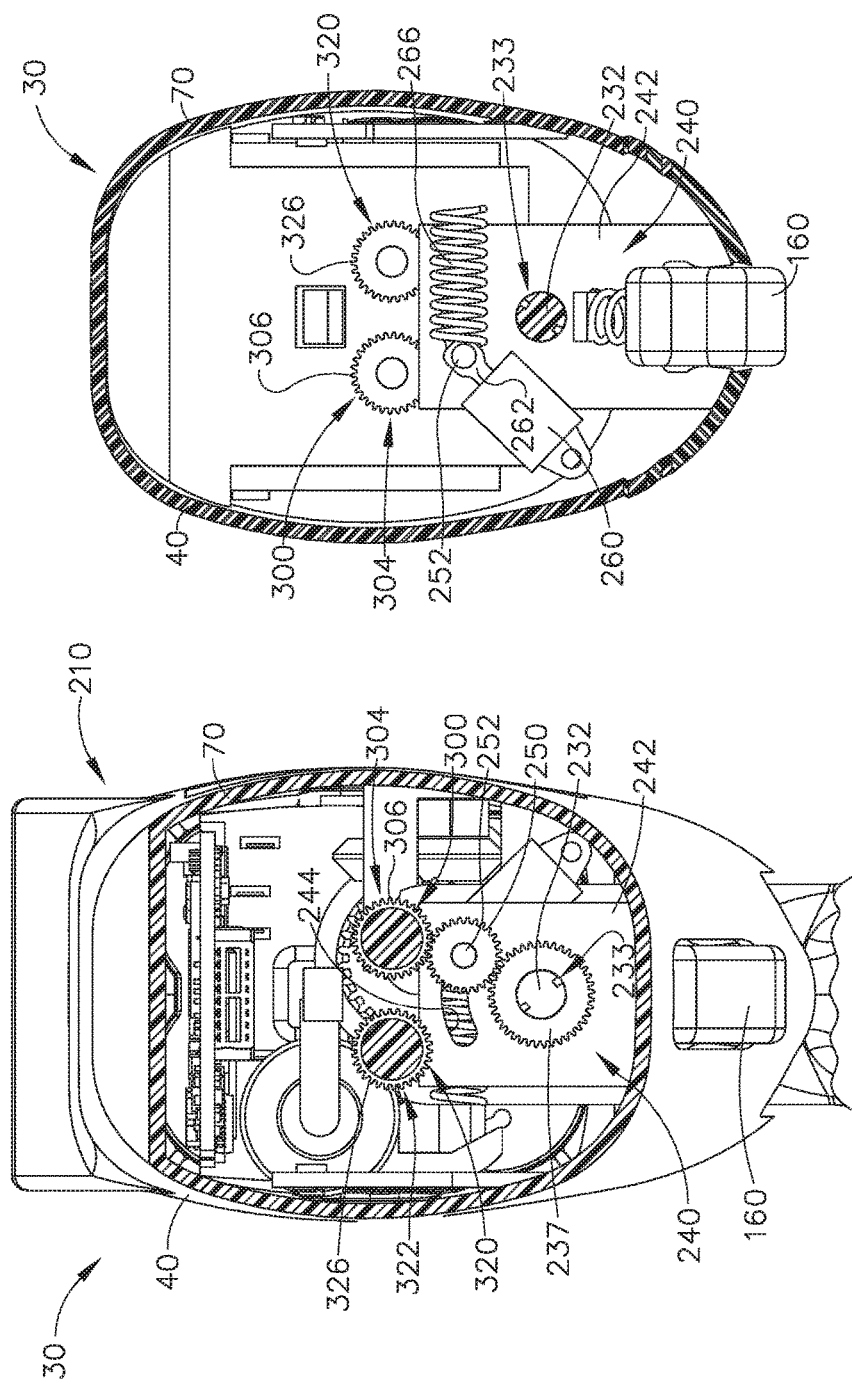
FIG. 6 is an end cross-sectional view of the handle assembly of FIGS. 2-5 taken along line 6-6 in FIG. 5.
FIG. 7 is another end cross-sectional view of the handle assembly of FIGS. 2-6 taken along line 7-7 in FIG. 5.

As indicated above, in the illustrated example, the rotary drive selector system 240 includes a shifter gear 250. As can be seen in FIGS. 6-9, the shifter gear 250 is rotatably mounted on an idler shaft 252 that is movably supported in an arcuate slot 244 in the shifter mounting plate 242. The shifter gear 250 is mounted so as to freely rotate on the idler shaft 252 and remain in meshing engagement with the central drive gear 234. The idler shaft 252 is coupled to an end of a shaft 262 of a shifter solenoid 260. The shifter solenoid 260 is pinned or otherwise mounted with the primary handle housing 30 such that when the shifter solenoid 260 is actuated, the shifter gear 250 is moved into meshing engagement with one of the first driven gear 306 or the second driven gear 326. For example, in one arrangement, when the solenoid shaft is 262 is retracted (FIGS. 6 and 7), the shifter gear 250 is in meshing engagement with the central drive gear 234 and the first driven gear 306 such that actuation of the motor 200 will result in rotation of the first drive socket 302. As can be seen in FIGS. 6 and 7, a shifter spring 266 may be employed to bias the shifter gear 250 into that first actuation position. Thus, should power be lost to the surgical instrument 10, the shifter spring 266 will automatically bias the shifter gear 250 into the first position. When the shifter gear 250 is in that position, subsequent actuation of the motor 200 will result in rotation of the first drive socket 302 of the first rotary drive system 300. When the shifter solenoid is actuated, the shifter gear 250 is moved into meshing engagement with the second driven gear 326 on the second drive socket 322. Thereafter, actuation of the motor 200 will result in actuation or rotation of the second drive socket 322 of the second rotary drive system 320.

As will be discussed in further detail below, the first and second rotary drive systems 300, 320 may be used to power various component portions of the interchangeable surgical tool assembly that is coupled thereto. As indicated above, in at least one arrangement, if during the actuation of the interchangeable surgical tool assembly, power was lost to the motor, the shifter spring 266 will bias the shifter gear 250 to the first position. Depending upon which component portion of the interchangeable surgical tool assembly was being operated, it may be necessary to reverse the application of the rotary drive motion to the first drive system 300 to enable the interchangeable surgical tool assembly to be removed from the patient. The handle assembly 20 of the illustrated example employs a manually actuatable "bailout" system, generally designated as 330, for manually applying a rotary drive motion to the first rotary drive system 300 in the above described scenario, for example.

Figure 10:
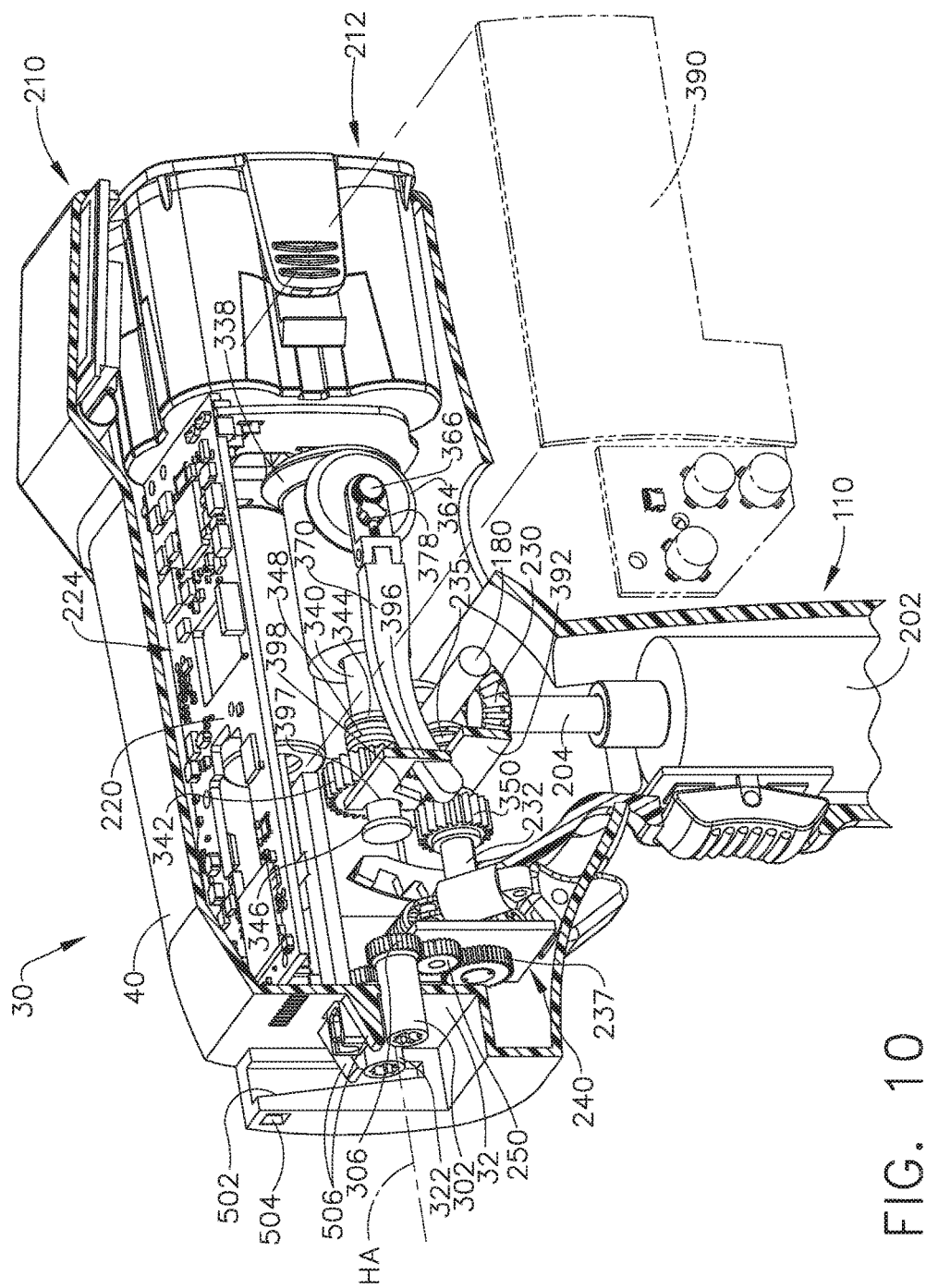
FIG. 10 is another perspective view of the handle assembly of FIGS. 2-9 with certain portions thereof shown in cross-section and with an access panel portion thereof shown in phantom.
Figure 11:
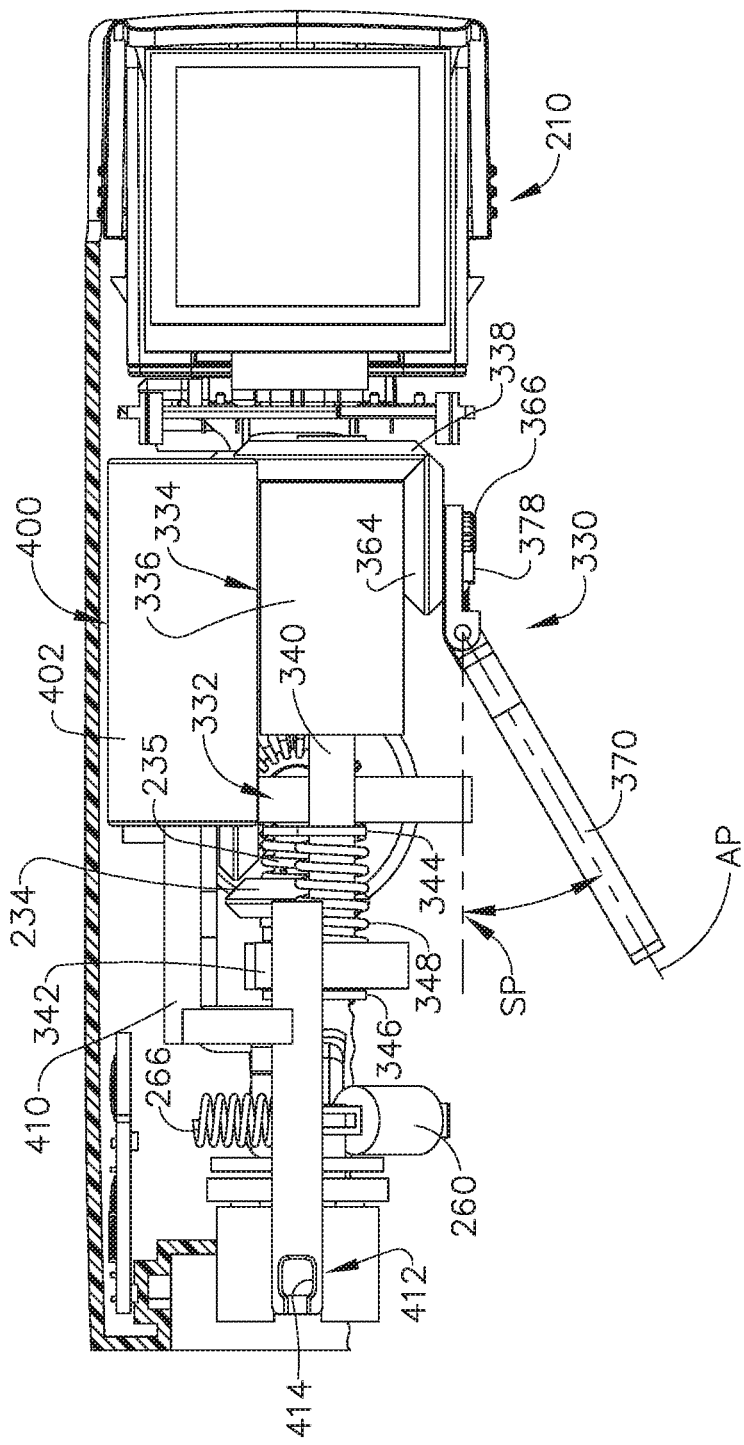
FIG. 11 is a top view of the handle assembly of FIGS. 2-11 with a bailout system shown in an actuatable position.

Referring now to FIGS. 3, 10 and 11, the illustrated bailout system 330 comprises a bailout drive train 332 that includes a planetary gear assembly 334. In at least one form, the planetary gear assembly 334 includes a planetary gear housing 336 that houses a planetary gear arrangement (not shown) that includes a planetary bevel gear 338. The planetary gear assembly 334 includes a bailout drive shaft 340 that is operably coupled to the planetary gear arrangement within the planetary gear housing 336. Rotation of the planetary bevel gear 338 rotates the planetary gear arrangement which ultimately rotates the bailout drive shaft 340. A bailout drive gear 342 is journaled on the bailout drive shaft 340 so that the bailout drive gear 342 can move axially on the bailout drive shaft 340, yet rotate therewith. The bailout drive gear 342 is movable between a spring stop flange 344 that is formed on the bailout drive shaft 340 and a shaft end stop 346 that is formed on the distal end of the bailout drive shaft 340. A bailout shaft spring 348 is journaled on the bailout drive shaft 340 between the bailout drive gear 342 and the spring stop flange 344. The bailout shaft spring 348 biases the bailout drive gear 342 distally on the bailout drive shaft 340. When the bailout drive gear 342 is in its distal-most position on the bail out drive shaft 340, it is in meshing engagement with a bailout driven gear 350 that is non-rotatably mounted to the system drive shaft 232. See FIG. 14.

Figure 12:
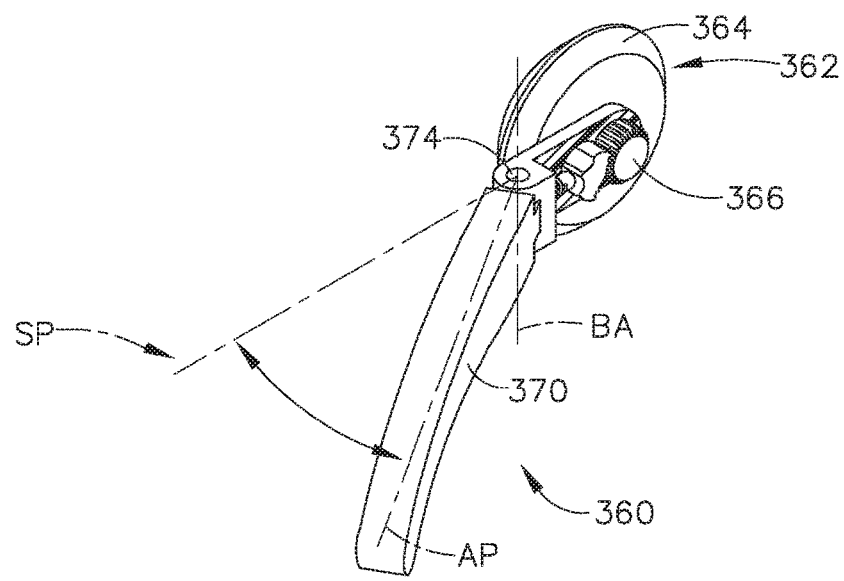
FIG. 12 is a perspective view of a bailout handle of the bailout system depicted in FIGS. 2-11.
Figure 13:
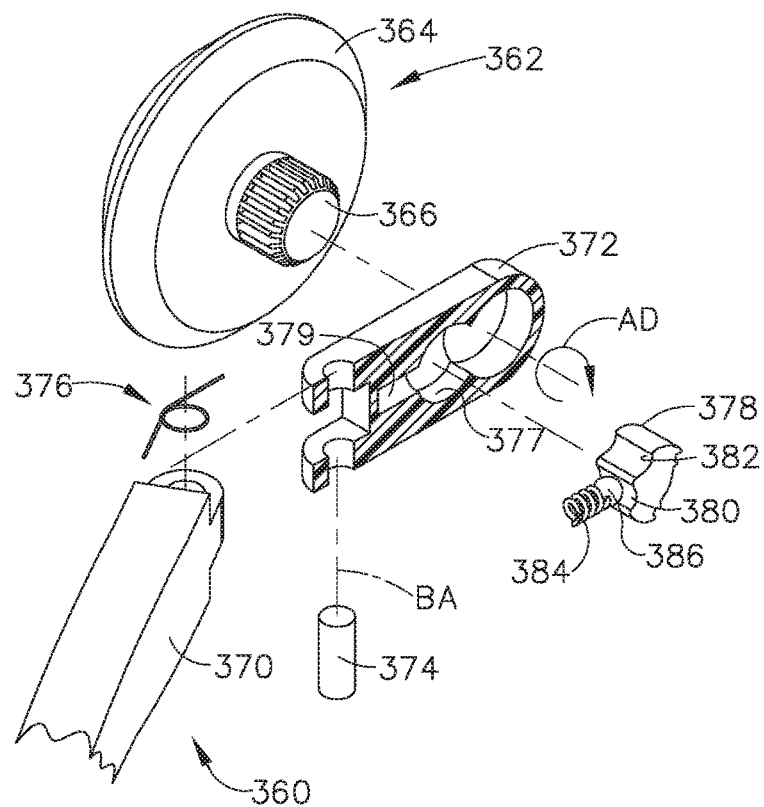
FIG. 13 is an exploded assembly view of portions of the bailout handle of FIG. 12 with portions thereof shown in cross-section.

Referring now to FIGS. 12 and 13, the bailout system 330 includes a bailout actuator assembly or bailout handle assembly 360 that facilitates the manual application of a bailout drive motion to the bailout drive train 332. As can be seen in those Figures, the bailout handle assembly 360 includes a bailout bevel gear assembly 362 that comprises a bailout bevel gear 364 and a ratchet gear 366. The bailout handle assembly 360 further includes a bailout handle 370 that is movably coupled to the bailout bevel gear assembly 362 by a pivot yoke 372 that is pivotally mounted on the ratchet gear 366. The bailout handle 370 is pivotally coupled to the pivot yoke 372 by a pin 374 for selective pivotal travel between a stored position "SP" and an actuation position "AP". See FIG. 12. A handle spring 376 is employed to bias the bailout handle 370 into the actuation position AP. In at least one arrangement, the angle between the axis SP representing the stored position and the axis AP representing the actuation position may be approximately thirty degrees, for example. See FIG. 13. As can also be seen in FIG. 13, the bailout handle assembly 360 further includes a ratchet pawl 378 that is rotatably mounted in a cavity or hole 377 in the pivot yoke 372. The ratchet pawl 378 is configured to meshingly engage the ratchet gear 366 when rotated in an actuation direction "AD" and then rotate out of meshing engagement when rotated in the opposite direction. A ratchet spring 384 and ball member 386 are movably supported in a cavity 379 in the pivot yoke 372 and serve to lockingly engage detents 380, 382 in the ratchet pawl 378 as the bailout handle 370 is actuated (ratcheted).

Referring now to FIGS. 3 and 10, the bailout system 330 further includes a bailout access panel 390 that is maneuverable between an open position and a closed position. In the illustrated arrangement, the bailout access panel 390 is configured to be removably coupled to the housing segment 70 of the primary housing portion 30. Thus, in at least that embodiment, when the bailout access panel 390 is removed or detached from the primary housing portion 30, it is said to be in an "open" position and when the bailout access panel 390 is attached to the primary housing portion 30 as illustrated, it is said to be in a "closed" position. Other embodiments are contemplated, however, wherein the access panel is movably coupled to the primary housing portion such that when the access panel is in the open position, it remains attached thereto. For example, in such embodiments, the access panel may be pivotally attached to the primary housing portion or slidably attached to the primary housing portion and be maneuverable between an open position and a closed position. In the illustrated example, the bailout access panel 390 is configured to snappingly engage corresponding portions of the housing segment 70 to removably retain it in a "closed" position. Other forms of mechanical fasteners such as screws, pins, etc. could also be used.

Regardless of whether the bailout access panel 390 is detachable from the primary housing portion 30 or it remains movably attached to the primary housing portion 30, the bailout access panel 390 includes a drive system locking member or yoke 392 and a bailout locking member or yoke 396 that each protrudes out from the backside thereof or are otherwise formed thereon. The drive system locking yoke 392 includes a drive shaft notch 394 that is configured to receive a portion of the system drive shaft 232 therein when the bailout access panel 390 is installed in the primary housing portion 30 (i.e., the bailout access panel is in the "closed" position). When the bailout access panel 390 is positioned or installed in the closed position, the drive system locking yoke 392 serves to bias the driven bevel gear 234 into meshing engagement with the driver bevel gear 230 (against the bias of the drive system spring 235). In addition, the bailout locking yoke 396 includes a bailout drive shaft notch 397 that is configured to receive a portion of the bailout drive shaft 340 therein when the bailout access panel 390 is installed or positioned in the closed position. As can be seen in FIGS. 5 and 10, the bailout locking yoke 396 also serves to bias the bailout drive gear 342 out of meshing engagement with the bailout driven gear 350 (against the bias of the bailout shaft spring 348). Thus, the bailout locking yoke 396 prevents the bailout drive gear 342 from interfering with rotation of the system drive shaft 232 when the bailout access panel 390 is installed or in the closed position. In addition, the bailout locking yoke 396 includes a handle notch 398 for engaging the bailout handle 370 and retaining it in the stored position SP.

FIGS. 4, 5 and 10 illustrate the configurations of the drive system components and the bailout system components when the bailout access panel 390 is installed or is in the closed position. As can be seen in those Figures, the drive system locking member 392 biases the driven bevel gear 234 into meshing engagement with the driver bevel gear 230. Thus, when the bailout access panel 390 is installed or is in the closed position, actuation of the motor 200 will result in the rotation of the driver bevel gear 230 and ultimately the system drive shaft 232. Also, when in that position, the bailout locking yoke 396 serves to bias the bailout drive gear 342 out of meshing engagement with the bailout driven gear 350 on the system drive shaft 232. Thus, when the bailout access panel 390 is installed or is in the closed position, the drive system is actuatable by the motor 200 and the bailout system 330 is disconnected or prevented from applying any actuation motion to the system drive shaft 232. To activate the bailout system 330, the clinician first removes the bailout access panel 390 or otherwise moves the bailout access panel 390 to the open position. This action removes the drive system locking member 392 from engagement with the driven bevel gear 234 which thereby permits the drive system spring 235 to bias the driven bevel gear 234 out of meshing engagement with the driver bevel gear 230. In addition, removal of the bailout access panel 390 or movement of the bailout access panel to an open position also results in the disengagement of the bailout locking yoke 396 with the bailout drive gear 342 which thereby permits the bailout shaft spring 348 to bias the bailout drive gear 342 into meshing engagement with the bailout driven gear 350 on the system drive shaft 232. Thus, rotation of the bailout drive gear 342 will result in rotation of the bailout driven gear 350 and the system drive shaft 232. Removal of the bailout access panel 390 or otherwise movement of the bailout access panel 390 to an open position also permits the handle spring 376 to bias the bailout handle 370 into the actuation position shown in FIGS. 11 and 14. When in that position, the clinician can manually ratchet the bailout handle 370 in the ratchet directions RD which results in the rotation of the ratchet bevel gear 364 (in a clockwise direction in FIG. 14, for example) which ultimately results in the application of a retraction rotary motion to the system drive shaft 232 through the bailout drive train 332. The clinician may ratchet the bailout handle 370 a number of times until the system drive shaft 232 has been sufficiently rotated a number of times to retract a component of the surgical end effector portion of the surgical tool assembly that is attached to the handle assembly 20. Once the bailout system 330 has been sufficiently manually actuated, the clinician may then replace the bailout access panel 390 (i.e., return the bailout access panel 390 to the closed position) to thereby cause the drive system locking member 392 to bias the driven bevel gear 234 into meshing engagement with the driver bevel gear 230 and the bailout locking yoke 396 to bias the bailout drive gear 342 out of meshing engagement with the bailout driven gear 350. As was discussed above, should power be lost or interrupted, the shifter spring 266 will bias the shifter solenoid 260 into the first actuation position. As such, actuation of the bailout system 330 will result in the application of reversing or retraction motions to the first rotary drive system 300.

As discussed above, a surgical stapling instrument can comprise a manually-actuated bailout system configured to retract a staple firing drive, for example. In many instances, the bailout system may need to be operated and/or cranked more than one time to fully retract the staple firing drive. In such instances, the user of the stapling instrument may lose track of how many times they have cranked the bailout and/or otherwise become confused as to how much further the firing drive needs to be retracted. Various embodiments are envisioned in which the stapling instrument comprises a system configured to detect the position of a firing member of the firing drive, determine the distance in which the firing member needs to be retracted, and display that distance to the user of the surgical instrument.

In at least one embodiment, a surgical stapling instrument comprises one or more sensors configured to detect the position of the firing member. In at least one instance, the sensors comprise Hall Effect sensors, for example, and can be positioned in a shaft and/or end effector of the stapling instrument. The sensors are in signal communication with a controller of the surgical stapling instrument which is, in turn, in signal communication with a display on the surgical stapling instrument. The controller comprises a microprocessor configured to compare the actual position of the firing member to a datum, or reference, position—which comprises a fully retracted position of the firing member—and calculate the distance, i.e., the remaining distance, between the actual position of the firing member and the reference position.

Further to the above, the display comprises an electronic display, for example, and the controller is configured to display the remaining distance on the electronic display in any suitable manner. In at least one instance, the controller displays a progress bar on the display. In such instances, an empty progress bar can represent that the firing member is at the end of its firing stroke and a full progress bar can represent that the firing member has been fully retracted, for example. In at least one instance, 0% can represent that the firing member is at the end of its firing stroke and 100% can represent that the firing member has been fully retracted, for example. In certain instances, the controller is configured to display how many actuations of the bailout mechanism are required to retract the firing member to its fully retracted position on the display.

Further to the above, the actuation of the bailout mechanism can operably disconnect a battery, or power source, of the surgical stapling instrument from an electric motor of the firing drive. In at least one embodiment, the actuation of the bailout mechanism flips a switch which electrically decouples the battery from the electric motor. Such a system would prevent the electric motor from resisting the manual retraction of the firing member.

The illustrated handle assembly 20 also supports a third axial drive system that is generally designated as 400. As can be seen in FIGS. 3 and 4, the third axial drive system 400, in at least one form, comprises a solenoid 402 that has a third drive actuator member or rod 410 protruding therefrom. The distal end 412 of the third drive actuator member 410 has a third drive cradle or socket 414 formed therein for receiving a corresponding portion of a drive system component of an interchangeable surgical tool assembly that is operably attached thereto. The solenoid 402 is wired to or otherwise communicates with the handle circuit board assembly 220 and the control system or CPU 224. In at least one arrangement, the solenoid 402 is "spring loaded" such that when the solenoid 402 is unactuated, the spring component thereof biases the third drive actuator 410 back to an unactuated starting position.

As indicated above, the reconfigurable handle assembly 20 may be advantageously employed to actuate a variety of different interchangeable surgical tool assemblies. To that end, the handle assembly 20 includes a tool mounting portion that is generally designated as 500 for operably coupling an interchangeable surgical tool assembly thereto. In the illustrated example, the tool mounting portion 500 includes two inwardly facing dovetail receiving slots 502 that are configured to engage corresponding portions of a tool attachment module portion of the interchangeable surgical tool assembly. Each dovetail receiving slot 502 may be tapered or, stated another way, be somewhat V-shaped. The dovetail receiving slots 502 are configured to releasably receive corresponding tapered attachment or lug portions that are formed on a portion of the tool attachment nozzle portion of the interchangeable surgical tool assembly. Each interchangeable surgical tool assembly may also be equipped with a latching system that is configured to releasable engage corresponding retention pockets 504 that are formed in the tool mounting portion 500 of the handle assembly 20.

The various interchangeable surgical tool assemblies may have a "primary" rotary drive system that is configured to be operably coupled to or interface with the first rotary drive system 310 as well as a "secondary" rotary drive system that is configured to be operably coupled to or interface with the second rotary drive system 320. The primary and secondary rotary drive systems may be configured to provide various rotary motions to portions of the particular type of surgical end effector that comprises a portion of the interchangeable surgical tool assembly. To facilitate operable coupling of the primary rotary drive system to the first rotary drive system and the secondary drive system to the second rotary drive system 320, the tool mounting portion 500 of the handle assembly 20 also includes a pair of insertion ramps 506 that are configured to bias portions of the primary and secondary rotary drive systems of the interchangeable surgical tool assembly distally during the coupling process so as to facilitate alignment and operable coupling of the primary rotary drive system to the first rotary drive system 300 on the handle assembly 20 and the secondary rotary drive system to the second rotary drive system 320 on the handle assembly 20.

The interchangeable surgical tool assembly may also include a "tertiary" axial drive system for applying axial motion(s) to corresponding portions of the surgical end effector of the interchangeable surgical tool assembly. To facilitate operable coupling of the tertiary axial drive system to the third axial drive system 400 on the handle assembly 20, the third drive actuator member 410 is provided with a socket 414 that is configured to operably receive a lug or other portion of the tertiary axial drive system therein.

Figure 15:
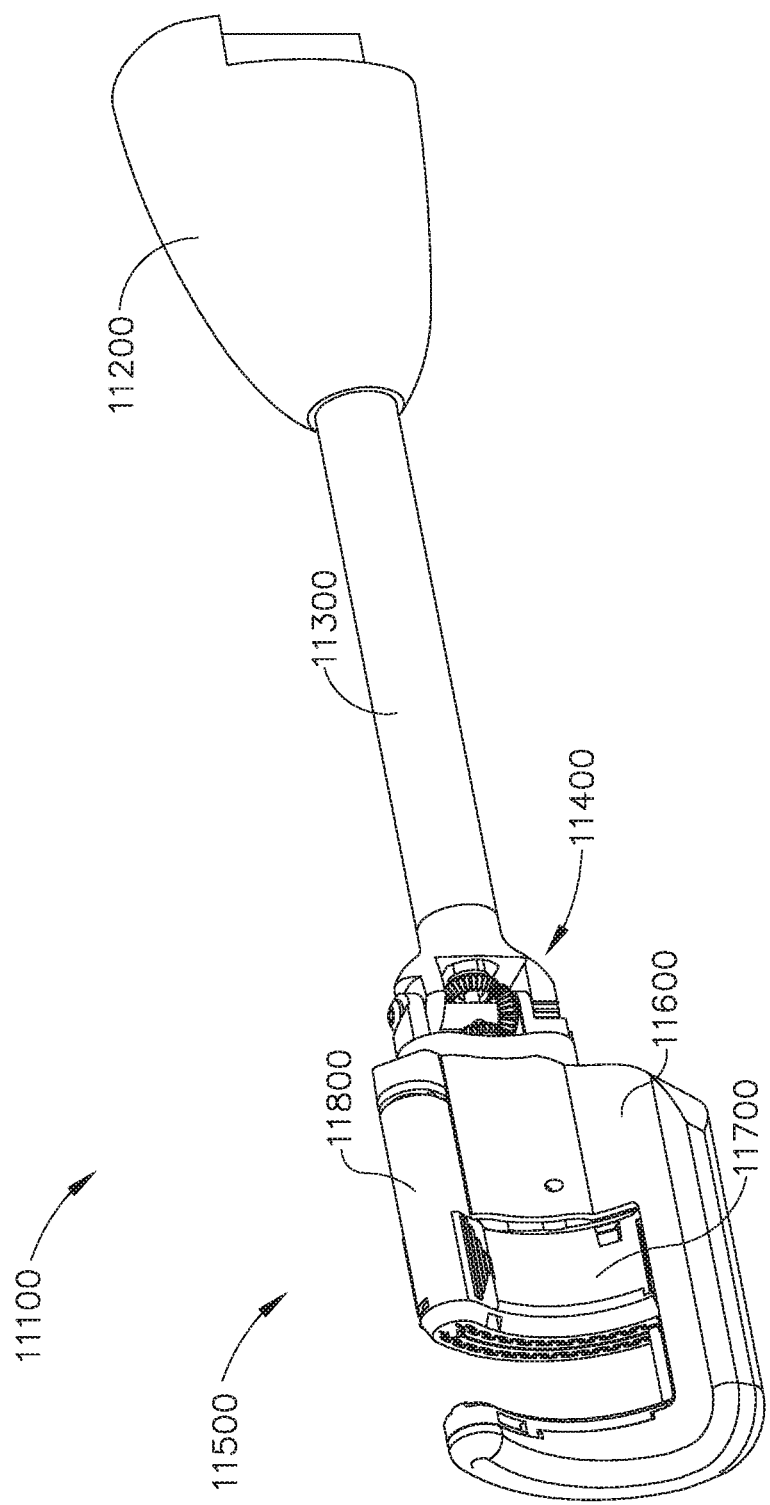
FIG. 15 is a perspective view of a surgical stapling attachment comprising an attachment portion, a shaft assembly, an articulation joint, and an end effector assembly.

A surgical stapling tool assembly, or attachment, 11100 is depicted in FIGS. 15-30. The tool assembly 11100 is configured to capture, clamp, staple, and cut tissue during a surgical procedure. Referring primarily to FIG. 15, the tool assembly 11100 comprises an attachment portion 11200, a shaft assembly 11300, an articulation joint 11400, and an end effector assembly 11500. The tool assembly 11100 is configured to be attached to an instrument interface by way of the attachment portion 11200. The instrument interface can comprise a surgical instrument handle such as those disclosed herein. Other embodiments are envisioned where the tool assembly 11100 is not readily attachable to and detachable from an instrument interface and, instead, is part of a unitary instrument. The attachment portion 11200 is configured to receive rotary control motions from the instrument interface to which the tool assembly 11100 is attached and transfer the rotary control motions to the shaft assembly 11300. The shaft assembly 11300 communicates these rotary control motions to the end effector assembly 11500 through the articulation joint 11400.

Figure 18:
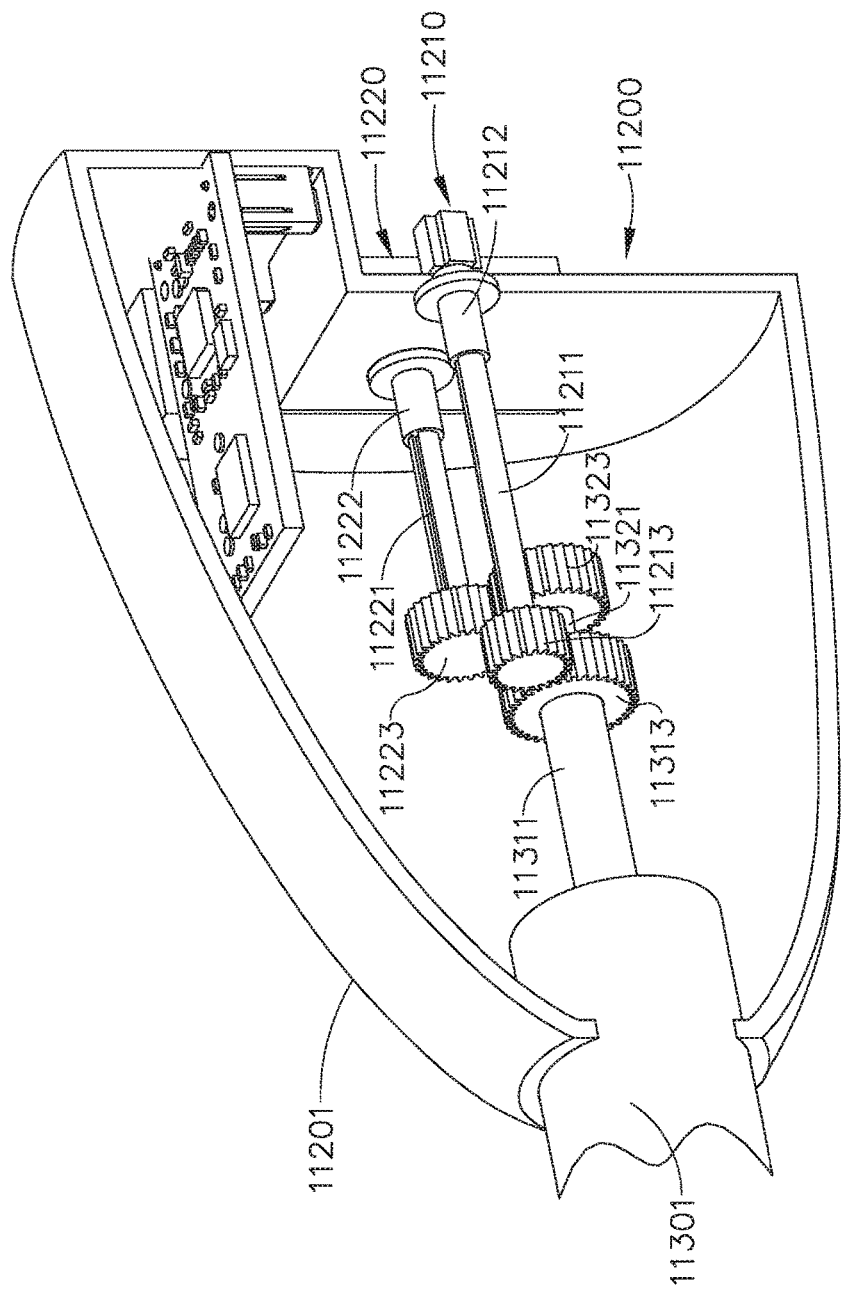
FIG. 18 is a partial perspective view of the attachment portion and the shaft assembly of the surgical stapling attachment of FIG. 15.

The attachment portion 11200, illustrated in greater detail in FIG. 18, is configured to be attached to an instrument interface to provide the rotary control motions generated by the instrument interface to the shaft assembly 11300. The attachment portion 11200 comprises a primary attachment interface 11210 and a secondary attachment interface 11220 supported by an attachment portion housing 11201. The attachment interfaces 11210, 11220 are configured to be mated, or coupled, with corresponding attachment interfaces of the instrument interface. The corresponding attachment interfaces of a surgical instrument handle, for example, can comprise of gear trains configured to be rotated by one or more motors when actuated by a user which, when rotated, rotates the primary attachment interface 11210 and the secondary attachment interface 11220.

The user may choose to rotate both interfaces 11210, 11220 simultaneously or, in the alternative, to rotate the interfaces 11210, 11220 independently. The primary attachment interface 11210 is configured to rotate an input drive shaft 11211 and an input drive gear 11213 mounted thereto. The input drive shaft 11211 comprises a housing bearing 11212 configured to abut the housing 11201 and prevent the shaft 11211 from translating distally. The input drive gear 11213 is operably intermeshed with a transfer gear 11313 of the shaft assembly 11300 which is mounted to a main drive shaft 11311. As a result, the rotation of interface 11210 is transferred to shaft 11311. A similar arrangement is used for the secondary attachment interface 11220. The secondary attachment interface 11220 is configured to rotate an input drive shaft 11221 and an input drive gear 11223 mounted thereto. The input drive shaft 11221 comprises a housing bearing 11222 configured to abut the housing 11201 and prevent the shaft 11221 from translating distally. The input drive gear 11223 is operably intermeshed with a transfer gear 11323 of the shaft assembly 11300 which is mounted to a secondary drive shaft 11321. As a result, the rotation of interface 11220 is transferred to shaft 11321. The main drive shaft 11311 is housed within a shaft assembly housing 11301. The drive shaft 11311 transfers the rotary control motions from the attachment interface 11210 to the end effector assembly 11500 through the articulation joint 11400. The secondary drive shaft 11321 is also housed within the shaft assembly housing 11301. The secondary drive shaft 11321 transfers the rotary control motions from the attachment interface 11220 to the end effector assembly 11500 through the articulation joint 11400.

Figure 19:
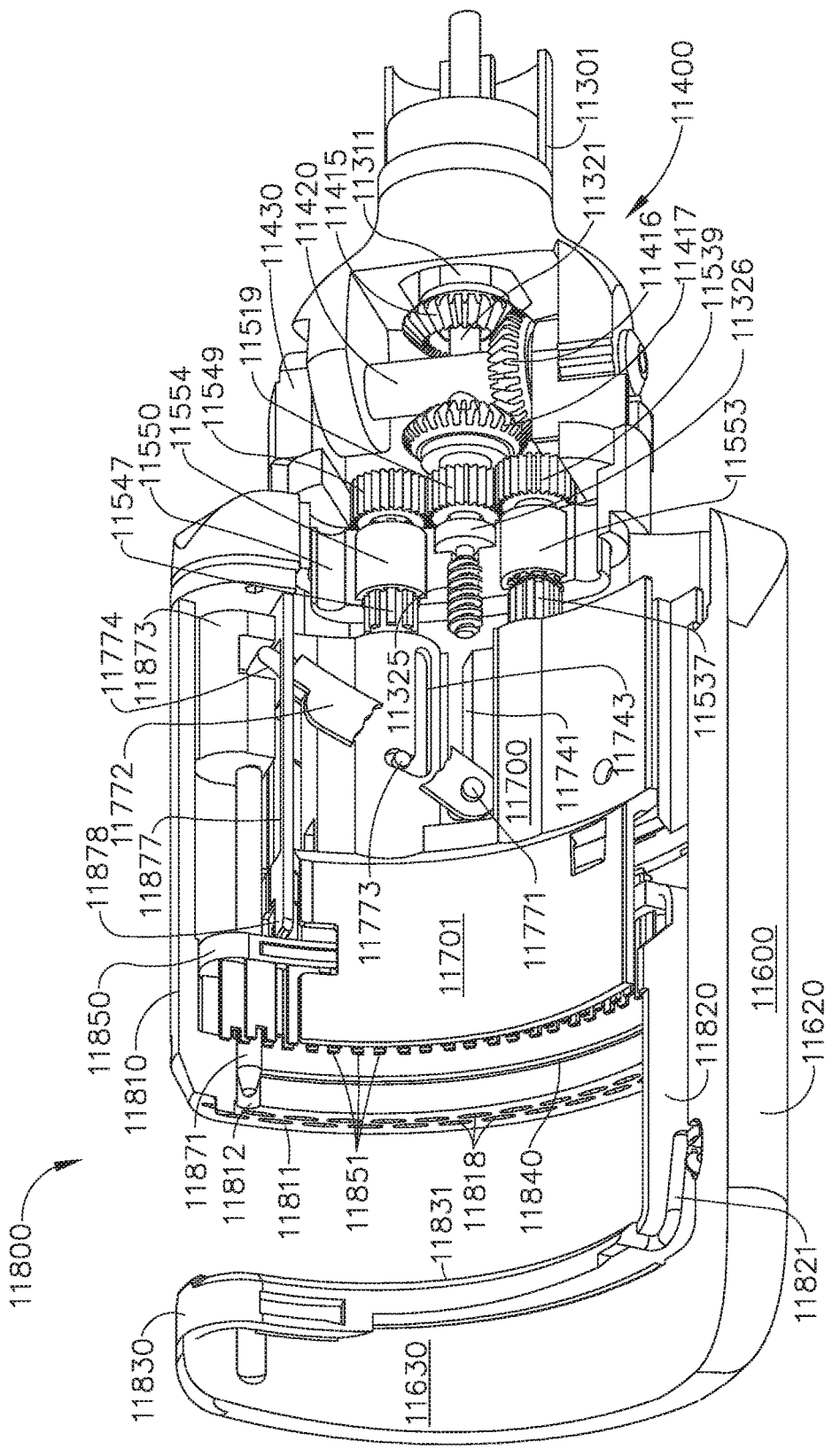
FIG. 19 is a partial perspective view of the end effector assembly, the articulation joint, and the shaft assembly of the surgical stapling attachment of FIG. 15, wherein the shaft assembly comprises a shifting assembly configured to shift between the drivability of a closure drive and a firing drive, and wherein the shifting assembly is illustrated in a position to drive the firing drive.
Figure 20:
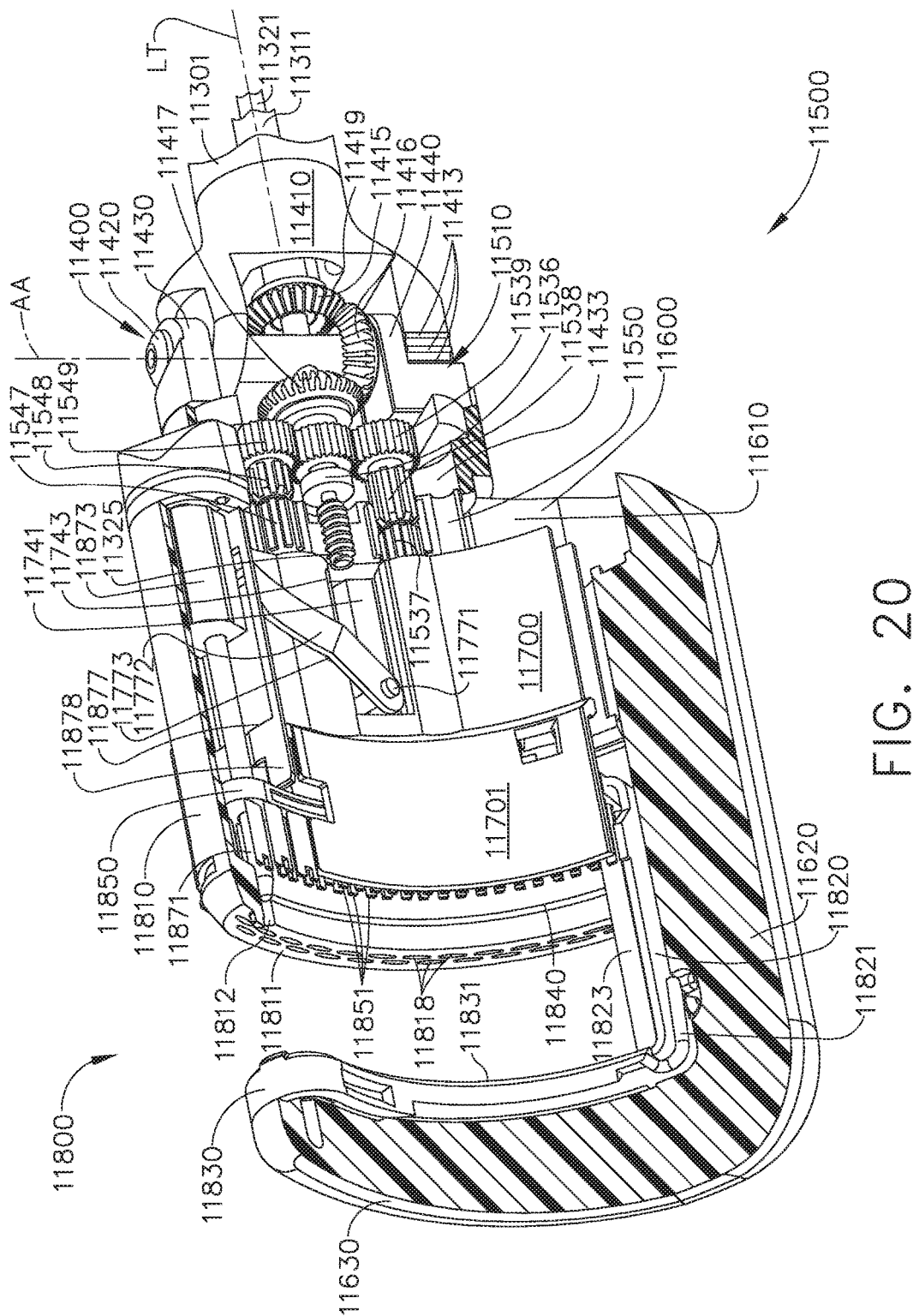
FIG. 20 is a partial perspective view of the end effector assembly, the articulation joint, and the shaft assembly of the surgical stapling attachment of FIG. 15, wherein the shifting assembly is illustrated in a position to drive the closure drive.

The articulation joint 11400 permits the end effector assembly 11500 to be passively articulated relative to the shaft assembly housing 11301. Referring primarily to FIGS. 19 and 20, the articulation joint 11400 comprises a proximal yoke 11410 attached to the shaft housing 11301, a distal yoke 11430 attached to the end effector assembly 11500, and an articulation pin 11420 pivotably coupling the proximal yoke 11410 and the distal yoke 11430. The articulation pin 11420 is rotatably received within proximal yoke apertures 11411 and distal yoke apertures 11431 defined in the proximal yoke 11410 and the distal yoke 11430, respectively. The end effector assembly 11500 is configured to be articulated about an articulation axis AA defined by the articulation pin 11420 in directions transverse to a longitudinal tool axis LT defined by the tool assembly 11100 and, more specifically, the shaft housing 11301. The proximal yoke 11410 comprises an aperture 11419 extending longitudinally therethrough permitting the concentric main drive shaft 11311 and the secondary drive shaft 11321 to extend therethrough. The articulation pin 11420 also comprises an aperture 11421 extending longitudinally therethrough permitting the secondary drive shaft 11321 to extend through the articulation pin 11420.

The articulation joint 11400 utilizes a passive articulation system comprising an articulation lock 11440 and detents 11413. A user may manually pivot the end effector assembly 11500 about the articulation pin 11420 causing the distal yoke 11430 to move the articulation lock 11440. As the articulation lock 11440 moves relative to the proximal yoke 11410 and rotates about the articulation pin 11420, the articulation lock 11440 is configured to grip, or incrementally lock with, detents 11413 defined in the proximal yoke 11410 to lock the distal yoke 11430 in position and, as a result, lock the end effector assembly 11500 into place. Stated another way, upon rotating the end effector assembly 11500 about the articulation pin 11420, the passive articulation system facilitates incremental articulation of the end effector assembly 11500 about the articulation axis AA.

The articulation joint 11400 is further configured to transfer, or communicate, rotation of the main drive shaft 11311 to the end effector assembly 11500. To transmit the rotary motion of the main drive shaft 11311 through, or across, the articulation joint 11400, the articulation joint 11400 further comprises an intermeshed gear train comprising an input bevel gear 11415 attached to the main drive shaft 11311, an idler bevel gear 11416 rotatable about the articulation pin 11420, and an output bevel gear 11417 attached to an input drive shaft 11518. As the main drive shaft 11311 rotates, the input bevel gear 11415 rotates which rotates the idler bevel gear 11416. Rotation of the idler bevel gear 11416 rotates the output bevel gear 11417 thus rotating the input drive shaft 11518 to which the output bevel gear 11417 is coupled. This arrangement permits the output bevel gear 11417 to rotate about the articulation pin 11420 when the end effector assembly 11500 is articulated while maintaining driving engagement with the main input drive shaft 11518.

A main input drive gear 11519 is attached to the main input drive shaft 11518 and is rotated when the main input drive shaft 11518 is rotated. The main input drive gear 11519 is configured to act as the single rotary input of the drive system 11510 which is discussed in greater detail below.

The articulation joint 11400 is further configured to permit the secondary drive shaft 11321 to pass therethrough so that a drive screw 11325 of the secondary drive shaft 11321 may engage a shifting assembly 11550 of the drive system 11510 discussed in greater detail below. The input bevel gear 11415, the output bevel gear 11417, and the main input drive shaft 11518 each comprise apertures configured to permit the secondary drive shaft 11321 to extend therethrough. The secondary drive shaft 11321 can be flexible, for example, to bend as the end effector assembly 11500 is articulated about the articulation axis AA. A thrust bearing 11326 is mounted to the secondary drive shaft 11321 to prevent the secondary drive shaft 11321 from being pulled through the main input drive shaft 11518 when the end effector assembly 11500 is articulated. The bearing 11326 abuts, or is bounded by, the main input drive gear 11519.

The articulation joint 11400 supports the end effector frame 11600 by attaching the proximal jaw 11610 of the end effector frame 11600 to the distal yoke 11430. The distal yoke 11430 comprises a sleeve portion 11433 having an outer surface and an inner surface where the outer surface is engaged by the end effector frame 11600 and the inner surface is configured to slidably support the shifting assembly 11550.

Figure 17:
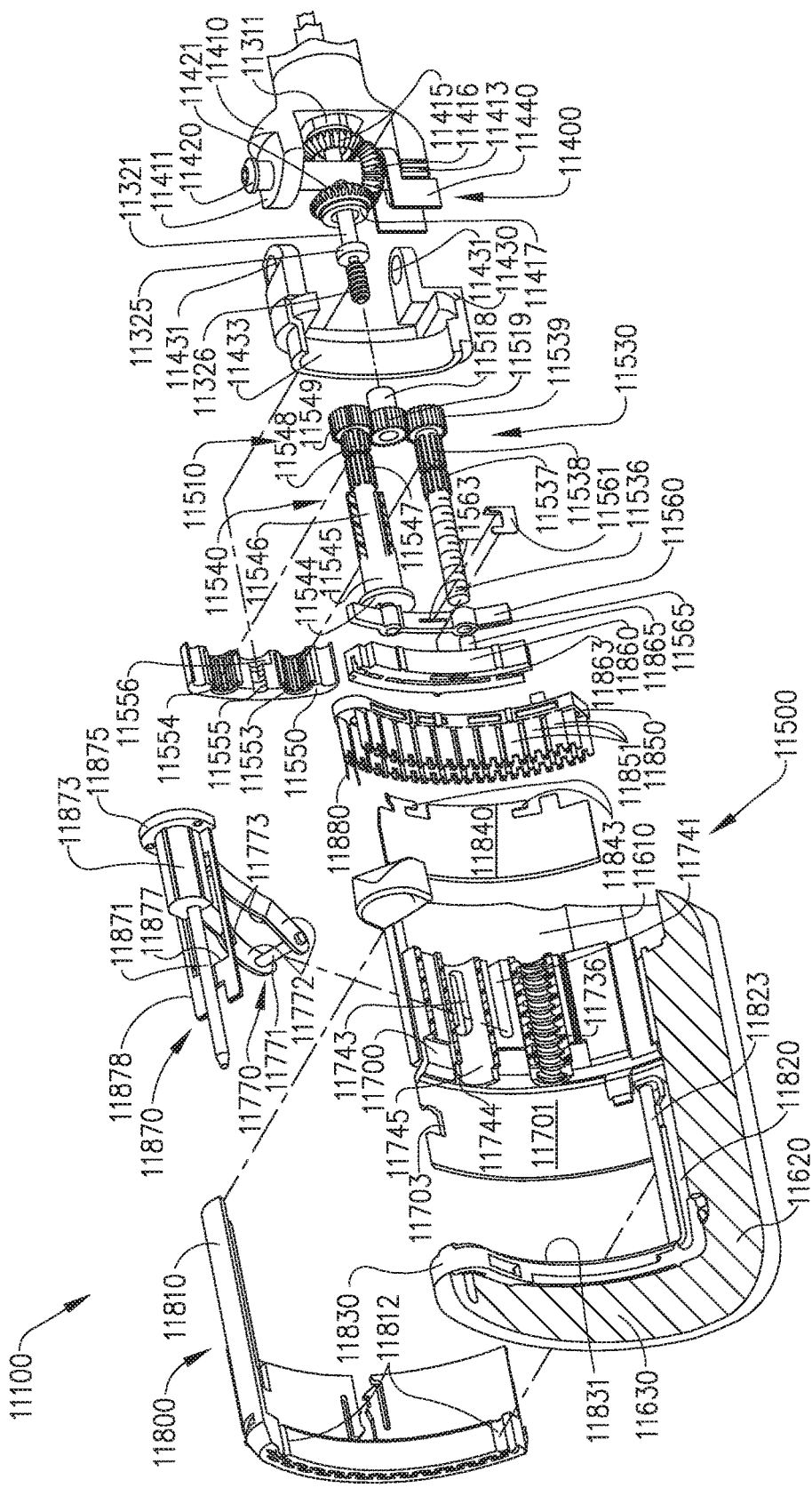
FIG. 17 is a partial exploded view of the end effector assembly, the articulation joint, and the shaft assembly of the surgical stapling attachment of FIG. 15.

Referring primarily to FIGS. 17 and 19, the end effector assembly 11500 comprises a drive system 11510, an end effector frame 11600, a closure frame 11700 moveable relative to the end effector frame 11600, and a replaceable staple cartridge assembly 11800 configured to be installed into the end effector frame 11600. The drive system 11510 comprises a single rotary input which is configured to receive the rotary control motions from the shaft assembly 11300 and the articulation joint 11400 to selectively drive a closure drive 11530 and a firing drive 11540 of the drive system 11510. The closure drive 11530 is configured to interact with the closure frame 11700 and portions of the staple cartridge assembly 11800 to move the closure frame 11700 and the staple cartridge assembly 11800 relative to the end effector frame 11600 into a capture stage position in order to capture tissue within the end effector assembly 11500. The capture stage involves automatically deploying a tissue-retention pin mechanism 11870 having a tissue-retention pin 11871. The closure drive can then be used to move the closure frame 11700 to a clamp stage position to clamp tissue with the staple cartridge assembly 11800. Once the tool assembly 11100 is in the fully clamped configuration, the firing drive 11540 can be operated to eject a plurality of staples 11880 from the staple cartridge assembly 11800 and deploy a knife 11840 from a staple cartridge body 11810 of the staple cartridge assembly to staple and cut tissue captured and clamped by the staple cartridge assembly 11800. The shifting assembly 11550 provides a user the ability to shift between the drivability of the closure drive 11530, the drivability of the firing drive 11540, and the simultaneous drivability of both the closure drive 11530 and the firing drive 11540.

Figure 16:
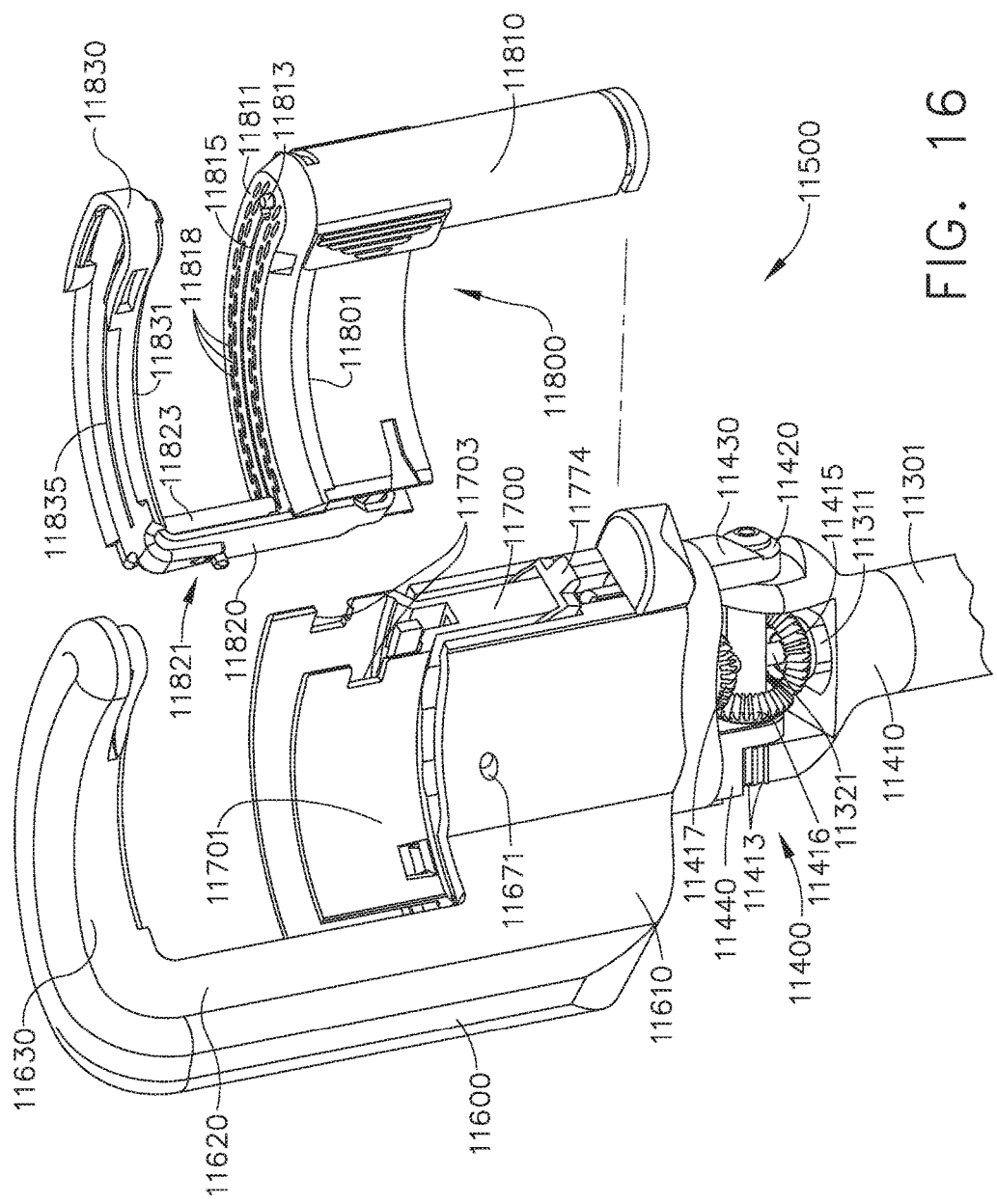
FIG. 16 is a partial perspective view of a staple cartridge assembly, the end effector assembly, and the articulation joint of the surgical stapling attachment of FIG. 15.

The staple cartridge assembly 11800 is configured to be replaceable. The staple cartridge assembly 11800 can be installed within the end effector frame 11600 such that, upon installation, the staple cartridge assembly 11800 is operably engaged with the closure frame 11700 and the drive system 11510. Referring now primarily to FIG. 16, the end effector frame 11600 comprises a proximal jaw 11610, a distal jaw 11630, and a connecting portion 11620 connecting the proximal jaw 11610 and the distal jaw 11630. The proximal jaw 11610 operably supports the drive system 11510 and the closure frame 11700 and is configured to slidably receive and moveably support the staple cartridge body 11810. The distal jaw 11630 is configured to slidably receive and fixedly support an anvil portion 11830 of the staple cartridge assembly 11800. The anvil portion 11830 comprises a staple forming surface 11831 configured to form the staples 11880 and a knife slot 11835 configured to at least partially receive the knife 11840 therein. The connecting portion 11620 is configured to receive and support an anvil frame 11820 of the staple cartridge assembly 11800 having a locator pin arrangement 11821. The locating pin arrangement 11821 can allow for quicker and/or easier loading of the staple cartridge assembly 11800 into the end effector assembly 11500. The locating pin feature 11821 corresponds to a locating pin indentation in the connecting portion 11620 of the end effector frame 11600. The staple cartridge assembly 11800 further comprises a guide pin 11823. The cartridge body 11810 is configured to move relative to the end effector frame 11600 using the knife and cartridge guide pin 11823 for support and guiding purposes.

The cartridge body 11810 comprises a cartridge deck 11811 having a plurality of staple cavities 11818 configured to removably store the staples 11880, a knife slot 11815 within which the knife 11840 is movably positioned, and a pair of pin slots 11812 configured to receive the pins 11823 and 11871 therein. The cartridge deck 11811 further comprises a closure stop 11813 that is configured to abut the anvil portion 11830 when the cartridge body 11810 is advanced toward the staple forming surface 11831. The closure stop 11813 defines a minimum distance achievable between the deck 11811 and the staple forming surface 11831 when the closure stop is abutted against the staple forming surface 11831. That said, it is envisioned that the closure stop 11813 may not contact the staple forming surface 11831 when thick tissue is being stapled, for example.

The closure frame 11700 comprises cartridge driving tabs 11701 and cartridge grasping recesses, or features, 11703 configured to engage the cartridge body 11810 and permit the closure frame 11700 to push the cartridge body 11810 toward the distal jaw 11630 and retract the cartridge body 11810 away from the distal jaw 11630. The cartridge driving tabs 11701 engage driving surfaces 11801 of the staple cartridge body 11810 such that the closure frame 11700 can push, or drive, the cartridge body 11810 toward the anvil portion 11830 when the closure frame 11700 is moved distally by the closure drive 11530. The cartridge grasping features 11703 act as hooks, or arms, and are configured to pull the cartridge 11810 proximally when the closure frame 11700 is moved proximally by the closure drive 11530.

Turning now to FIG. 17, the staple cartridge assembly 11800 further comprises a plurality of drivers 11851 supported by a staple driver base 11850. The drivers 11851 are configured to support the staples 11880 and push the staples 11880 out of their respective staple cavities 11818. The staple driver base 11850 and the knife 11840 are driven by a main driver 11860 which interacts with a firing bar 11560 of the drive system 11510. The knife 11840 is attached to the main driver 11860 by the knife supports 11843. The firing drive 11540 interacts with the main driver 11860 such that, when the firing drive 11540 is actuated, the firing bar 11560 pushes the main driver 11860 distally and ultimately ejects the staples 11880 from the staple cartridge assembly 11800 and deploys the knife 11840. The firing drive 11540 can be operated to retract the firing bar 11560 which retracts the main driver 11860 using a knife retraction arm 11561 engaged with the firing bar 11560 and the main driver 11860. The main driver 11860 comprises a slot 11863 configured to receive the knife retraction arm 11561 and, in addition, a firing bar guide pin 11865 configured to act as an alignment interface between the firing bar 11560 and the main driver 11860.

Figure 24:
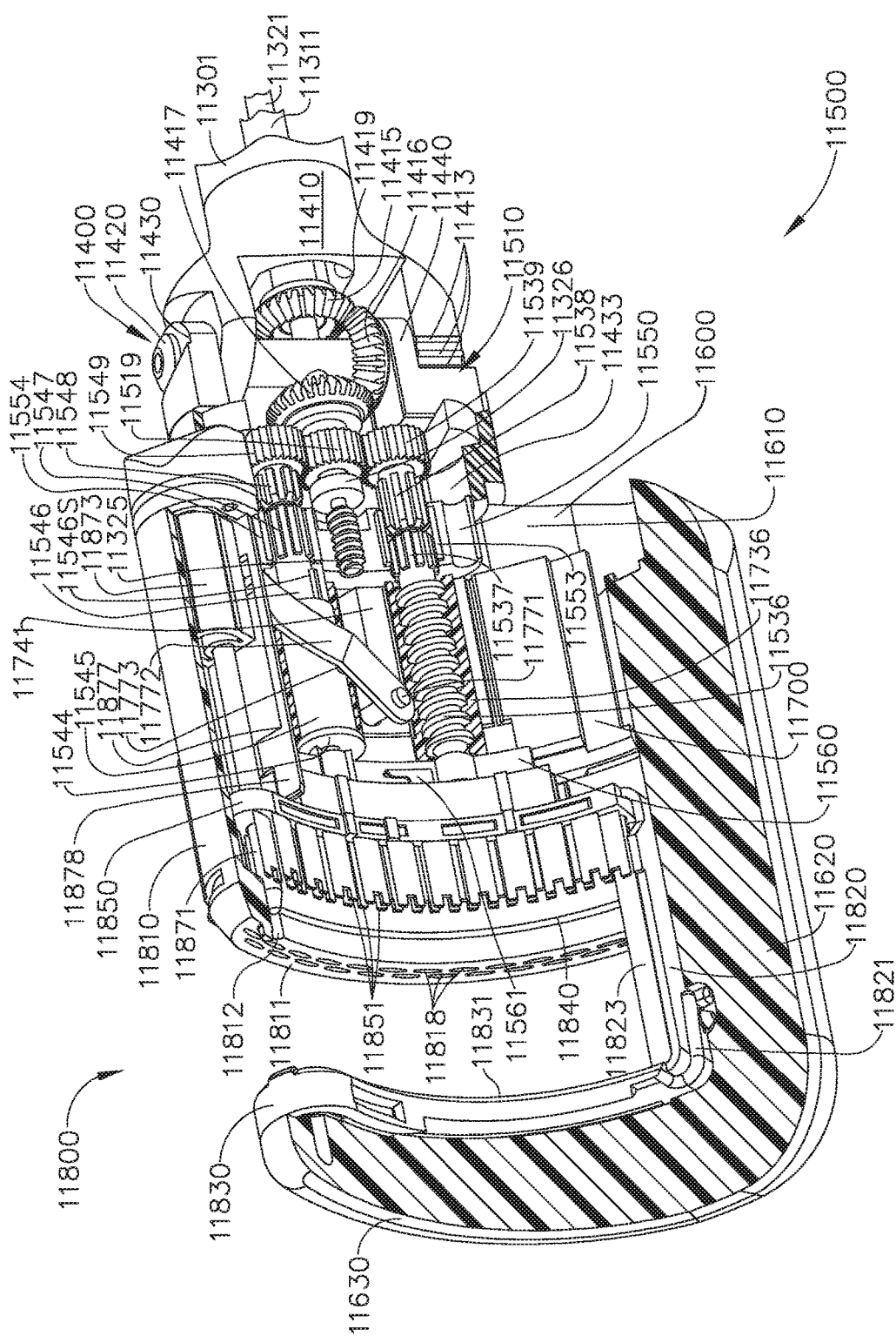
FIG. 24 is a partial perspective view of the end effector assembly, the articulation joint, and the shaft assembly of the surgical stapling attachment of FIG. 15, wherein the shifting assembly is illustrated in a position to drive the closure drive.

As discussed above, the drive system 11510 of the end effector assembly 11500 is engaged with the single rotary input, or the main input drive gear 11519, to effect multiple functions of the tool assembly 11100. Referring now to FIG. 24, the drive system 11510 comprises a closure drive 11530, a firing drive 11540, and the shifting assembly 11550 to selectively shift between the drivability of the closure drive 11530, the drivability of the firing drive 11540, and the simultaneous drivability of both the closure drive 11530 and the firing drive 11540. As discussed above, the interface 11220 can be selectively rotated to operate the shaft 11321. The shaft 11321 comprises a threaded portion, or drive screw, 11325 which is threadably engaged with the shifting assembly 11550. The shifting assembly 11550 is moveable longitudinally along the longitudinal tool axis LT using the drive screw 11325 of the secondary drive shaft 11321. When the secondary attachment interface 11220 is rotated, the shifting assembly 11550 moves relative to the distal yoke 11430. It is envisioned that a motor and/or solenoid is positioned within the end effector assembly 11500 in lieu of the shaft 11321 to move the shifting assembly 11550 between the described positions.

The closure drive 11530 comprises an input drive shaft having an input drive gear 11539 and an input splined portion 11538. The input drive gear 11539 is operably intermeshed with the main input drive gear 11519. The closure drive 11530 further comprises an output shaft having an output splined portion 11537 and a threaded portion 11536. The output shaft of the closure drive 11530 is aligned with the input drive shaft of the closure drive 11530. When the main input drive gear 11519 is rotated, the output shaft of the closure drive 11530 is rotated in unison with the input drive shaft of the closure drive 11530 only when the splined portions 11538, 11537 are coupled by the shifting assembly 11550. The threaded portion 11536 of the output shaft of the closure drive 11530 is threadably received by a threaded bore 11736 of the closure frame 11700. When the output shaft of the closure drive 11530 is rotated, the closure frame 11700 moves relative to the end effector frame 11600 causing the staple cartridge body 11810 to be advanced distally toward the anvil portion 11830 to clamp tissue within the end effector assembly 11500.

The firing drive 11540 also comprises an input drive shaft having the input drive gear 11549 and an input splined portion 11548. The input drive gear 11549 is also operably intermeshed with the main input drive gear 11519. The firing drive 11540 further comprises an output shaft having an output splined portion 11547 and an input splined portion 11546. The output shaft of the firing drive 11540 further comprises a tubular firing shaft 11545 which receives the input splined portion 11546 within a firing shaft bore 11545B. The tubular firing shaft 11545 is rotatably engaged with a rib 11546S of the input splined portion 11546 so that the tubular firing shaft 11545 can move longitudinally relative to the input splined portion 11546 while maintaining a rotating, drivable relationship with the input splined portion 11546. The output shaft of the firing drive 11540 is aligned with the input drive shaft of the firing drive 11540. When the main input drive gear 11519 is rotated, the output shaft of the firing drive 11540 is rotated in unison with the input drive shaft of the firing drive 11540 only when the splined portions 11548, 11547 are coupled by the shifting assembly 11550.

The tubular firing shaft 11545 further comprises a firing shaft ground 11544 and, in addition, a threaded output shaft 11543 threadably received by the firing bar 11560. When the closure frame 11700 is advanced distally by the closure drive 11530, the closure frame 11700 pushes the firing bar 11560 distally. As the firing bar is advanced distally by the closure frame 11700, the tubular firing shaft 11545 is pulled distally relative to the input splined portion 11546 by the firing bar 11560 owing to at least the threaded engagement of the threaded output shaft 11543 and the firing bar 11560. The tubular firing shaft 11545 is journally received by a firing bore 11745 defined in the closure frame 11700 to permit rotation of the tubular firing shaft 11545 within the closure frame 11700. When the splined portions 11548, 11547 are coupled, the tubular firing shaft 11545 of the firing drive 11540 is rotated by the input splined portion 11546 and, also, the firing shaft ground 11544 of the tubular firing shaft 11545 pushes against the firing ledge 11744 of the closure frame 11700. Utilizing the ledge 11744 as a movable grounding mechanism, the tubular firing shaft 11545 drives the firing bar 11560 distally, by the threaded output shaft 11543, thus deploying the knife 11840 and ejecting the staples 11880 from the staple cavities 11818.

The shifting assembly 11550 permits the user to shift between the drivability options discussed above by coupling and uncoupling the sets of splined portions 11537, 11538 and 11547, 11548. The shifting assembly 11550 comprises a threaded aperture 11555 threadably receiving the drive screw 11325 of the secondary drive shaft 11321 such that, when the drive screw 11325 is rotated, the shifter assembly 11550 moves longitudinally relative to the sets of splined portions 11537, 11538 and 11547, 11548. The shifting assembly 11550 further comprises a splined closure coupling, or clutch ring, 11553 corresponding to the closure drive 11530 and a splined firing coupling, or clutch ring, 11554 corresponding to the firing drive 11540. The splined couplings 11553, 11554 are cylindrical, tube-like couplings journably supported within the shifting assembly 11550 and are permitted to rotate within the shifting assembly 11550. The splined couplings 11553, 11554 each have inner shells comprising a splined configuration such that the couplings 11553, 11554 can couple, or mate, the sets of splined shaft portions 11537, 11538 and 11547, 11548, respectively. When the shifting assembly 11550 is shifted to place the end effector assembly 11500 in a tissue clamping configuration, the closure coupling 11553 is engaged with the splined portions 11537, 11538. The closure coupling 11553 transfers the rotation of the splined shaft portion 11538 to the splined shaft portion 11537, thus rotating the output shaft of the closure drive 11530. When the shifting assembly 11550 is shifted to place the end effector assembly 11500 in a tissue cutting and stapling configuration, the firing coupling 11554 is engaged with the splined portions 11547, 11548. The firing coupling 11554 transfers the rotation of the input splined portion 11548 to the output splined portion 11547, thus rotating the output shaft of the firing drive 11540. The shifting assembly 11550 also comprises a cylindrical recess 11556 permitting the shifting assembly 11550 to nest against the thrust bearing 11326 of the secondary drive shaft 11321 when moved proximally to the second position.

The user of the tool assembly 11100 can shift the tool assembly 11100 between a clamping condition and a staple forming condition depending on what function they wish to perform via a controller onboard the tool assembly 11100 and/or the instrument interface to which the tool assembly 11100 is attached. The controller would communicate to a motor to actuate either the primary attachment interface 11210, the secondary attachment interface 11220, or both the primary attachment interface 11210 and the secondary attachment interface 11220 simultaneously. Referring now to FIGS. 25-30, the interaction and engagement between the drive system 11510 and the end effector assembly 11500 will now be discussed in relation to the capable functions of the tool assembly 11100 including capturing, clamping, stapling, and cutting tissue.

Figure 25:
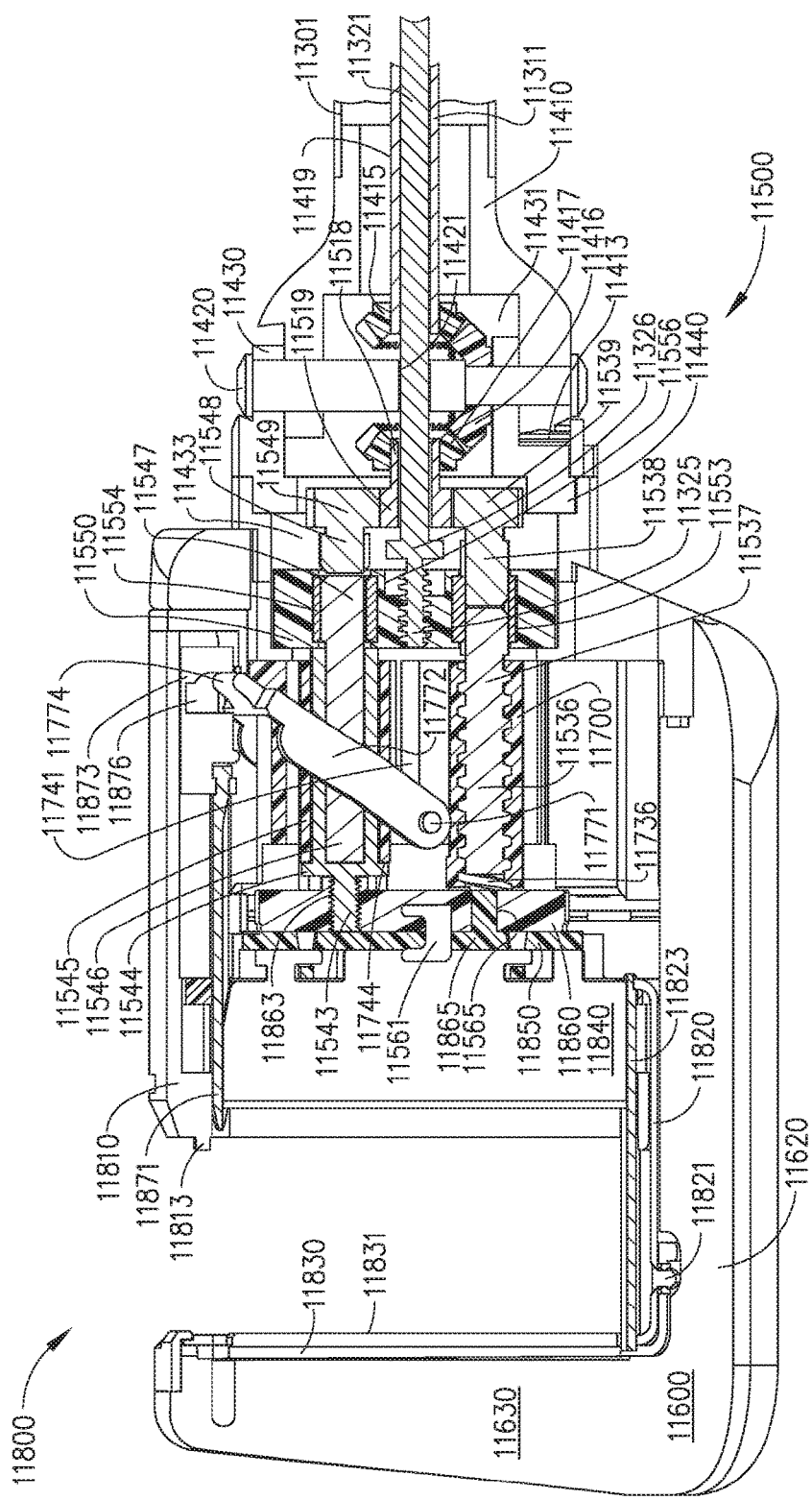
FIG. 25 is a longitudinal cross-sectional view of the end effector assembly, the articulation joint, and the shaft assembly of the surgical stapling attachment of FIG. 15, wherein the shifting assembly is in a first position to drive the closure drive and the end effector assembly is in an open configuration.
Figure 26:
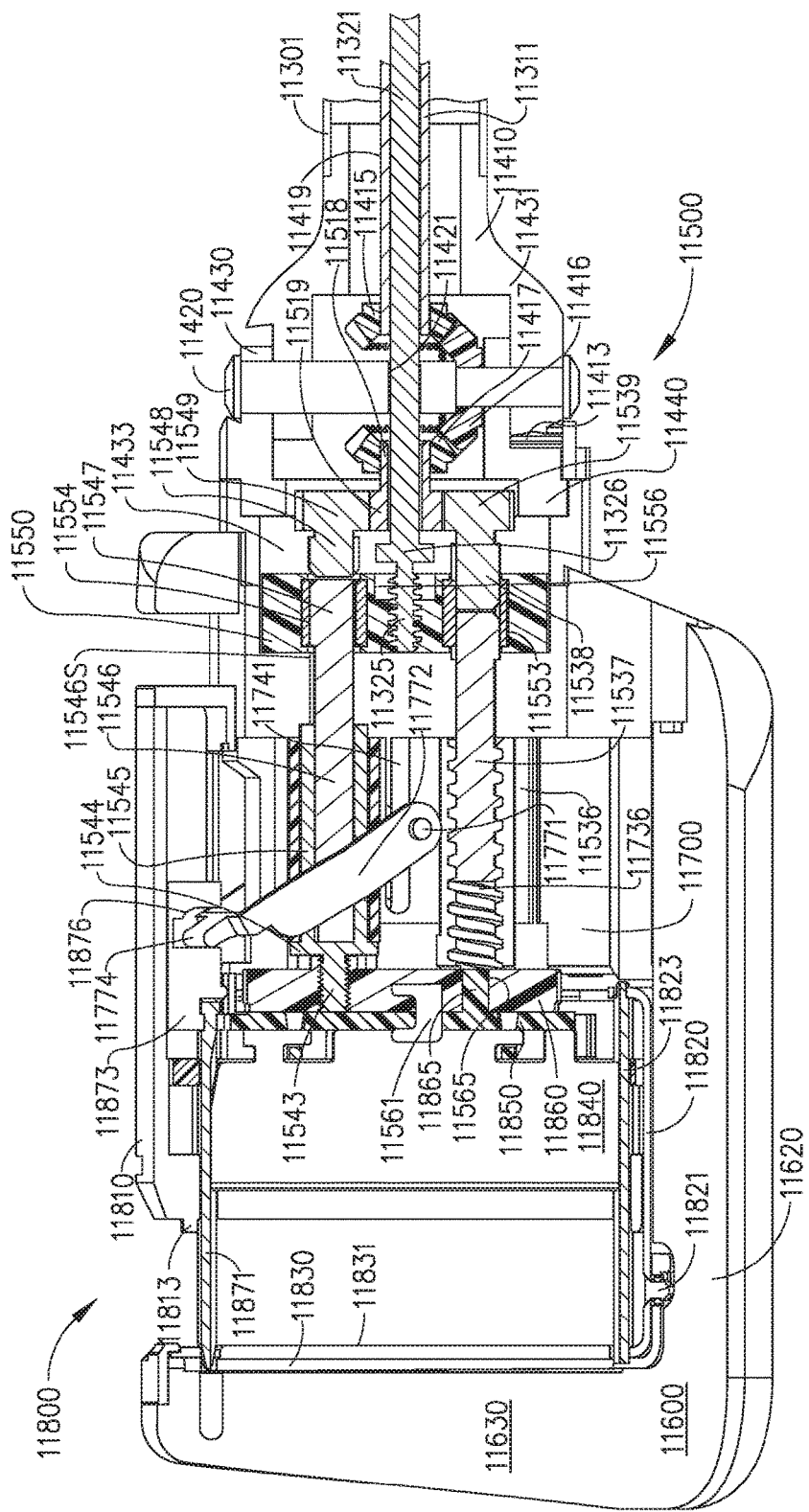
FIG. 26 is a longitudinal cross-sectional view of the end effector assembly, the articulation joint, and the shaft assembly of the surgical stapling attachment of FIG. 15, wherein the shifting assembly is in the first position and the end effector assembly is in a partially closed configuration.

FIG. 25 illustrates the tool assembly 11100 in an open, or initial, configuration. The shifting assembly 11550 is in a first position where the closure coupling 11553 couples the splined shaft portions 11538, 11537 of the closure drive 11530 enabling the output shaft of the closure drive 11530 to be driven upon rotation of the main input drive gear 11519. The firing coupling 11554 is in a position where it is only mated with the output shaft of the firing drive 11540.

In this instance, the firing coupling 11554 is not a position configured to mate the splined shaft portions 11538, 11537. In this position, the firing coupling 11554 does not rotate within the shifting assembly 11550 because the output shaft of the firing drive 11540 is not driven upon rotation of the main input drive gear 11519.

The actuation of the closure drive 11530 performs two functions; pin (capture) tissue within the end effector assembly 11500 and clamp the tissue within the end effector assembly 11500. To capture the tissue with the tissue-retention pin 11871, the primary attachment interface 11210 is actuated while the shifting assembly 11550 is in the first position. The main input drive gear 11519 is driven and, because the closure coupling is engaged with both splined portions 11538, 11537 of the closure drive 11530, the output shaft of the closure drive 11530 is rotated advancing the closure frame 11700 distally. This initial, distal movement of the closure frame 11700 automatically deploys the tissue-retention pin mechanism 11870 with a lever 11770. A coupler portion 11873 having a coupler recess 11876 is configured to receive a lever tip 11774 extending from a pair of lever arms 11772 to couple the tissue-retention pin mechanism 11870 and the lever 11770. A cartridge cap 11878 having a cap window 11877 and cap base 11875 permits the lever 11770 to engage the staple cartridge assembly 11800 to interact with the pin mechanism 11870. The cap base 11875 defines a ground position for pin the coupler portion 11873 and, thus, the pin mechanism 11870. To deploy the pin 11871, the lever 11770 interfaces with the end effector frame 11600, the closure frame 11700, and the tissue-retention pin mechanism 11870. The lever 11770 comprises a ground pin 11771 supported within a frame aperture 11671 of the end effector frame 11600 and a frame slot 11741 of the closure frame 11700. The ground pin 11771 defines a lever rotating axis. The lever 11770 also comprises lever arms 11772 having actuation tines 11773 configured for engagement with a closure frame cam slot 11743 of the closure frame 11700. The lever further comprises a lever tip 11774 configured for engagement with the coupler portion 11873 of the pin mechanism 11870.

Figure 21:
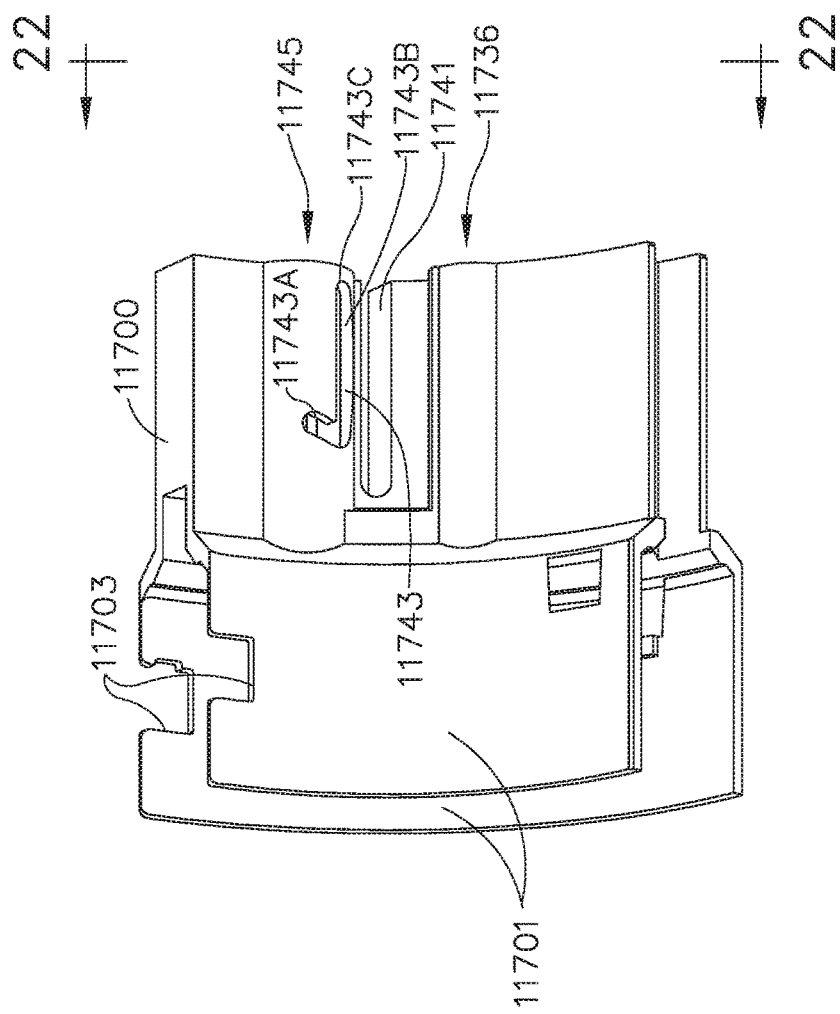
FIG. 21 is a perspective view of a closure frame of the end effector assembly of the surgical stapling attachment of FIG. 15, wherein the closure frame comprises corresponding slots to engage a tissue-retention pin mechanism of the end effector assembly and corresponding driving tabs to engage the staple cartridge assembly.

As best seen in FIGS. 21-23, the closure frame cam slot 11743 of the closure frame 11700 comprises an initial cam slot portion 11743A configured to drive the actuation tines 11773 distally causing the lever 11770 to rotate about the lever rotating axis thus lifting the lever tip 11774 to drive the pin 11871 out of its corresponding pin slot 11812 and toward the distal jaw 11630. The closure frame cam slot 11743 also comprises a final cam slot portion 11743B to permit clearance in the closure frame 11700 for the actuation tines 11773 during the clamping stage discussed in greater detail below. The actuation tines 11773 abut the final cam slot portion 11743B during the clamping stage to prevent the tissue-retention pin 11871 from retracting, or opening during the clamping and/or firing/stapling stage. The frame slot 11741 also provides clearance but for the ground pin 11771 during the clamping stage. This initial actuation stage of the closure drive 11530 completes an initial capture stage in which the tissue-retention pin 11871 is deployed into engagement with the distal jaw 11630 and/or anvil portion 11830 of the staple cartridge assembly 11800. This initial capture stage, seen in FIG. 26, can be sufficient to capture tissue with the tool assembly 11100.

During the initial capture stage, the closure frame 11700 also advances portions of the staple cartridge assembly 11800 and the firing bar 11560 toward the distal jaw 11630. The cartridge driving tabs 11701 drive the cartridge body 11810 and the closure frame 11700 drives the tubular firing shaft 11545 and the firing bar 11560. Other, and/or additional, contact points may be provided between the closure frame 11700, the firing drive 11540, and the staple cartridge assembly 11800 to aid in the advancement of certain parts of the end effector assembly 11500. As discussed above, the tubular firing shaft 11545 and the input splined portion 11546 of the output shaft of the firing drive 11540 can move longitudinally relative to each other while maintaining a rotatable driving relationship. This facilitates the extension of the output shaft of the firing drive 11540 so that the tubular firing shaft 11545 may be driven when the input splined portion 11546 is driven after the closure frame 11700 is advanced.

Figure 27:
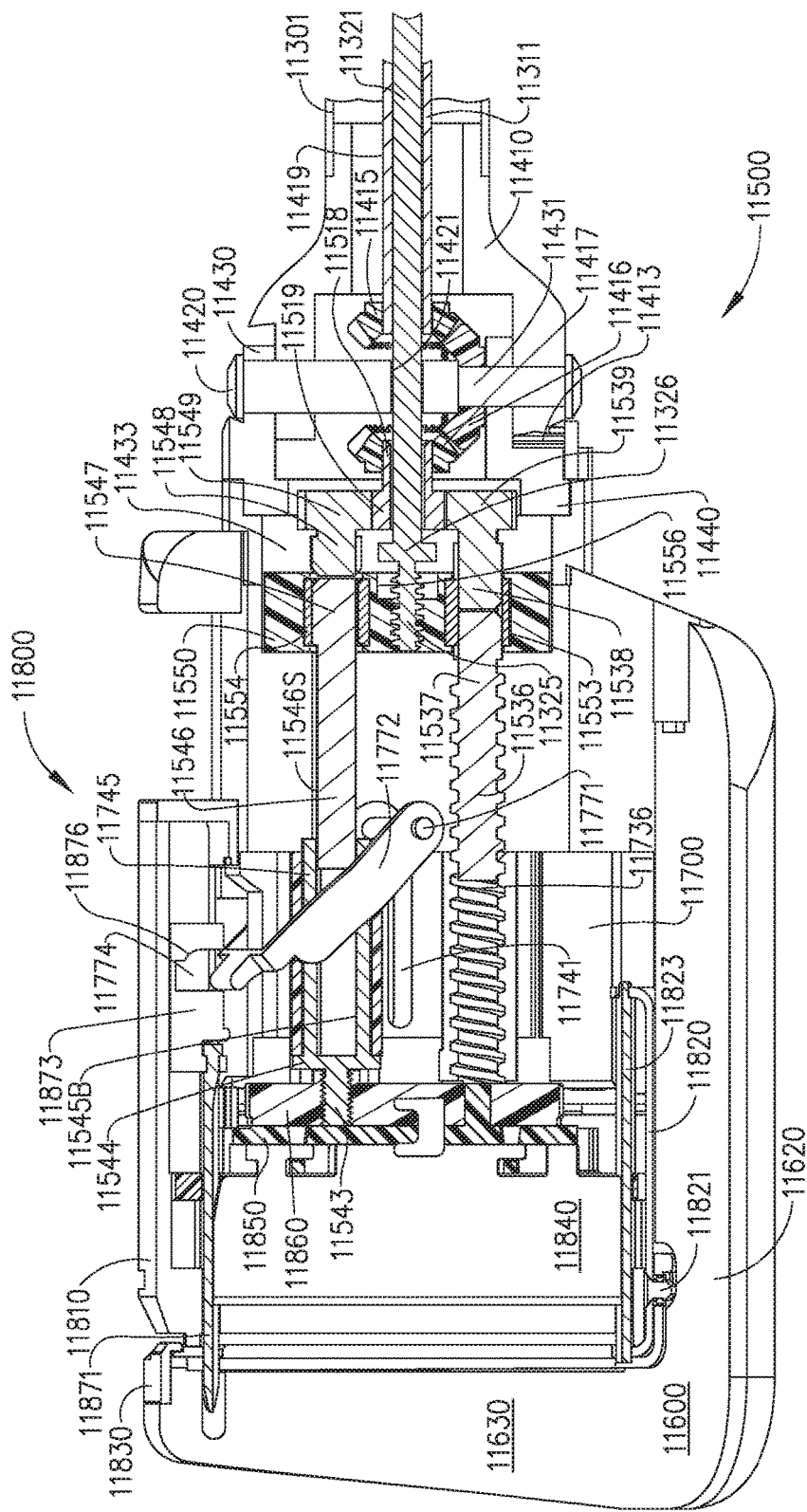
FIG. 27 is a longitudinal cross-sectional view of the end effector assembly, the articulation joint, and the shaft assembly of the surgical stapling attachment of FIG. 15, wherein the shifting assembly is in the first position and the end effector assembly is in a fully clamped configuration.

FIG. 27 illustrates the tool assembly 11100 in a fully clamped configuration after a final actuation stage of the closure drive 11530. The closure stop 11813 is bounded by the anvil portion 11830 and the tissue-retention pin mechanism 11870 is fully deployed. To fully deploy the tissue-retention pin mechanism 11870, the closure frame cam slot 11743 comprises a final cam slot end 11743 C to advance the actuation tines 11773 to a final position. This configuration of the tool assembly 11100 is considered to be a fully clamped position. The user may decide to actuate the closure drive in an opposite direction to retract the closure drive and thus unclamp and uncapture the tissue, or, the user may decide to shift the shifting assembly to a second position, shown in FIG. 28, to fire the tool assembly 11100.

Figure 28:
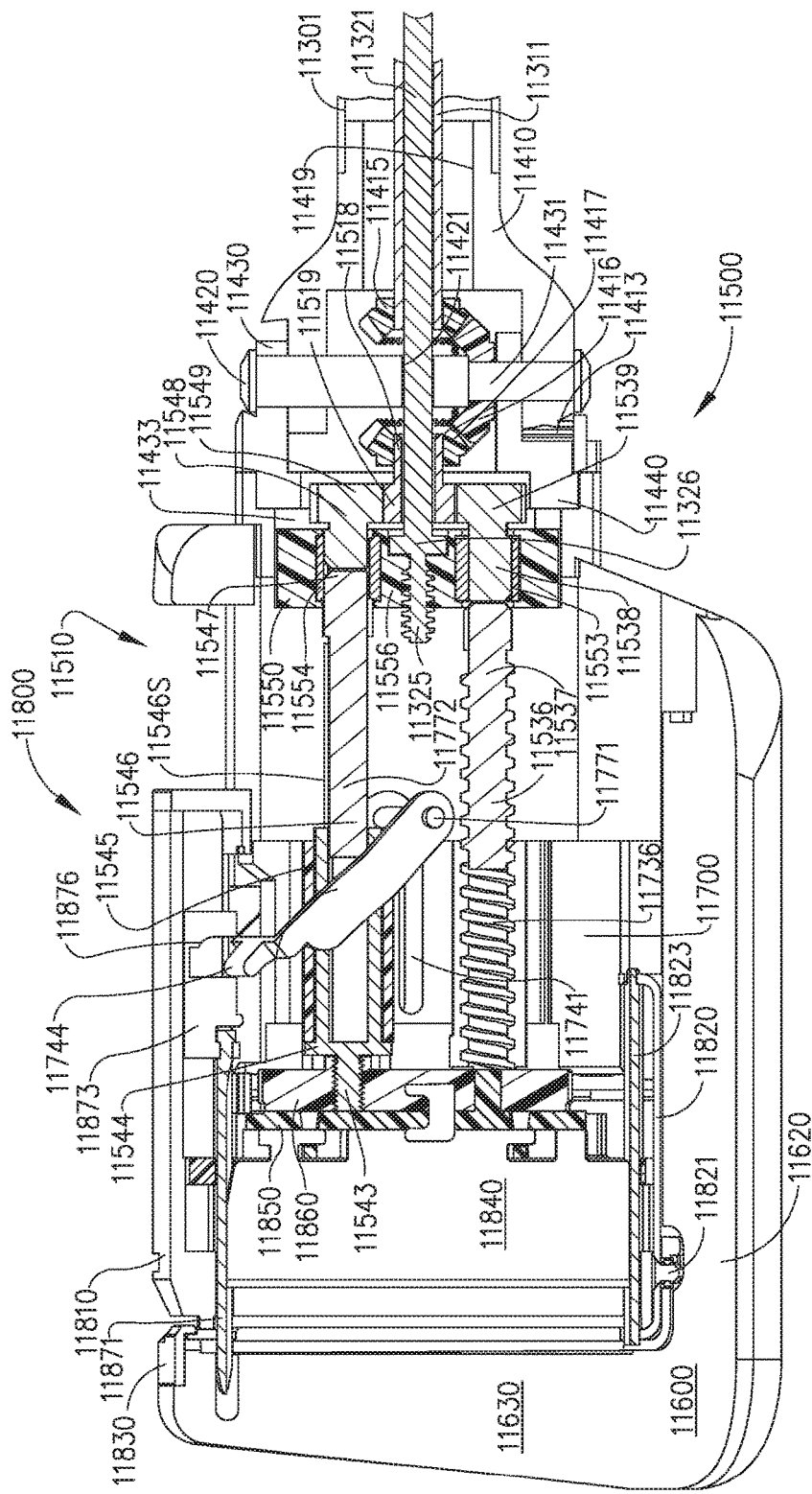
FIG. 28 is a longitudinal cross-sectional view of the end effector assembly, the articulation joint, and the shaft assembly of the surgical stapling attachment of FIG. 15, wherein the shifting assembly has shifted from the first position to a second position to drive the firing drive and the end effector assembly is in the fully clamped configuration.

To move the shifting assembly to the second position shown in FIG. 28, the user can actuate the secondary attachment interface 11220 thus rotating the drive screw 11325 to move the shifting assembly 11550 proximally to the second position. The shifting assembly 11550 is configured to nest against the thrust bearing 11326 upon moving to the second position. In the second position, the firing coupling 11554 of the shifting assembly 11550 couples the splined shaft portions 11548, 11547 of the firing drive 11540 enabling the output shaft of the firing drive 11540 to be driven upon rotation of the main input drive gear 11519. Moving the shifting assembly 11550 to the second position also decouples the splined shaft portions 11538, 11537 of the closure drive 11530. The closure coupling 11553 rotates within the shifting assembly 11550 when the main input drive gear 11519 is driven but, because the closure coupling 11553 is only mated to the input splined portion 11548, the output shaft of the closure drive 11530 will not rotate.

The user can now actuate the firing drive 11540 by driving the primary attachment interface 11210 to drive the main drive shaft 11311. Actuation of the firing drive 11540 rotates the output splined portion 11546 thus rotating the tubular firing shaft 11545. The tubular firing shaft 11545 rotates within the firing bore 11745 of the closure frame 11700. When the tubular firing shaft 11545 is rotated, the firing shaft ground 11544 of the tubular firing shaft 11545 pushes off of, or is grounded by, the firing ledge 11744 of the closure frame 11700. Rotation of the tubular firing shaft 11545 rotates the threaded output shaft 11543 thus driving the firing bar 11560 distally. The distal movement of the firing bar 11560 deploys the knife 11840 out of the cartridge body 11810 and drives the staples 11880 out of the staple cavities 11818 with the staple drivers 11851 and driver base 11850. The knife 11840 cuts the tissue clamped with the end effector assembly 11500 and the staples 11880 staple the tissue clamped with the end effector assembly.

Figure 29:
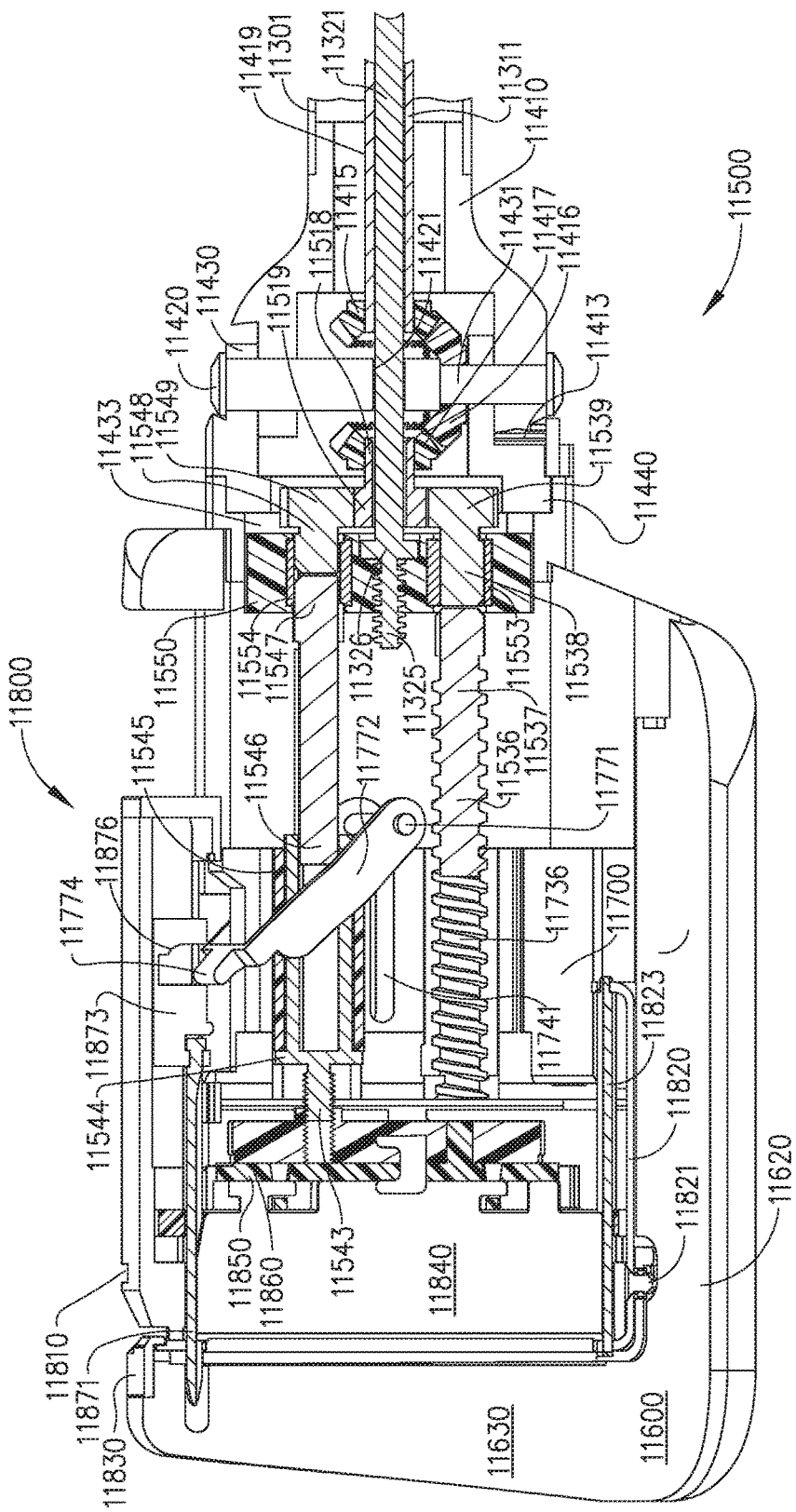
FIG. 29 is a longitudinal cross-sectional view of the end effector assembly, the articulation joint, and the shaft assembly of the surgical stapling attachment of FIG. 15, wherein the shifting assembly is in the second position and the surgical stapling attachment is in a fully fired configuration.

At the stage illustrated in FIG. 29, a user can retract the firing bar 11560 by actuating the primary attachment interface 11210 in an opposite direction thus pulling the drive bar 11560 and the knife 11840 proximally. The firing bar 11560 comprises an aperture 11565 configured to journably support the firing bar guide pin 11865 to maintain alignment of the firing bar 11560 and the main driver 11860 during movement of the firing bar 11560 and the main driver 11860. The firing bar 11560 also comprises a slot 11563 configured to receive the knife retraction arm 11561 such that when the firing bar 11560 is moved proximally, the firing bar 11560 can pull, or retract, the knife 11840 proximally. Another option for the user can involve shifting the shifting assembly 11550 to a third position which is intermediate the first position and the second position by actuating the secondary attachment interface 11220. This third position, illustrated in FIG. 30, places both of the couplings 11553, 11554 into coupling engagement with their respective sets of splined portions 11538, 11537 and 11548, 11547. The user can then actuate the primary attachment interface 11210 in a reversing direction to actuate the main input drive gear 11519 and drive both the output shaft of the closure drive 11530 and the output shaft of the firing drive 11540 simultaneously. A user may desire this simultaneous drivability at any point during use of the tool assembly 11100 to provide a quick retraction method in the event the user wants to withdraw the tool assembly 11100 from a surgical site. The controller onboard the instrument interface can be programmed to automatically shift the shifting assembly 11550 to the third position and reverse the main input drive gear 11519 by simultaneously actuating both attachment interfaces 11210, 11220.

Figure 30:
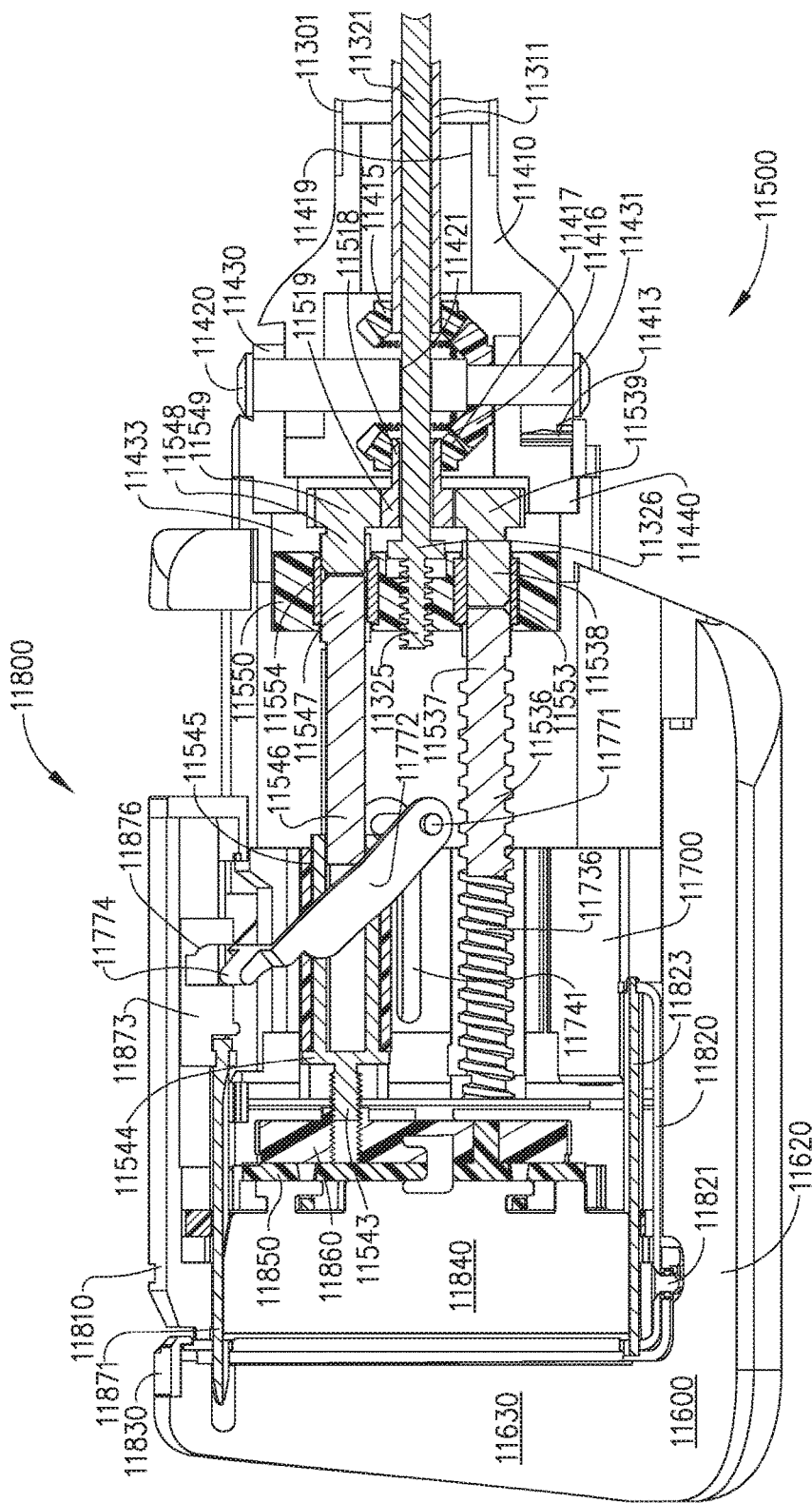
FIG. 30 is a longitudinal cross-sectional view of the end effector assembly, the articulation joint, and the shaft assembly of the surgical stapling attachment of FIG. 15, wherein the shifting assembly has shifted from the second position to a third position to drive the firing drive and the closure drive simultaneously, and wherein the surgical stapling attachment is in the fully fired configuration.
Figure 30A:
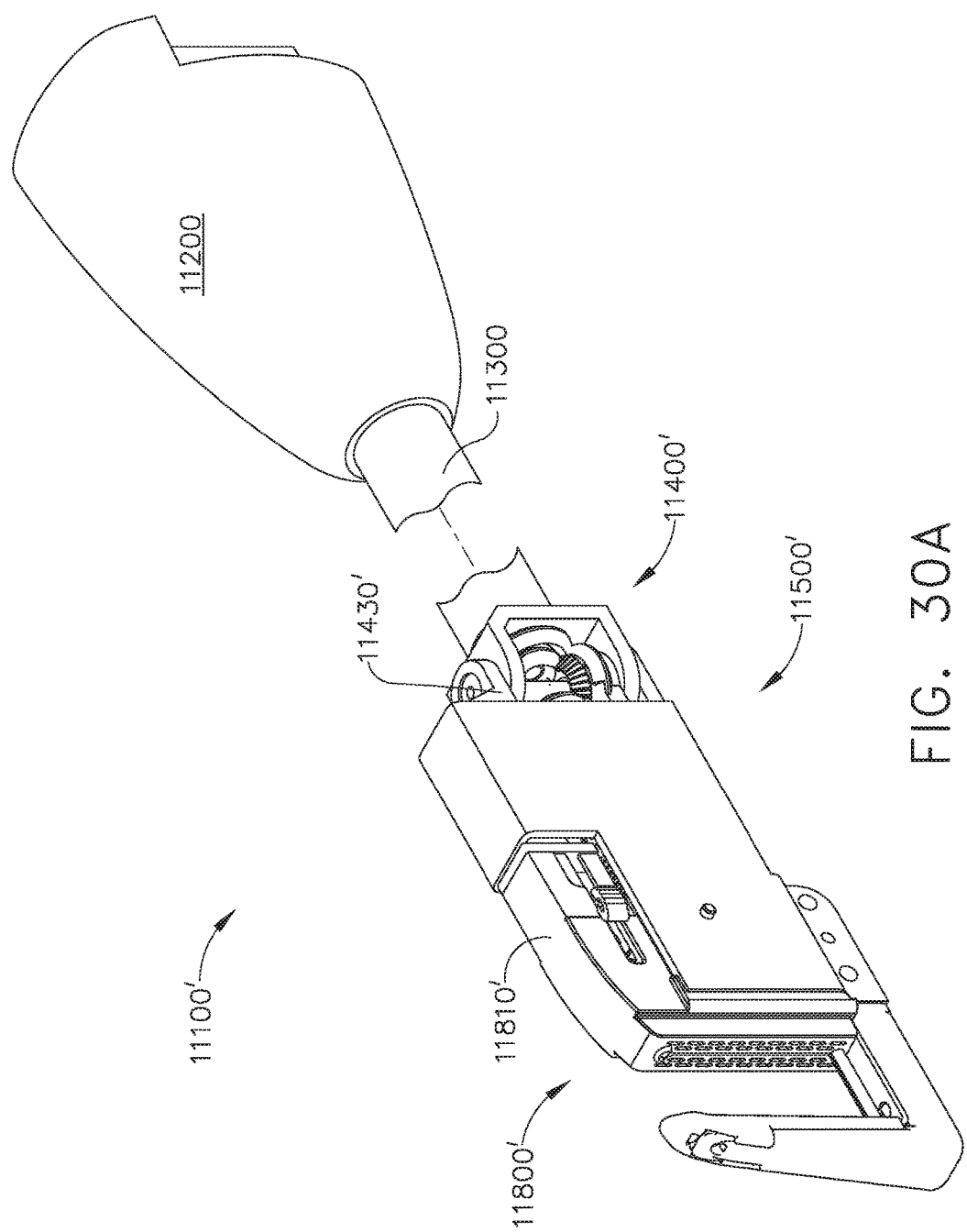
FIG. 30A is a perspective view of a shaft assembly comprising a staple cartridge in accordance with at least one embodiment.
Figure 30C:
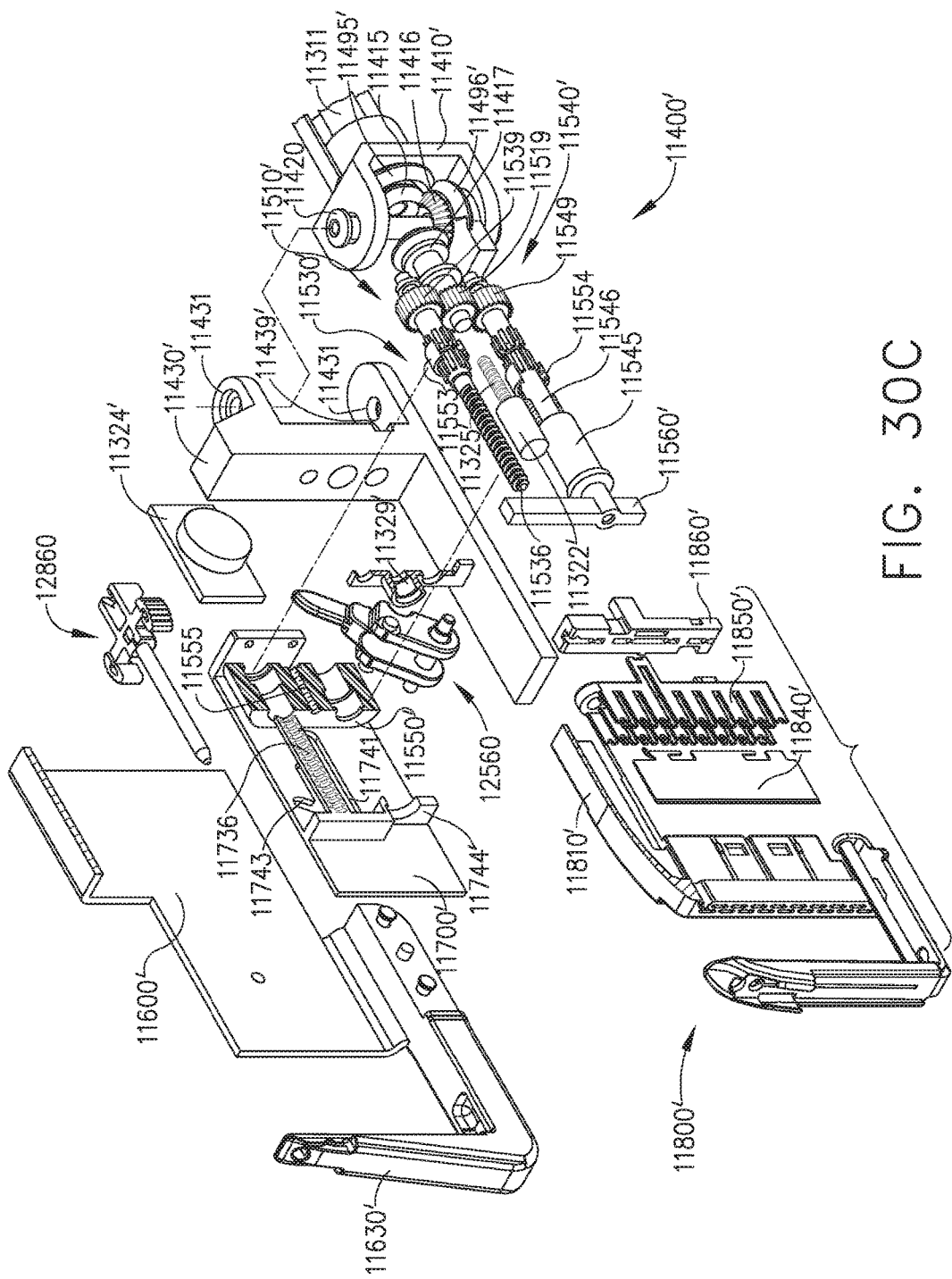
FIG. 30C is a partial exploded view of the shaft assembly of FIG. 30A.
Figure 30D:
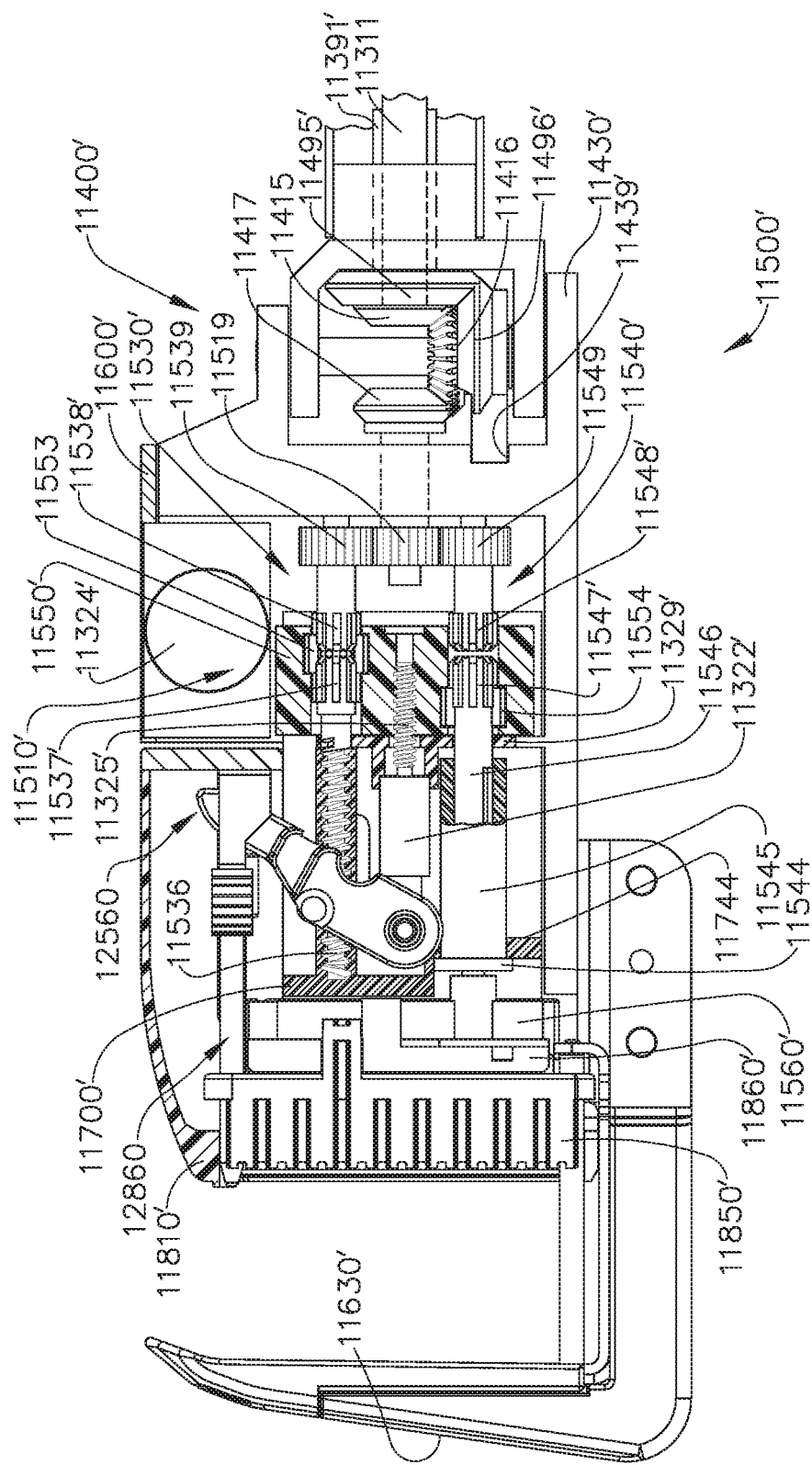
FIG. 30D is a partial cross-sectional view of the shaft assembly of FIG. 30A illustrated in an open, unclamped configuration.
Figure 30E:
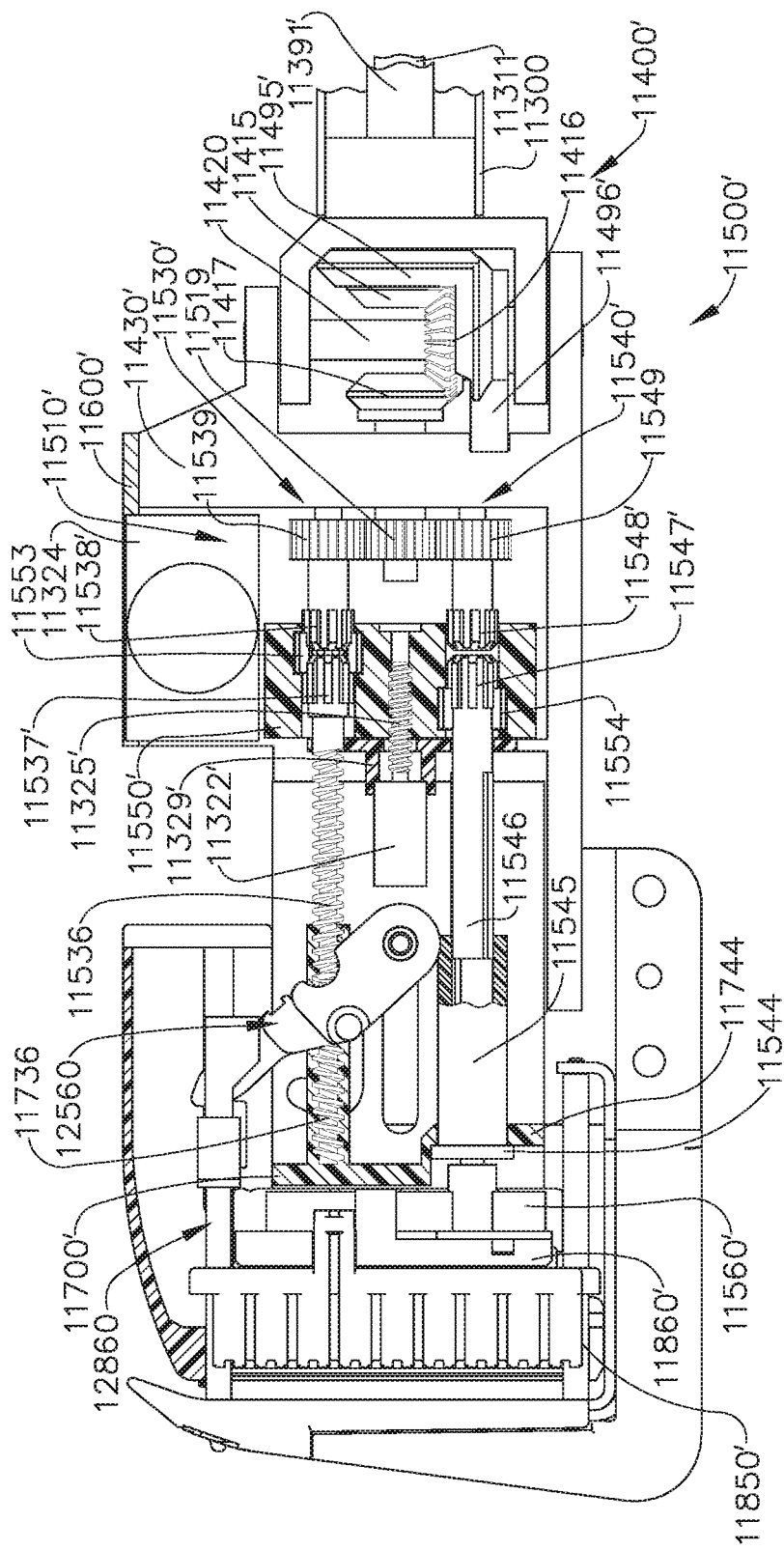
FIG. 30E is a partial cross-sectional view of the shaft assembly of FIG. 30A illustrated in a closed, clamped configuration.
Figure 30F:
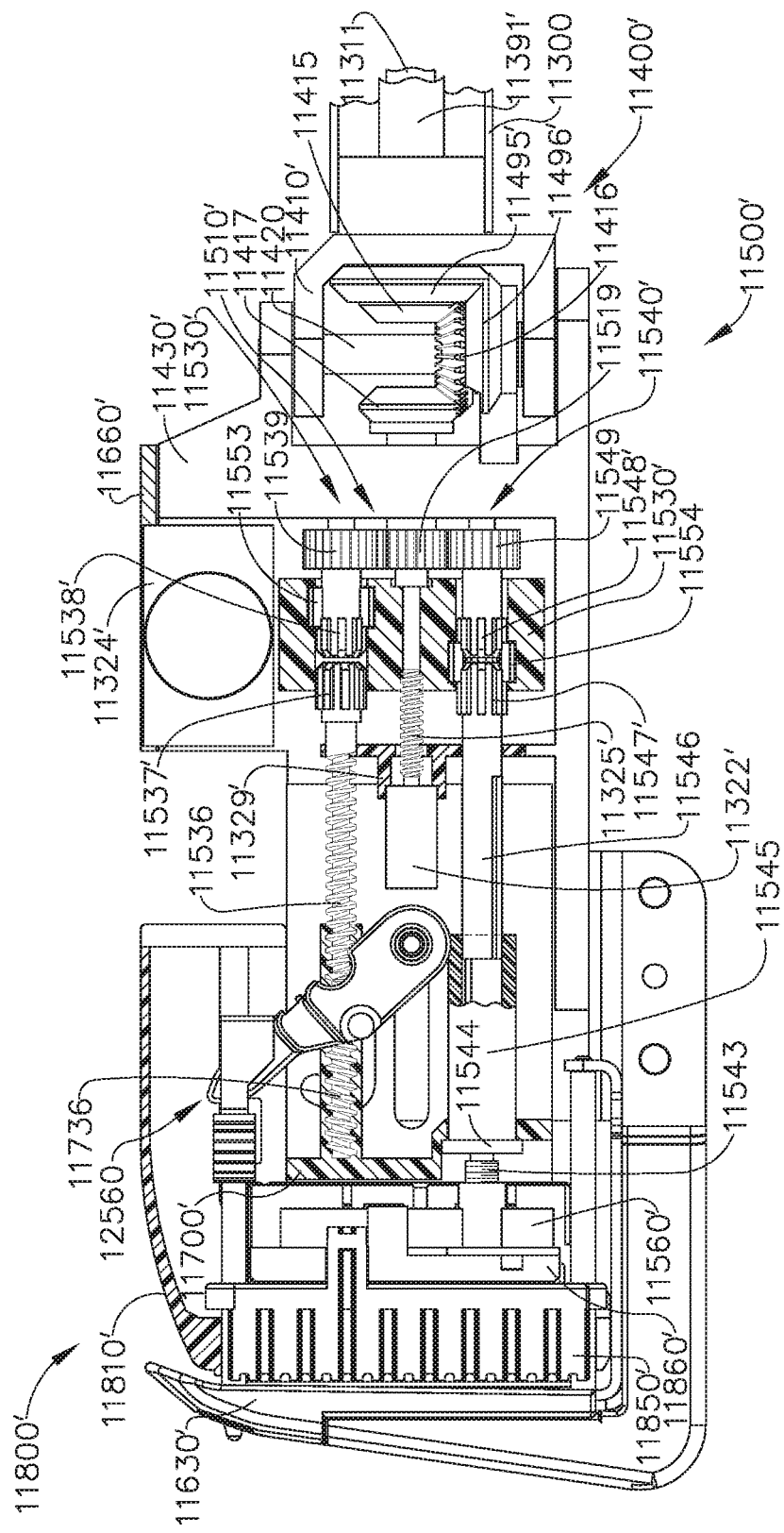
FIG. 30F is a partial cross-sectional view of the shaft assembly of FIG. 30A illustrated in a fired configuration.

A tool assembly 11100' is illustrated in FIGS. 30A-30G. The tool assembly 11100' is similar to the tool assembly 11100 in many respects. Referring primarily to FIG. 30A, the tool assembly 11100' comprises an attachment portion 11200, a shaft 11300 extending from the attachment portion 11200, an end effector 11500', and an articulation joint 11400' connecting the end effector 11500' to the shaft 11300. Referring primarily to FIG. 30B, the end effector 11500' comprises an end effector frame 11600', a staple cartridge 11800' which is insertable into and removable from the end effector frame 11600', and an anvil jaw 11630'. The staple cartridge 11800' comprises a cartridge body 11810' which is slidable relative to the anvil jaw 11630' between an open, unclamped position (FIG. 30D) and a closed, clamped position (FIG. 30E). As described in greater detail below, the tool assembly 11100' comprises a closure drive 11530' configured to move the cartridge body 11810' between its unclamped and clamped positions. Referring primarily to FIG. 30F, the tool assembly 11100' also comprises a firing drive 11540' configured to eject staples removably stored in the staple cartridge 11800' after the cartridge body 11810' has been moved into its clamped position, which is also described in greater detail below.

As described above, the articulation joint 11400 comprises a proximal yoke 11410 and a distal yoke 11430 which are rotatably connected by a pin 11420. The articulation joint 11400' comprises a similar arrangement including a proximal yoke 11410' and a distal yoke 11430'. Furthermore, as also described above, the articulation joint 11400 comprises bevel gears 11415, 11416, and 11417 which are operably intermeshed to transmit the rotation of a drive shaft 11311 to a drive system 11510. The articulation joint 11400' comprises a similar arrangement of bevel gears configured to transmit the rotary motion of shaft 11311 to a drive system 11510'. Moreover, the articulation joint 11400' comprises a second set of intermeshed bevel gears 11495' and 11496' nested with the bevel gears 11415, 11416, and 11417 which are configured to articulate the end effector 11500' relative to the shaft 11300. The bevel gear 11495' is rotatably supported by the proximal yoke 11410' and is operably engaged with an articulation input shaft 11391' (FIG. 30D) and the bevel gear 11496'. The bevel gear 11496' is fixedly mounted to the distal yoke 11430'. A portion of the bevel gear 11496' extends into a notch 11439' of the distal yoke 11430'. Rotation of the input shaft 11391' in a first direction rotates the end effector 11500' in a first direction and, similarly, rotation of the input shaft 11391' in a second, or opposite, direction rotates the end effector 11500' in a second, or opposite, direction. The tool assembly 11100' may be actuated by an electric motor of the instrument interface to which the assembly 11100' is attached to rotate the input shaft 11391'; however, the tool assembly 11100' can be actuated by any suitable means.

Similar to the drive system 11510 of the end effector 11500, the drive system 11510' of the end effector 11500' comprises an input gear 11519 which is operably engaged with the bevel gear 11417 and operably intermeshed with a drive gear 11539 of the closure drive 11530' and a drive gear 11549 of the firing drive 11540'. Also similar to the drive system 11510, the drive system 11510' comprises a shifter block, or assembly, 11550' movable between a first position (FIGS. 30D and 30E) and a second position (FIG. 30F) to shift the shaft assembly 11100' between a closing, or clamping, operating mode and a firing operating mode, respectively. The drive gear 11539 is mounted to a spline shaft 11538' and, when the shifter block 11550' is in its first position (FIGS. 30D and 30E), the spline shaft 11538' is rotatably coupled to a spline shaft 11537' of the closure drive 11530'. The spline shaft 11537' comprises a threaded distal end 11536 threadably engaged with a closure frame 11700' and, when the spline shaft 11537' is rotated by the spline shaft 11538' in a first direction, the closure frame 11700' and the cartridge body 11810' are displaced distally as illustrated in FIG. 30E to close the end effector 11500'. Notably, the rotation of the drive gear 11549 of the firing drive 11540' is not transmitted through the shifter block 11550' to the distal portion of the firing drive 11540' when the shifter block 11550' is in its first position. As a result, the closure drive 11530' operates independently of the firing drive 11540' and, moreover, the firing drive 11540' cannot be operated until the shifter block 11550' is shifted into its second position.

Further to the above, the drive gear 11549 is mounted to a spline shaft 11548' and, when the shifter block 11550' is in its second position (FIG. 30F), the shifter block 11550' rotatably couples the spline shaft 11548' to a spline shaft 11547' of the firing drive 11540'. The spline shaft 11547' comprises a distal end 11546 keyed to a rotatable drive shaft 11545 of the firing drive 11540' such that the spline shaft 11547' and the drive shaft 11545 rotate together. The drive shaft 11545 includes a threaded distal end 11543 threadably engaged with a firing block 11560' wherein, when the spline shaft 11547' is rotated by the spline shaft 11548' in a first direction, the firing block 11560' is displaced distally to fire the staples from the staple cartridge 11800' and cut the tissue captured between the staple cartridge body 11810' and the anvil jaw 11630' Similar to the firing drive 11540, described above, the firing drive 11540' comprises a staple driver 11850', a knife block 11860', and a knife 11840' which are pushed distally by the firing block 11560' during a firing stroke of the firing drive 11540'. Notably, the rotation of the drive gear 11539 of the closure drive 11530' is not transmitted through the shifter block 11550' to the distal portion of the closure drive 11530' when the shifter block 11550' is in its second position. As a result, the firing drive 11540' operates independently of the closure drive 11530'.

Upon comparing FIGS. 30D and 30E, further to the above, the reader should appreciate that the firing drive

11540' extends, or telescopes, when the closure drive 11530' is operated to close the end effector 11550'. As a result, the distal end 11546 of the spline shaft 11547' remains rotatably engaged with the drive shaft 11545. Referring primarily to FIG. 30C, the closure frame 11700' comprises a hook 11744' configured to abut a collar 11544 defined on the drive shaft 11545 and pull the drive shaft 11545 distally when the closure frame 11700' is driven distally to close the end effector 11550'. When the closure drive 11530' is operated to re-open the end effector 11500', as described below, the drive shaft 11545 is pushed proximally to collapse the firing drive 11540'.

After the firing stroke of the firing drive 11540', the spline shaft 11548' is rotated in a second, or opposite, direction to pull the firing block 11560', the knife block 11860', and the knife 11840' proximally. Notably, the staple driver 11850' is not retracted with the firing block 11560'; however, the staple driver 11850' could be retracted in other embodiments. Once the knife 11840' has been retracted sufficiently below the deck of the cartridge body 11810', the shifter block 11550' can be shifted back into its first position to operably decouple the firing drive 11540' from the drive shaft 11311 and, also, operably recouple the closure drive 11530' with the drive shaft 11311. At such point, the spline shaft 11538' can be rotated in a second, or opposite, direction to pull the cartridge body 11810' and the closure frame 11700' proximally and re-open the end effector 11500'.

The end effector 11500' comprises a motor 11322' configured to move the shifter block 11550' between its first and second positions, as described above. The motor 11322' comprises a housing positioned within a motor support 11329' mounted in the closure frame 11700'. The housing of the motor 11322' is fixedly mounted within the motor support 11329' such that the housing does not move relative to the motor support 11329'. The motor 11322' further comprises a rotatable output shaft 11325' which is threadably engaged with a threaded aperture 11555 defined in the shifter block 11550'. When the motor 11322' is operated in a first direction, the threaded output shaft 11325' moves the shifter block 11550' into its first position. When the motor 11322' is operated in a second direction, the threaded output shaft 11325' moves the shifter block 11550' into its second position.

Figure 30G:
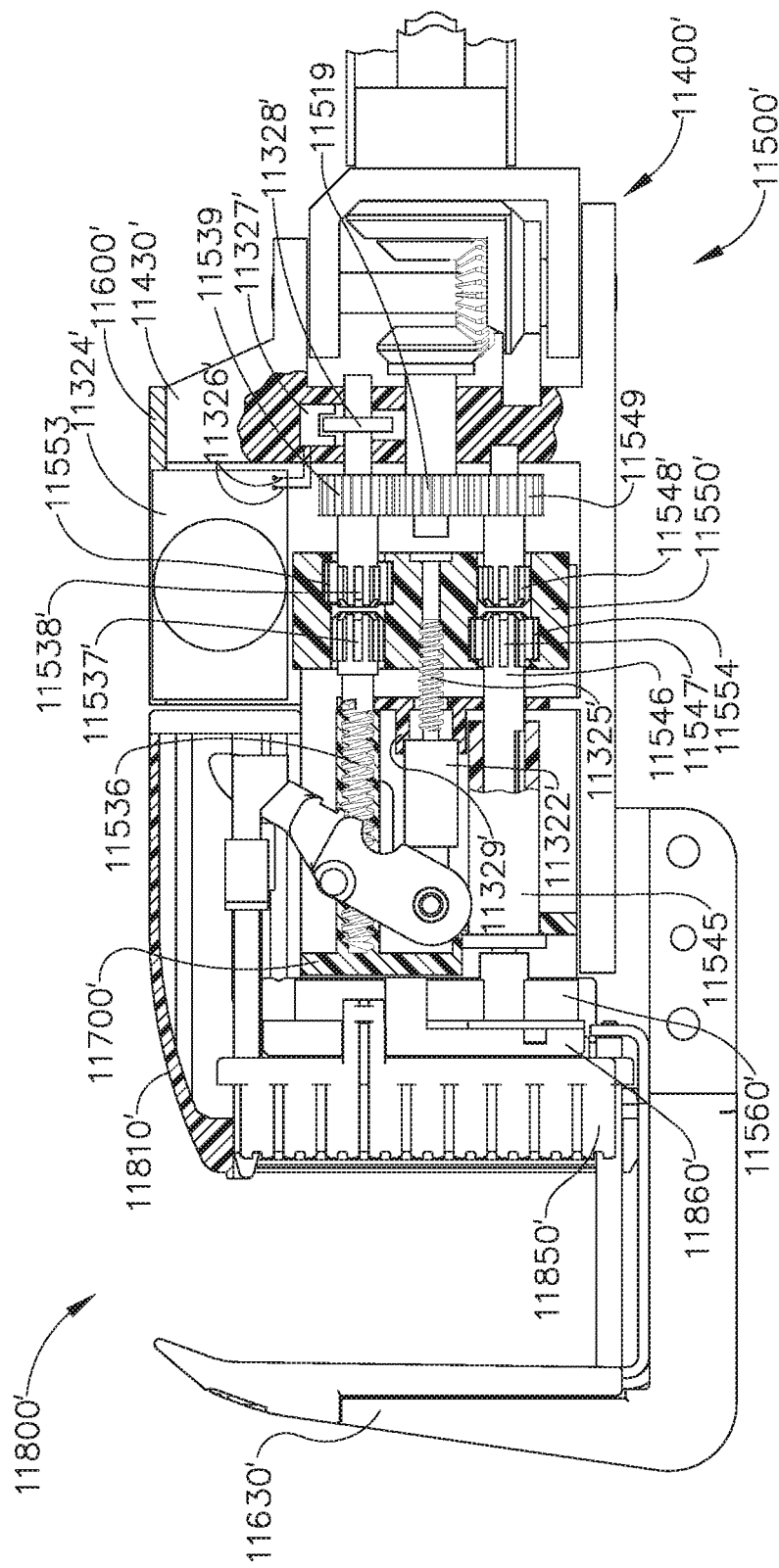
FIG. 30G is a partial cross-sectional view of the shaft assembly of FIG. 30A illustrating a power harvesting system in accordance with at least one embodiment.

Referring primarily to FIG. 30G, a battery and controller system 11324' is configured to communicate with and power the motor 11322'. When a user and/or computer of the surgical instrument interface to which the instrument 11100' is attached wants to shift the shifting block 11550', a signal is wirelessly sent to the battery and controller system 11324, for example. In other instances, the signal can be communicated to the system 11324' via conductor. This signal is then communicated to the motor 11322' to activate the motor 11322'. In at least one alternative embodiment, a solenoid can be utilized to shift the shifter block 11550'.

As the reader should appreciate, it can be important to prolong the battery life for such a system. The instrument 11100' is configured to harvest kinetic energy during various stages of operation. The instrument 11100' comprises an energy-harvesting system that can convert the movement of the drive system 11510' to electrical energy and story that energy in the battery. The energy-harvesting system comprises a coil 11327' housed with the distal yoke 11430' and positioned near a proximal portion of the closure drive 11530'. The coil 11327' is electrically coupled to the battery and controller system 11324' via conductors 11326'. A shaft extending proximally from the drive gear 11539 comprises a magnetic disc 11328' mounted thereon. As the closure drive 11530' is rotated, the magnetic disc 11328' rotates in close proximity with the coil 11327' to generate a current within the energy-harvesting system.

The energy-harvesting system can act as a generator when the shifter block 11550' is in a neutral position (FIG. 30G). In this neutral position, the splined coupling 11554 is meshed only with the spline shaft 11547' and, similarly, the splined coupling 11553 is meshed only with the spline shaft 11537'. Thus, when the drive input 11519 is rotated, the energy-harvesting system is configured to generate energy to recharge the battery though not performing any instrument functions. Notably, the energy-harvesting system can also act as a generator when the shifter block 11550' is in its first position and its second position. While clamping and/or firing, in such instances, the magnetic disc 11328' is rotated by the input 11539 regardless of which instrument function is being actuated. The energy harvested may be supplied to the battery and/or the motor 11322' during the clamping and/or firing operations of the end effector 11500'.

Figure 31:
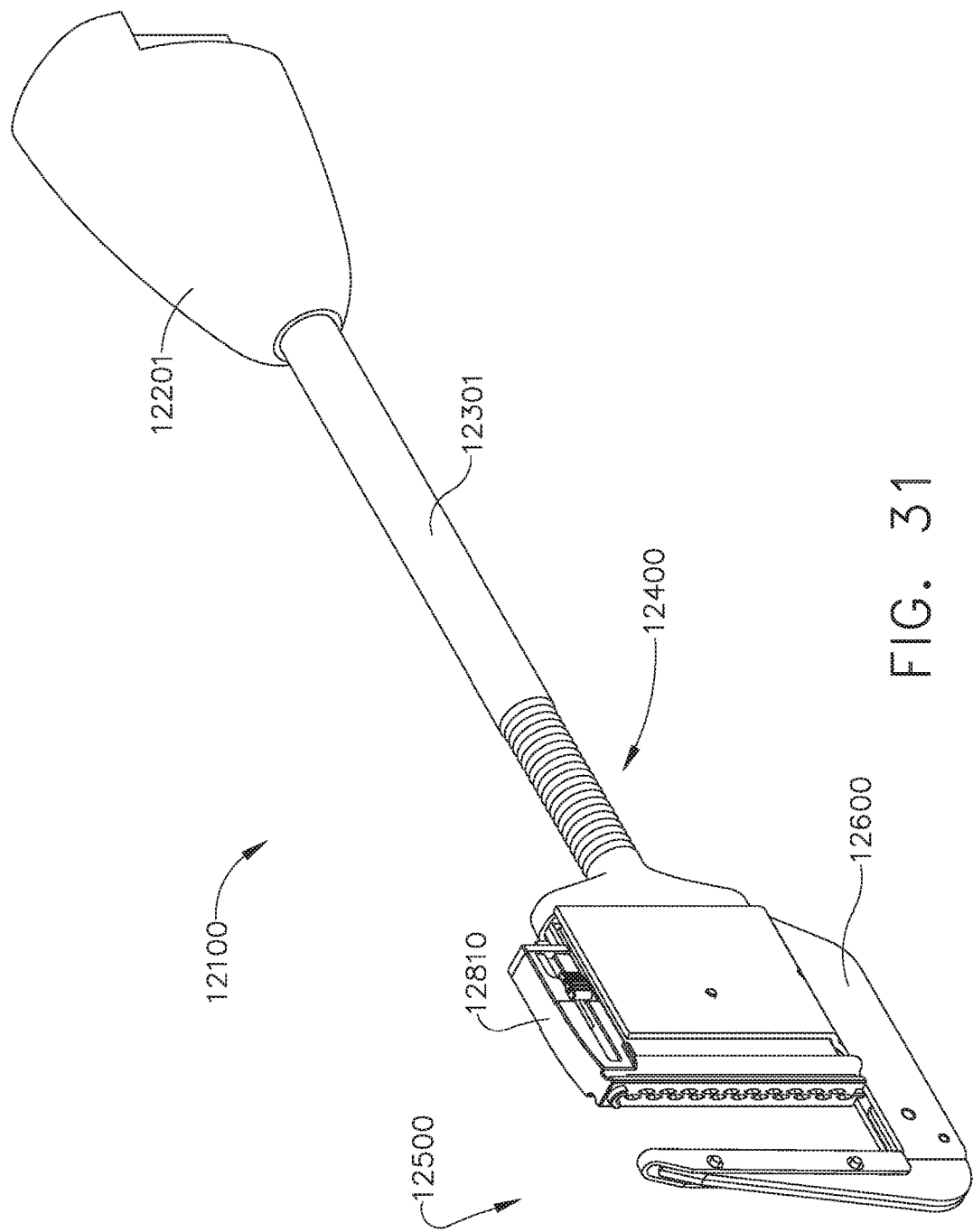
FIG. 31 is a perspective view of a surgical stapling attachment, or instrument, comprising an attachment portion, a shaft assembly, an articulation joint, and an end effector assembly.
Figure 32:
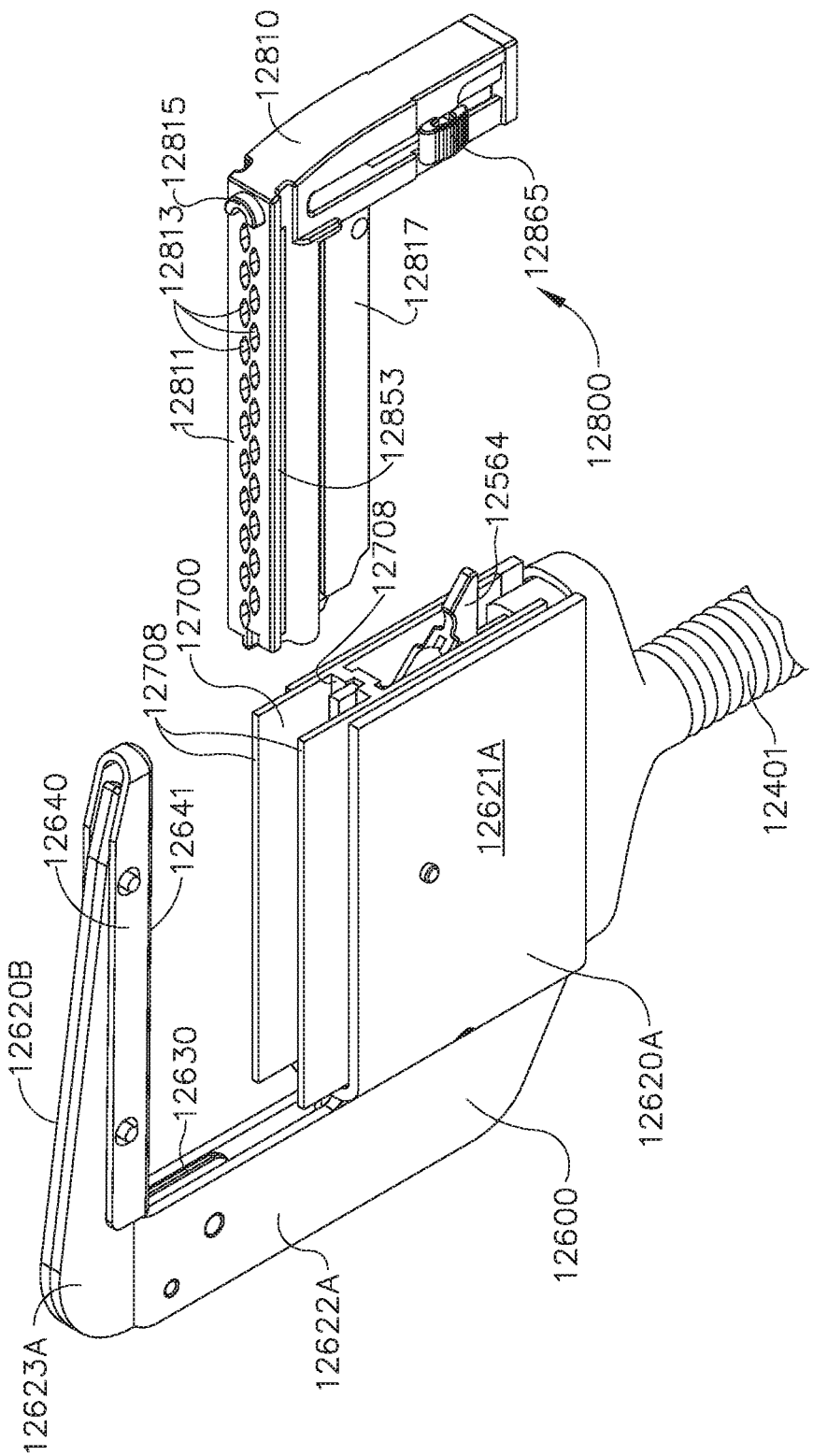
FIG. 32 is a partial perspective view of the articulation joint and the end effector assembly of the instrument of FIG. 31, wherein the end effector assembly comprises an end effector frame, a closure frame, and a staple cartridge assembly.
Figure 33:
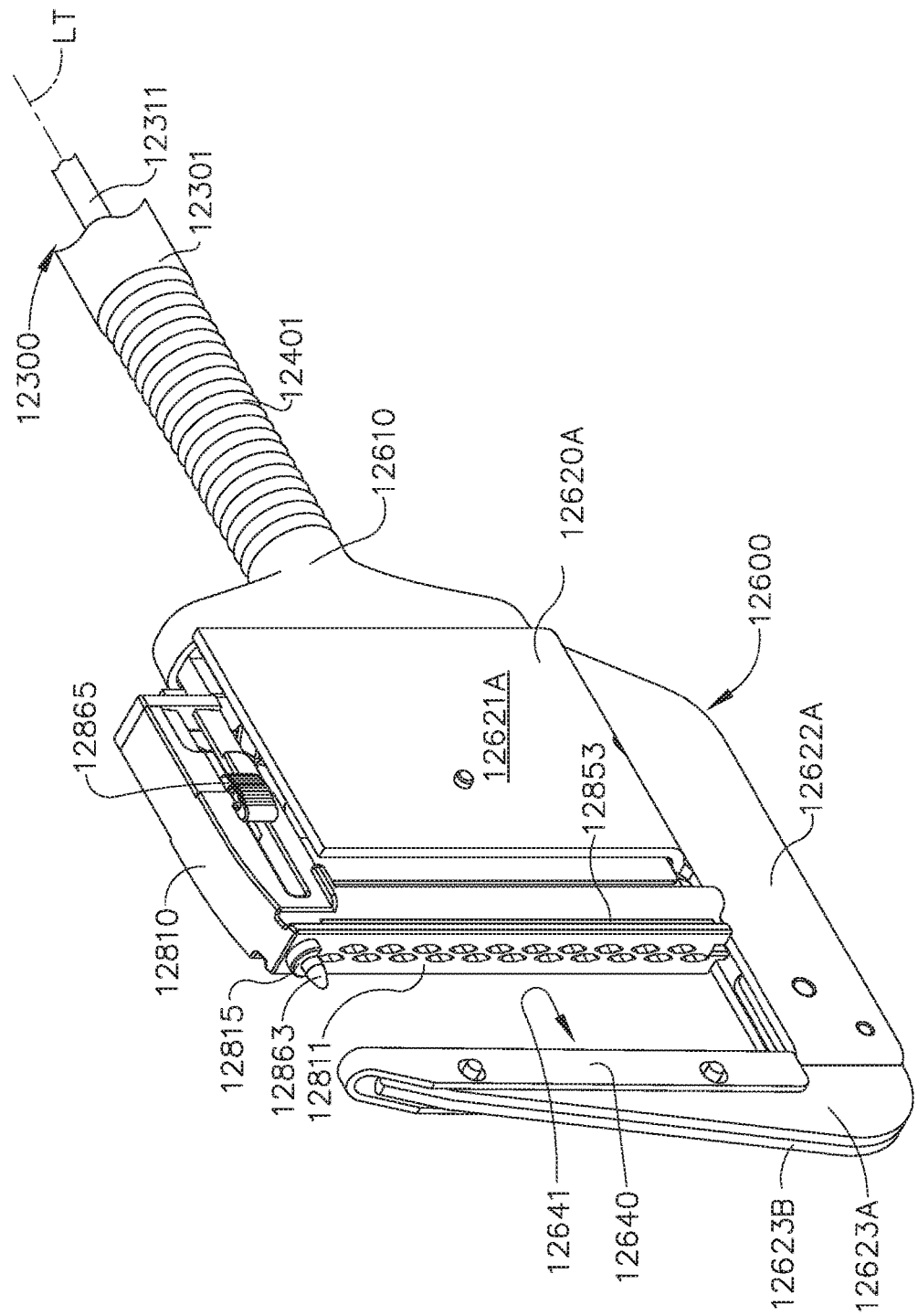
FIG. 33 is a partial perspective view of the shaft assembly, the articulation joint, and the end effector assembly of the instrument of FIG. 31 illustrating the staple cartridge assembly installed within the end effector assembly.
Figure 34:
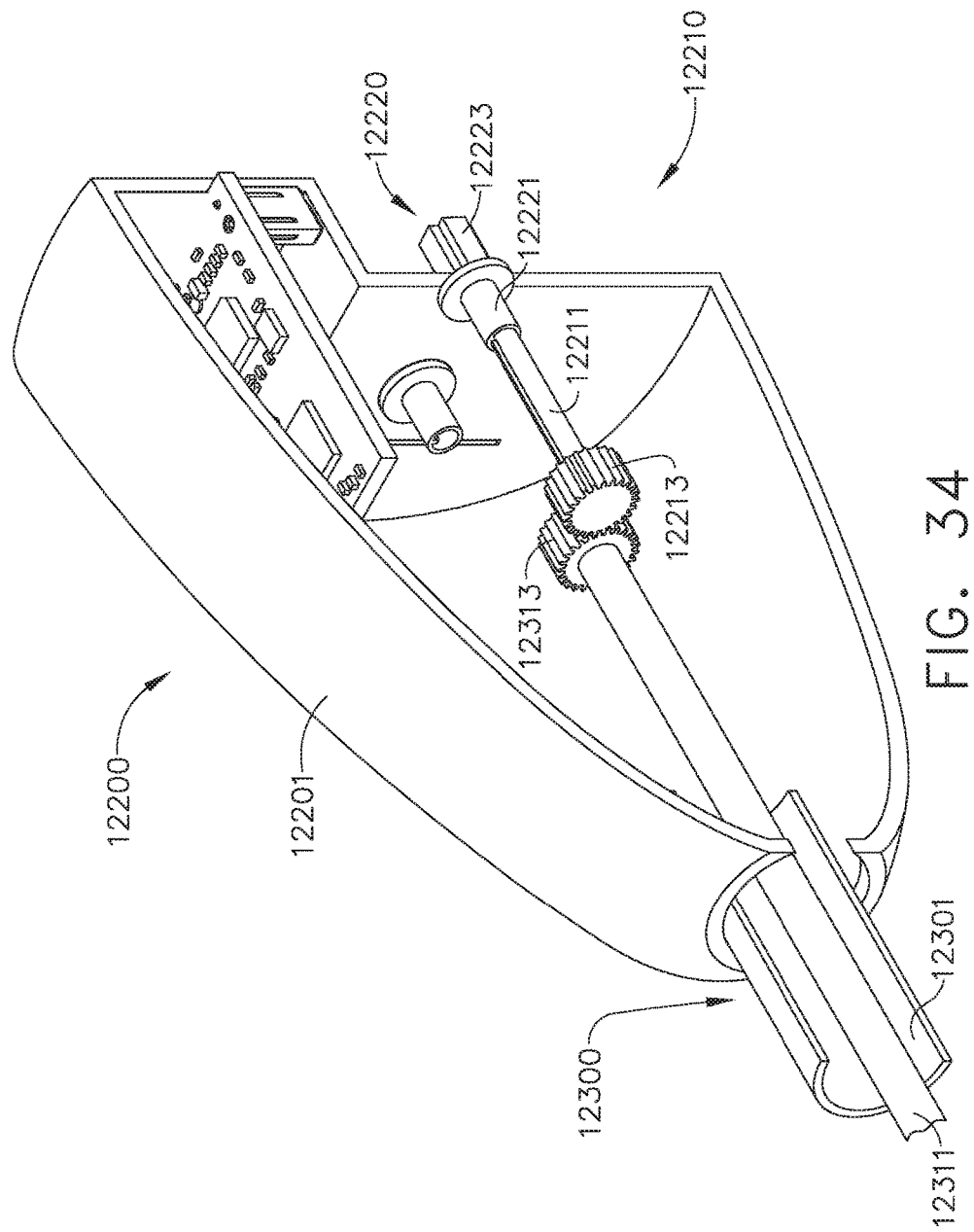
FIG. 34 is a cross-sectional perspective view of the attachment portion and the shaft assembly of the instrument of FIG. 31, wherein the attachment portion comprises an attachment interface and a transmission configured to transmit rotary control motions received by an instrument interface to a main drive shaft of the shaft assembly.
Figure 35:
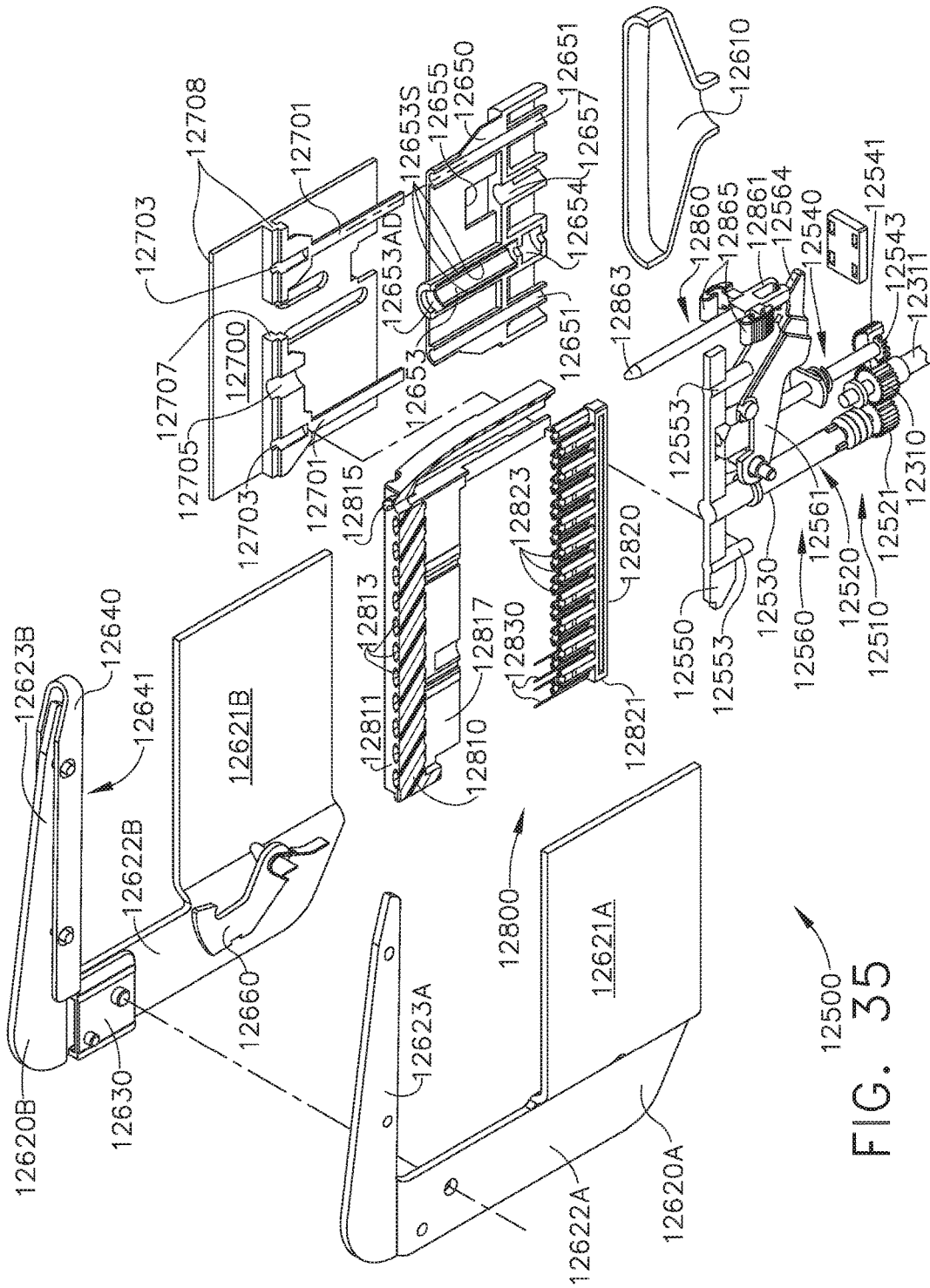
FIG. 35 is an exploded view of the end effector assembly and the shaft assembly of the instrument of FIG. 31.

A surgical stapling attachment, or tool assembly, 12100 is depicted in FIGS. 31-50. The tool assembly, or instrument, 12100 is configured to capture, clamp, and staple tissue during a surgical procedure. Referring primarily to FIGS. 31-33, the tool assembly 12100 comprises an attachment portion 12200, a shaft assembly 12300, an articulation joint 12400, and an end effector assembly 12500. The tool assembly 12100 is configured to be attached to an instrument interface by way of the attachment portion 12200. The instrument interface can comprise a surgical instrument handle such as those disclosed herein. Other embodiments are envisioned where the tool assembly 12100 is not readily attachable to and detachable from an instrument interface and, instead, is part of a unitary instrument. The attachment portion 12200 is configured to receive rotary control motions from the instrument interface to which the tool assembly 12100 is attached and transfer the rotary control motions to the shaft assembly 12300. The shaft assembly 12300 communicates these rotary control motions through the articulation joint 12400 and to the end effector assembly 12500.

The attachment portion 12200 comprises a transmission system 12210. Shown in FIG. 34, the transmission system 12210, housed within an attachment portion housing 12201, comprises an attachment interface 12220 comprising a coupler portion 12223. The coupler portion 12223 is configured to be operably coupled to an instrument interface. The transmission further comprises a housing bearing 12221, an input shaft 12211 coupled to the coupler portion 12223, and an input drive gear 12213 attached to the input shaft 12211. Upon actuation of the coupler portion 12223 by the instrument interface, the input drive gear 12213 drives a main drive shaft gear 12313 to drive a main drive shaft 12311 attached to the main drive shaft gear 12313.

Referring primarily to FIGS. 35-38, the end effector assembly 12500 comprises a drive system 12510, an end effector frame 12600, a closure frame 12700 moveable relative to the end effector frame 12600, and a replaceable staple cartridge assembly 12800 configured to be installed into the end effector frame 12600. The drive system 12510 comprises a single rotary input which is configured to receive the rotary control motions from the shaft assembly 12300 and drive a main drive 12520 to clamp tissue with the tool assembly 12100. The main drive 12520 is configured to interact with the end effector assembly 12500 to move the closure frame 12700 and, as a result, the staple cartridge assembly 12800 distally. Distal movement of the closure frame 12700 also results in an automatic deployment of a tissue-retention pin 12860 of the staple cartridge assembly 12800 to capture tissue. The main drive 12520 is further configured to fire the tool assembly 12100 once the tool assembly 12100 attains a fully clamped configuration. Firing the tool assembly 12100 includes deploying a plurality of staples from the staple cartridge assembly 12800 to staple tissue captured and clamped by the tool assembly 12100.

The end effector frame 12600 houses the various components of the end effector assembly 12500. The end effector frame 12600 houses the closure frame 12700 and the staple cartridge assembly 12800. Relative movement of the closure frame 12700 and the staple cartridge assembly 12800 within the end effector frame 12600 is permitted. The end effector frame 12600 comprises a proximal neck portion 12610, a first side frame 12620A, and a second side frame 12620B. The proximal neck portion 12610 is attached, or coupled, to the articulation joint 12400. The articulation joint 12400 comprises a flexible neck 12401 configured to permit a user of the tool assembly 12100 to passively articulate the end effector assembly 12500 relative to a shaft housing 12301. Embodiments are envisioned where the tool assembly 12100 does not comprise an articulation joint and the proximal neck portion 12610 is attached directly to the shaft housing 12301 of the shaft assembly 12300.

The proximal neck portion 12610 and the first and second side frames 12620A, 12620B house certain components of the end effector assembly 12500 including the drive system 12510. The first and second side frames 12620A, 12620B each comprise a proximal jaw portion 12621A, 12621B, an intermediate jaw portion 12622A, 12622B, and a distal jaw portion 12623A, 12623B, respectively. The distal jaw portions 12623A, 12623B are held together at least by an anvil 12640 having a staple forming surface 12641. Bolts, screws, and/or rivet configurations, for example, can be used to attach the side frames 12620A, 12620B to each other. The end effector frame 12600 further comprises a spacer member 12630 positioned between the intermediate jaw portions 12622A, 12622B to provide a gap for a portion or portions of the staple cartridge assembly 12800 to slide between the intermediate portions 12622A, 12622B of the side frames 12620A, 12620B upon moving relative to the end effector frame 12600.

The closure frame 12700 is configured to push the staple cartridge assembly 12800 distally toward the anvil 12640 upon actuation of the main drive 12510. The closure frame 12700 comprises cartridge body driving surfaces 12708 to contact and drive a staple cartridge body 12810 of the staple cartridge assembly 12800. The staple cartridge body 12810 comprises a deck 12811, a plurality of staple cavities 12813, and a closure stop 12815. The staple cartridge assembly 12800 also comprises a plurality staples 12830 removably stored within the staple cavities 12813. The plurality of staples 12830 are configured to be formed against the staple forming surface 12641. The tool assembly 12100 is assumed to have reached a fully-clamped configuration when the closure stop 12815 abuts the staple forming surface 12641 and/or is seated within a recess defined in the anvil 12640. Embodiments are also envisioned where the closure stop 12815 never reaches the anvil 12640 or the staple forming surface 12641 and, instead, is positioned adjacent to the staple forming surface 12641 when the staple cartridge assembly 12800 reaches its fully clamped position. Controlling the distance between the deck 12811 and the staple forming surface 12641 in fully-clamped configuration can be accomplished using the drive system 12510 discussed in greater detailed below.

Figure 36:
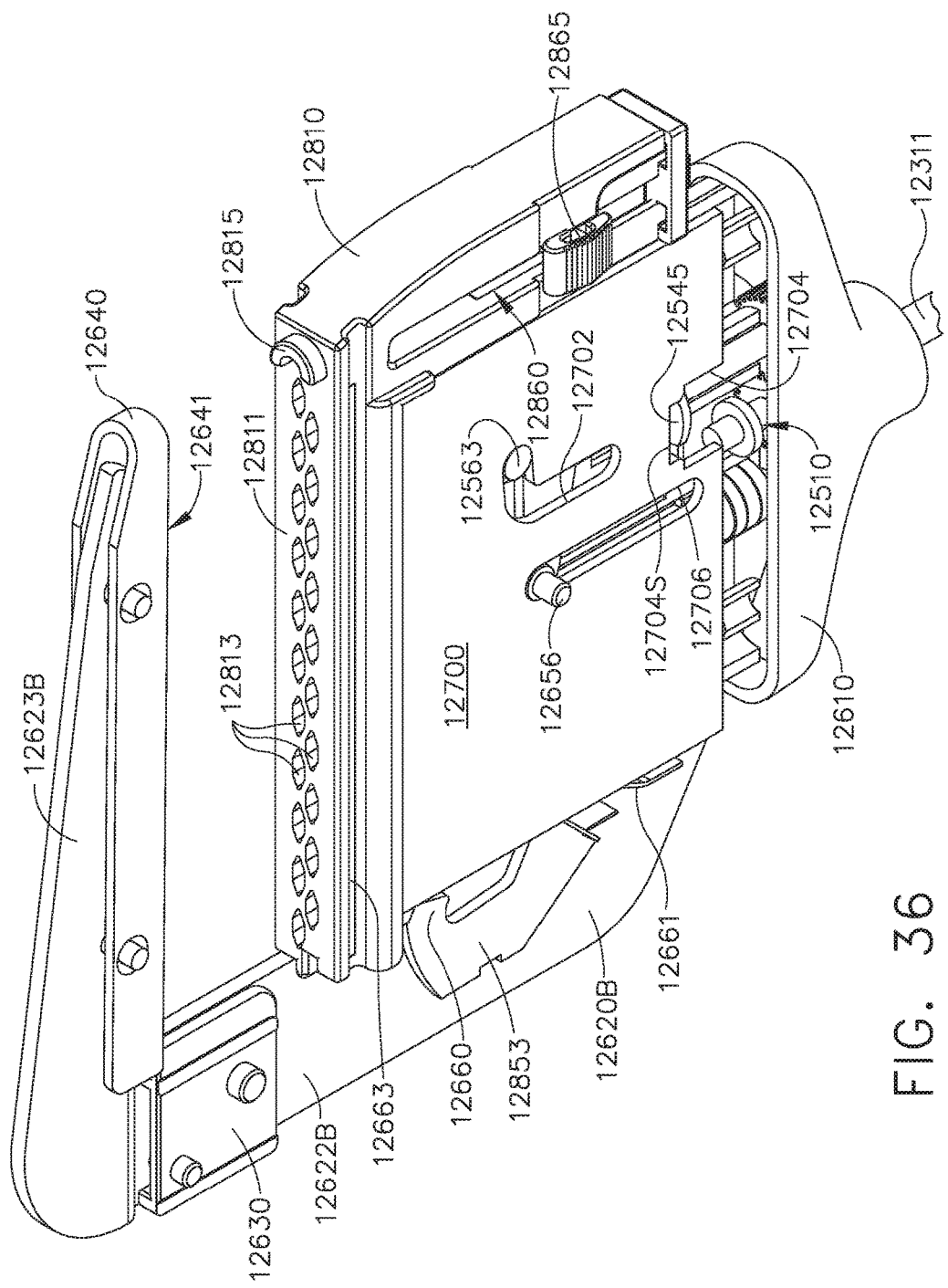
FIG. 36 is a partial perspective view of the end effector assembly of the instrument of FIG. 31.
Figure 37:
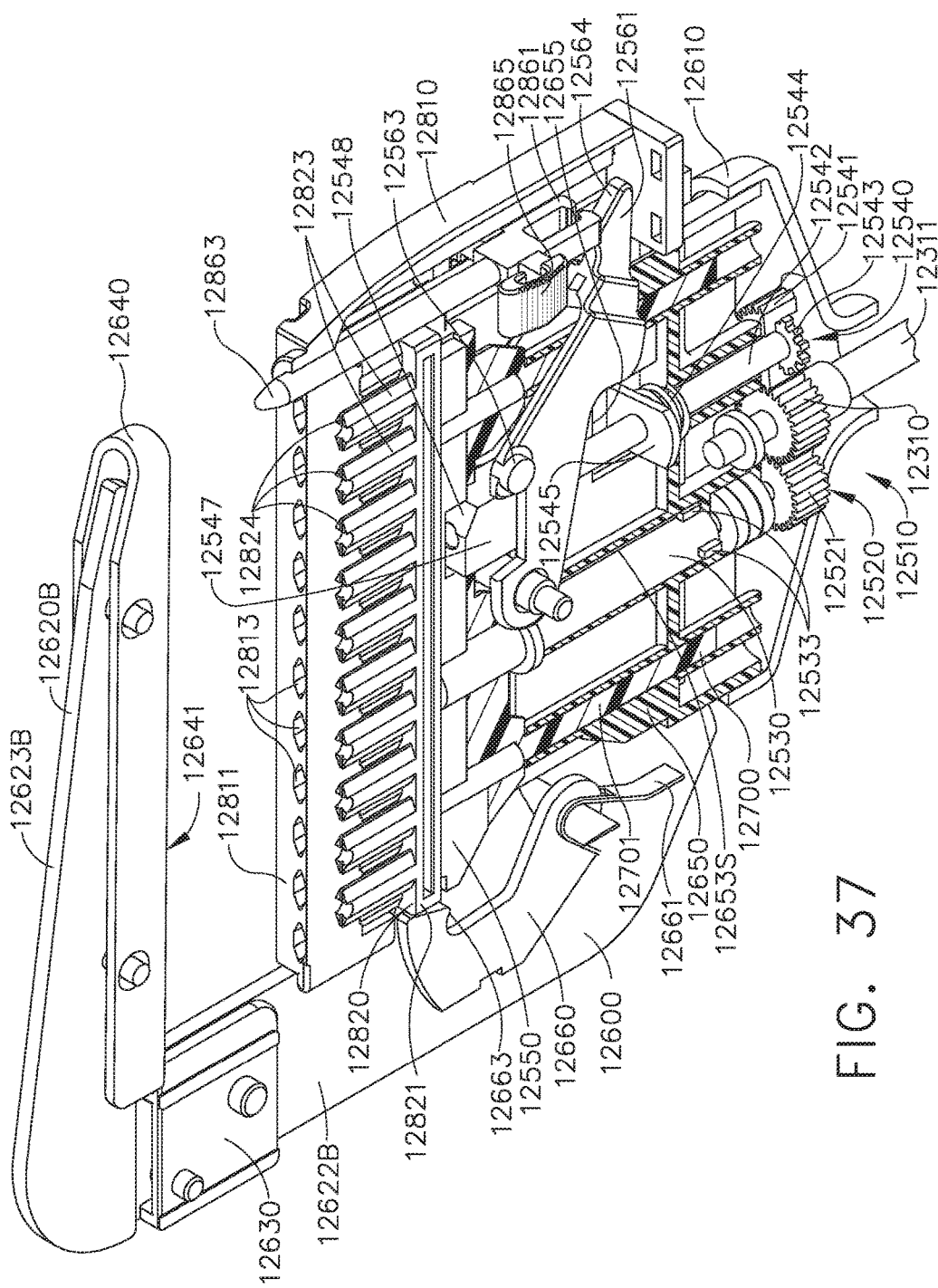
FIG. 37 is a partial perspective view of the end effector assembly and the shaft assembly of the instrument of FIG. 31, wherein portions of the end effector assembly are fully or partially removed to expose a drive system, multiple lock arrangements, and a tissue-retention pin mechanism of the end effector assembly.
Figure 38:
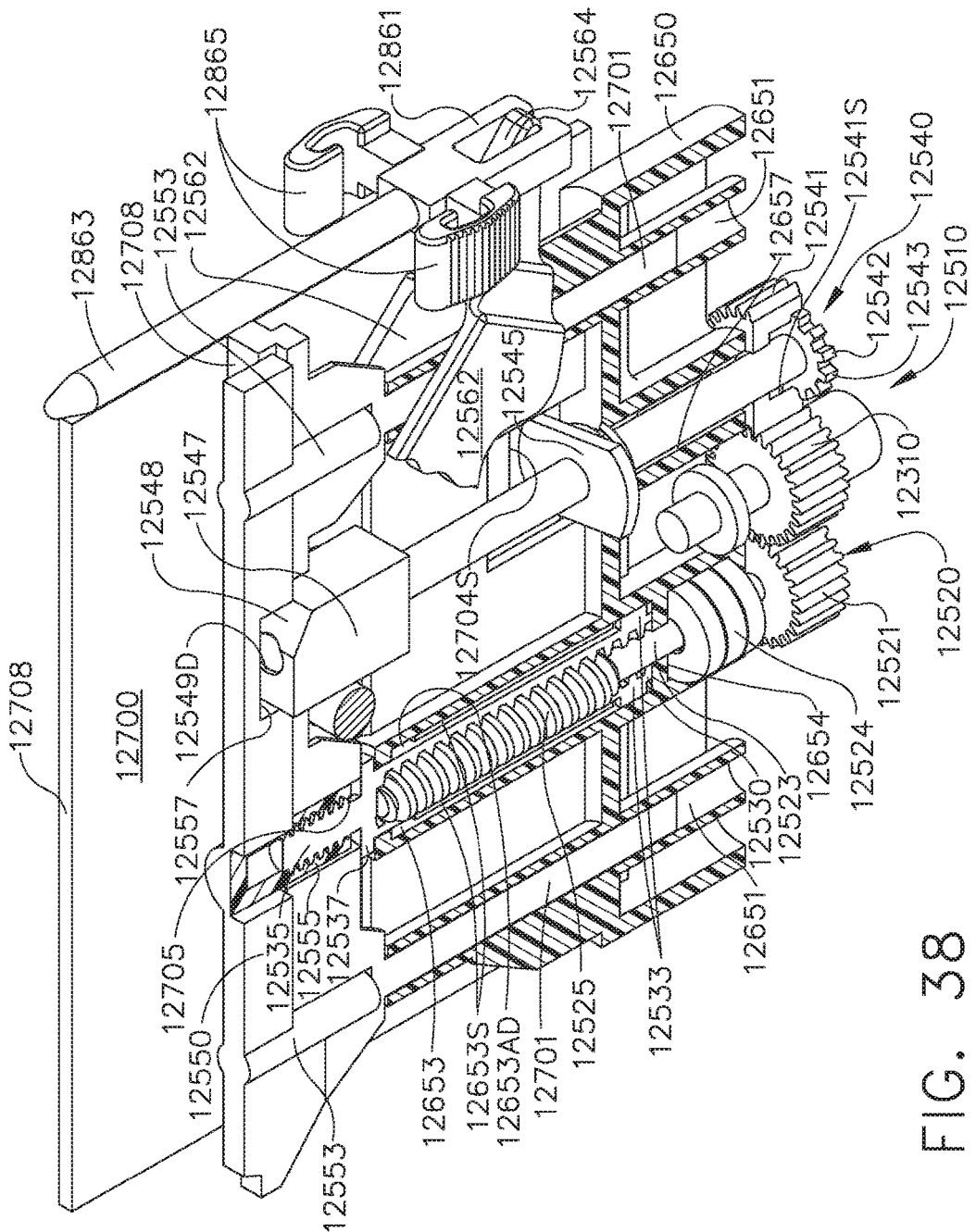
FIG. 38 is a partial perspective view of portions of the closure frame and the end effector frame, wherein portions have been removed to expose the drive system, a lock arrangement, and the tissue-retention pin mechanism of the instrument of FIG. 31.
Figure 39:
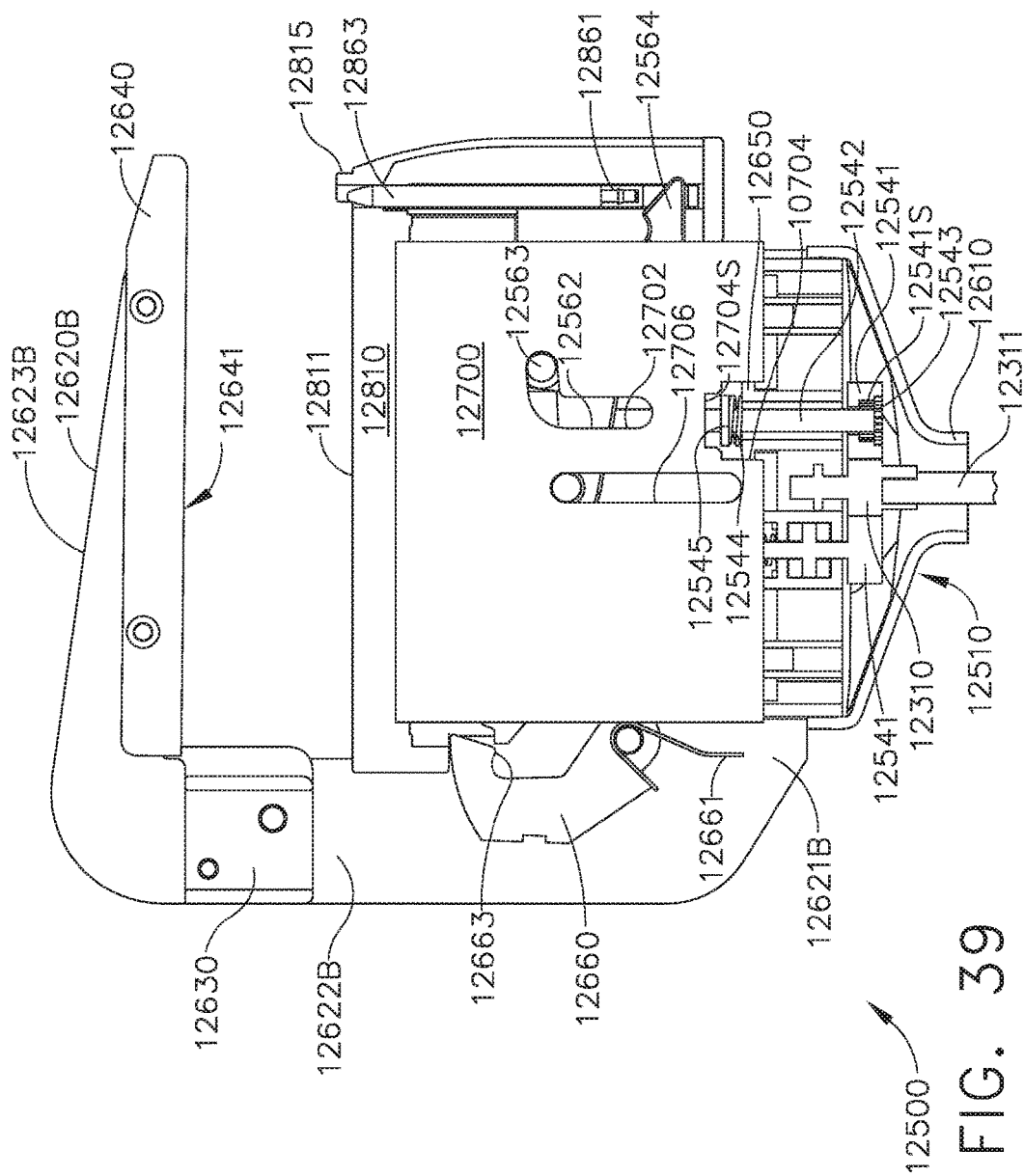
FIG. 39 is a partial, cross-sectional elevational view of the end effector assembly of the instrument of FIG. 31 illustrated in an uncaptured, unclamped, unfired, unlocked configuration.
Figure 40:
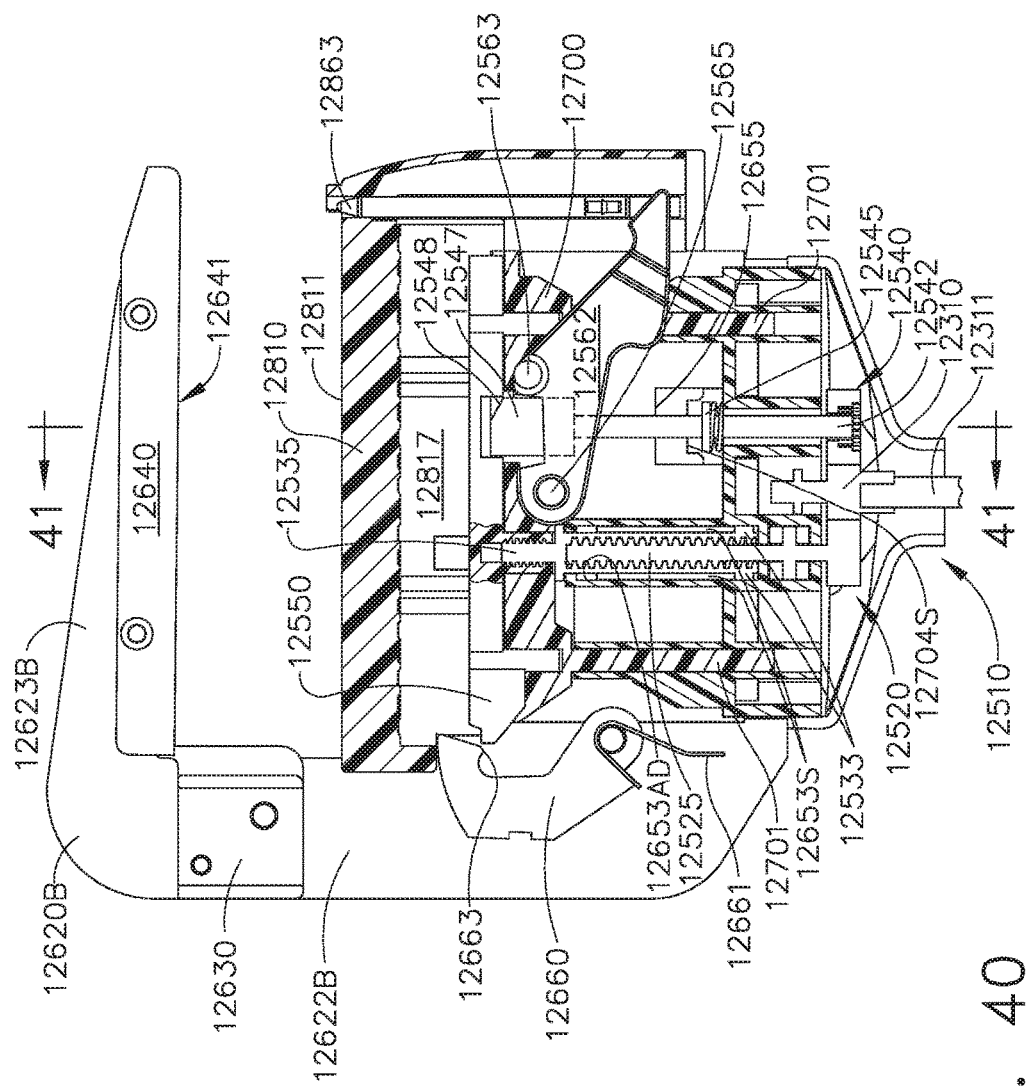
FIG. 40 is a partial, cross-sectional elevational view of the end effector assembly of the instrument of FIG. 31 illustrated in the uncaptured, unclamped, unfired, unlocked configuration of FIG. 39.

Referring to FIGS. 36-38, the end effector assembly 12500 is illustrated in an unlocked configuration prior to actuation of the drive system 12510. The end effector assembly 12500 is configured to utilize the rotary motions provided by the main drive shaft 12311 to capture, clamp, and staple tissue with the tool assembly 12100. To capture tissue with the tool assembly 12100, the closure frame 12700 is advanced, or actuated, to actuate the pin actuation mechanism 12560. Actuation of the pin actuation mechanism 12560 deploys a tissue-retention pin 12860 of the staple cartridge assembly 12800. The pin actuation mechanism 12560 comprises a pin lever 12561 and a ground pin 12565 extending fixedly from the end effector frame 12600. The ground pin 12565 defines a retaining pin axis about which the pin lever 12561 rotates. The closure frame 12700 comprises a pair of ground pin slots 12706 defined on opposite sides thereof to provide clearance for the ground pin 12565 so that the closure frame 12700 can move relative to the ground pin 12565. The pin lever 12561 comprises a pair of lever arms 12562 comprising a pair of actuation projections, or tines, 12563 received within a pair of cam slots 12702 defined in the closure frame 12700. The cam slots 12702 are configured to displace the actuation projections 12563 distally and laterally as the closure frame 12700 moves longitudinally within the end effector frame 12600 to rotate the pin actuation mechanism 12560 about the retaining pin axis. The pin lever 12561 further comprises a lever tip 12564 extending from the lever arms 12562. The lever tip 12564 extends into a coupler portion 12861 of the tissue-retention pin 12860 to couple the pin actuation mechanism 12560 to the pin 12860. The tissue-retention pin 12860 further comprises a pin shaft, or rod, 12863 and manual override knobs 12865. When the pin actuation mechanism 12560 is actuated by the closure frame 12700, the lever tip 12564 advances the pin shaft 12863 toward the anvil 12640.

The manual override knobs 12865 of the pin 12860 are configured to permit a user of the tool assembly 12100 to manually retract the pin shaft 12863 back into the staple cartridge assembly 12800 in the event that the drive system 12510 jams or there is a loss of power, for example. The actuation projections 12563 may be comprised of a more fragile material and/or geometry than the lever arms 12562 in order to provide the user with the ability to shear the projections 12563 from the lever arms 12562 and therefore allow the pin lever 12561 to freely rotate about the ground pin 12565. As a result of this free rotation, the coupler portion 12861 is permitted to be moved proximally relative to the staple cartridge body 12810 with out much, if any, resistance, therefore permitting the pin shaft 12863 to be retracted manually In addition to or in lieu of the above, the actuation projections 12563 may comprise of a substantially thin configuration, or profile, which permits the lever arms 12562 to collapse, or bend, inward when pulling the manual override knobs 12865 proximally thus urging the actuation projections 12563 inward and out of the cam slots 12702 to provide the free rotation discussed above.

When an unspent, or unfired, cartridge is installed within the end effector assembly 12500 the main drive 12520 can be actuated. As discussed in greater detail below, the end effector assembly 12500 comprises one or more lockouts that are defeated when an unspent staple cartridge is inserted into the end effector assembly 12500. In any event, the main drive 12520 is responsible for moving the closure frame 12700 and the staple cartridge assembly 12800 toward the anvil 12640 to capture and clamp tissue with the end effector assembly 12500 as well as the firing the tool assembly 12100 to staple tissue. The main drive 12520 comprises an input drive gear 12521 drivably intermeshed with a main input gear 12310. The input drive gear 12521 is mounted to a main drive shaft 12523 comprising a drive screw portion 12525. The main drive 12520 also comprises a thrust bearing configuration 12524 configured to support the shaft 12523. The drive screw portion 12525 is threadably received within a threaded aperture 12531 of a closure nut tube, or closure drive, 12530. The closure nut tube 12530 is moveably supported within a frame bore 12653 of the interior frame structure 12650 and comprises a plurality of tabs 12533 received within a plurality of longitudinally extending slots 12653 S within the frame bore 12653 which prevent the closure nut tube 12530 from rotating with the drive screw portion 12525. Though the illustrated embodiment contains four tabs 12533, only one tab 12533 and corresponding slot 12653 S may be sufficient. When the drive screw portion 12525 is rotated in a first direction, the closure nut tube 12530 moves, or slides, longitudinally within the frame bore 12653 but does not rotate within the frame bore 12653. As a result of this distal movement, a ledge 12537 of the closure nut tube 12530 pushes on the closure frame 12700 causing the closure frame 12700 to move distally. When the drive screw portion 12525 is rotated in a second direction, the drive screw portion 12525 pulls the closure nut tube 12530 proximally.

When the closure tube 12530 reaches a distal-most position associated with the fully clamped position of the staple cartridge 12800, the tabs 12533 enter a distal annular recess 12653AD defined in the closure tube 12530. The annular recess 12653AD provides clearance for the tabs 12533. When the tabs 12533 are aligned with the annular recess 12653AD, the tabs 12533 no longer prevent the rotation of the closure nut tube 12530. As a result, rotation of the drive screw portion 12525 when the closure nut tube 12530 has reached this distal-most position results in rotation of both the closure nut tube 12530 and the drive screw portion 12525 simultaneously.

At this stage, further actuation of the drive system 12510 in the same direction results in firing of the tool assembly 12100. In various instances, the drive system 12510 may make this transition from clamping to firing continuously without interruption. In various other instances, the tool assembly 12100 may be configured to interrupt actuation of the drive system 12510 when the closure nut tube 12530 reaches its distal-most position. In either event, the tool assembly 12100 is configured to be fired after the drive system 12510 has moved the cartridge assembly 12800 into the fully clamped position. The closure nut tube 12530 further comprises a firing screw portion, or firing drive, 12535 threadably received by a firing nut portion 12555 of the driver bar 12550. Since the closure nut tube 12530 is now free to rotate, the firing screw portion 12535 will now rotate as the drive screw 12525 rotates and drive the driver bar 12550 distally. The driver bar 12550 pushes a staple cartridge driver 12820 distally thus ejecting the staples 12830 from the staple cartridge assembly 12800. The staple driver 12820 supports the plurality of staples 12830 with a plurality of staple drivers 12823 each having a support cradle 12824. The staple driver 12820 moves distally within the staple cartridge body 12810 toward the anvil 12640 to eject the staples 12830 out of the staple cavities 12813 toward the stapling forming surface 12641. Although only two rows of staples are illustrated, any suitable number of rows may be employed. The driver bar 12550 is guided by the closure frame 12700 using guide pins 12553 and corresponding guide pin slots 12703.

As discussed above, the main drive 12520 is actuated to capture and clamp tissue within the end effector assembly 12500 by advancing the closure frame 12700 and then staple tissue by advancing the driver bar 12550 distally. However, as mentioned above, the main drive 12520 can not be actuated until an unspent staple cartridge assembly is installed within the end effector assembly 12500. A lockout drive 12540 is provided to provide this type of locking arrangement. As discussed in greater detail below, the lockout drive 12540 utilizes the same input as the main drive 12520, and, if the lockout drive 12540 is in a locked configuration, the main drive 12520 is prevented from being driven. If the lockout drive 12540 is in an unlocked configuration, the main drive 12520 is permitted to be driven.

Figure 41:
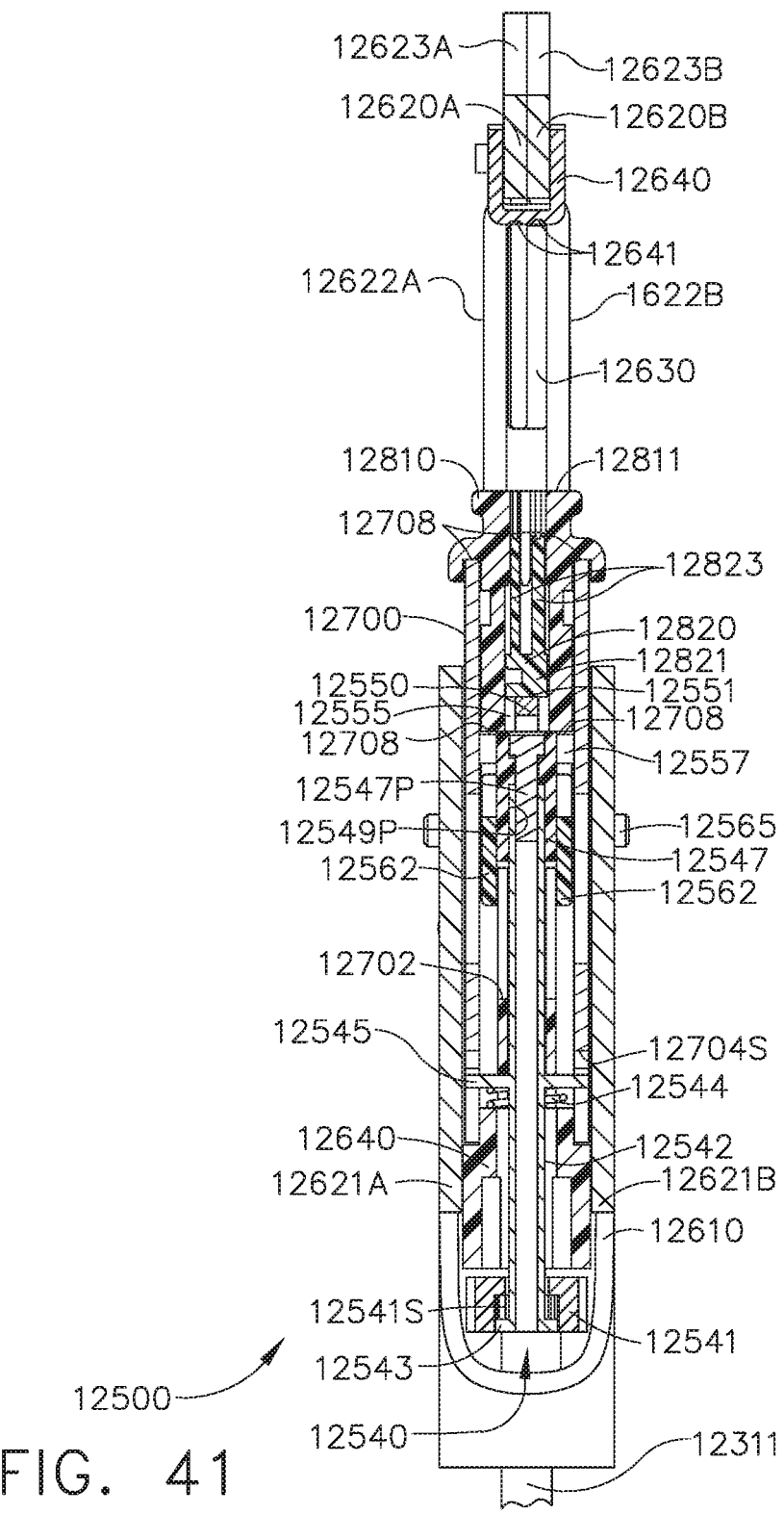
FIG. 41 is a cross-sectional elevational view of the end effector assembly of the instrument of FIG. 31 illustrated in the uncaptured, unclamped, unfired, unlocked configuration of FIG. 39 taken along line 41-41 in FIG. 40.

Referring to FIGS. 38 and 41, the lockout drive 12540 comprises an outer drive gear 12541 operably intermeshed with the main input gear, or common drive input, 12310 attached to the main drive shaft 12311. The lockout drive 12540 further comprises a shaft 12542, a spring-loaded interference gear 12545 grounded against an interior frame structure 12650 of the end effector frame 12600, and a distal lock portion 12547 configured to be engaged by a key portion 12817 of the staple cartridge assembly 12800. The closure frame 12700 comprises a window 12707 (FIG. 35) to permit relative movement between the closure frame 12700 and the distal lock portion 12547. The outer drive gear 12541 comprises an inner splined, or toothed, portion 12541S configured to slidably support and mesh with an inner drive gear 12543 attached to the shaft 12542. This configuration permits relative, longitudinal movement between the shaft 12542 and the outer drive gear 12541 while maintaining a driving relationship between the inner drive gear 12543 and the outer drive gear 12541. The interference gear 12545, having a press fit relationship with the shaft 12542, for example, is spring-loaded against the interior frame structure 12650 of the end effector frame 12600 by a spring 12544. The spring 12544 may comprise of a compression spring, for example. The shaft 12542 is always urged distally by the spring 12544 urging the interference gear 12545 toward a lockout slot 12704S of a lockout window 12704 in the closure frame 12700. When the interference gear 12545 is in the lockout slot 12704S, the shaft 12542 is in the locked configuration. This locked configuration prevents the shaft 12542 from rotating thus preventing the outer drive gear 12541 from being driven. Preventing the outer drive gear 12541 from being driven prevents the drive system 12510 from being actuated. In the locked configuration, the drive system 12510 may be in a binding state, for example. A controller of an instrument handle and/or an onboard controller may sense a binding relationship by measuring an energy spike, for example, and then, upon reaching an energy threshold, seize power delivery to the motor.

To put the lockout drive 12540 in an unlocked configuration, a staple cartridge assembly must be installed within the end effector assembly 12500. The key portion 12817 of the staple cartridge assembly 12800 is configured to contact a ramp surface 12548 of the distal lock portion 12547 to push the distal lock portion 12547 proximally. Pushing the distal lock portion 12547 proximally causes the shaft 12542 to be urged proximally. Pushing the shaft 12542 proximally moves the interference gear 12545 out of the lockout slot 12704S and into a freely rotating position within the lockout window 12704. When the interference gear 12545 is permitted to rotate freely, the shaft 12542 is permitted to rotate. When the shaft 12542 is permitted to rotate, the lockout drive 12540 is in an unlocked configuration allowing the input gear 12310 to drive the main drive 12520 and the lockout drive 12540 simultaneously. In the unlocked configuration, the drive system 12510 is no longer in a binding state.

The distal lock portion 12547 is pinned to the shaft 12542 by a pin 12547P. The pin 12547P is received within a shaft aperture 12549P of the shaft 12542 such that the shaft 12542 and the pin 12547P rotate together owing to an interference fit, for example, when the lockout drive 12540 is driven. Thus, the pin 12547P can rotate within the distal lock portion 12547. Accordingly, in addition to the spring-loaded interference gear 12545 urging the shaft 12542 distally when shifting to the locked configuration, the distal lock portion 12547 will push a pin head of the pin 12547P distally, resulting in the distal lock portion 12547 pulling the shaft 12542 distally as well (see FIG. 41). The distal lock portion 12547 is sandwiched, or nested, between the lever arms 12562. The driver bar 12550 comprises a clearance slot 12557 for the distal lock portion 12547.

Another lockout is provided to prevent the drive system 12510 from being actuated when a spent staple cartridge assembly is installed within the end effector assembly 12500. A spent cartridge lockout member, or cartridge driver engagement arm, 12660 is positioned between the side frames 12620A, 12620B. The lockout member 12660 comprises a spring member 12661 and a driver bar catch feature, or hook, 12663. The lockout member 12660 is illustrated in the unlocked configuration in FIGS. 35-38. The staple cartridge assembly 12800 installed within the end effector assembly 12500 is unspent in FIGS. 35-37. An unspent cartridge contains a staple driver 12820 which has not been fired and is in its proximal-most position. Since, in various embodiments, a staple driver such as the staple driver 12820 is not retracted after being fired, a staple driver in a spent cartridge remains in a distal-most position it achieves when fired. Thus, the lockout member 12660 is urged by the spring member 12661 to catch the driver bar 12550 in the absence of a staple driver whether the absence is due to the absence of a staple cartridge assembly altogether or is due to a spent cartridge being present. At any rate, when caught by the cartridge driver catch feature 12663, the drive system 12510 is prevented from being actuated. This lockout configuration also puts the drive system 12510 in a binding state.

Referring primarily to FIGS. 39-46, operation of the tool assembly 12100 will now be described with respect to a surgical stapling procedure, or operation. The tool assembly 12100 is illustrated in the uncaptured, unclamped, unfired, unlocked configuration in FIGS. 39-41. The tool assembly 12100 is unlocked because the unspent staple cartridge assembly 12800 is installed within the end effector assembly 12500. The interference gear 12545 is pushed out of the lockout slot 127045 and is free to rotate within the lockout window 12704 and the lockout window, or cavity, 12655 of the interior frame structure 12650. The lockout member 12660 is pushed away from the driver bar 12550 by the staple driver 12820 of the unspent staple cartridge assembly 12800 thus providing an unobstructed path for the driver bar 12550 to travel. The actuation tines 12563 of the pin actuation mechanism 12560 are in a first portion of the cam slots 12702. A user of the instrument may now place tissue between the cartridge deck 12811 and the anvil 12640 of the instrument to prepare for capturing of the tissue.

Figure 42:
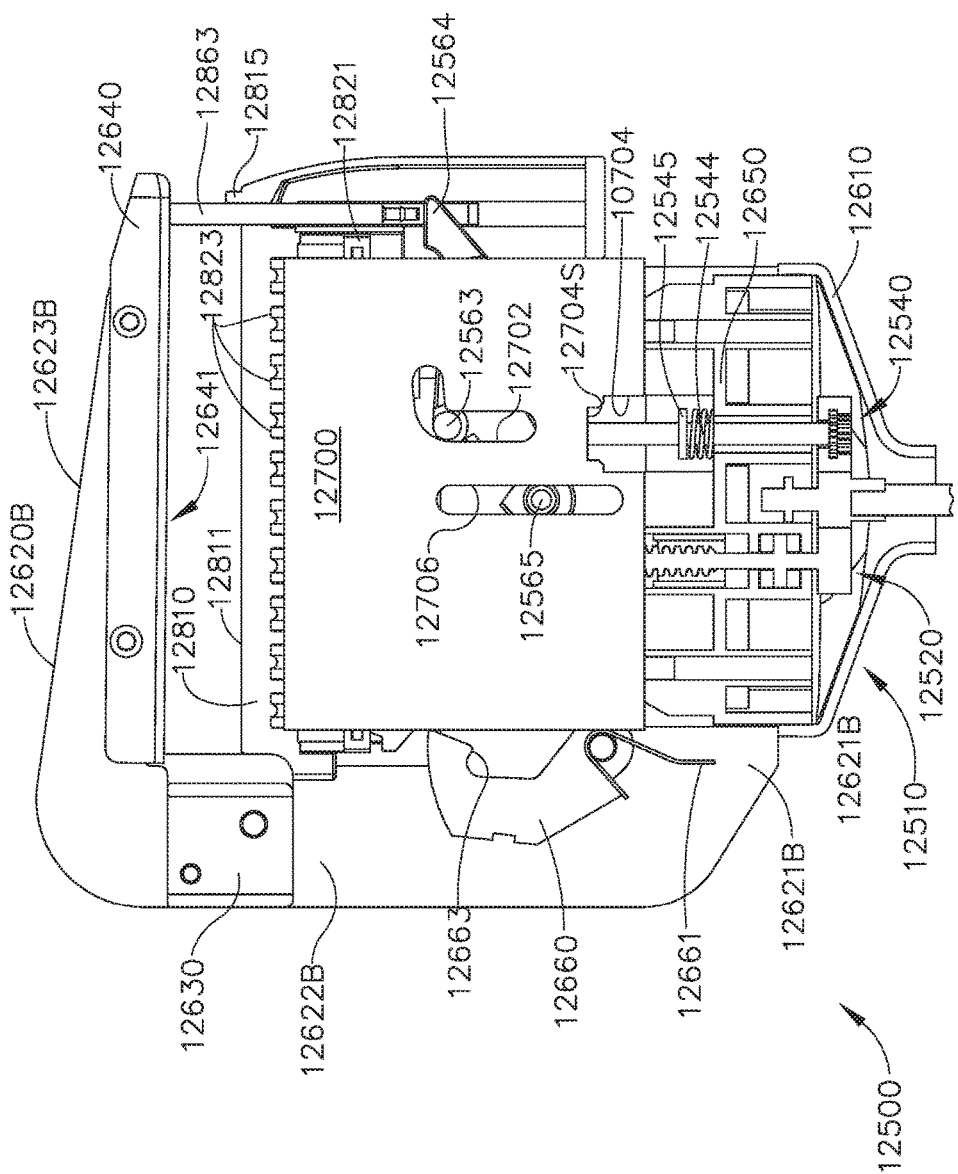
FIG. 42 is a partial, cross-sectional elevational view of the end effector assembly of the instrument of FIG. 31 illustrated in a captured, partially-clamped, unfired configuration.
Figure 43:
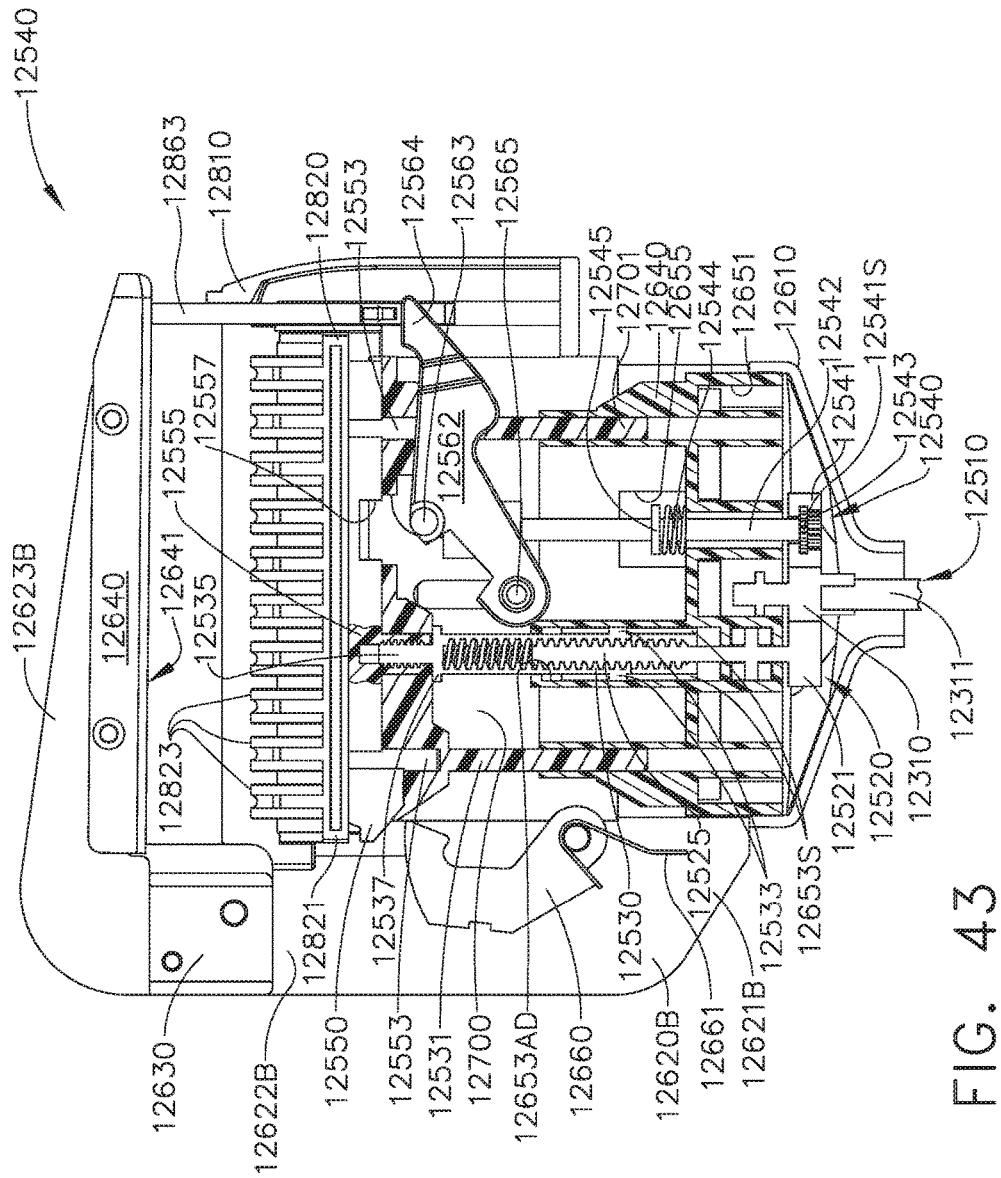
FIG. 43 is a partial, cross-sectional elevational view of the end effector assembly of the instrument of FIG. 31 illustrated in the captured, partially-clamped, unfired configuration of FIG. 42.

Referring now to FIGS. 42 and 43, the drive system 12510 has been actuated to capture tissue with the tool assembly 12100. The closure frame 12700 automatically deployed the pin actuation mechanism 12560 and pin 12860 by camming the actuation projections 12563 with the cam slots 12702.

The pin 12860 contacts the anvil 12640 defining a completed tissue capture stage. The closure frame 12700 has also advanced the staple cartridge assembly 12800 distally toward the anvil. At this point, the tool assembly 12100 may continuously actuate the main drive 12520 to proceed to fully clamping the tissue. However, if the user desires to uncapture the currently captured tissue (tissue not shown), the user may actuate the drive system 12510 in a reverse direction to reverse the drive system 12510 thereby rotating the pin actuation mechanism 12560 about the pin retaining axis to retract the pin shaft 12863. The instrument may be fitted with a sensor to detect when the pin shaft 12863 reaches a fully deployed position, for example. Detecting full deployment of the pin may result in a temporary pause in actuation to allow the user to determine if the tissue captured at this stage is the tissue to be clamped and, eventually, stapled. Once the user decides the tissue that is captured is the tissue to be clamped and, eventually, stapled, the user may trigger further actuation of the main drive system 12510 to proceed to the clamping stage.

In FIGS. 42 and 43, the shaft 12542 of the lockout drive 12540 sprung back to its original position upon losing contact with its biasing member, the key portion 12817 of the staple cartridge body 12810. In other words, the spring 12544 is in its neutral, or uncompressed, state. The interference gear 12545 is still in a freely rotating position due to, one, the lockout window 12655 of the interior frame structure 12650 and, two, the distal movement of the closure frame 12700. The inner drive gear 12543 has moved longitudinally within but maintained a meshing relationship with the inner splined portion 12541S permitting the lockout drive 12540 to rotate when the drive system 12510 is actuated. The tabs 12533 of the closure nut tube 12530 are positioned within the slots 12653S causing the closure nut tube 12530 to translate within the frame bore 12653 as the drive screw portion 12525 rotates.

Figure 44:
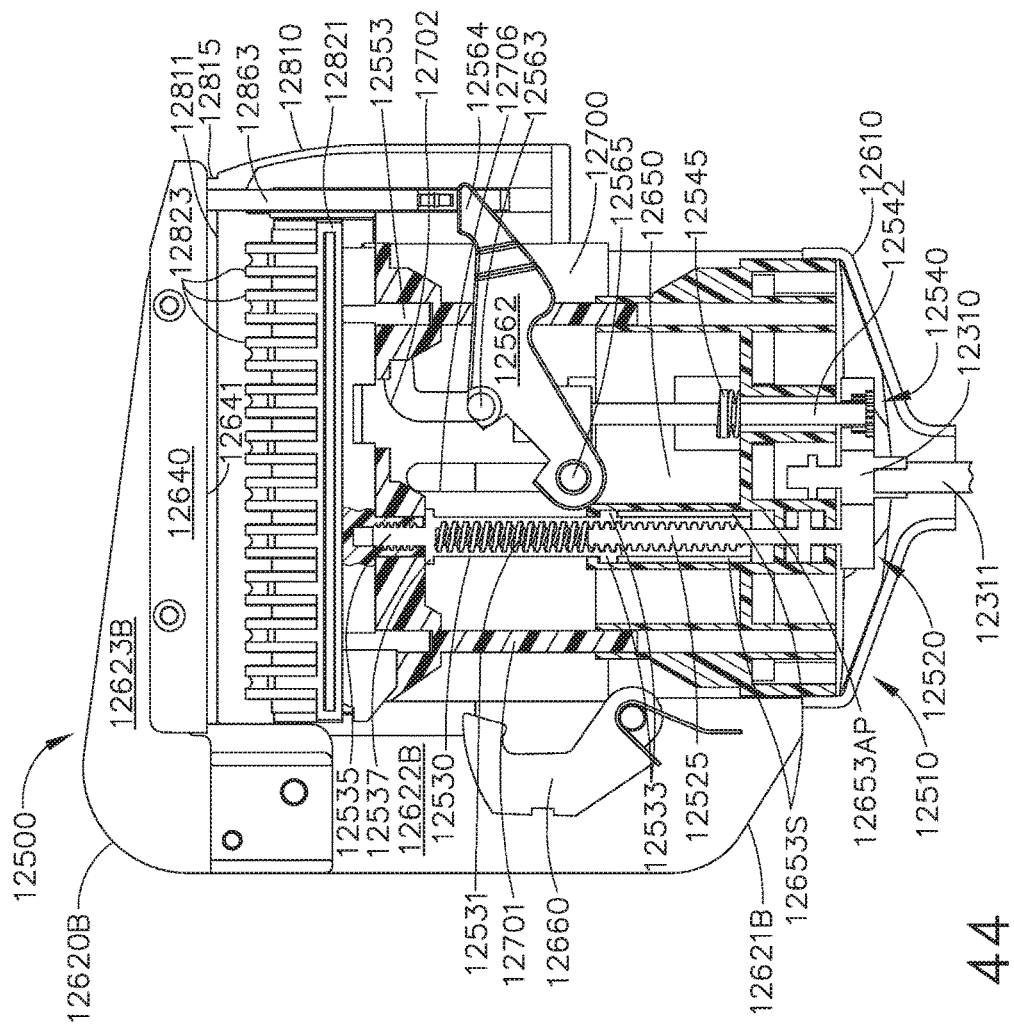
FIG. 44 is a partial, cross-sectional elevational view of the end effector assembly of the instrument of FIG. 31 illustrated in a fully-clamped, unfired configuration.

Turning now to FIG. 44, the tool assembly 12100 is illustrated in the fully clamped configuration. The tabs 12533 of the closure nut tube 12530 have reached their distal most position now permitting the closure nut tube 12530 to be rotated. The tool assembly 12100 may be further configured to temporarily pause actuation of the main drive 12510 upon reaching the fully clamped position so that the user of the tool assembly 12100 can check if the captured, and now clamped, tissue is the target tissue to be stapled. In the event that the user of the tool assembly 12100 wants to unclamp the tissue, the drive system 12510 may be reversed to place the tabs 12533 of the closure nut tube 12530 back within the slots 12653S of the bore 12653 so that the drive screw portion 12525 may pull the closure nut tube 12530 and, as a result, the closure frame 12700 proximally. If the user decides that the captured, and now clamped, tissue is the target tissue to be stapled, the user may trigger further actuation of the main drive 12510 to fire the tool assembly 12100.

Figure 45:
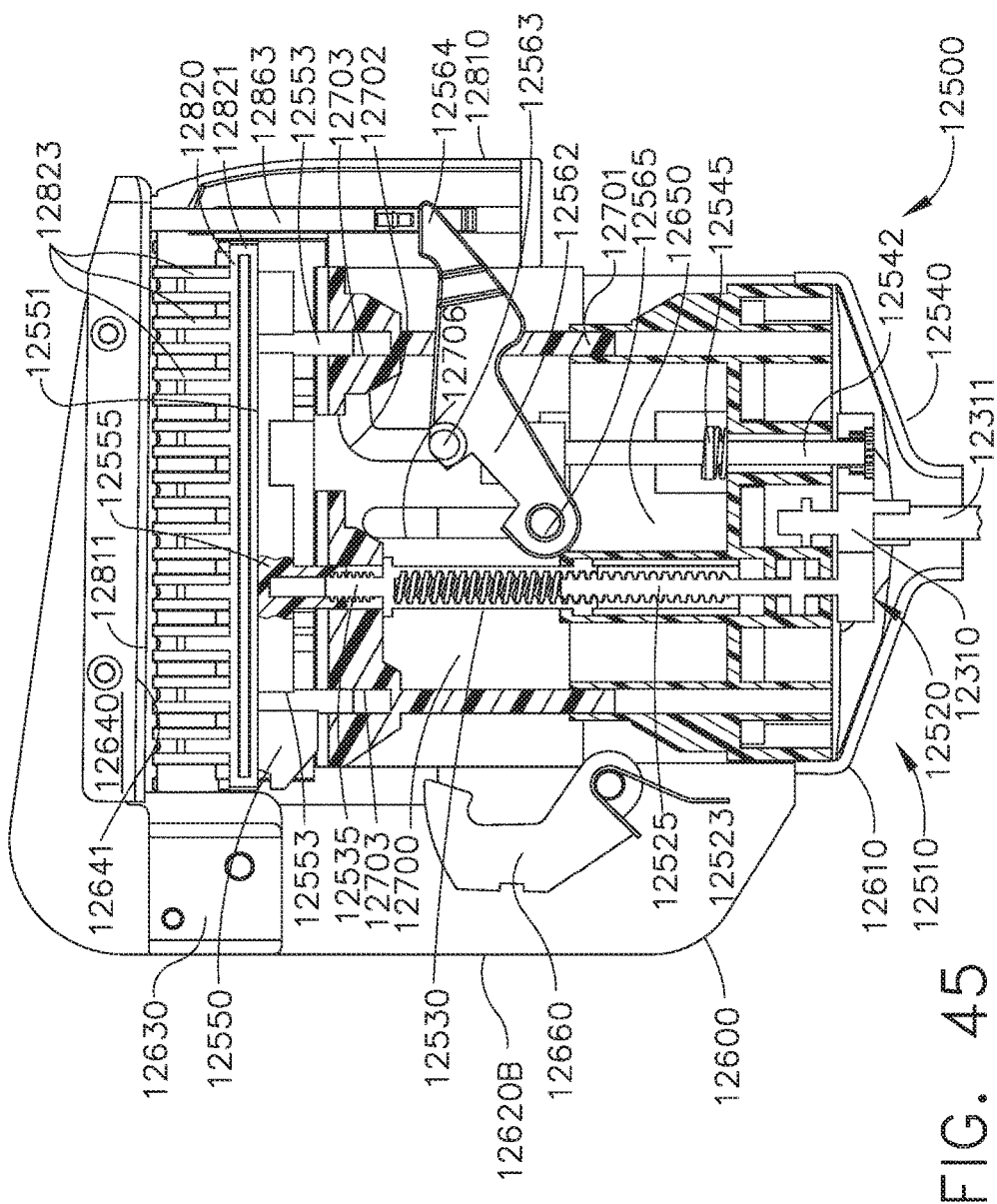
FIG. 45 is a partial, cross-sectional elevational view of the end effector assembly of the instrument of FIG. 31 illustrated in a fully-clamped, fired configuration.

FIG. 45 illustrates the tool assembly 12100 in a fully fired configuration. The firing screw portion 12535 has been rotated to advance the driver bar 12550 toward the anvil 12640 pushing the staple driver 12820 distally within the staple cartridge body 12810. This distal advancement of the staple driver 12820 results in the deployment of the staples 12830 from the staple cavities 12813. The guide pins 12553 have been partially advanced out of their respective guide pin slots 12703 in the closure frame 12700. Upon fully firing the tool assembly 12100, the tool assembly 12100 may automatically reverse the drive system 12510 to retract the staple cartridge assembly 12800 to unclamp and uncapture the tissue that has just been stapled. This automatic retraction may be due to any suitable sensor configuration to identify that the staples 12830 have been fully fired, for example. In one instance, full actuation of the driver bar 12550 may be detected. In another instance, the firing screw portion 12535 can be configured to rotate a set number of rotations to advance the staple driver a set distance; upon completing the set number of rotations, the tool assembly 12100 and/or instrument interface to which the tool assembly 12100 is attached, may initialize the automatic retraction. This may be advantageous when different staple cartridge assemblies are used and the distance that the driver bar 12550 is required to travel changes to accommodate different staple heights, for example.

Figure 46:
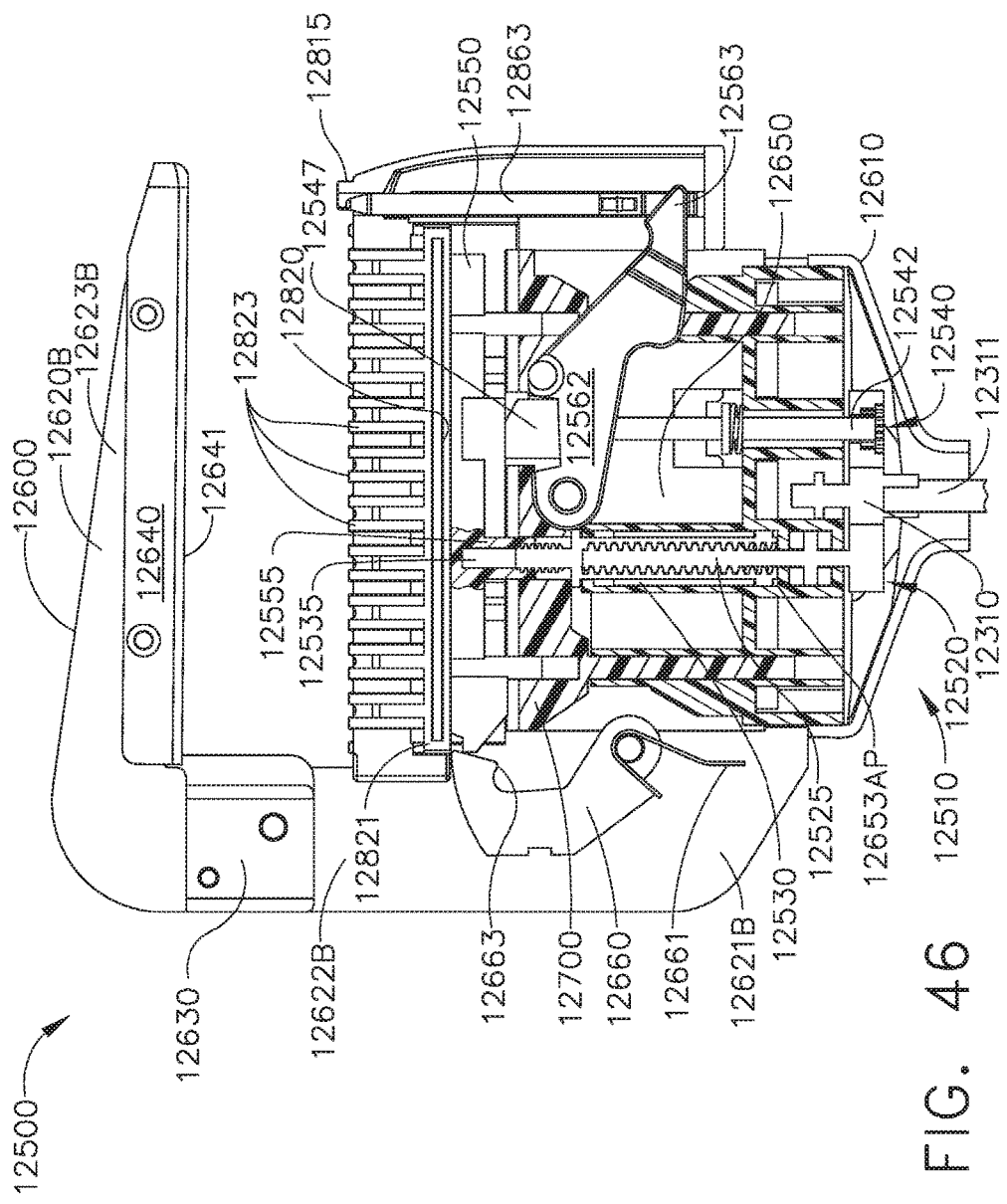
FIG. 46 is a partial, cross-sectional elevational view of the end effector assembly of the instrument of FIG. 31 illustrated in a partially-retracted, fired configuration.

Referring now to FIG. 46, the tool assembly 12100 is illustrated in an uncaptured, unclamped, fully-fired configuration. The lock member 12660 has been pushed outwardly by the driver bar 12550. The lock member 12660 has also nudged its catch feature 12663 directly under the staple driver 12820. The catch feature 12663 may, alone, prevent the staple driver 12820 of the now spent staple cartridge assembly 12800 from being moved proximally for any reason. The tabs 12533 of the closure nut tube 12530 are in their proximal most position. This proximal most position puts the tabs 12533 within a proximal annular recess 12653AP within the firing bore 12653. The annular recess 12653AP permits the closure tube to rotate simultaneously with the drive screw portion 12525 to retract the driver bar 12550.

Figure 47:
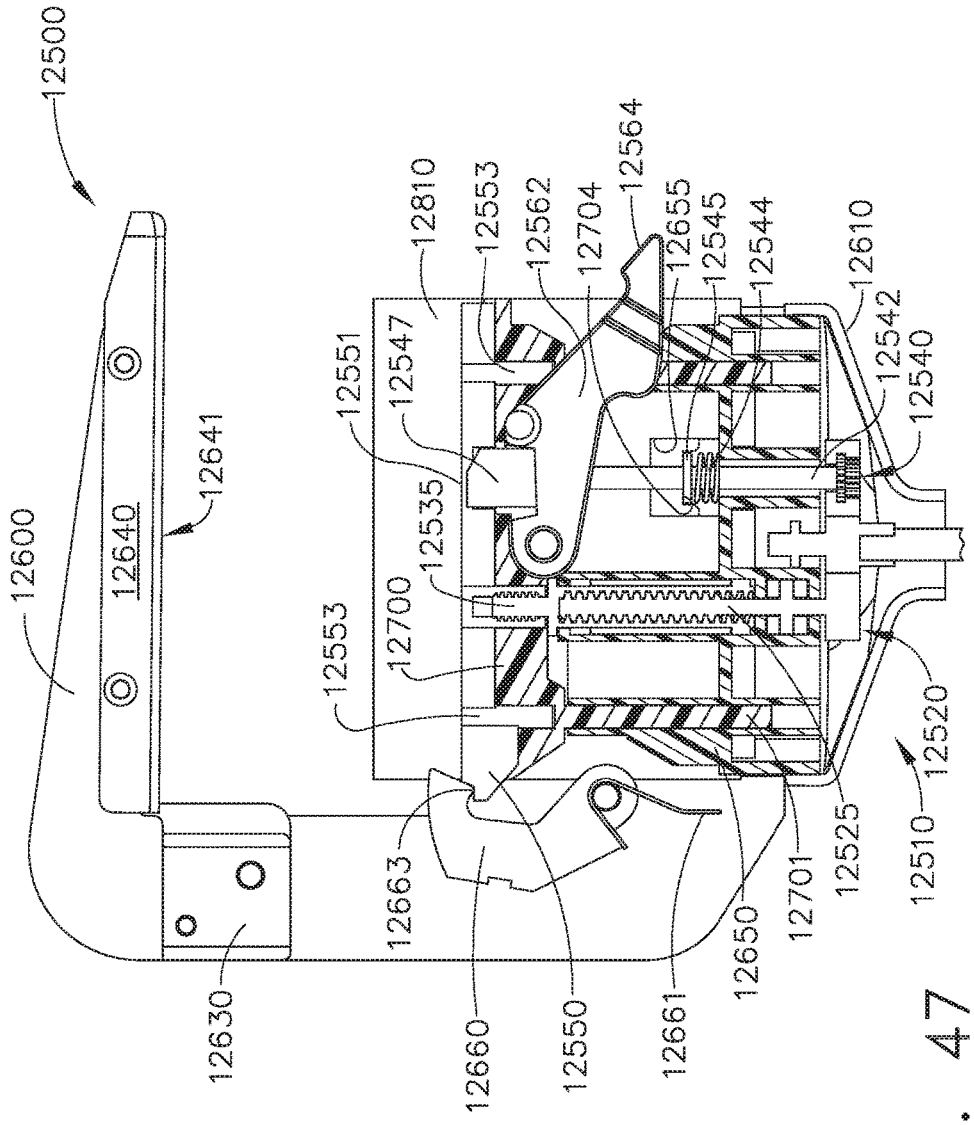
FIG. 47 is a partial, cross-sectional elevational view of the end effector assembly of the instrument of FIG. 31 illustrated in a fully-retracted, locked configuration, wherein the spent staple cartridge assembly has been removed from the end effector assembly.

FIG. 47 illustrates the tool assembly 12100 with the staple cartridge assembly 12800 uninstalled within the end effector assembly 12500. Prior to uninstalling the staple cartridge assembly 12800, the catch feature 12663 of the lock member 12660 was urged inward by the spring member 12661 to catch the driver bar 12550. In this position, the drive system 12510 is in a binding state since the driver bar 12550 can not be advanced. The lock member 12660 remains in this position when the spent staple cartridge assembly 12800 is removed from the tool assembly 12100. The lockout drive 12540 initiates its locking function upon removal of the staple cartridge assembly 12800. Since the distal lock portion 12547 is not pushed proximally by a cartridge body key member, the spring 12544 motivates the interference gear 12545 and, thus, the shaft 12542 distally placing the interference gear 12545 in the lockout slot 12704S of the lockout window 12704. Without a staple cartridge assembly installed within the end effector assembly 12500, the lockout member 12660 and lockout drive 12540 provide two actuation prevention devices, or mechanisms, to prevent the drive system 12510 from being actuated.

Figure 48:
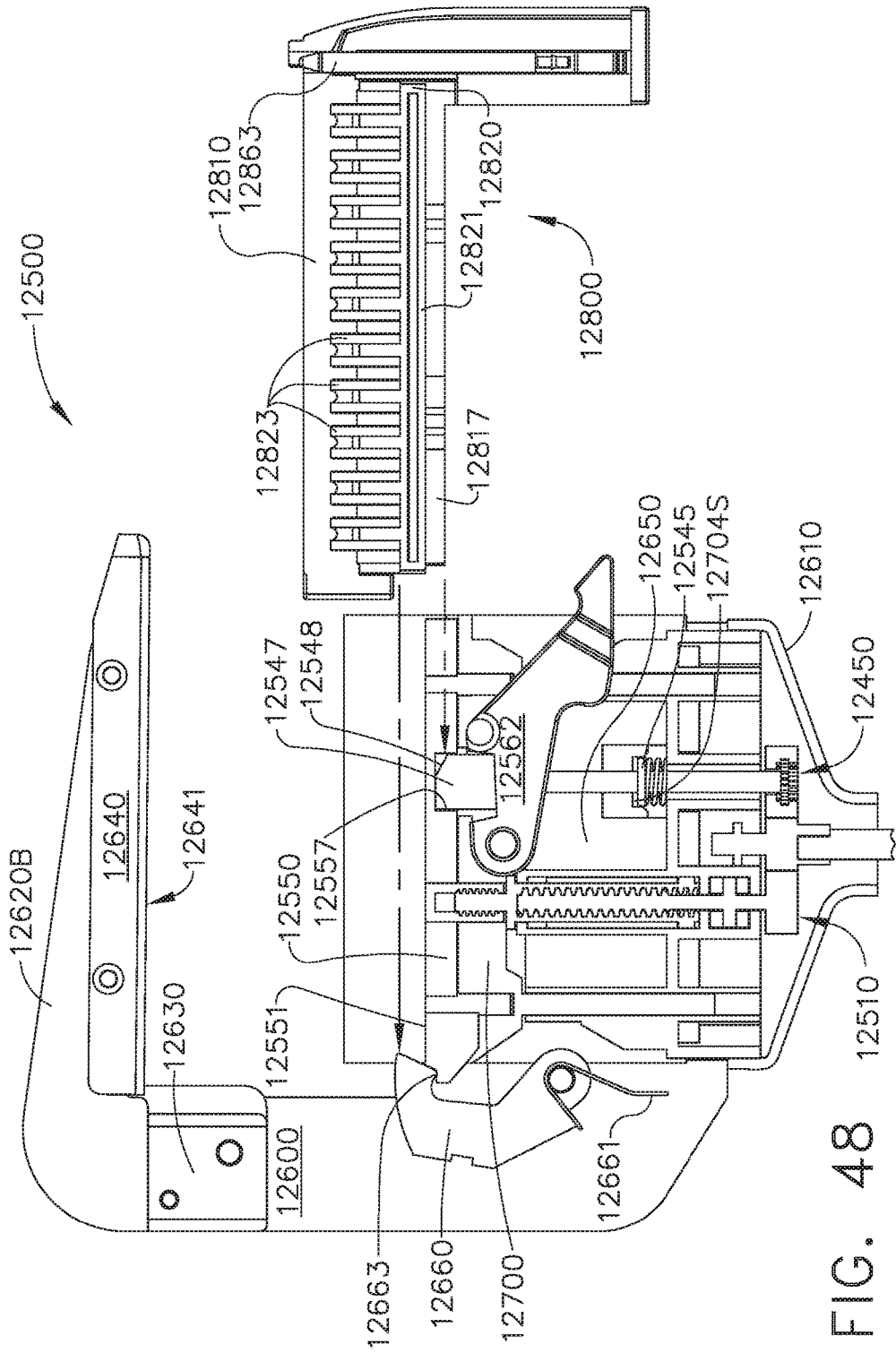
FIG. 48 is a partial, cross-sectional elevational view of the end effector assembly of the instrument of FIG. 31 illustrated in the fully-retracted, locked configuration of FIG. 46, wherein an unspent staple cartridge assembly is ready to be installed within the end effector assembly.

Referring now to FIG. 48, the unspent staple cartridge assembly 12800 is illustrated not installed within the end effector assembly 12500. A base portion 12821 of the staple driver 12820 is configured to unlock the lock member 12660 by contacting the catch feature 12663 and pushing the catch feature 12663 away from the driver bar 12550. As discussed above, the key portion 12817 is configured to engage the ramp surface 12548 of the distal lock portion 12547 to push the interference gear 12545 out of the lockout slot 12704S and into a freely rotating position.

Figure 49:
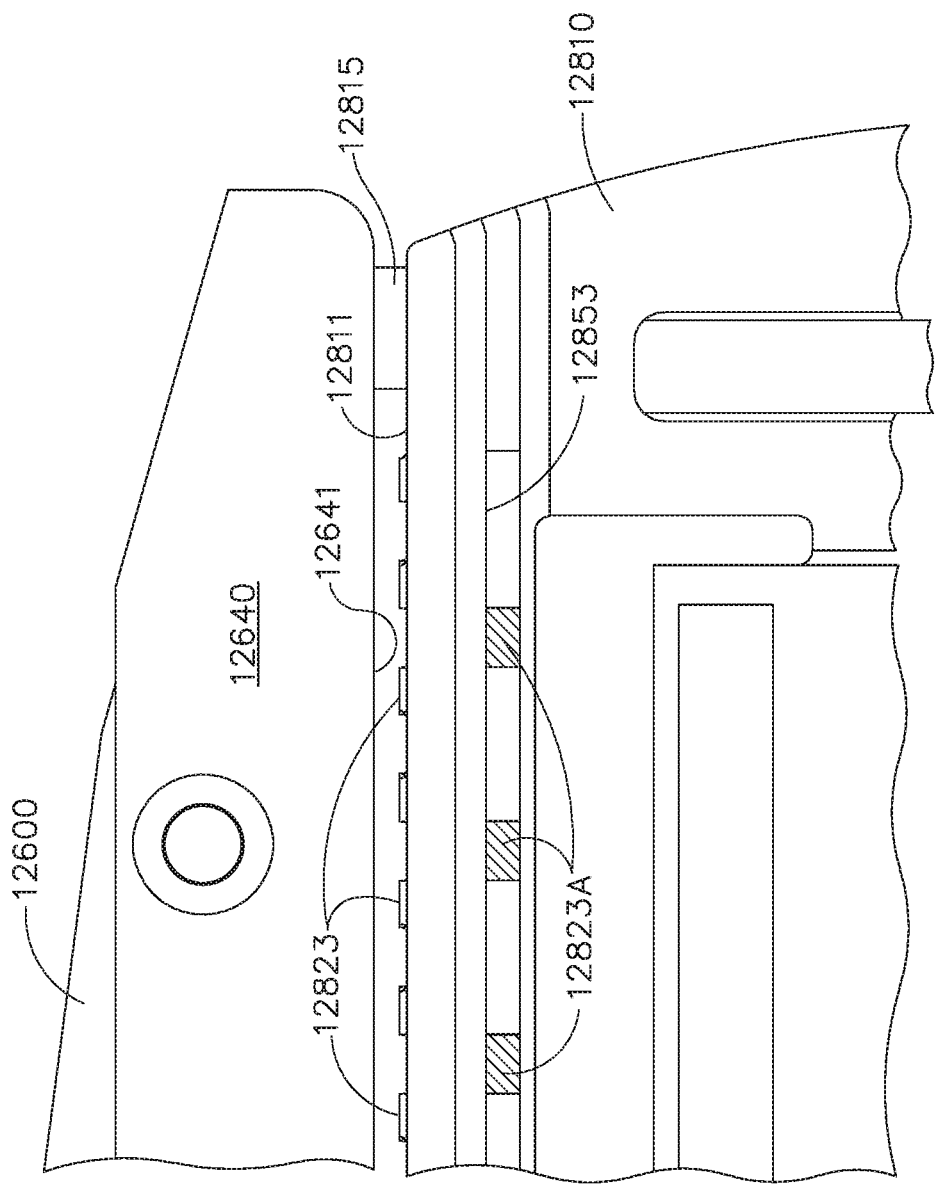
FIG. 49 is a partial, cross-sectional elevational view of the end effector assembly of the instrument of FIG. 31 illustrated in a fully-clamped, partially-fired configuration, wherein the staple cartridge assembly comprises a firing status indicator system and the firing status indicator system indicates that the instrument is in the fully-clamped, partially-fired configuration.
Figure 50:
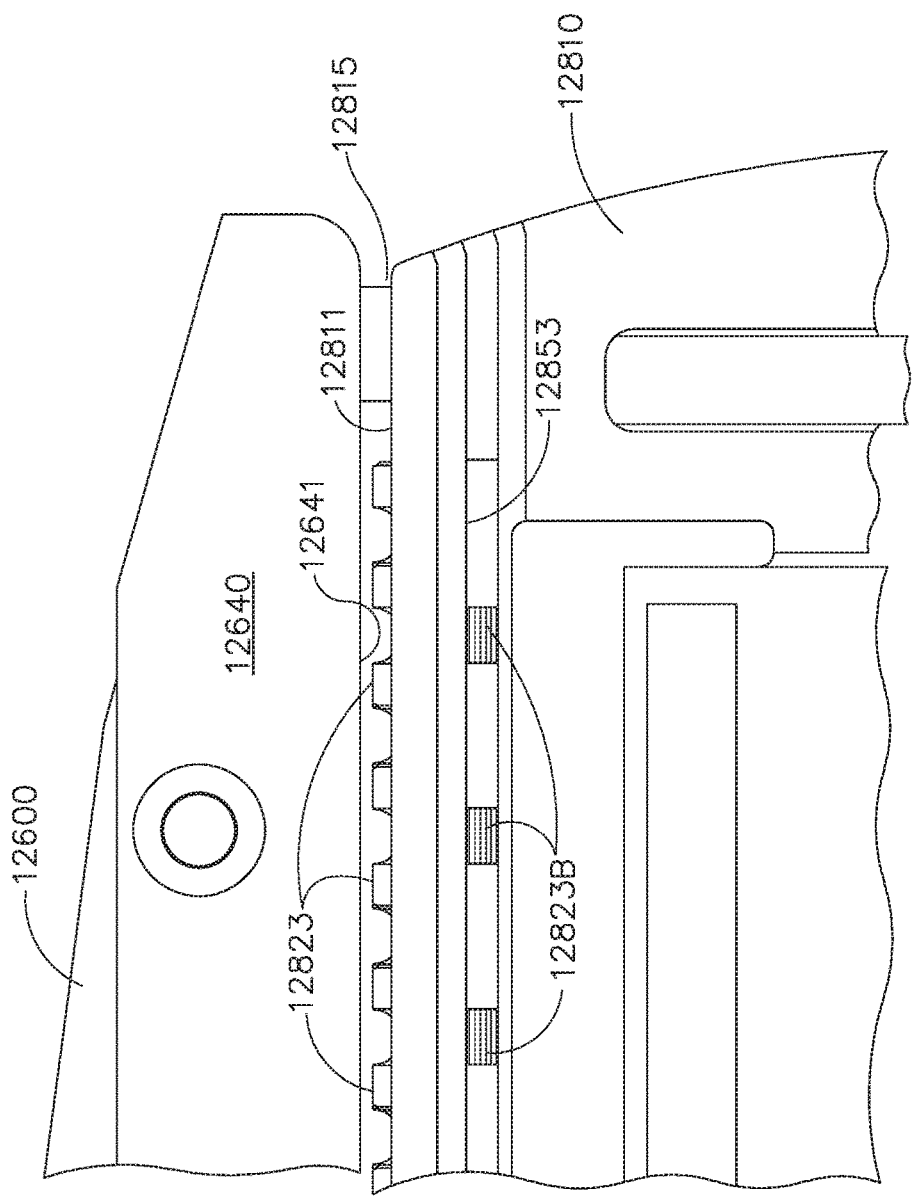
FIG. 50 is a partial, cross-sectional elevational view of the end effector assembly of the instrument of FIG. 31 illustrated in a fully-clamped, fully-fired configuration, wherein the firing status indicator system indicates that the instrument is in the fully-clamped, fully-fired configuration.
Figure 51:
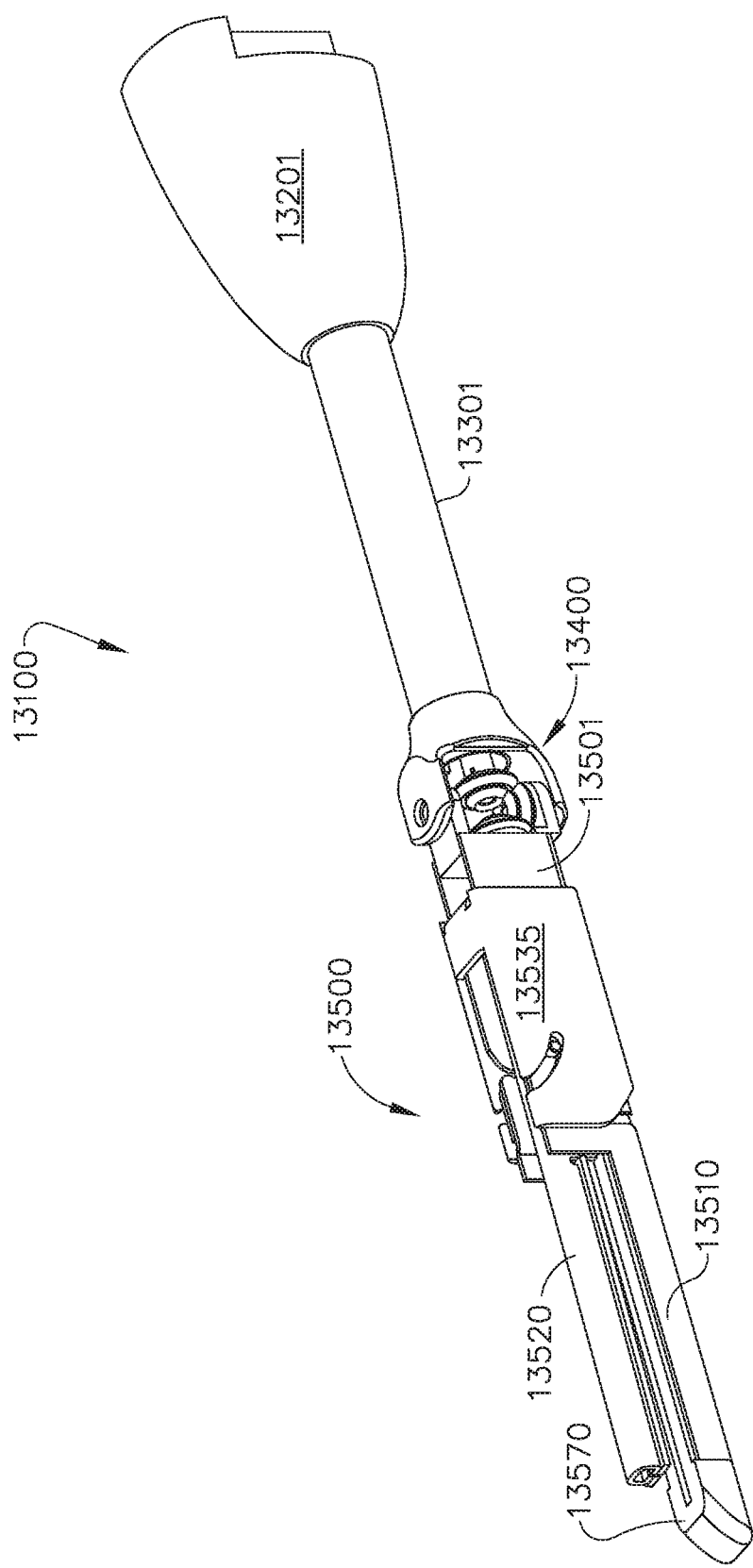
FIG. 51 is a perspective view of a surgical stapling attachment, or instrument, comprising an attachment portion, a shaft assembly, an articulation joint, and an end effector assembly.

The staple cartridge assembly 12800 further comprises a status indicator system to visually indicate to a user of the tool assembly 12100 the status of the staples 12830. Referring now to FIGS. 49 and 50, the staple cartridge assembly 12800 is illustrated in a fully clamped, partially fired configuration where the staple drivers 12823 of the staple driver 12820 are extended partially above the deck 12811 of the cartridge body 12810. A cartridge window 12853 is provided within the staple cartridge body 12810 for displaying the movement of the staple drivers 12823. The movement of the staple drivers is indicated by visual indicia 12823A, 12823B on the staple drivers 12823 themselves. For example, the visual indicia 12823A, 12823B may comprise a single color varying in intensity, or shade, for example, to illustrate the progression of the staple drivers 12823 within the cartridge body 12810. A greater intensity may indicate that the staple drivers 12823 are approaching, or have reached, a fully fired position. In other instances, the staple drivers 12823 may comprise two colors; a first color 12823A, such as blue, for example, to indicate that the staple drivers 12823 are in mid progression, and, a second color 12823B, such as red, for example, to indicate that the staple drivers 12823 have reached the fully fired position.

A surgical stapling attachment, or tool assembly, 13100 is depicted in FIGS. 51-69. The tool assembly, or instrument, 13100 is configured to clamp, staple, and cut tissue during a surgical procedure. Referring primarily to FIGS. 51-55, the tool assembly 13100 comprises an attachment portion 13200, a shaft assembly 13300, an articulation joint 13400, and an end effector assembly 13500. The attachment portion 13200 is configured to be attached to an interface of a surgical instrument. The instrument interface can comprise a handle such as those disclosed herein for example. Other embodiments are envisioned where the tool assembly 13100 is not readily attachable to and detachable from an instrument interface and, instead, is part of a unitary instrument. The attachment portion 13200 is configured to receive rotary control motions from the instrument interface to which the tool assembly 13100 is attached and transfer the rotary control motions to the shaft assembly 13300. As discussed in greater detail below, the shaft assembly 13300 communicates these rotary control motions to the end effector assembly 13500 through the articulation joint 13400.

Figure 56:
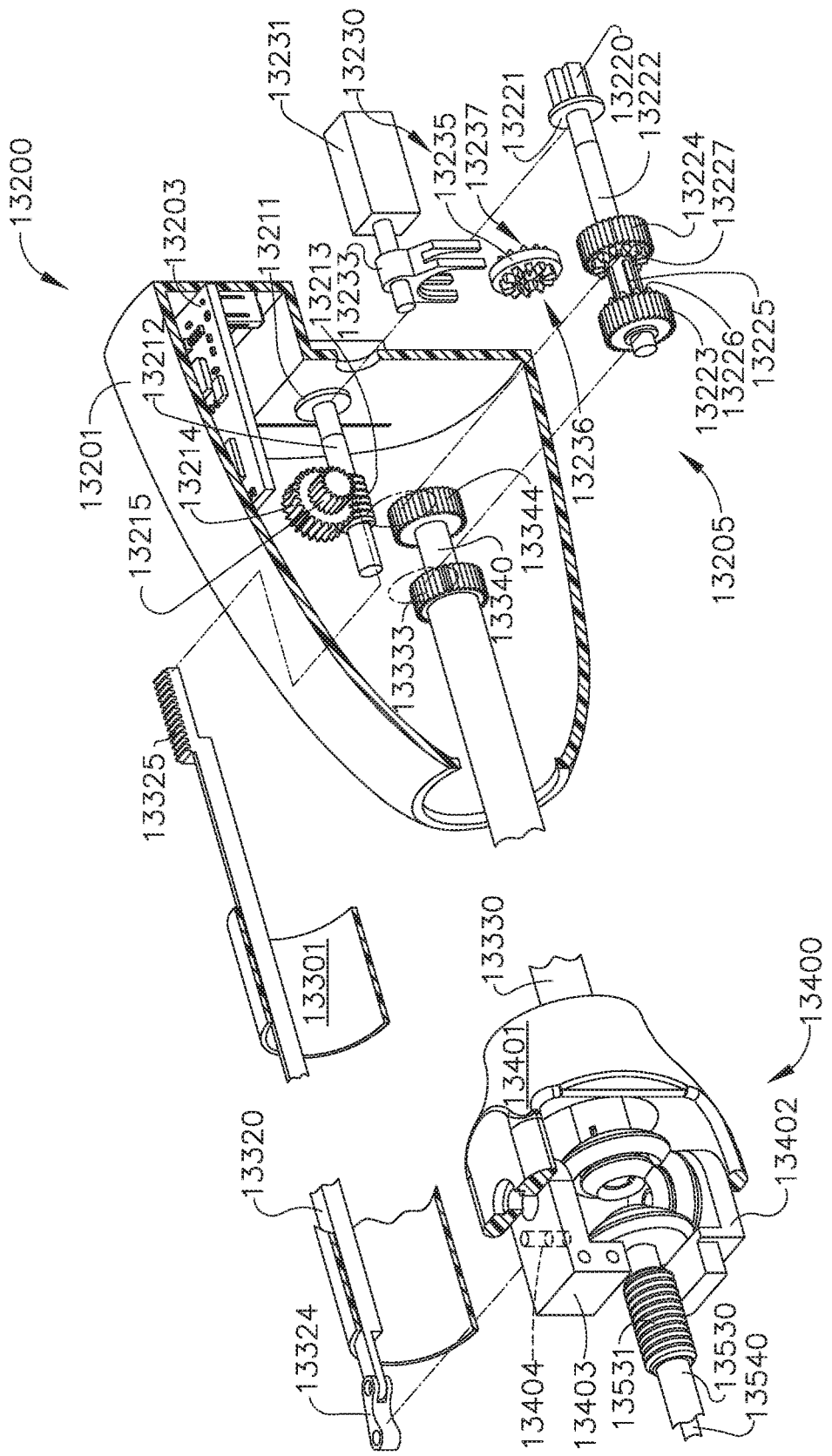
FIG. 56 is a partial exploded view of the attachment portion, the shaft assembly, and the articulation joint of the instrument of FIG. 51.

The attachment portion 13200 comprises a housing 13201 and a transmission 13205 including an articulation transmission and, in addition, an end effector transmission. With reference to FIG. 56, the articulation transmission comprises a articulation drive coupler 13210 (FIG. 52) configured to receive rotary motion from the instrument, an input shaft 13212, and a housing bearing 13211. The bearing 13211 rotatably supports the input shaft 13212. The input shaft 13212 comprises a worm gear portion 13213 meshed with a worm wheel 13214. The worm wheel 13214 is coupled with a translation, or pinion, gear 13215 to actuate an articulation shaft, or rod, 13320 of the shaft assembly 13300. The gear 13215 rotates with the worm wheel 13214. The articulation shaft 13320 comprises a rack 13325 disposed on a proximal portion thereof which is meshed with the pinion gear 13215 such that, when the pinion gear 13215 is rotated by the input shaft 13212, the articulation shaft, or link, 13320 is moved longitudinally to articulate the end effector assembly 13500.

Figure 65:
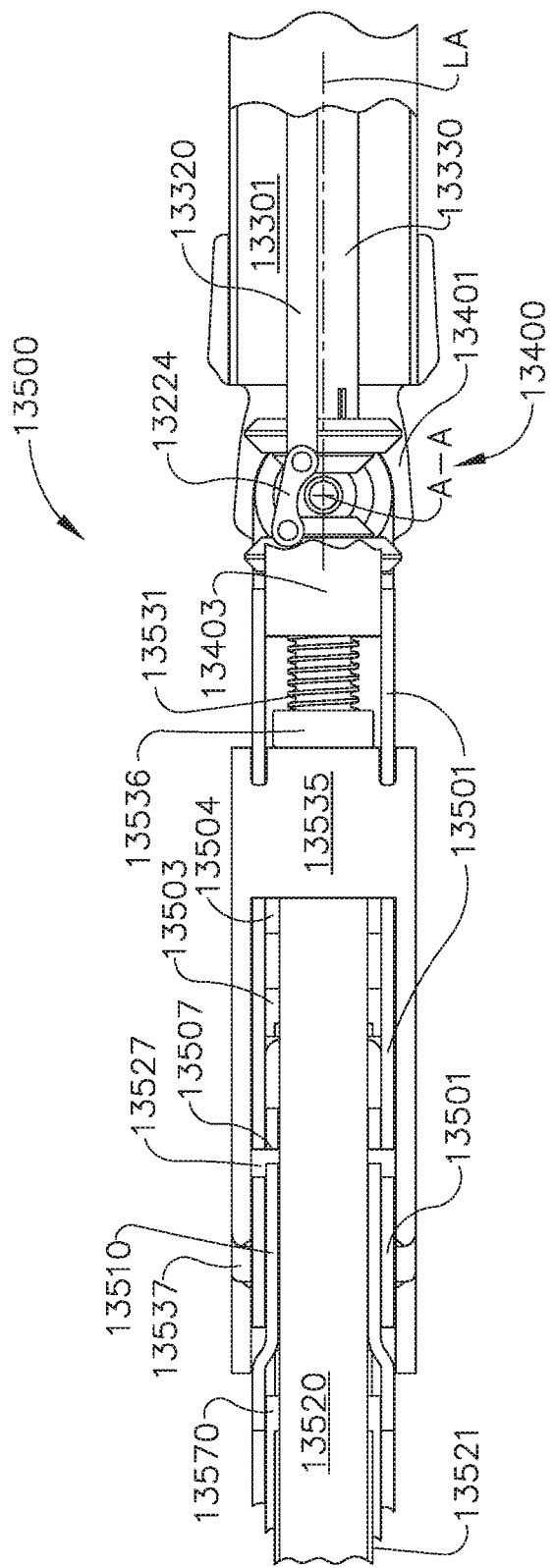
FIG. 65 is a partial, top view of the end effector assembly, the articulation joint, and the shaft assembly of the instrument of FIG. 51 illustrated in a clamped, unarticulated configuration.
Figure 66:
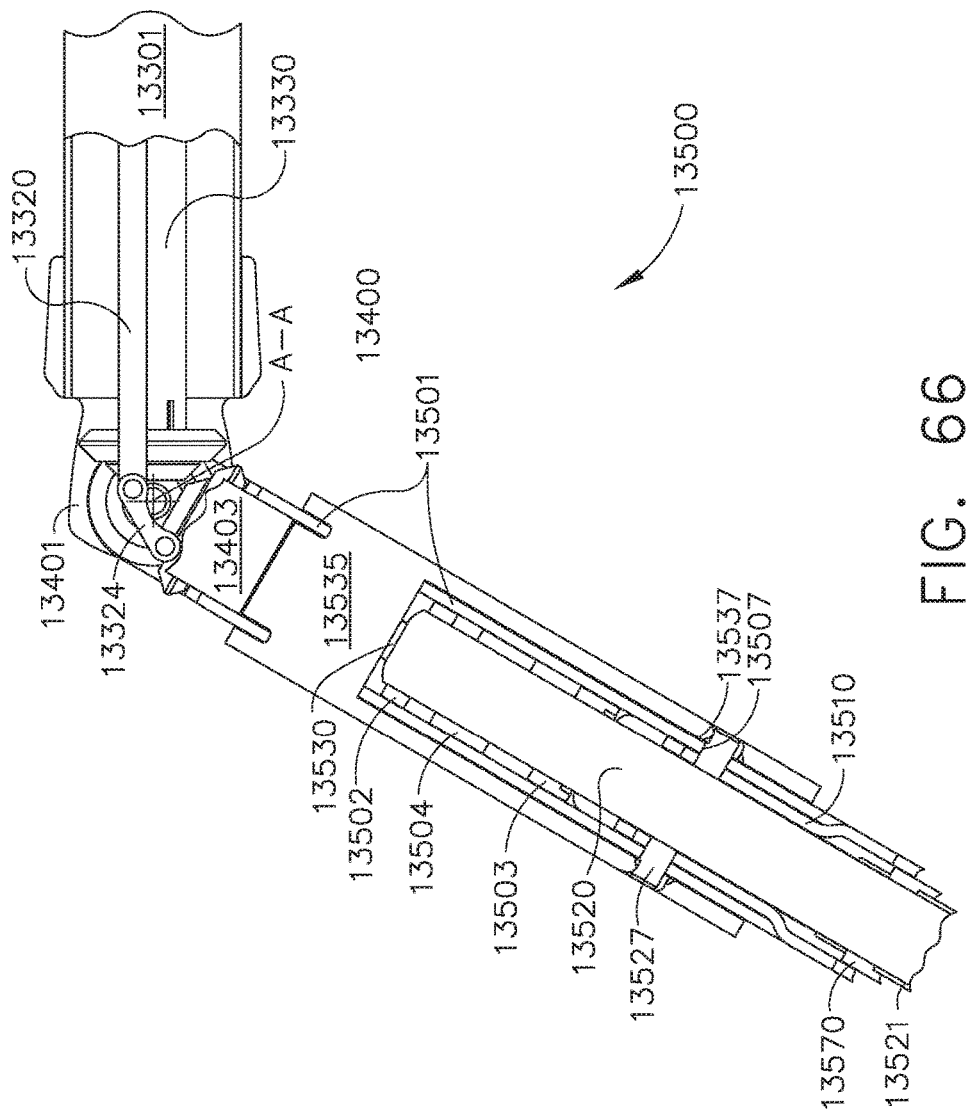
FIG. 66 is a partial, top view of the end effector assembly, the articulation joint, and the shaft assembly of the instrument of FIG. 51 illustrated in an unclamped, articulated configuration.
Figure 67:
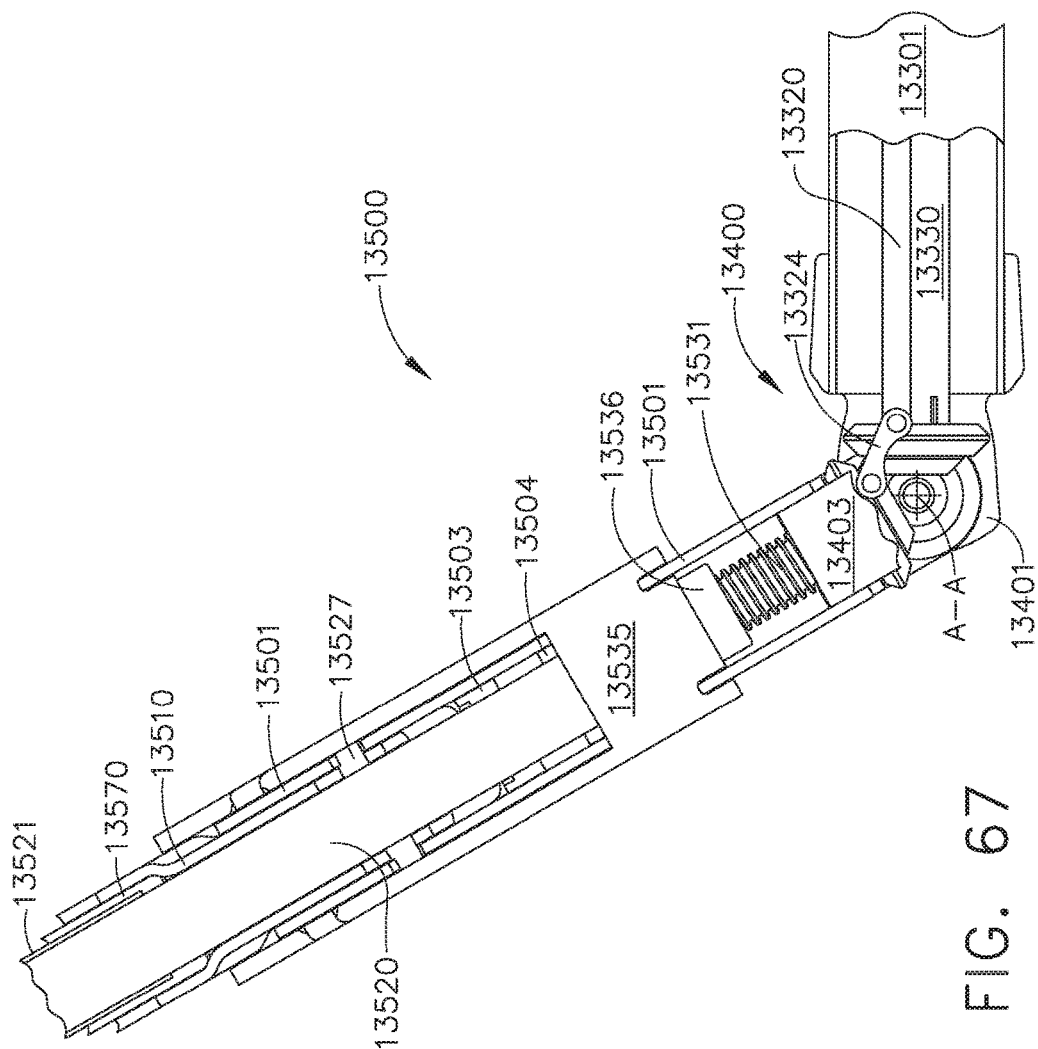
FIG. 67 is a partial, top view of the end effector assembly, the articulation joint, and the shaft assembly of the instrument of FIG. 51 illustrated in a clamped, articulated configuration.
Figure 68:
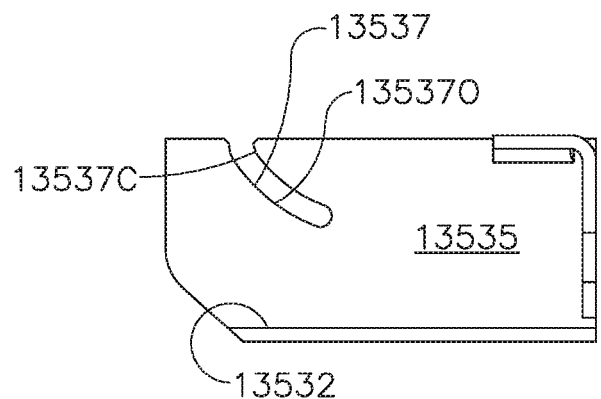
FIG. 68 is a cross-sectional elevational view of a closure frame of the end effector assembly of the instrument of FIG. 51.

The end effector assembly 13500 is illustrated in an unarticulated, or neutral, configuration in FIG. 65. As illustrated in FIG. 66, the articulation shaft 13320 can be pushed distally to articulate the end effector 13500 in a first direction. Similarly, as illustrated in FIG. 67, the articulation shaft 13320 can be pulled proximally to articulate the end effector 13500 in a second, or opposite, direction. As illustrated in FIGS. 65-67, the articulation shaft 13320 is not directly attached to the end effector 13500; rather, the articulation shaft 13320 is attached to the end effector 13500 via an articulation link 13324. In the neutral, or unarticulated, configuration of the end effector 13500, as illustrated in FIG. 55, the articulation link 13324 extends from a region proximal to the articulation axis A-A to a region distal to the articulation axis A-A. Also, in the neutral configuration of the end effector 13500, the articulation link 13324 is positioned only one side of a longitudinal axis LA defined by the tool assembly 13100 and/or shaft housing 13301. The articulation link 13324 comprises a curved configuration configured to encourage the end effector assembly 13500 to articulate about the articulation axis A-A when the articulation shaft, or drive, 13320 is translated proximally and/or distally by the articulation transmission.

The end effector assembly 13500 comprises a frame, or spine, 13501 extending distally from the articulation joint 13400. The articulation joint 13400 comprises a proximal yoke 13401 fixedly attached to the shaft housing 13301, a lower, distal yoke arm 13402 fixedly attached to the end effector spine 13501, and an upper, distal yoke arm 13403 also fixedly attached to the end effector spine 13501. The yoke arms 13402, 13403 are configured to be rotated relative to the yoke 13401 about an articulation axis A-A. Although not illustrated, a pin or rod may be positioned along the articulation axis A-A for the proximal yoke 13401 and the yoke arms 13402, 13403 to pivot about. The articulation link 13324 is coupled to the upper, distal yoke arm 13403 by a pin 13404 so that, when the articulation shaft 13320 is moved longitudinally relative to the shaft housing 13301, the articulation shaft 13320 can push or pull the upper yoke arm 13403 to articulate the end effector assembly 13500 about the articulation axis A-A.

The end effector transmission of the transmission 13205 comprises a drive input, or primary drive coupler, 13220 configured to receive rotary motion from the instrument interface. The end effector transmission further comprises an input shaft 13222 and a housing bearing 13221 which rotatably supports the input shaft 13222. The input shaft 13222 comprises a closure drive gear 13223 journably supported thereon, a firing drive gear 13224 journably supported thereon, and a splined shaft portion 13225 disposed between the closure drive gear 13223 and the firing drive gear 13224. The closure drive gear 13223 is meshed with a corresponding output closure drive gear 13333 of the shaft assembly 13300 while the firing drive gear 13224 is meshed with a corresponding output firing drive gear 13344 of the shaft assembly 13300.

A shifter mechanism 13230 of the end effector transmission is capable of shifting between the drivability of the closure drive gear 13223 and the drivability of the firing drive gear 13224. The closure drive gear 13223 and the firing drive gear 13224 do not rotate unless engaged by the shifter mechanism 13230. The closure drive gear 13223 comprises a set of teeth, or projections, 13226 disposed on a side of the closure drive gear 13223 which faces the firing drive gear 13224. The firing drive gear 13224 comprises a set of teeth, or projections, 13227 disposed on a side of the firing drive gear 13224 which faces the closure drive gear 13223. A shifter body, or disk, 13235 comprises teeth, or projections, 13236 disposed on a first side of the disk 13235 that faces the closure drive gear 13223 and teeth, or projections, 13237 disposed on a second side of the disk 13235 that faces the firing drive gear 13224. The shift disk 13235 is meshed with and slidable relative to the splined shaft portion 13225. The shift disk 13235 is held by a shifter arm 13233 actuatable by a shift solenoid 13231 to move the shifter arm 13233 between a first position in which the disk 13235 is in meshing engagement with the closure drive gear 13223 and a second position in which the disk 13235 is in meshing engagement with the firing drive gear 13224. When the disk 13235 is engaged with the closure drive gear 13223, rotation of the drive coupler 13220 causes rotation of the closure drive gear 13223 and, thus, the closure shaft 13330. Similarly, when the disk 13235 is engaged with the firing drive gear 13224, rotation of the drive coupler 13220 causes rotation of the firing drive gear 13224 and, thus, the firing shaft 13340. Activating the shift solenoid 13231 may be achieved through an onboard controller 13203 configured to receive signals from the instrument interface and transmit these signals to the shift solenoid 13231.

Figure 57:
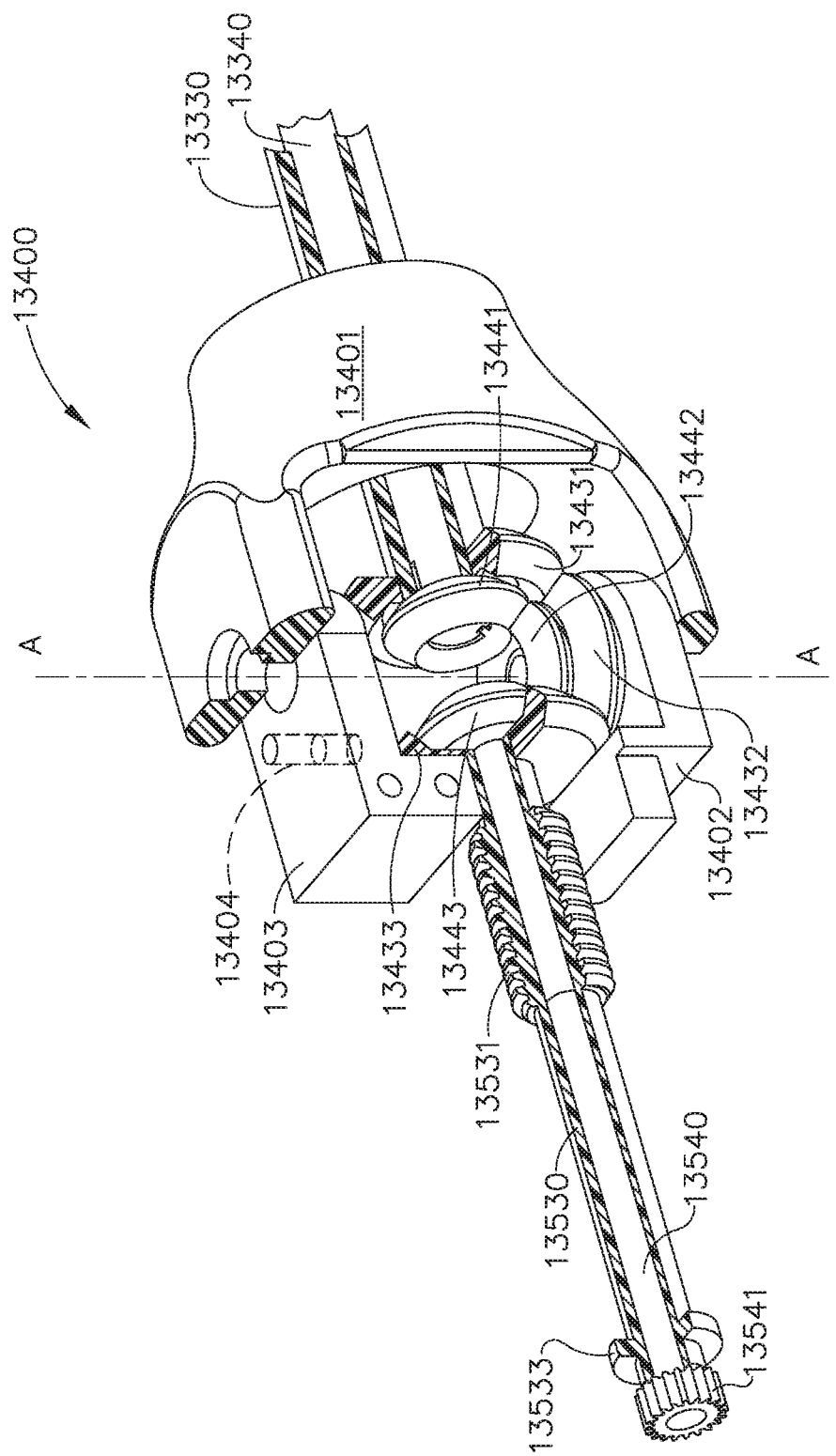
FIG. 57 is a partial cross-sectioned perspective view of the articulation joint of the instrument of FIG. 51.

Turning now to FIG. 57, the articulation joint 13400, as discussed above, is configured to receive rotary control motions from the shaft assembly 13300 and transmit, or communicate, these rotary control motions to the end effector assembly 13500. In order to transfer the rotary motion of the closure shaft 13330 of the shaft assembly 13300 to a closure shaft, or drive, 13530 of the end effector assembly 13500 and, in addition, transfer the rotary motion of the firing shaft 13340 to a firing shaft, or drive, 13540 of the end effector assembly 13500 while maintaining the ability to articulate the end effector assembly 13500 relative to the shaft assembly 13300, the articulation joint 13400 comprises an arrangement of bevel gears. The firing shaft 13340 comprises an input bevel gear 13441 attached to a distal end of the firing shaft 13340, an idler bevel gear 13442 meshed with the input bevel gear 13441, and an output bevel gear 13443 meshed with the idler bevel gear 13442 and attached to the firing shaft 13540 of the drive system of the end effector assembly 13500. The idler bevel gear 13442 has a rotation axis common to the articulation axis A-A. Further to the above, the closure shaft 13330 comprises an input bevel gear 13431 attached to a distal end of the closure shaft 13330, an idler bevel gear 13432 having a rotation axis common to the articulation axis A-A and meshed with the input bevel gear 13431, and an output bevel gear 13433 meshed with the idler bevel gear 13432 and attached to a closure shaft 13530 of the drive system of the end effector assembly 13500. The bevel gears 13441, 13442, 13443 are in a nested configuration within the bevel gears 13431, 13432, 13433 such that the (inner) firing bevel gears 13441, 13442, 13443 can rotate relative to the (outer) closure bevel gears 13431, 13432, 13433 and vice-versa.

The output bevel gears 13433, 13443 are rotatable about the articulation axis A-A. As the end effector assembly 13500 is articulated, the output bevel gears 13433, 13443 can be configured to back rotate both idler bevel gears 13432, 13442. Back rotation of the idler bevel gears 13432, 13442 will cause back rotation of the input bevel gears 13431, 13441 and thus, cause rotation of the closure shaft 13330 and the firing shaft 13340. To avoid binding in the end effector transmission while the end effector assembly 13500 is articulated, the onboard controller 13203 of the attachment portion 13200 may signal the shift solenoid 13231 to place the shift disk 13235 in a neutral position where the shift disk 13235 is not engaged with either journably supported drive gears 13223, 13224 when the user actuates the articulation drive coupler 13210. As a result, the drive gears 13223, 13224 will rotate freely relative to the input shaft therefore diffusing the rotation of bevel gear assembly due to articulation.

Figure 58:
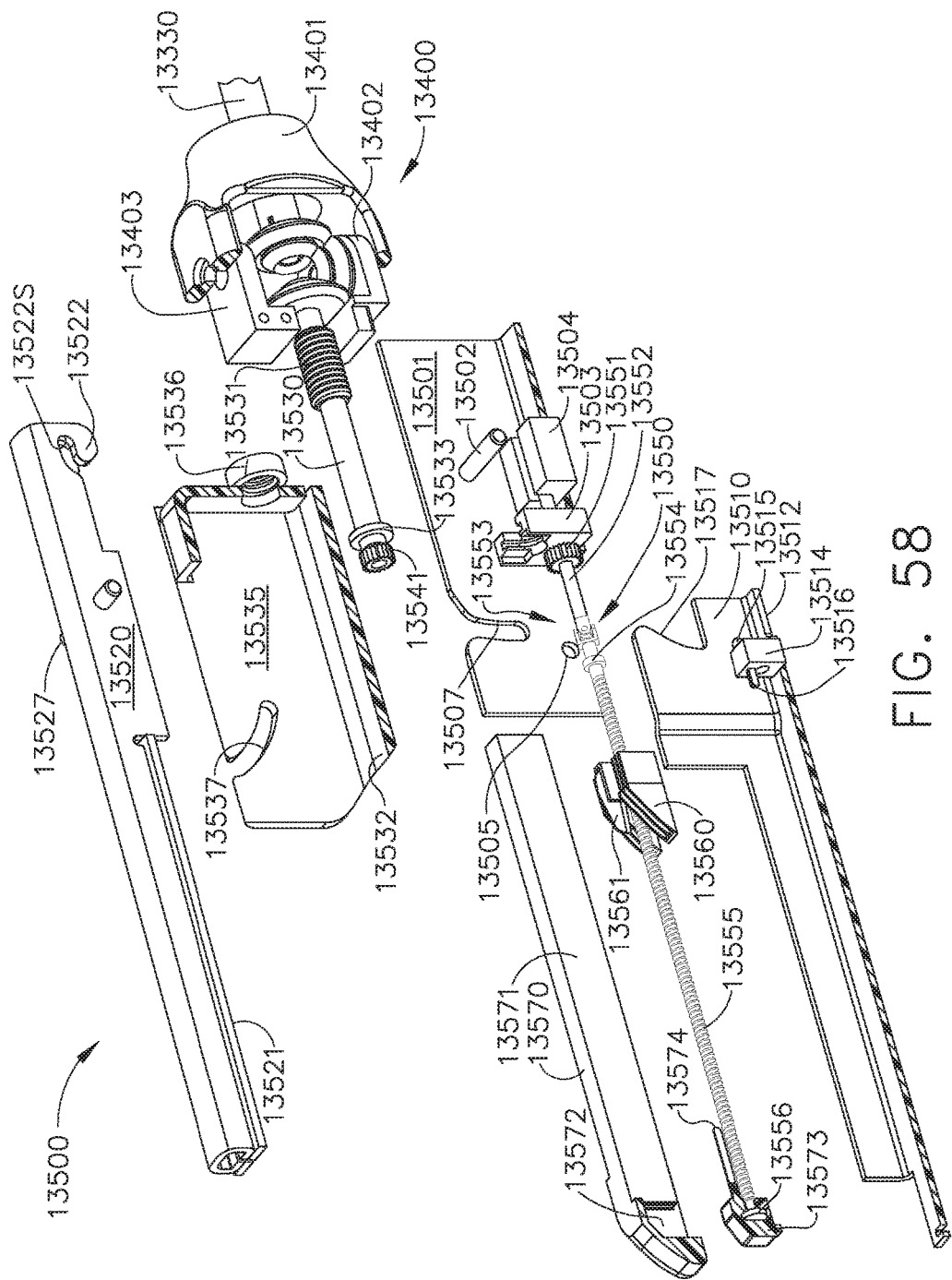
FIG. 58 is a perspective view of the articulation joint and the end effector assembly of the instrument of FIG. 51, wherein the end effector assembly comprises a pair of moveable jaws, a staple cartridge, and a drive system.
Figure 59:
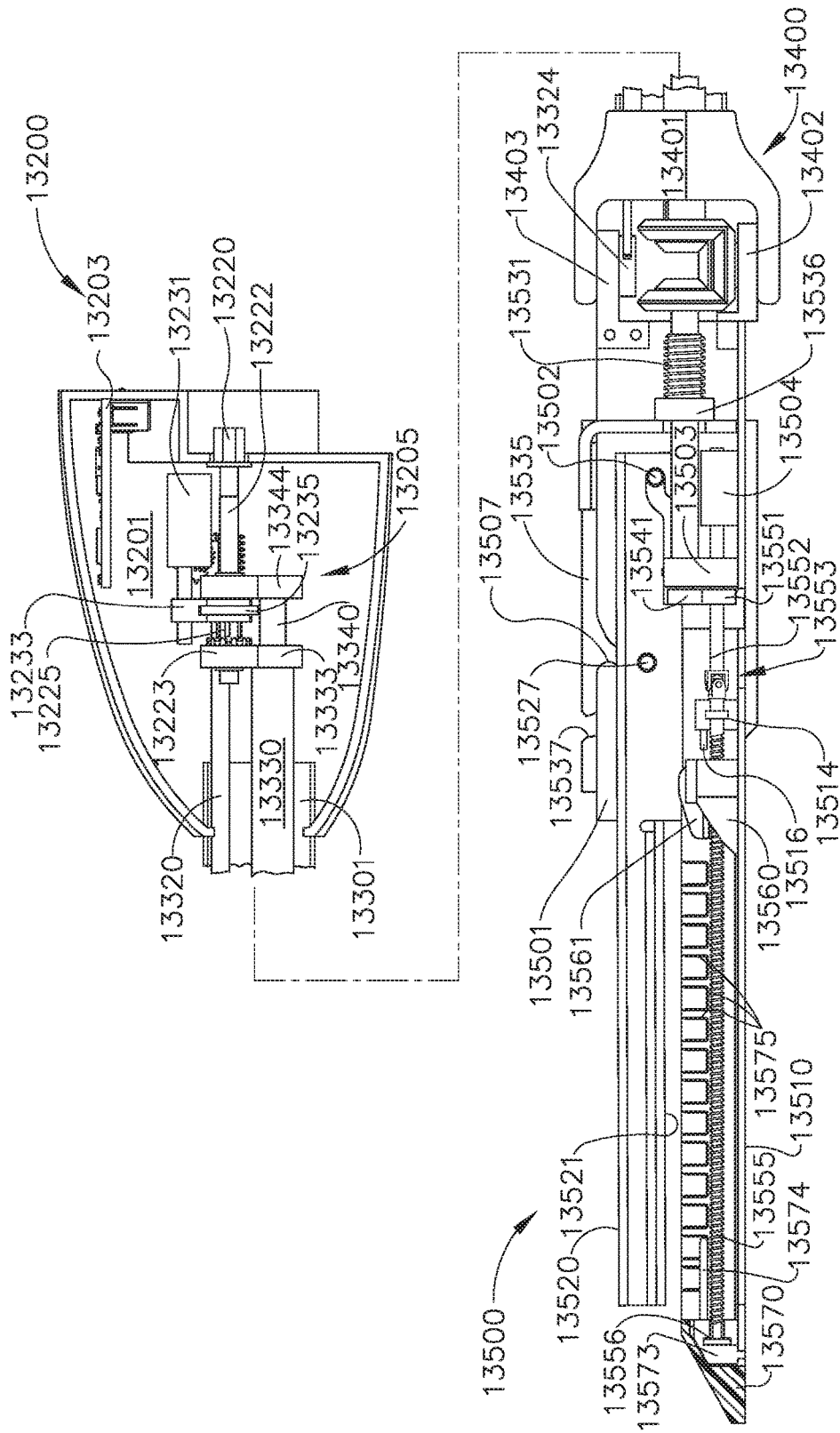
FIG. 59 is a cross-sectional elevational view of the instrument of FIG. 51 illustrated in a clamped, unfired configuration.

The end effector assembly 13500 further comprises a first jaw 13510 and a second jaw 13520 which are movable relative to one another. Turning now to FIG. 58, the end effector assembly 13500 comprises a closure system configured to move the jaws 13510, 13520 between open and closed positions. The closure system comprises a closure frame 13535 having a closure nut 13536 threadably engaged with a closure screw portion 13531 of the closure shaft 13530. The closure frame 13535 is moveable relative to the end effector frame 13501 upon actuation, or rotation, of the closure shaft 13530. Rotation of the closure shaft 13530 in a first rotational direction causes distal movement of the frame 13501. Rotation of the closure shaft 13530 in a second rotational direction opposite the first rotational direction causes proximal movement of the frame 13501. A thrust bearing 13533 positioned at a distal end of the closure shaft 13530 is supported within a frame support 13503 of the end effector frame 13501. Discussed in greater detail below, the end effector assembly 13500 also comprises a firing system 13550 actuated by a firing drive gear 13541 of the firing shaft 13540. The closure shaft 13530 and the firing shaft 13540 are configured to rotate independently of each other.

Figure 64:
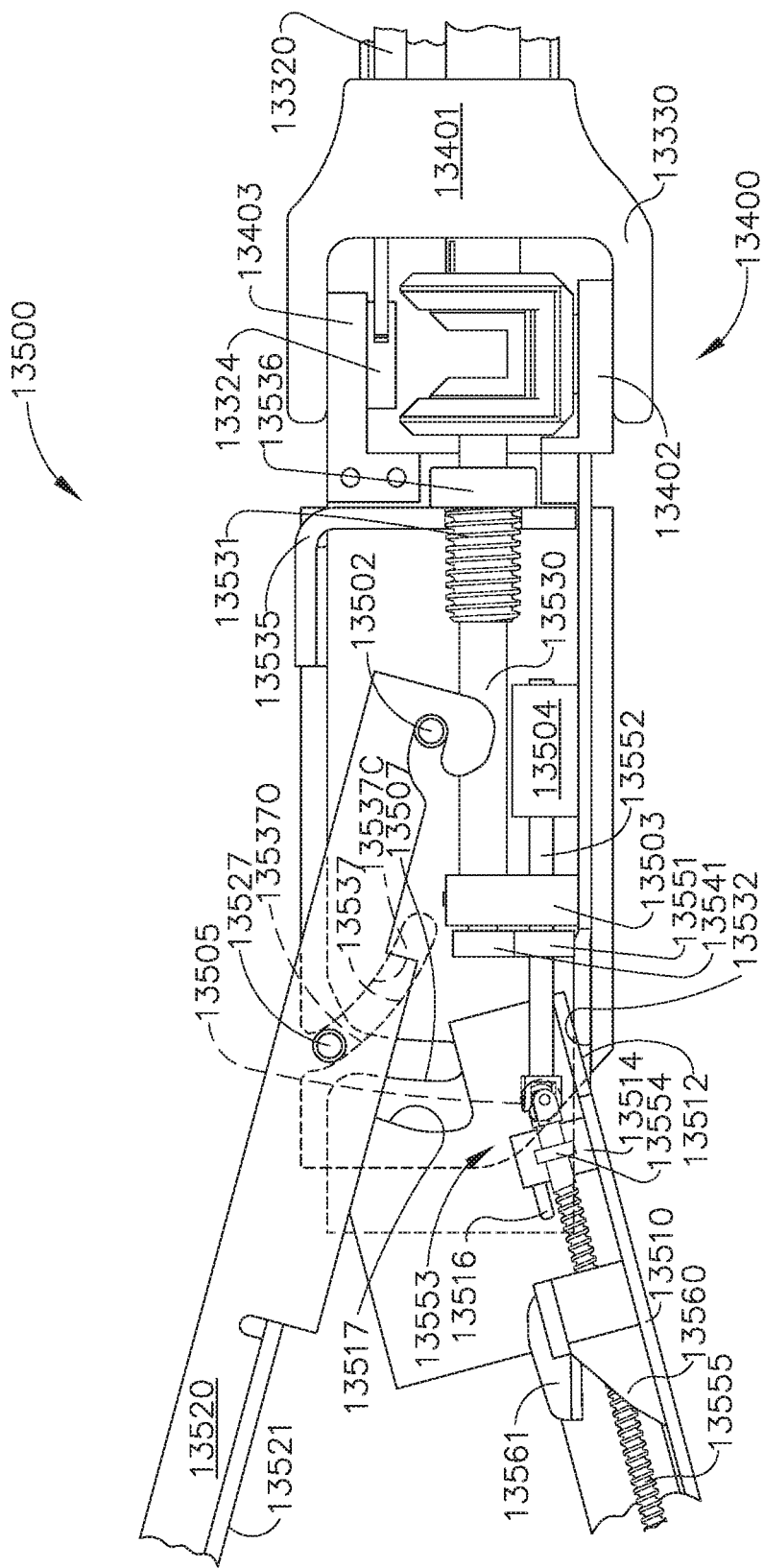
FIG. 64 is a partial, cross-sectional elevational view of the end effector assembly of the instrument of FIG. 51 illustrated in an unclamped, or open, configuration.

FIG. 64 is a partial view of the end effector assembly 13500 in an open, or unclamped, configuration. To clamp tissue with the tool assembly 13100, both jaws 13510, 13520 are moved from open positions to closed positions by actuation of the closure drive 13530. Rotation of the closure drive 13530 rotates the closure screw portion 13531. Rotation of the closure screw portion 13531 causes the closure nut 13536, and thus, the closure frame 13535 to translate relative to the end effector frame 13501. Upon fully retracting the closure frame 13535, the closure nut 13536 is configured to be received within a recess defined between the yoke arms 13402, 13403.

The end effector frame 13501 is positioned at least partially within the closure frame 13535 such that two lateral sides of the end effector frame 13501 are received within corresponding slots of the closure frame 13535. Such an arrangement permits the end effector frame 13501 to extend through the closure frame 13535 and permits the closure frame 13535 to move relative to the end effector frame 13501. The end effector assembly 13500 further comprises an anvil portion 13521 disposed on the jaw 13520 configured to form staples 13575. The jaw 13520 is at least partially positioned within the end effector frame 13501. The jaw 13520 comprises a pair of actuation pins 13527 movable within a pair of closure frame slots 13537 defined in the closure frame 13535 and a pair of end effector frame slots 13507 defined in the end effector frame 13501. The jaw 13520 further comprises a proximal hook portion 13522 comprising a pair of slots 13522S positioned therein. The proximal hook portion 13522 is configured to be hooked, or latched, on a frame pin 13502 of the end effector frame 13501. The jaw 13520 is pivotable about the frame pin 13502. The open slot configuration of the hook portion 13522 permits the jaw 13520 to be removed from the end effector assembly 13500 in the event that a user would like to replace the jaw 13520 for any reason.

The jaw 13520, grounded by and rotatable about the pin 13502, is rotated to a closed position by advancing the closure frame 13535 distally causing a pair of closure cam surfaces 13537C of the closure frame slot 13537 to cam the pins 13527 of the jaw 13520 toward the jaw 13510. The jaw 13510, grounded by the pins 13515 and rotatable about the pin axis defined by the pins 13515, is moved to a rotated position by advancing the closure frame 13535 distally causing a closure cam surface 13532 of the closure frame 13535 to cam a bottom surface 13512 of the jaw 13510 toward the jaw 13520. Similarly, the jaw 13520 is moved to an open position by moving the closure frame 13535 proximally causing a pair of opening cam surfaces 13537O (see FIG. 68) of the closure frame slot 13537 to cam the pins 13527 of the jaw 13520 upward. The end effector frame slots 13507 are clearance slots for the pins 13527 as the pins 13527 are cammed upward and downward relative to the frame 13501. The jaw 13510 is moved to an open position by moving the closure frame 13535 proximally causing the closure cam surface 13532 to be moved proximally permitting the jaw 13510 to fall open relative to the frame 13501. The jaw 13510 comprises a pair of curved recesses 13517 to provide clearance for the pins 13527.

Figure 69:
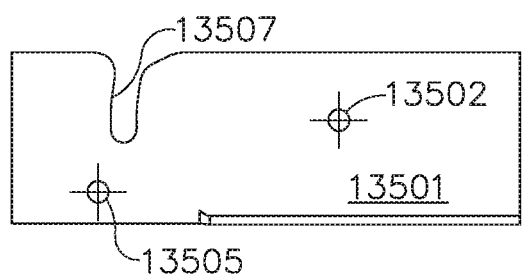
FIG. 69 is a cross-sectional elevational view of an end effector frame of the instrument of FIG. 51.

Further to the above, as can be seen in FIG. 69, the axis about which the jaw 13510 rotates and the axis about which the jaw 13520 rotates are not identical. The axes are vertically and horizontally offset from each other. The axis about which the jaw 13510 rotates is distal with respect to the axis about which the jaw 13520 rotates. The vertical distance between the axes may define a predetermined tissue gap distance and/or clamp distance between the cartridge 13570 and the anvil 13521.

When the tool assembly 13100 is in an unclamped configuration (FIG. 66), further to the above, the closure nut 13536 is in its proximal-most position which is a recess defined between the yoke arms 13402, 13403. In the unclamped configuration, a top surface of the jaw 13520 is completely exposed permitting a user of the tool assembly 13100 to remove the jaw 13520 from the instrument. This provides a readily replaceable anvil configuration.

The end effector frame 13501 supports the firing system 13550 which is configured to staple and/or cut tissue clamped with the tool assembly 13100. The firing system 13550, discussed in greater detail below, is configured to be actuated by the firing drive gear 13541 of the firing shaft 13540. The jaw, or cartridge support channel, 13510 comprises a pair pivot pins 13515 extending outwardly with respect to the jaw 13510 configured to be received within a pair of corresponding frame apertures 13505 permitting the jaw 13510, and as a result, the staple cartridge 13570 to pivot about a pivot axis defined by the pins 13515 relative to the end effector frame 13501.

The firing system 13550 comprises a drive gear 13551 meshed with the firing drive gear 13541. The drive gear 13551 is positioned on a proximal firing shaft 13552 which is rotatably supported by a frame support 13504 of the end effector frame 13501. The firing system 13550 further comprises a firing screw shaft 13555 comprising a proximal thrust bearing 13554 supported within a thrust bearing support 13514 of the jaw 13510 and a distal thrust bearing 13556 supported within a top and bottom bushing assembly 13573. The bushing assembly 13573 is positioned within a distal cartridge cavity 13572. The firing system 13550 further comprises a U-joint 13553 operably coupling the firing shaft 13552 and the firing screw shaft 13555. The U-joint 13553 permits the jaw 13510 to be rotated about the pivot axis defined by the pins 13515 while maintaining a driving relationship between the proximal firing shaft 13552 and the firing screw shaft 13555. In various instances, the U-joint 13553 is positioned at the axis defined by the pivot pins 13515; however, the U-joint 13553 may be located at any suitable location.

The firing system 13550 further comprises a firing member, or sled, 13560. The sled 13560 comprises a threaded aperture extending therethrough which is threadably engaged with the firing screw shaft 13555. The sled 13560 is constrained from rotating, or at least substantially rotating, with the firing screw shaft 13555 and, as a result, the firing screw shaft 13555 displaces the sled 13560 longitudinally when the firing screw shaft 13555 is rotated about its longitudinal axis. In use, the sled 13560 is displaced distally when the firing screw shaft 13555 is rotated in a first direction and displaced proximally when the firing screw shaft 13555 is rotated in a second direction.

Figure 61:
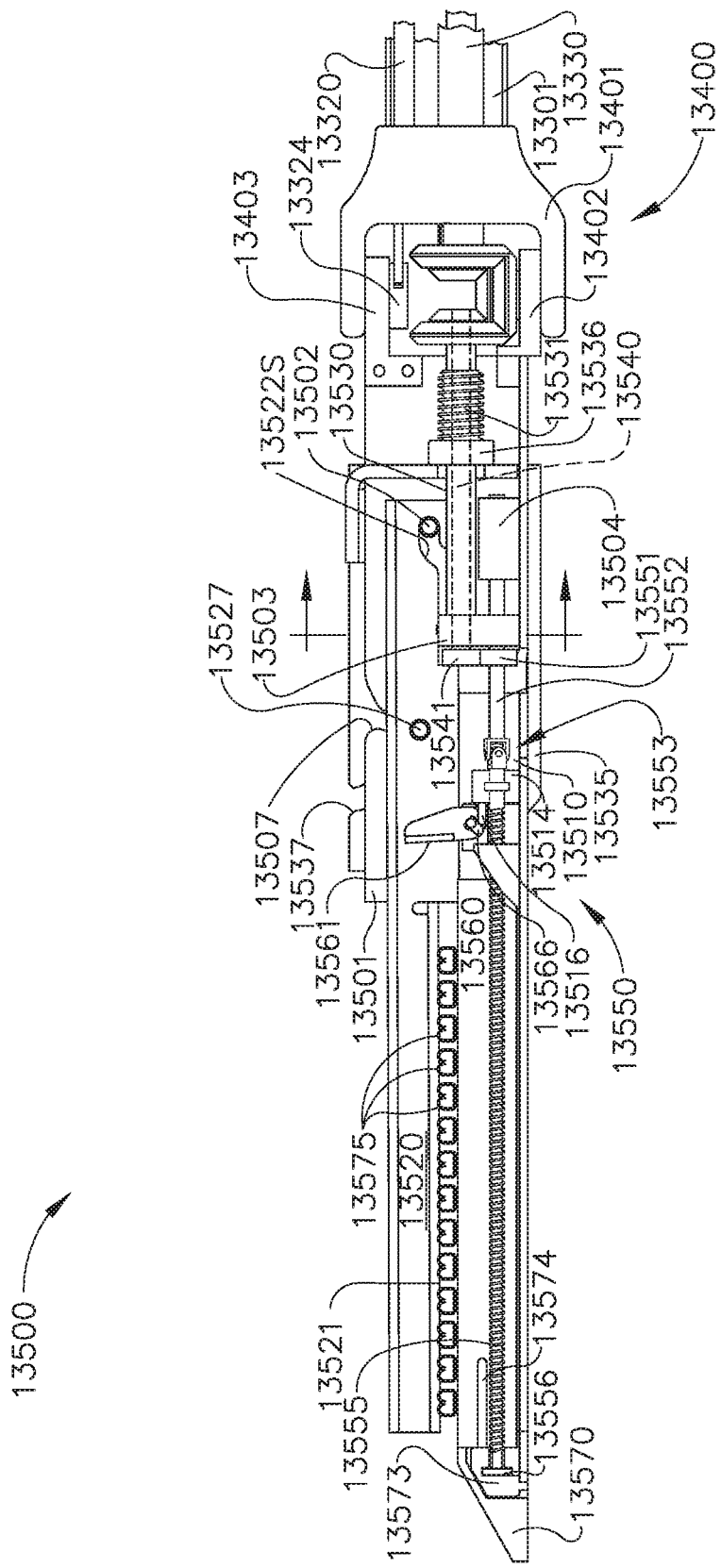
FIG. 61 is a cross-sectional elevational view of the end effector assembly of the instrument of FIG. 51 illustrated in a retracted configuration.
Figures 62, 63:
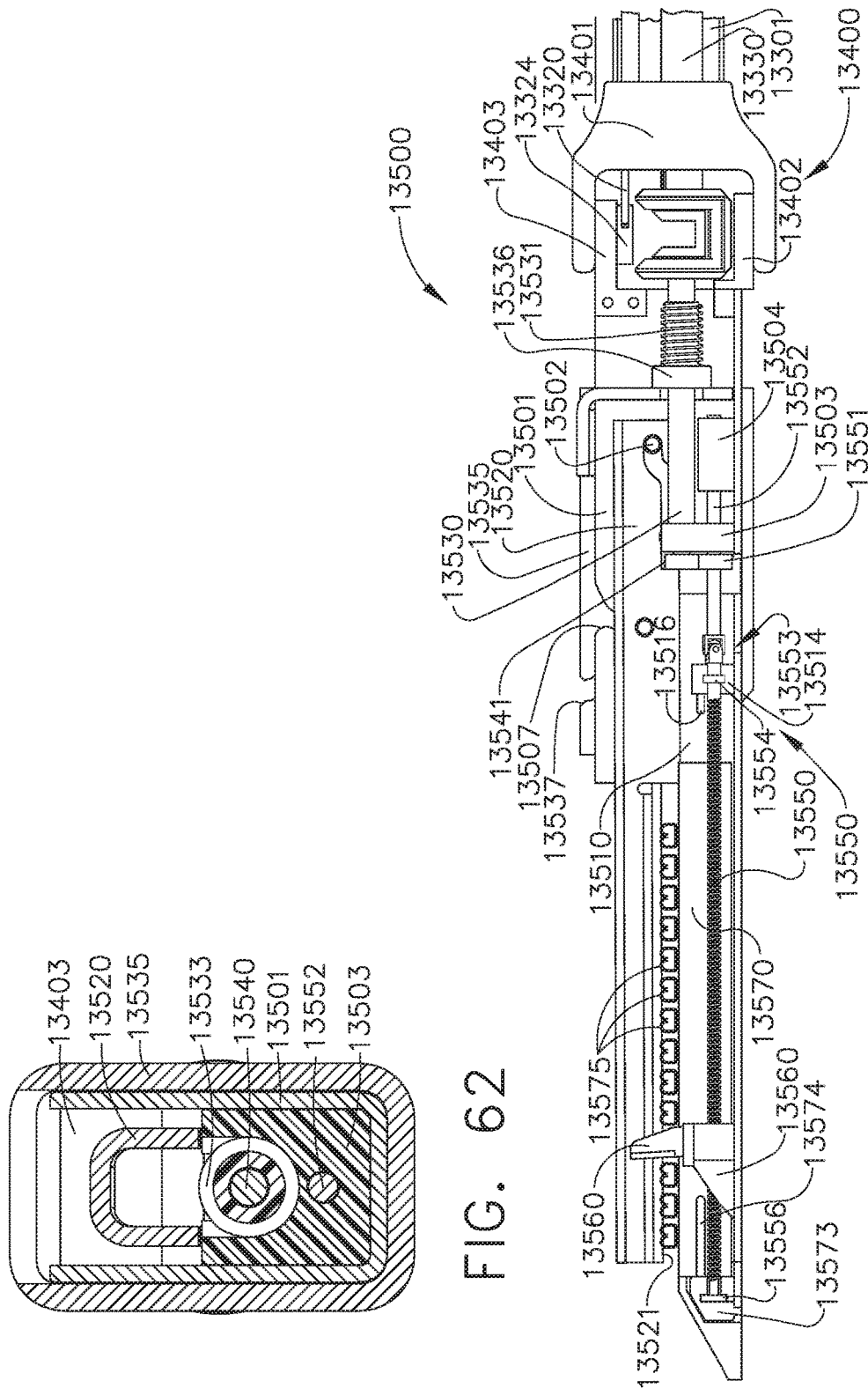
FIG. 62 is a cross-sectional elevational view of the end effector assembly of the instrument of FIG. 51 taken along line 62-62 in FIG. 61.
FIG. 63 is a cross-sectional elevational view of the end effector assembly of the instrument of FIG. 51 illustrated in a clamped, fully stapled, partially cut configuration.

As described in greater detail below, the sled 13560 is displaced distally between an unfired position (FIG. 59) and a fired position (FIG. 60) during a staple firing stroke to eject the staples 13575 from the staple cartridge 13570 and staple the tissue captured between the anvil portion 13521 and the staple cartridge 13570. The reader should appreciate from FIGS. 59 and 60 that the tissue is not cut while it is stapled. More specifically, the sled 13560 comprises a knife, or cutting member, 13561 which remains in an undeployed, or lowered, position during the staple firing stroke. After the staple firing stroke has been completed, referring now to FIG. 61, the sled 13560 is retracted proximally. The sled 13560 is retracted proximally until the cutting member 13561 contacts a pin, or cam, 13516 extending from the frame of the staple cartridge 13570. The cutting member 13561 is rotatably mounted to the sled 13560 and, when the cutting member 13561 contacts the pin 13516, the cutting member 13561 rotates upwardly into a deployed position. At such point, the sled 13560 can be advanced distally once again to cut the stapled tissue during a cutting stroke, as illustrated in FIG. 63.

The cutting member 13561 moves within a longitudinal slot 13571 defined in the staple cartridge 13570. The pin 13516 extends from the thrust bearing support 13514 and is aligned with the longitudinal slot 13571. When the sled 13560 is in its unfired position (FIG. 59), the cutting member 13561 is not in contact with the pin 13516; however, when the sled 13560 is retracted proximally relative to its unfired position, as illustrated in FIG. 61, the cutting member 13561 contacts the pin 13516 and is rotated into its deployed position. More specifically, a cam arm 13566 of the cutting member 13561 engages the pin 13516 and rotates upwardly from its non-cutting position to its cutting position.

As discussed above, FIG. 59 illustrates the tool assembly 13100 in an unfired, or initial, configuration. In such an unfired configuration of the tool assembly 13100, as also discussed above, the sled 13560 is in its unfired position and the cutting member 13561 in its non-cutting position. The tool assembly 13100 can be configured to detect whether the sled 13560 is in its unfired position and/or whether the cutting member 13561 is in its non-cutting position. In at least one instance, the staple cartridge 13570 can comprise a first sensor configured to detect the presence of the sled 13560 if the sled 13560 is in its unfired position. Similarly, the staple cartridge 13570 can comprise a second sensor configured to detect the presence of the cutting member 13561 if the cutting member 13561 is in its cutting position. The first sensor and the second sensor can comprise proximity sensors, for example, and can be in signal communication with a controller of the tool assembly 13100.

Figure 60:
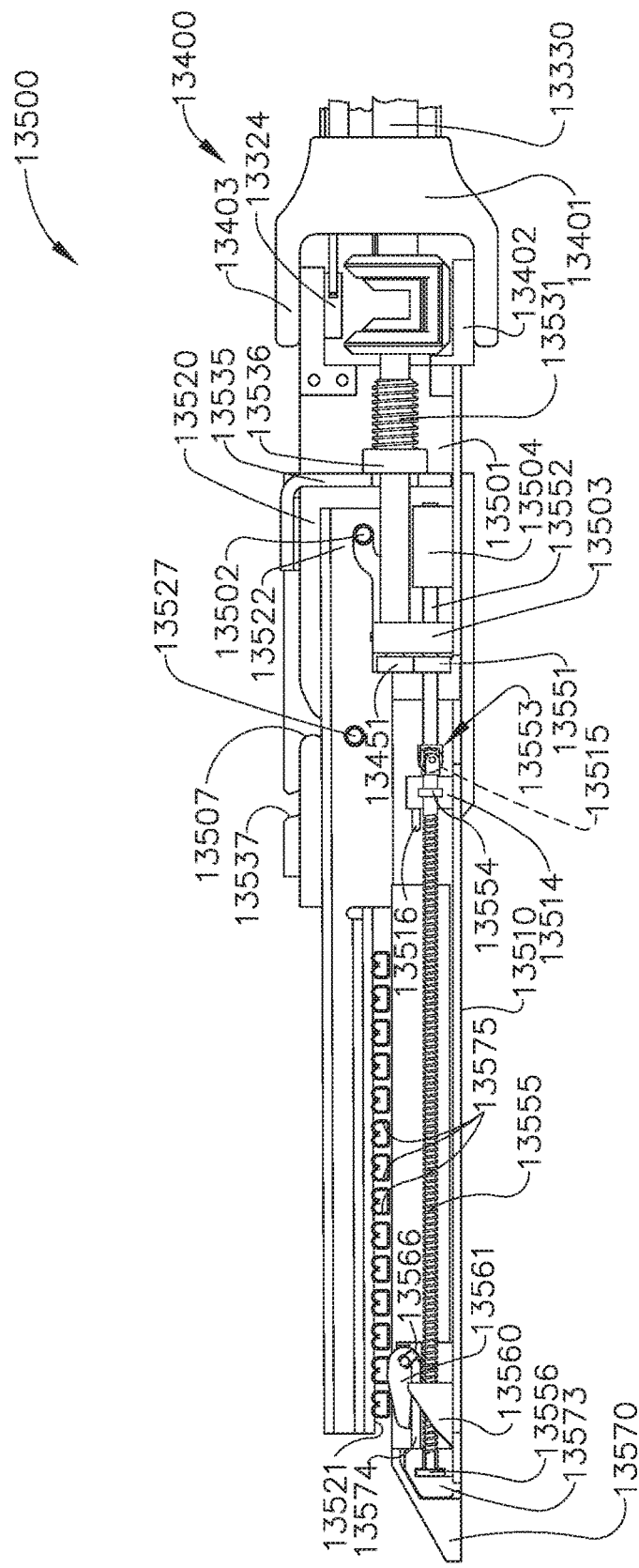
FIG. 60 is a cross-sectional elevational view of the end effector assembly of the instrument of FIG. 51 illustrated in a clamped, fully stapled configuration.

When the sled 13560 reaches its distal-most position of its firing stroke, as illustrated in FIG. 60, all of the staples 13575 will have been deployed from the staple cartridge 13570. In various instances, a sensor is disposed at a distal end of the end effector assembly which is configured to detect whether the sled 13560 has reached its distal-most position. The sensor may comprise a proximity sensor, for example, in signal communication with a controller of the tool assembly 13100. Once all of the staples 13575 have been fired, the instrument controller can signal to the user that the firing stroke has been completed. At such point, the user can operate the tool assembly 13100 to retract the sled 13560 in order to prepare the tool assembly 13100 for the cutting portion of the procedure. Alternatively, the tool assembly 13100 can be configured to automatically retract the sled 13560 after the firing stroke has been completed.

As discussed above, FIG. 61 illustrates the tool assembly 13100 in a configuration in which all of the staples have been fired and the firing member has been retracted to a proximal-most, or mode-switching, position. As also discussed above, this mode-switching position permits the pin 13516 to engage the cam arm 13566 of the cutting member 13561 and rotate the cutting member 13561 to its cutting position. In various instances, the sled 13560 may be prevented from reaching this mode-switching position until the instrument controller has received a signal that the staple firing stroke has been completed. In at least one such instance, the instrument controller can interrupt the electrical power supply to the motor of the firing drive once the sled 13560 has reached its unfired position in the event that the instrument controller does not receive a signal from the end-of-firing-stroke sensor confirming that the firing stroke was completed. In the event that the instrument controller receives a signal that the staple firing stroke has been completed, the instrument controller can permit the sled 13560 to be retracted proximally beyond its unfired position into its mode-switching position.

Once the sled 13560 has been moved into the mode-switching position, the instrument controller can permit the sled 13560 to be advanced distally once again. In various instances, the instrument can comprise a tissue-cutting switch which, when depressed, can actuate the firing drive 13540 once again to drive the sled 13560 through the staple cartridge 13570 through a second, or cutting, stroke. As the cutting member 13561 has now been raised into its cutting position, the cutting member 13561 will incise the stapled tissue.

Further to the above, the tool assembly 13100 is configured to lower the cutting member 13561 to its non-cutting position after the sled 13560 has completed its tissue cutting stroke. More specifically, referring primarily to FIG. 63, the cam portion 13566 of the cutting member 13561 is configured to contact a distal pin, or cam, 13574 at the end of the tissue cutting stroke wherein such interaction rotates the cutting member 13561 downwardly into its noncutting position. As a result, the sled 13560 can be retracted without the cutting member 13561 being exposed to the tissue. Also, as a result, the jaws 13510, 13520 can be unclamped from the tissue after the cutting stroke without the cutting member 13561 being exposed. The reader should appreciate that the cutting member 13561 does not interact with the distal pin 13574 at the end of the firing stroke because the cutting member 13561 is already in its lowered position during the firing stroke.

As outlined above, the tool assembly 13100 is configured to prohibit the cutting of tissue clamped by the tool assembly 13100 until all of the staples 13575 have been fired, or fully formed. As also outlined above, this bifurcation of functions is possible as the cutting member 13561 is pivotable between a non-cutting position and a cutting position.

FIG. 70 is a perspective view of a portion of a staple cartridge 4410 for use with a circular surgical stapling instrument in accordance with at least one embodiment. A variety of circular surgical stapling instruments are known. For example, U.S. patent application Ser. No. 14/836,110, filed Aug. 26, 2015, entitled SURGICAL STAPLING CONFIGURATIONS FOR CURVED AND CIRCULAR STAPLING INSTRUMENTS, which is hereby incorporated by reference in its entirety, discloses various circular surgical stapling instrument arrangements. U.S. patent application Ser. No. 14/498,070, filed Sep. 26, 2014, entitled CIRCULAR FASTENER CARTRIDGES FOR APPLYING RADIALLY EXPANDING FASTENER LINES, the entire disclosure of which is hereby incorporated by reference herein also discloses various circular surgical stapler arrangements. As discussed in those references, a circular surgical stapler generally comprises a frame assembly that comprises an attachment portion that is configured to operably couple an anvil to the circular surgical stapler.

In general, the anvil includes an anvil head that supports an annular line or lines of staple-forming pockets. An anvil stem or trocar portion is attached to the anvil head and is configured to be removably coupled to the anvil attachment portion of the circular stapling instrument. Various circular surgical stapling instruments include means for selectively moving the anvil toward and away from the surgical staple cartridge such that the target tissue may be clamped between the anvil and the deck of the surgical staple cartridge. The surgical staple cartridge removably stores a plurality of surgical staples therein that are arranged in one or more annular arrays that correspond to the arrangement of staple forming pockets provided in the anvil. The staples are removably stored within corresponding staple cavities that are formed in the staple cartridge and are supported on corresponding portions of a selectively movable pusher assembly that is operably received within the circular stapler. The circular stapler further includes an annular knife or cutting member that is configured to incise the tissue that is clamped between the anvil and the staple cartridge.

Referring again to FIG. 70, the staple cartridge 4410 comprises a cartridge body 4411 that defines an annular cartridge deck surface 4412. The cartridge body 4411 comprises an inner annular row 4420 of spaced inner staple cavities 4422 and an outer annular row 4440 of spaced outer staple cavities 4442. The inner staple cavities 4422 are staggered relative to the outer spaced staple cavities 4442 as can be seen in FIG. 70. Supported within each inner staple cavity 4422 is an inner surgical staple 4430 and supported within each outer staple cavity 4442 is an outer surgical staple 4450. The outer staples 4450 in the outer annular row 4440 may have different characteristics than the inner staples 4430 in the inner annular row 4420. For example, as illustrated in the embodiment of FIG. 71, the outer staples 4450 have an unformed "gullwing" configuration. In particular, each outer staple 4450 includes a pair of legs 4454, 4464 that extend from a staple crown 4452. Each leg 4454, 4464 includes a vertical portion 4456, 4466, respectively that extends from the crown 4452. The vertical portions 4456, 4466 may be parallel to each other in one embodiment. However, in the illustrated arrangement, the vertical portions 4456, 4466 are not parallel to each other. For example, the angle $A_1$ between the crown 4452 and the vertical portions 4456, 4466 in the illustrated arrangement is greater than ninety degrees. See FIG. 71. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, the entire disclosure of which is hereby incorporated by reference herein. However, other the vertical portions 4456, 4466 may be arranged at other angles with respect to the crown 4452. One advantage of having the vertical leg portions 4456, 4466 oriented at angles greater than ninety degrees relative to the crown 4452 is that such arrangement may assist in the temporary retention of the staple within its corresponding staple cavity.

At least one leg 4454, 4464 includes an inwardly extending end portion. In the embodiment depicted in FIG. 71 for example, each leg 4454, 4464 includes an inwardly extending leg portion. In the illustrated arrangement, leg portion 4458 extends inwardly from the vertical leg portion 4456 and the leg portion 4468 extends inwardly from the vertical leg portion 4466. As can be seen in FIG. 71, the leg portion 4458 is shorter than the leg portion 4468. Stated another way, the distance $H_A$ between the staple crown 4452 and the point where the leg portion 4458 angles inward from the vertical leg portion 4456 is greater than the distance $H_C$ between the staple crown 4452 and the point where the leg portion 4468 angles inward from the vertical leg portion 4466. Thus, distance $H_B$ in at least one embodiment is shorter than the length $H_D$. The angle $A_2$ at which the leg portion 4458 angles relative to the vertical leg portion 4556 may be equal to the angle $A_3$ at which the leg portion 4468 angles relative to the vertical leg portion 4466 or angles $A_2$ and $A_3$ may be different from each other. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, which has been herein incorporated by reference.

In at least one embodiment, each inner surgical staple 4430 may have the configuration illustrated in FIG. 71. As can be seen in FIG. 71, the inner surgical staple 4430 has a crown 4432 and two vertical legs 4434, 4436 extending therefrom. The vertical legs 4434, 4436 may extend relatively perpendicularly from the crown 4432 or they may extend at angles $A_4$ that may be greater than ninety degrees. Such arrangement may assist in the temporary retention of the staples 4430 within their corresponding staple cavity 4422. However, vertical legs 4434, 4436 may extend from the crown 4432 at different angles. In some embodiments, angles $A_4$ are equal to each other. In other embodiments, angles $A_4$ are different from each other. In the illustrated embodiment, the inner staples 4430 and the outer staples 4450 each have the same unformed height UFH. The inner and outer staples 4430, 4450 are formed from conventional surgical staple wire. In at least one embodiment, the diameter of the staple wire used to form the outer staples 4450 is greater than the diameter of the staple wire used to form the inner staples 4430. In other embodiments, the inner and outer staples may have the same diameters and be formed from wires with other diameters. In some arrangements, the inner and outer staples may be formed from the same type of staple wire. Thus, in such arrangement, the wire diameters of the inner and outer staples would be the same. In yet another embodiment, however, the inner and outer staples may have the same unformed shapes/configurations, yet be formed from two different staple wires that have different wire diameters. Also in at least one arrangement, the crown width $CW_O$ of each outer staple 4450 is larger than the crown width $CW_I$ of each inner staple 4430. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, which has been herein incorporated by reference.

Returning to FIG. 70, the staple cartridge 4410 includes an outer rim 4414 that extends above the deck surface 4412. During surgery, the clinician can adjust the location of the anvil relative to the cartridge of a circular stapler. In at least one such embodiment, the staple cartridge 4410 further comprises deck features 4416 and 4418 that extend from the deck surface 4412. As can be seen in FIG. 70, a series of inner deck features 4416 are provided between the inner row 4420 of staple cavities 4422 and a centrally-disposed knife opening 4413 through which the knife or cutting member will pass during the firing process. The deck features 4416 may be shaped and located relative to the inner staple cavities and opening 4413 as shown in FIGS. 70, 72 and 73. For example, each inner deck feature 4416 may have a flat wall portion 4415 that is coextensive with the wall of the knife opening 4413 and a conical or sloping body portion 4417 that is adjacent to the row of inner staple cavities 4422. See FIGS. 72 and 73. In the embodiment depicted in FIG. 70, the deck features 4416 are oriented in the gap between two adjacent inner staple cavities 4422 and are staggered between pairs of staple cavities 4422 as shown. The cavity extension arrangements or deck features in this system may serve to lower pressure that is commonly encountered in flat deck cartridges. This disclosed arrangement may also help to mitigate tissue movement and slippage. Since slippage of the tissue is generally undesirable, the outside diameter holding features may be bigger and more numerous. The internal diameter features may serve to increase tissue tension/shear as the blade passes next to the inside internal diameter which may make the system cut better. However, the deck features 4416 may have different shapes and configurations and may be located in different locations on the deck surface 4412.

As can also be seen in FIGS. 70, 72 and 73, every other outer staple cavity 4442 includes an outer deck feature 4418 that is associated with each end thereof. Outer deck features 4418 extend above the deck surface 4412 and guide the outer staples 4450 toward the anvil when the staples 4450 are being ejected from the staple cartridge 4410. In such embodiments, the outer staples 4450 may not extend above the outer deck features 4418 until they are moved toward the anvil by the firing member. Referring primarily to FIG. 70, in at least one embodiment, the outer deck features 4418 do not extend around the entirety of the corresponding outer staple cavity 4442. A first outer deck feature 4418 is positioned adjacent a first end of a corresponding outer cavity 4442 and a second outer deck feature 4418 is positioned adjacent a second end of the outer cavity 4442. As can be seen in FIG. 70, the outer deck features 4418 are associated with every other one of the outer staple cavities 4442. Such arrangement may serve to lower overall pressure and minimize tissue stretch and movement. In other embodiments, first and second outer deck features 4418 may be associated with every one of the outer staple cavities 4442, however. In yet other embodiments, an outer deck feature may extend around the entire perimeter of a corresponding outer cavity. As can be seen in FIG. 72, the inner deck features 4416 are shorter than the outer deck features 4418. Stated another way, each inner deck feature protrudes above the deck surface 4412 a distance that is less than the distance that each outer deck feature 4418 protrudes above the deck surface 4412. Each outer deck feature may protrude above the deck surface 4412 the same distance that the outer rim 4414 protrudes above the deck surface 4412. In addition, as can also be seen in FIG. 72, each outer deck feature 4418 has a generally conical or tapered outer profile which may help to prevent tissue from snagging on the deck features during insertion of the stapler head through a patient's colon and rectum.

The above-mentioned deck feature arrangements may provide one or more advantages. For example, the upstanding outer rim may help to prevent tissue from sliding across the cartridge deck. This upstanding rim could also comprise a repeating pattern of highs and lows rather than being one continuous lip formation. The inside upstanding features may also help to retain the tissue adjacent to the blade and lead to improved cutting. The inside deck features could be between every cavity or in alternative arrangements, the deck feature(s) may comprise one continuous upstanding lip. It may be desirable to balance the number of deck features to minimize the number of high force/compression zones while attaining a desired amount of tissue immobilization. The cavity concentric features may serve the additional purpose of minimization of tissue flow in the areas where the staple legs project from. Such arrangements also facilitate desirable staple formation as the staple legs eject and transition to the receiving anvil pocket which may consist of corresponding forming pockets. Such localized pocket features increase the low compression zones while facilitating leg support from the cartridge as the staple exits the cartridge. This arrangement thereby minimizes the distance that the staple must "jump" before it meets the anvil pocket. Tissue flow tends to increase going from the center of the cartridge radially outward.

FIGS. 72 and 73 illustrate use of the surgical staple cartridge 4410 in connection with an anvil 4480. The anvil 4480 comprises an anvil head portion 4482 that operably supports a staple forming insert or portion 4484 and a knife washer 4490. The knife washer 4490 is supported in confronting relationship to the knife 4492 that is supported in the stapler head. In the illustrated embodiment, the staple forming insert 4484 is fabricated from, for example, steel, stainless steel, etc. and contains an inner row of inner staple forming pockets 4486 and an outer row of outer staple forming pockets 4488. Each inner staple forming pocket 4486 corresponds to one of the inner staple cavities 4422 and each outer staple forming pocket 4488 corresponds to one of the outer staple cavities 4442. In the illustrated arrangement, when the anvil 4480 is moved to its firing position relative to the cartridge deck surface 4412, the inner staple forming pockets 4486 are closer to the cartridge deck surface 4412 than are the outer staple forming pockets 4488. Stated another way, the first gap $g_1$ or first staple forming distance between a first staple forming portion 4485 and the cartridge deck surface 4412 is less than the second gap $g_2$ or second staple forming distance between a second staple forming portion 4487 and the cartridge deck surface 4412.

As can be further seen in FIGS. 72 and 73, the inner staples 4430 are each supported within their corresponding inner staple cavity 4422 on a corresponding inner driver portion 4502 of a pusher assembly 4500 and each of the outer staples 4450 are supported within their corresponding outer staple cavity 4442 on a corresponding outer driver portion 4504. Advancement of the pusher assembly 4500 toward the anvil 4480 will cause the inner and outer staples 4430, 4450 to be driven into forming contact with their respective corresponding staple forming pockets 4486, 4488 as shown in FIG. 73. In addition, the knife 4492 is advanced distally through the tissue that is clamped between the anvil 4480 and the deck surface 4412 and through a frangible bottom 4491 of the knife washer 4490. Such arrangement serves to provide the outer staples 4450 with a formed height $FH_O$ that is larger than the formed height $FH_I$ of the inner staples 4430. Stated another way, the outer row 4440 of outer staples 4450 are formed into a larger "B" formation resulting in a greater capture volume and/or taller staple forming height to alleviate high tissue compression near the outer row of staples 4440. A larger B formation may also improve blood flow toward the inner rows. In various instances, the outer row 4440 of outer staples 4450 comprise a greater resistance to unfolding by utilizing a larger staple crown, staple leg widths, and/or staple leg thicknesses.

The quantity of staples used in each row of staples can vary. In one embodiment, for example, there are more outer staples 4450 than there are inner staples 4430. Another embodiment employs more inner staples 4430 than outer staples 4450. In various instances, the wire diameter of the outer staples 4450 is larger than the wire diameter of the inner staples 4430. The inner and outer staples 4430, 4450 may have the same unformed heights UFH. The crown widths $CW_O$ in the outer row 4440 of outer staples 4450 are larger than the crown widths $CW_I$ of the inner row 4420 of inner staples 4430. The gullwing configuration of the outer staples 4450 employs bends that are located at different distances from their respective crown. Use of the stepped anvil configuration with a flat (unstepped) cartridge deck surface 4412 with uniform driver or pusher travel yield staples with different formed heights.

Figure 74:
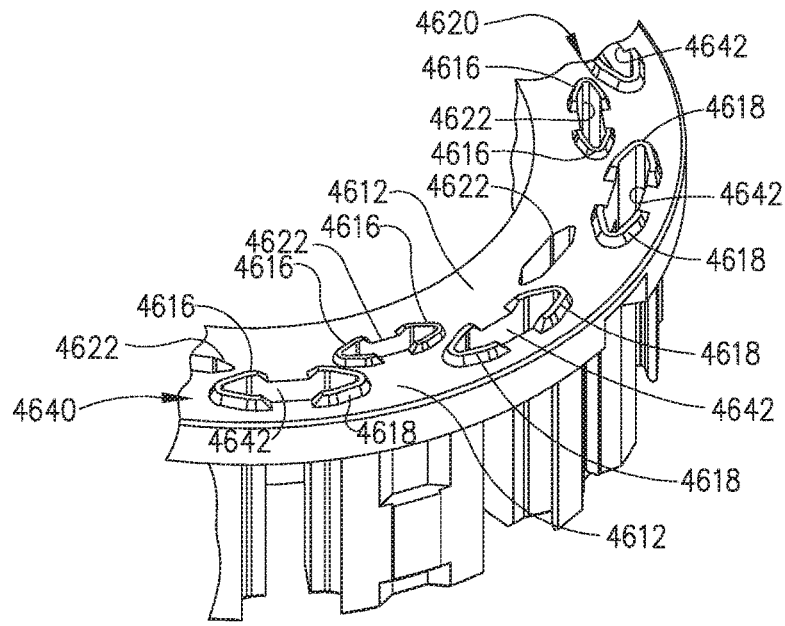
FIG. 74 is a perspective view of a portion of a surgical staple cartridge for use with a circular surgical stapling instrument in accordance with at least one embodiment.

FIG. 74 illustrates another staple cartridge embodiment 4610. As can be seen in FIG. 74, the staple cartridge 4610 includes a cartridge deck 4612 that includes an inner annular row 4620 of spaced inner staple cavities 4622 and an outer annular row 4640 of outer spaced staple cavities 4642. The inner staple cavities 4622 are staggered relative to the outer spaced staple cavities 4642 as can be seen in FIG. 74. Supported within each inner staple cavity 4622 is an inner surgical staple 4630 and supported within each outer staple cavity 4642 is an outer surgical staple 4650. In addition, an outer rim 4614 extends above the deck surface 4612. In various embodiments, further to the above, the staples 4630, 4650 do not protrude above the deck surface 4612 until they are moved toward the anvil by the firing member. Such embodiments may frequently utilize small staples relative to the depth of their respective staple cavity in which they are stored. In other embodiments, the legs of the staples protrude above the deck surface 4612 when the staples are in their unfired positions. In at least one such embodiment, the staple cartridge 4610 further comprises deck features 4616 and 4618 that extend from the deck surface 4612.

As can also be seen in FIG. 74, every other inner staple cavity 4622 includes an inner deck feature 4616 that is associated with each end thereof. Inner deck features 4616 extend above the deck surface 4612 and guide the corresponding inner staples 4630 toward the anvil when the corresponding inner staples 4630 are being ejected from the staple cartridge 4610. In such embodiments, the inner staples 4630 may not extend above the inner deck features 4616 until they are moved toward the anvil by the firing member. In the illustrated example, the inner deck features 4616 do not extend around the entirety of the corresponding inner staple cavity 4622. A first inner deck feature 4616 is positioned adjacent a first end of a corresponding inner cavity 4622 and a second inner deck feature 4616 is positioned adjacent a second end of the inner cavity 4622. In other embodiments, the inner deck features 4416 may be associated with every one of the inner staple cavities 4622, however. In yet other embodiments, an inner deck feature may extend around the entire perimeter of a corresponding inner staple cavity. By employing deck features that have different heights in concentric patterns wherein they are associated with every other cavity may provide more lower pressure tissue gap areas, while balancing them with the desire to guide as many and as much of the staple leg for as long as possible. Stated another way, such arrangement may minimize the amount of tissue flow reducing the overall amount of pressure applied to the target tissue.

Figure 75:
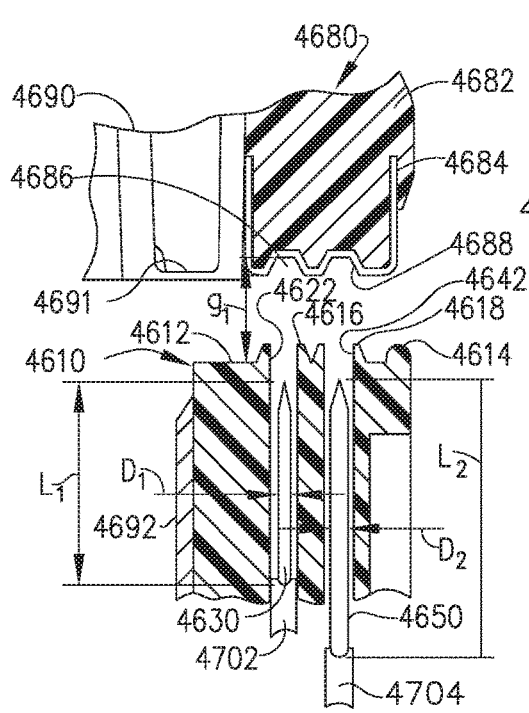
FIG. 75 is a cross-sectional view of a portion of an anvil in relation to a portion of the surgical staple cartridge of FIG. 74 prior to actuation of the staple forming process.
Figure 76:
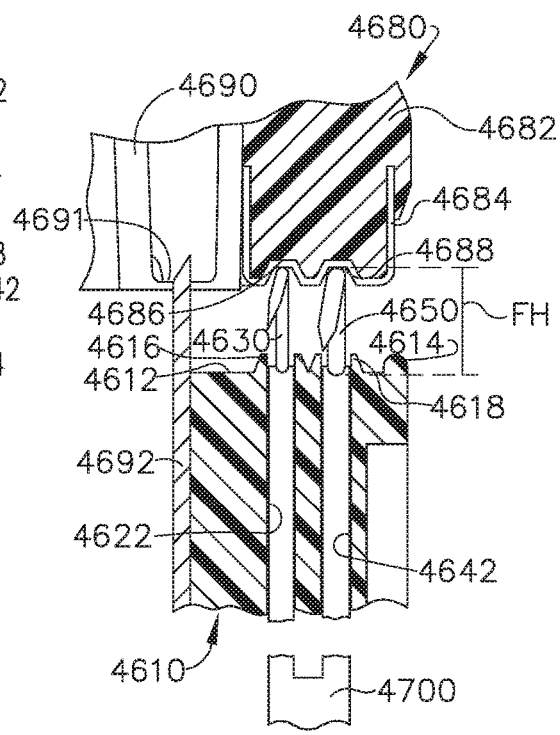
FIG. 76 is another cross-sectional view of the anvil and staple cartridge of FIG. 75 after the staples have been formed.

Still referring to FIG. 74, each outer staple cavity 4642 includes an outer deck feature 4618 that is associated with each end thereof. Outer deck features 4618 extend above the deck surface 4612 and guide the outer staples 4650 toward the anvil when the staples 4650 are being ejected from the staple cartridge 4610. In such embodiments, the outer staples 4650 may not extend above the outer deck features 4618 until they are moved toward the anvil by the firing member. As can be seen in FIG. 74, in the illustrated example, the outer deck features 4618 do not extend around the entirety of the corresponding outer staple cavity 4642. A first outer deck feature 4618 is positioned adjacent a first end of a corresponding outer cavity 4642 and a second outer deck feature 4618 is positioned adjacent a second end of the outer cavity 4642. As can be seen in FIG. 74, outer deck features 4618 are associated with every one of the outer staple cavities 4642. In other embodiments, first and second outer deck features 4618 may be associated with every other one of the outer staple cavities 4642, however. In yet other embodiments, an outer deck feature may extend around the entire perimeter of a corresponding outer cavity. As can be seen in FIGS. 75 and 76, the inner deck features 4616 and the outer deck features 4618 extend above the deck surface 4612 the same distance. Stated another way, they have the same heights. In addition, as can also be seen in FIGS. 75 and 76, each inner deck feature 4416 and each outer deck feature 4618 has a generally conical or tapered outer profile which may help to prevent tissue from snagging on the deck features during insertion of the stapler head through a patient's colon and rectum.

FIGS. 75 and 76 illustrate use of the surgical staple cartridge 4610 in connection with an anvil 4680. The anvil 4680 comprises an anvil head portion 4682 that operably supports a staple forming insert or portion 4684 and a knife washer 4690. The knife washer 4690 is supported in confronting relationship to a knife 4692 that is supported in the stapler head. In the illustrated embodiment, the staple forming insert 4684 is fabricated from, for example, steel, stainless steel, etc. and contains an inner row of inner staple forming pockets 4686 and an outer row of outer staple forming pockets 4688. Each inner staple forming pocket 4686 corresponds to one of the inner staple cavities 4622 and each outer staple forming pocket 4688 corresponds to one of the outer staple cavities 4642. In the illustrated arrangement, the inner staple forming pockets 4686 are located the same distance $g_1$ from the deck surface 4612 as are the outer staple forming pockets 4688.

As can be further seen in FIGS. 75 and 76, an inner staple 4630 is supported within a corresponding inner staple cavity 4622 on a corresponding inner driver portion 4702 of a pusher assembly 4700. An outer staple 4650 is supported within a corresponding outer staple cavity 4642 on a corresponding outer driver portion 4704. Advancement of the pusher assembly 4700 toward the anvil 4680 will cause the inner and outer staples 4630, 4650 to be driven into forming contact with their respective corresponding staple forming pockets 4686, 4688 as shown in FIG. 76. In addition, the knife 4692 is advanced distally through the tissue that is clamped between the anvil 4680 and the deck surface 4612 and through a frangible bottom 4691 of the knife washer 4690. In the example illustrated in FIGS. 75 and 76, each inner staple 4630 is formed from a first staple wire that has a first wire diameter $D_1$ and has a first unformed height $L_1$. For example, the first wire diameter $D_1$ may be approximately 0.0079"-0.015" (increments are usually 0.0089", 0.0094", and 0.00145") and the first unformed height $L_1$ may be approximately 0.198"-0.250". Each outer staple 4650 is formed from a second staple wire that has a second wire diameter $D_2$ and has a second unformed height $L_2$. In the embodiment depicted in FIGS. 75 and 76, $D_1 < D_2$ and $L_1 < L_2$. However, as can be seen in FIG. 76, the inner and outer staples 4630, 4650 are formed with the same formed heights FH's. The thicker wire staples on the outside tend to provide high tear and burst strengths as compared to the inside row of smaller diameter staples which tend to hold better hemostatically. Stated another way, the tighter inside rows of staples may hold better hemostatically while the outer rows of less compressed staples may facilitate better healing and blood flow. In addition, the staples with longer legs, even when formed at the same heights as staples with shorter legs, may ensure more B-bending which may make the longer legged staples stronger and more likely to be properly formed enough to hold in high load conditions. The quantity of staples used in each row of staples can vary. In one embodiment, for example, the inner row 4620 has the same number of inner staples 4630 as does the outer row 4640 of outer staples 4650. In various arrangements, the crown widths of the staples 4650 is larger than the crown widths of the inner staples 4630. In other embodiments, the staples 4630, 4650 may have identical crown widths. In other arrangements, the staples 4630, 4650 may be of the gullwing design described above. For example, at least one leg of the staple may include an end portion that is bent inwardly or both legs may include end portions that are bent inwardly toward each other. Such staples may be employed in the inner annular row or the outer annular row or in both of the inner and outer annular rows.

Figure 77:
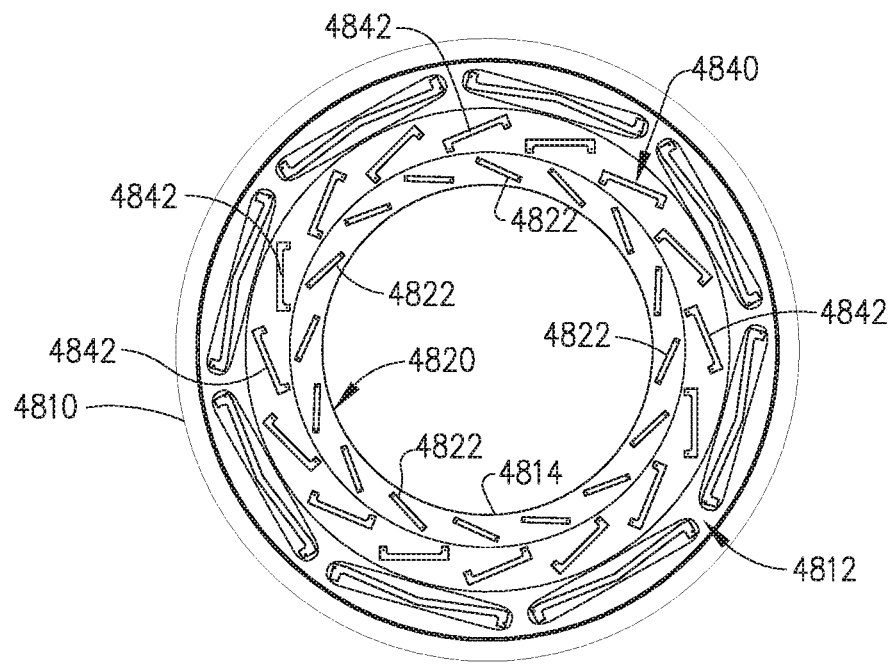
FIG. 77 is a top view of a staple cartridge in accordance with at least one embodiment.
Figure 80:
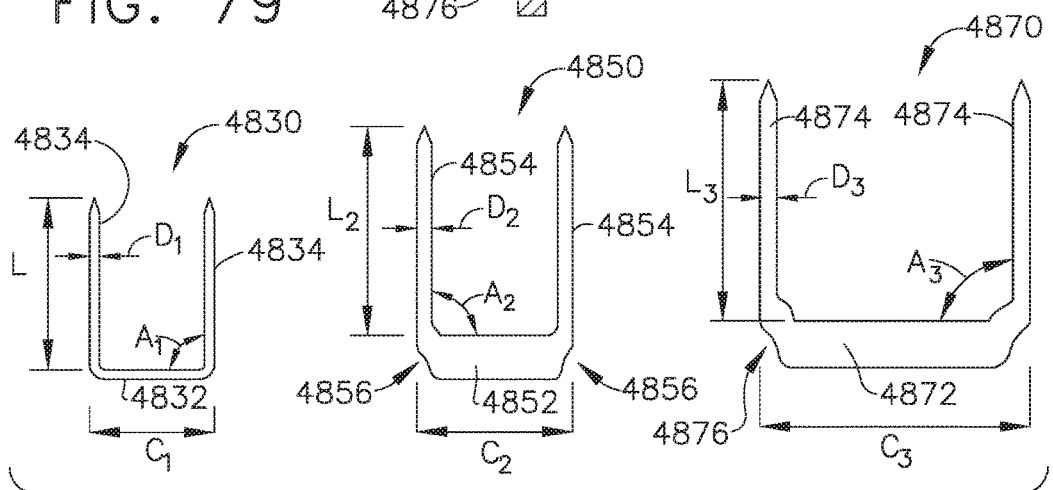
FIG. 80 depicts three unformed surgical staples.
Figure 81:
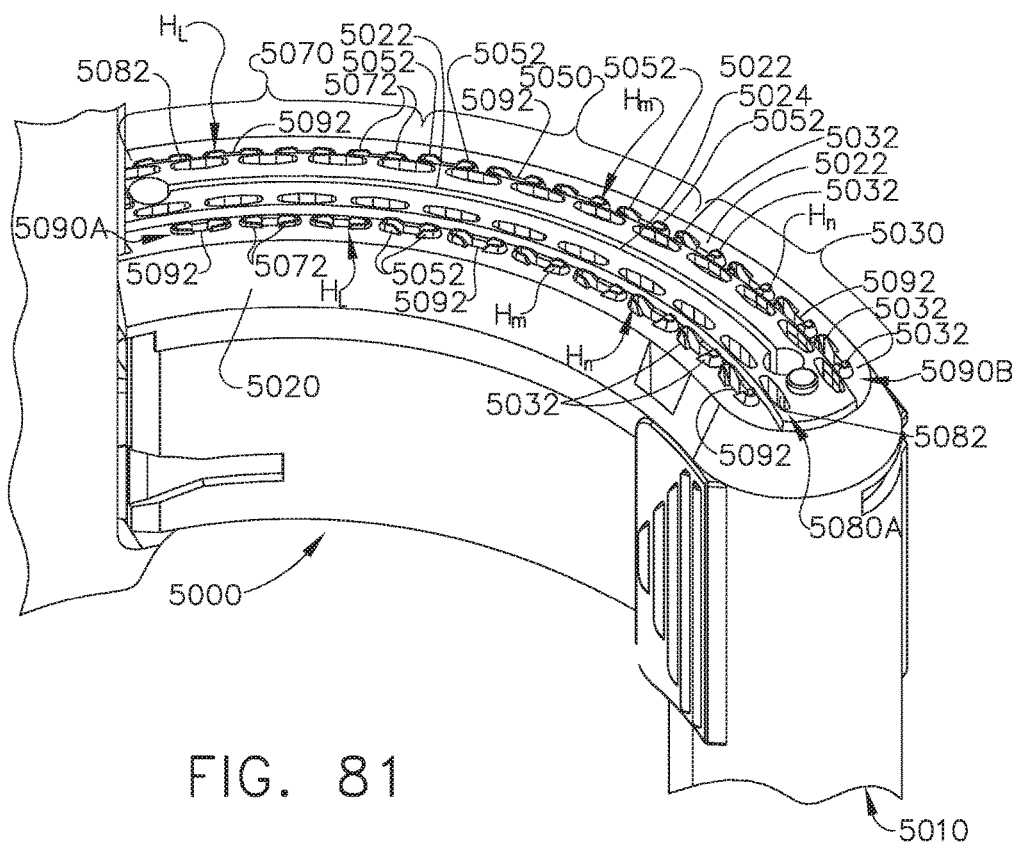
FIG. 81 is a perspective view of a portion of a surgical stapling device according to at least one embodiment.

FIG. 77 illustrates another circular staple cartridge embodiment 4810 that includes a cartridge deck 4812 that includes three annular rows 4820, 4840, 4860 of spaced staple cavities. The inner or first row 4820 contains a first plurality of inner or first staple cavities 4822 that are each arranged at a first angle. Each inner staple cavity 4822 operably supports a corresponding inner or first staple 4830 therein. The inner cavities 4822 orient the first staples 4830 at the same uniform angle relative to the tangential direction. In the illustrated example, each inner staple 4830 is formed from a first staple wire that has a first staple diameter $D_1$. In one example, the first staple wire diameter $D_1$ may be approximately 0.0079"-0.015" (increments are usually 0.0089", 0.0094", and 0.00145"). Referring to FIG. 80, each inner staple 4830 includes a first crown 4832 and two first legs 4834. The first crown has a first crown width $C_1$ and each first leg 4834 has a first unformed leg length $L_1$. In one example, the first crown width $C_1$ may be approximately 0.100"-0.300" and the first unformed leg length $L_1$ may be approximately 0.198"-0.250". The first legs 4834 may be each arranged at an angle $A_1$ relative to the first staple crown 4832. The angle $A_1$ may be approximately 90° or it may be slightly greater than 90° such that the first legs 4834 are slightly splayed outward to assist in retaining the first staple 4830 in its corresponding first staple cavity 4822.

Figure 78:
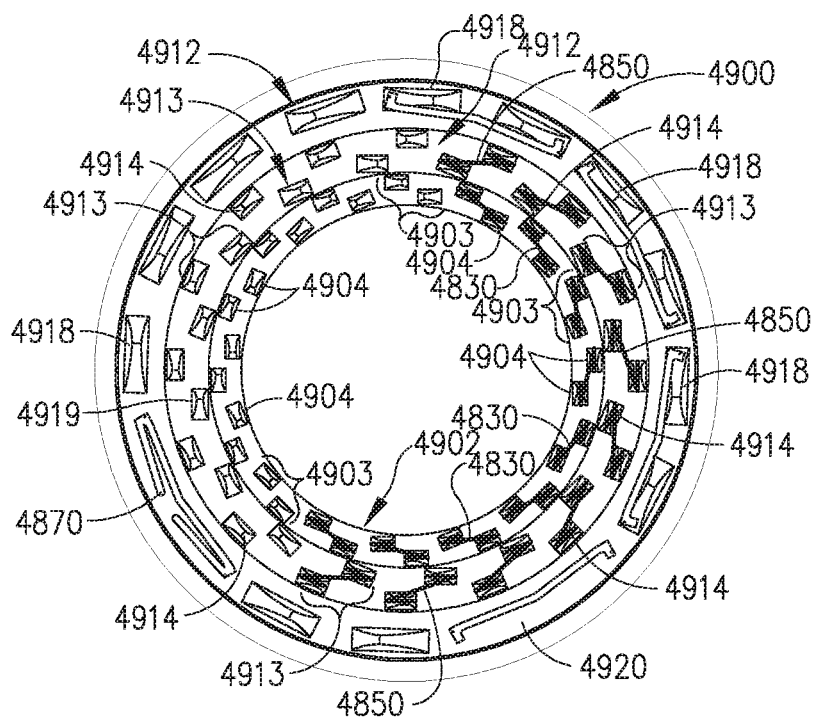
FIG. 78 is a bottom view of an anvil in accordance with at least one embodiment.
Figure 79:
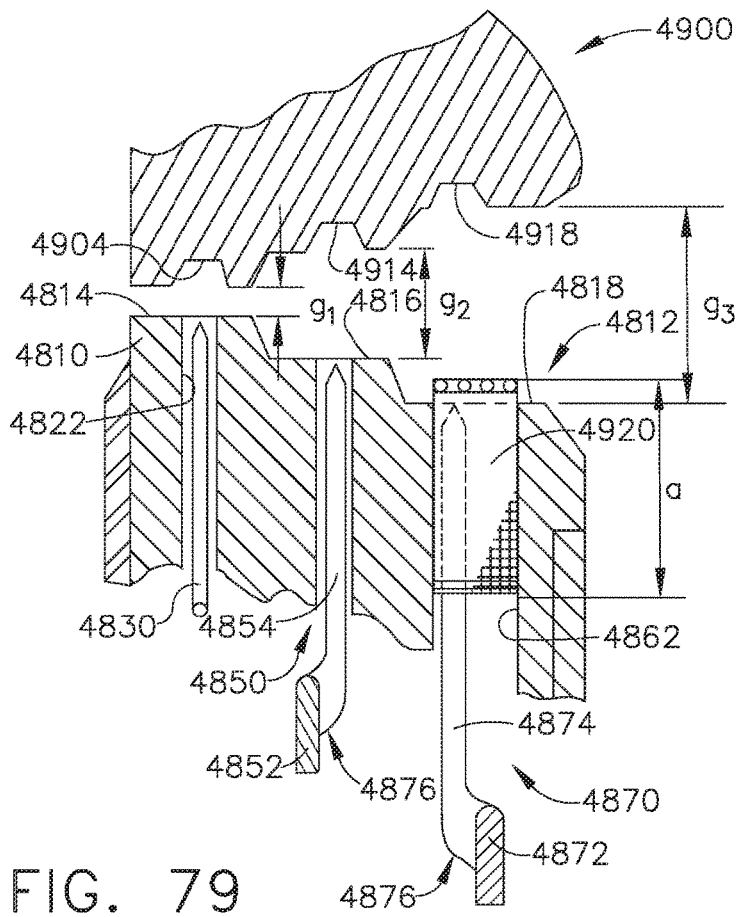
FIG. 79 is a cross-sectional view of a portion of an anvil in relation to a portion of a surgical staple cartridge.

Turning to FIGS. 78 and 79, the staple cartridge 4810 is intended to be used in connection with an anvil 4900 that includes two inner or first rows 4902 of staggered or angled first pairs 4903 of first staple forming pockets 4904. Each first pair 4903 of first staple forming pockets 4904 correspond to one first staple 4830. One first staple forming pocket 4904 corresponds to one first staple leg 4834 and the other first staple forming pocket 4904 of the pair 4903 corresponds to the other first staple leg 4834. Such arrangement serves to establish a formed staple configuration wherein the first staple legs 4834 of a first staple 4830 are formed out of plane with the first crown 4832 of that particular first staple 4830 such that one first leg 4834 is formed on one side of the first crown 4832 and the other first leg 4834 is formed on the other side of the first crown 4832. This "three-dimensional" formed staple configuration is shown with respect to some of the first staple forming pockets 4904 in FIG. 78.

As can be most particularly seen in FIG. 79, the cartridge deck 4812 is of "stepped" construction. The cartridge deck 4812 includes an inner or first cartridge deck portion 4814 that corresponds to the inner or first annular row 4820 of inner or first staple cavities 4822. As can be further seen in FIG. 79, when the anvil 4900 is moved to the closed or clamping position, the portion of the anvil 4900 containing the first staple forming pockets 4904 is spaced from the deck portion 4814 a first gap distance $g_1$.

Referring again to FIGS. 77, 79 and 80, the middle or second row 4840 contains a second plurality of middle or second staple cavities 4842 that are each arranged at a second angle. Each middle staple cavity 4842 operably supports a corresponding middle or second staple 4850 therein. The middle cavities 4842 orient the middle or second staples 4850 at the same uniform second angle relative to the tangential direction. However, the second angle differs from the first angle. Stated another way, when the first and second staples are supported in their respective first and second cavities, the axis of the first crown of each first staple 4830, when extended, would ultimately intersect the extended axis of the second crown of an adjacent second staple 4850. As can be seen in FIGS. 79 and 80, each second or middle staple 4850 comprises a second staple crown or base 4852 and two second legs 4854. The staple base 4852 may have a somewhat rectangular cross-sectional shape and be formed from a flat sheet of material. The second staple legs 4854 may have a round cross-sectional profile, for example. The second or middle staples may comprise various staple configurations disclosed in, for example, U.S. patent application Ser. No. 14/836,110, filed Aug. 26, 2015, entitled SURGICAL STAPLING CONFIGURATIONS FOR CURVED AND CIRCULAR STAPLING INSTRUMENTS, which has been herein incorporated by reference in its entirety. Having round staple legs that extend from a staple base portion having the rectangular cross-sectional profile can provide a staple base portion and staple legs with no preferential bending planes. The second staple 4850 comprises bend portions 4856 where the staple legs 4854 extend from the staple base portion 4852. The bend portions 4856 may comprise a substantially square cross-sectional profile. The square profile and the rectangular profile of the bend portions 4856 and the staple base portion 4852, respectively, provide a stiff connection and backbone to the round staple legs 4854. The round staple legs 4854 eliminate preferential bending planes that staple legs with a square, rectangular, or any shape with vertices or a non-uniform shape, cross-sections could have. Each of the second staple legs 4854 has a second diameter $D_2$. In at least one embodiment, $D_2 > D_1$. The second base or crown 4852 has a second crown width $C_2$. In one arrangement, $C_2 > C_1$. The second legs 4854 may be each arranged at an angle $A_2$ relative to the second base or crown 4852. The angle $A_2$ may be approximately 90° or it may be slightly greater than 90° such that the second legs 4854 are slightly splayed outward to assist in retaining the second staple 4850 in its corresponding second staple cavity 4842.

Turning to FIGS. 78 and 79, the anvil 4900 further comprises two middle or second rows 4912 of staggered or angled second pairs 4913 of second staple forming pockets 4914. Each second pair 4913 of second staple forming pockets 4914 correspond to one second staple 4850. One second staple forming pocket 4914 corresponds to one second staple leg 4854 and the other second staple forming pocket 4914 of the pair 4913 corresponds to the other second staple leg 4854. Such arrangement serves to establish a formed staple configuration wherein the second legs 4854 are formed out of plane with the second base 4852 of the particular second staple 4850. This "three-dimensional" formed staple configuration is shown with respect to some of the second staple forming pockets 4914 in FIG. 78.

As can be most particularly seen in FIG. 79, the cartridge deck 4812 further comprises a second cartridge deck portion 4816 that corresponds to the middle or second annular row 4840 of middle or second staple cavities 4842. As can be further seen in FIG. 79, when the anvil 4900 is moved to the closed or clamping position, the portion of the anvil 4900 containing the second staple forming pockets 4914 is spaced from the deck portion 4816 a second gap distance $g_2$ In the illustrated example, $g_2 > g_1$.

Referring again to FIGS. 77, 79 and 80, the outside or third row 4860 contains a third plurality of outside or third staple cavities 4862 that are sized relative to the second staple cavities 4842 such that each outer or third staple cavity 4862 spans a distance between two adjacent second cavities 4842. Each outer staple cavity 4862 operably supports a corresponding outer or third staple 4870 therein. The outer cavities 4862 orient the outer or third staples 4870 tangent to the circumferential direction. As can be seen in FIGS. 79 and 80, each third or outer staple 4870 comprises a third staple crown or base 4872 and two third legs 4874. The staple base 4872 may have a somewhat rectangular cross-sectional shape and be formed from a flat sheet of material. The third staple legs 4874 may have a round cross-sectional profile, for example. The third or outer staples 4870 may comprise various staple configurations disclosed in, for example, U.S. patent application Ser. No. 14/836,110, filed Aug. 26, 2015, entitled SURGICAL STAPLING CONFIGURATIONS FOR CURVED AND CIRCULAR STAPLING INSTRUMENTS, which has been herein incorporated by reference in its entirety. Having round staple legs that extend from a staple base portion having the rectangular cross-sectional profile can provide a staple base portion and staple legs with no preferential bending planes. The third staple 4870 comprises bend portions 4876 where the staple legs 4874 extend from the staple base portion 4872. The bend portions 4876 may comprise a substantially square cross-sectional profile. The square profile and the rectangular profile of the bend portions 4876 and the staple base portion 4872, respectively, provide a stiff connection and backbone to the round staple legs 4874. The round staple legs 4874 eliminate preferential bending planes that staple legs with a square, rectangular, or any shape with vertices or a non-uniform shape, cross-sections could have. In at least one embodiment, $D_3 > D_2$ The third base or crown 4872 has a third crown width $C_3$ and each third leg 4874 has a third unformed leg length $L_3$. In one arrangement, $C_3 > C_2$ and $L_3 > L_2$ The third legs 4874 may be each arranged at an angle $A_3$ relative to the third base or crown 4872. The angle $A_3$ may be approximately 90° or it may be slightly greater than 90° such that the third legs 4874 are slightly splayed outward to assist in retaining the third staple 4870 in its corresponding third staple cavity 4862.

Turning to FIGS. 78 and 79, the anvil 4900 further comprises an outer row 4916 of outer or third staple forming pockets 4918. Each third staple forming pocket 4918 corresponds to one third staple 4870. As can be most particularly seen in FIG. 79, the cartridge deck 4812 further comprises a third cartridge deck portion 4818 that corresponds to the outer or third row 4860 of outer or third staple cavities 4862. As can be further seen in FIG. 79, when the anvil 4900 is moved to the closed or clamping position, the portion of the anvil 4900 containing the third staple forming pockets 4918 is spaced from the deck portion 4818 a third gap distance $g_3$. In the illustrated example, $g_3 > g_2$. As can be further seen in FIG. 79, in at least one embodiment, a tissue thickness compensator 4920 is employed in connection with each outer or third staple 4870. The tissue thickness compensator may comprise a woven material that is embedded with oxidized regenerated cellulose (ORC) to promote hemostasis. The tissue thickness compensator 4920 may comprise any of the various tissue thickness compensator arrangements disclosed in U.S. patent application Ser. No. 14/187,389, filed Feb. 24, 2014, entitled IMPLANTABLE LAYER ASSEMBLIES, U.S. Patent Application Publication No. 2015/0238187, the entire disclosure of which is hereby incorporated by reference herein. As can be seen in FIG. 79, the tissue thickness compensator 4920 has a thickness designated as "a". In one embodiment, the tissue thickness compensator has a thickness of approximately 0.015"-0.045". However, other thicknesses may be employed.

Thus, in at east one embodiment as depicted in FIGS. 77-80, the staple cartridge 4810 may employ a different number of staples in each of the three rows of staples. In one arrangement, the inner row of staples comprises conventional staples with the smallest wire diameter and the shortest unformed leg length. Each first staple has the shortest crown width and each first staple is oriented at a uniform angle relative to the tangential direction. The middle staples have a configuration that differs from the first staple configuration. Each leg of the middle staples comprises a moderate wire diameter and unformed leg length. Each middle staple has a slightly larger crown width than the crown widths of the inner staples and each middle staple is oriented at a uniform angle relative to the tangential direction, but at a different angle relative to the inner row of inner staples. Each outer staple has a configuration that is similar to the configuration of the middle staples. Each of the third legs of each outer staple comprises the largest wire diameter as compared to the wire diameters of the legs of the inner and middle staples. The crown width of each outer staple is significantly larger than the crown widths of the inner and middle staples. Each outer staple is oriented tangentially to the circumferential direction of the cartridge. The outer row of staples employs woven tissue thickness compensators (spacer fabric) that is embedded with ORC to promote hemostasis. The stepped anvil and the stepped cartridge deck yield different formed staple heights with the staples having the shortest formed heights being in the inner row and the staples having the longest formed heights being in the outer row. The anvil pockets corresponding to the inner and middle rows of staples are "tilted" to create three dimensional staples in the inner and middle rows. "Bathtub-type" anvil pockets correspond to the outer row of staples. In at least one embodiment, the staples may be sequentially fired. For example, the staples in the inner and middle rows may be fired first and the staples in the outer row fired thereafter. The annular knife cuts the clamped tissue during the firing process.

FIGS. 81-84 depict portions of a curved stapling instrument 5000 in accordance with at least one embodiment configured to capture, incise, and staple tissue. The curved stapling instrument 5000 comprises a frame assembly 5010, a staple cartridge 5020, and an anvil (not shown) that is configured to be supported in confronting relationship relative to the deck of the staple cartridge. As will be discussed in further detail below, upon receiving a first actuation force, the staple cartridge 5020 is driven toward the anvil to capture tissue therebetween. The curved stapling instrument 5000 further comprises a knife assembly comprising a cutting member (not shown) that is configured to incise the tissue captured between the staple cartridge 5020 and the anvil. The staple cartridge 5020 comprises a deck 5022 comprising a cutting slot 5024 that is configured to receive the cutting member, a plurality of staple cavities 5030A and 5030B, and a plurality of staples 5040 (FIG. 84) removably stored within the staple cavities 5030A, 5030B. The curved stapling instrument 5000 further comprises a driver assembly 5100 comprising a main driver 5102 that is configured for axial displacement within the frame assembly 5010. Upon actuation of the firing system, the main driver 5102 moves axially in a direction toward the anvil. In at least one arrangement, the axial movement of the main driver 5102 will also advance the cutting member out of the cutting slot 5024 to cut the tissue clamped between the cartridge 5020 and the anvil.

Figure 82:
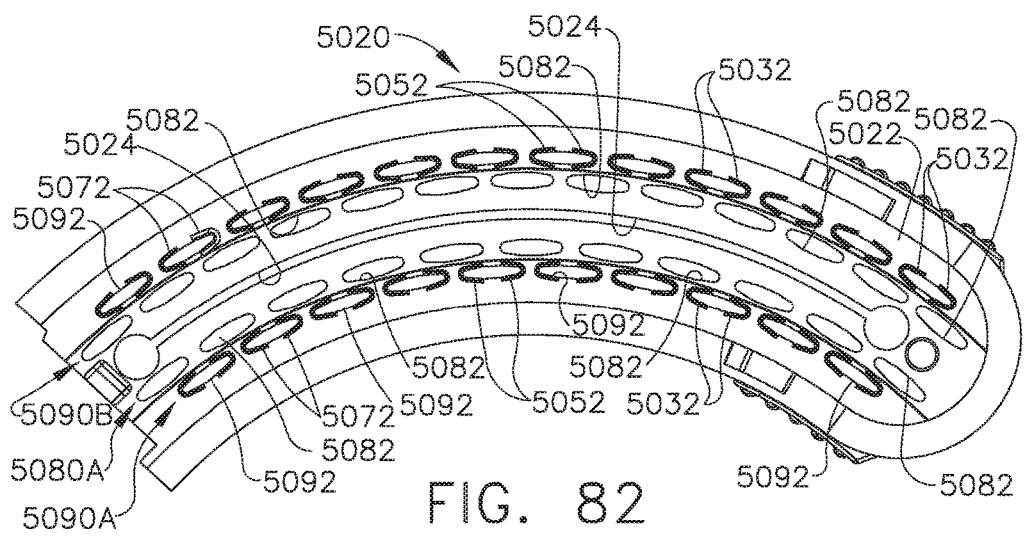
FIG. 82 is a top view of a surgical staple cartridge of the stapling device of FIG. 81.
Figure 83:
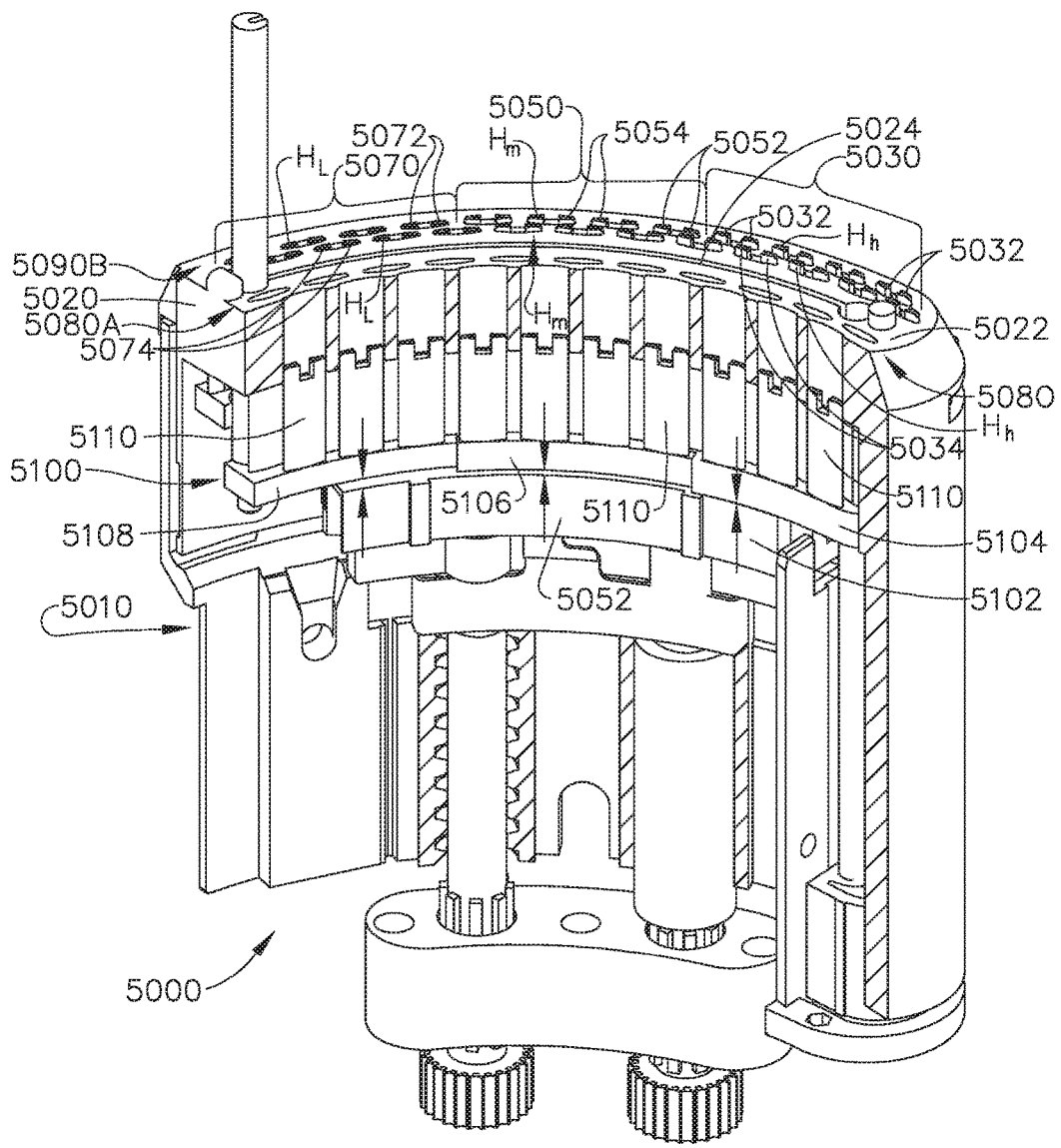
FIG. 83 is a perspective view of a portion of the surgical stapling device of FIG. 81.

In the illustrated example, the cartridge 5020 is divided longitudinally into three sections: the "high" section 5030, the "medium" section 5050, and the "low" section 5070. The cutting slot 5024 bifurcates each of the high, medium and low sections 5030, 5050, 5070 such that two rows of staple cavities are located on each side of the cutting slot 5024. As can be seen in FIG. 82, for example, the staple cartridge 5020 comprises two inner rows 5080A, 5080B of inner staple cavities 5082 and two outer rows 5090A, 5090B of outer staple cavities 5092. The staple cartridge 5020 further comprises a plurality of deck features extending from the deck 5022. For example, referring to FIGS. 81 and 82, the outer rows 5090A, 5090B of staple cavities 5092 have a collection of deck features associated therewith. In the illustrated example, those staple cavities 5092 associated with the high section 5030 include deck features 5032 that extend above the deck surface 5022 a feature height $H_h$. Those staple cavities 5092 associated with the medium section 5050 include deck features 5052 that extend above the deck surface 5022 a feature height $H_m$. Those staple cavities 5092 associated with the low section 5070 include deck features 5072 that extend above the deck surface 5022 a feature height $H_L$. $H_h > H_m > H_L$. In at least one embodiment, for example, $H_h$ may be approximately 0.020", $H_m$ may be approximately 0.015", and $H_L$ may be approximately 0.010". The deck features 5032, 5052, and 5072 may be molded into the deck surface 5022. Embodiments are envisioned where the deck features 5032, 5052, 5072 are separate portions configured to be attached to the deck surface 5022. The deck features 5032, 5052, and 5072 can be extensions of the staple cavities 5092 in order to support, guide, and/or control the staples, while loading the staples into the cartridge 5020, while housing, or supporting, the staples 5112 before ejecting the staples 5112, and/or while ejecting the staples from the cartridge 5020. A single deck feature 5032, 5052, 5072 supports two different staple legs of neighboring staples 5112. The deck features 5032, 5052, and 5072 can comprise multiple support walls configured to support one or more sides, faces, and/or edges of each staple leg. Embodiments are envisioned where the deck features 5032, 5052, 5072 on the outer staple rows 5090A, 5090B only correlate with every other staple cavity 5092 in each outer row 5090A, 5090B. In the embodiment depicted in FIG. 83, the staple cavities 5082 of inner rows 5080A, 5080B (only row 5080B can be seen in FIG. 83) each have deck features associated therewith. For example, those staple cavities 5082 associated with the high section 5030 include deck features 5034 that extend above the deck surface 5022 a feature height $H_h$. Those staple cavities 5082 associated with the medium section 5050 include deck features 5054 that extend above the deck surface 5022 a feature height $H_m$. Those staple cavities 5082 associated with the low section 5070 include deck features 5074 that extend above the deck surface 5022 a feature height $H_L$.

The staple cartridge 5020 includes a driver assembly 5100 that is configured to drive the staples supported within the staple cavities 5082, 5092 toward the anvil upon the application of an actuation force. In the arrangement illustrated in FIGS. 83 and 84, for example, the driver assembly 5100 includes a main driver 5102 that is configured to move toward the anvil upon application of an actuation motion thereto and away from anvil upon application of a retraction motion thereto. The driver assembly 5100 further comprises a pair of high driver portions 5104 (one on each side of the cutting slot 5024), a pair of medium driver portions 5106 (one on each side of the cutting slot 5024), and a pair of low driver portions 5108 (one on each side of the cutting slot 5024). Each of the driver portions 5104, 5106, 5108 has a plurality of staple support drivers 5110 associated therewith. A staple support driver 5110 is supported in each of the staple cavities 5082, 5092 and supports a staple 5112 thereon. See, e.g., FIG. 84. Thus, when the stapling device is fired, the staples 5112 may be formed with different formed staple heights. For example, the formed heights of the staples 5112 associated with the high section 5030 may have a formed height that is shorter than the formed height of those staples associated with the medium section 5050 and the formed height of the staples 5112 associated with the medium section 5050 may be shorter than the formed height of the staples 5112 associated with the low section 5070. Furthermore, by driving the staples different distances may help to accommodate for anvil deflection. However, in instances where there is no anvil deflection, such arrangement provides staples with formed heights that vary by region. Actuation of the driver assembly 5100 will also result in the cutting member being driven through the clamped tissue. The reader will appreciate that different staples with different leg and/or crown configurations and/or wire diameters and/or unformed heights may be employed in the different sections 5030, 5050, 5070 to achieve desired formed staple heights and arrangements on each side of the tissue cut line.

Figure 85:
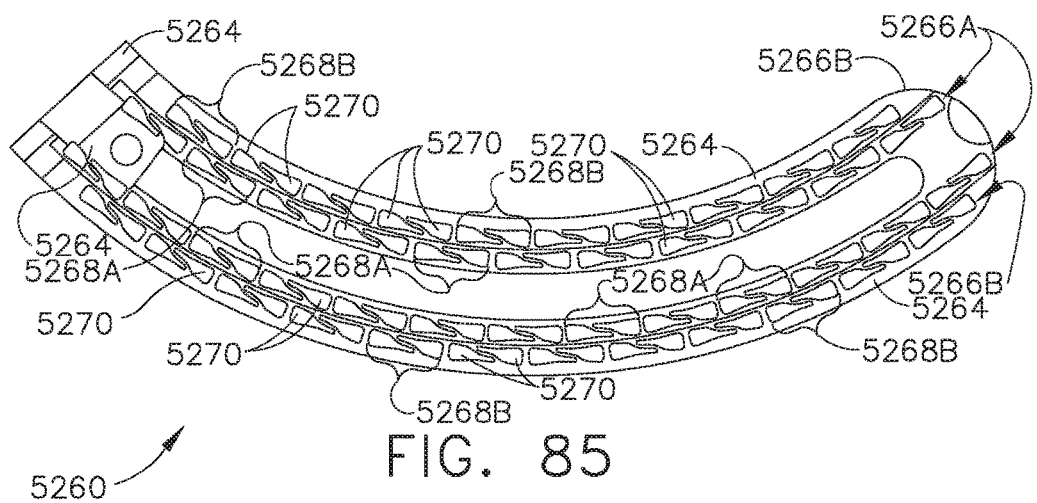
FIG. 85 is a bottom view of an anvil according to at least one embodiment.
Figure 86:
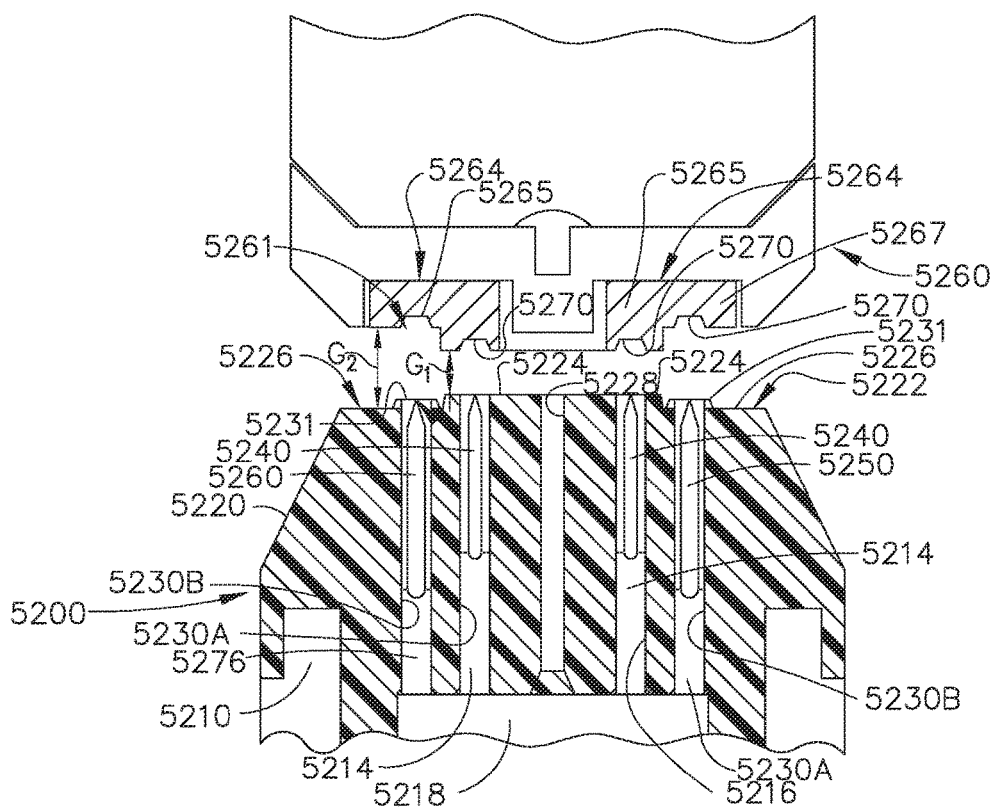
FIG. 86 is a side elevational cross-sectional view of a portion of a surgical stapling device employing the anvil of FIG. 85.

FIGS. 85-88 illustrate various portions of another curved stapling instrument 5200 in accordance with at least one embodiment configured to capture, incise, and staple tissue. Referring first to FIG. 86, the curved stapling instrument 5200 comprises a frame assembly 5210, a staple cartridge 5220, and an anvil 5260 that is configured to be supported in confronting relationship relative to the deck 5222 of the staple cartridge 5220. The curved stapling instrument 5200 further comprises a knife assembly comprising a cutting member (not shown) that is configured to incise the tissue captured between the staple cartridge 5220 and the anvil 5260. In the embodiment illustrated in FIG. 86, the deck 5222 comprises a "stepped" deck that includes a centrally-disposed cutting slot 5228 that is configured to receive the cutting member. The deck 5222 further comprises a centrally-disposed high deck portion 5224 through which the cutting slot 5228 extends and a low deck portion 5226. An inner row of inner staple cavities 5230A are provided in the high deck portion 5224 on each side of the cutting slot 5228. Each low deck portion 5226 has a corresponding row of outer staple cavities 5230B therein. As can be seen in FIG. 86, a deck feature 5231 of the various configurations disclosed herein may be associated with each of the outer staple cavities 5230B or every other one of the outer staple cavities 5230B in each outer row of outer staple cavities 5230B. In other arrangements, deck features may additionally be associated with each of the inner staple cavities 5230A or every other inner staple cavity 5230A in each row of inner staple cavities 5230A. In still other arrangements, no deck features may be employed in connection with any of the inner and outer staple cavities 5230A, 5230B.

Figure 88:
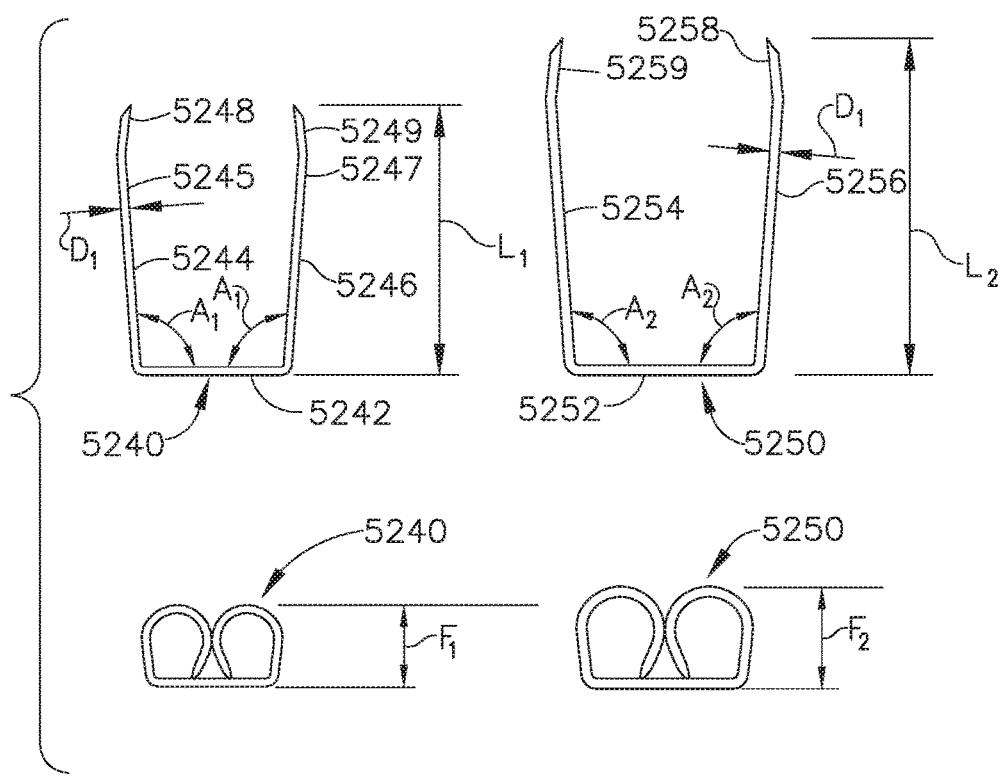
FIG. 88 depicts staples in accordance with at least one embodiment in unformed and formed configurations.

Referring now to FIGS. 86 and 88, in at least one arrangement, each staple cavity 5230A removably stores an inner staple 5240 therein and each staple cavity 5230B removably stores an outer staple 5250 therein. Each inner staple 5240 is supported on a corresponding driver 5214 and each outer staple 5250 is supported on a corresponding driver 5216. The drivers 5214, 5216 form a portion of a movable driver assembly 5218 that is operably supported in the stapling instrument 5200. It will be understood that the application of an actuation motion to the driver assembly 5218 will result in the advancement of each staple 5240, 5250 into forming contact with the anvil 5260.

The inner rows of inner staples 5240 may comprise different characteristics than the outer row of outer staples 5250. For example as illustrated in the embodiment of FIG. 88, the legs of the inner staples 5240 have a "gullwing" configuration. In particular, each inner staple 5240 includes a pair of legs 5244, 5246 that extend from a staple crown 5242. Each leg 5244, 5246 includes a vertical portion 5245, 5247 that extends from the crown 5242. The vertical portions 5245, 5247 may be parallel to each other in one embodiment. However, in the illustrated arrangement, the vertical portions 5245, 5247 are not parallel to each other. See FIG. 88. However, the vertical leg portions 5245, 5247 may be arranged at other angles with respect to the crown 5242. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, which is hereby incorporated by reference herein in its entirety. One advantage of having the vertical leg portions 5245, 5247 oriented at angles greater than ninety degrees relative to the crown 5242 is that such arrangement may assist in the temporary retention of the staple within its corresponding staple cavity. Still referring to FIG. 88, each leg 5244, 5246 further includes an inwardly extending leg portion. In the illustrated arrangement, leg portion 5248 extends inwardly from the vertical leg portion 5244 and the leg portion 5249 extends inwardly from the vertical leg portion 5246. As can be seen in that Figure, the leg portion 5248 is shorter than the leg portion 5244. Each inner staple 5240 has an unformed height $L_1$.

As can also be seen in FIG. 88, the legs of the outer staples 5250 also have a "gullwing" configuration. In particular, each outer staple 5250 includes a pair of legs 5254, 5256 that extend from a staple crown 5252. Each leg 5254, 5256 includes a vertical portion 5255, 5257 that extends from the crown 5252. The vertical portions 5255, 5257 may be parallel to each other in one embodiment. However, in the illustrated arrangement, the vertical portions 5255, 5257 are not parallel to each other. See FIG. 88. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, which is hereby incorporated by reference herein in its entirety. However, the vertical leg portions 5245, 5247 may be arranged at other angles with respect to the crown 5242. One advantage of having the vertical leg portions 5255, 5257 oriented at angles greater than ninety degrees relative to the crown 5252 is that such arrangement may assist in the temporary retention of the staple within its corresponding staple cavity. Still referring to FIG. 88, each leg 5254, 5256 further includes an inwardly extending leg portion. In the illustrated arrangement, leg portion 5258 extends inwardly from the vertical leg portion 5254 and the leg portion 5259 extends inwardly from the vertical leg portion 5256. As can be seen in that Figure, the leg portion 5258 is shorter than the leg portion 5254. Each outer staple 5250 has an unformed height $L_2$. In the illustrated arrangement, $L_2>L_1$. In the illustrated embodiment, the inner and outer staples 5240, 5250 have the same wire diameters $D_1$. However, in other embodiments, the inner and outer staples 5240, 5250 have different wire diameters. In still other embodiments, staples 5240 may be provided in the staple cavities 5230B and staples 5250 may be provided in staple cavities 5230A such that the longer unformed staples are in the inner lines of staple cavities and the shorter staples are in the outer lines of staple cavities.

The stapling instrument 5200 may employ an anvil 5260 as shown in FIGS. 85 and 86. Referring first to FIG. 85, the anvil 5260 may include two inserts 5264 that are supported in the anvil body 5260 such that one insert 5264 corresponds to the staples located on one side of the cutting slot 5228 and the other insert 5264 corresponds to the staple located on the other side of the cutting slot 5228. As can be seen in FIG. 86, the inserts 5264 provide the anvil 5260 with a stepped staple forming undersurface 5261. Each insert 5264 includes an inner portion 5265 and an outer portion 5267. When the anvil 5260 is positioned in a closed orientation for clamping tissue, a gap $G_1$ is provided between the inner portion 5265 of the insert 5264 and the corresponding deck portion 5224 and a gap $G_2$ is formed between the outer portion 5267 of the insert 5264 and the corresponding deck portion 5226. In the illustrated arrangement $G_2>G_1$. The inner portion 5265 comprises an inner row 5266A of pairs 5268A of inner staple forming cavities 5270. The outer portion 5267 of each insert 5264 comprises an outer row 5266B of outer pockets 5258B of outer staple forming pockets 5270.

Figure 87:
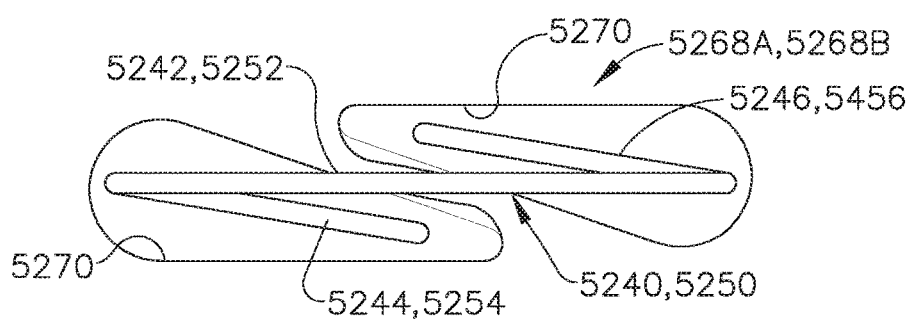
FIG. 87 is an enlarged view of staple forming pockets of the anvil of FIG. 85 with a corresponding formed staple.

Turning now to FIG. 87, in at least one embodiment, each staple forming pocket 5270 of each pair 5268A, 5268B of staple forming pockets 5270 has a triangular shape. The forming pockets 5270 in a single pair 5268A, 5268B are spaced from each other and are configured to receive and form a corresponding leg of a particular staple. Such arrangement serves to provide the formed staple with a three-dimensional configuration. That is, each leg of the formed staple does not lie in the same plane as the staple crown. See FIG. 87. In one arrangement, the formed height $F_2$ of each outer staple 5250 is greater than the formed height $F_1$ of each inner staple 5240 as illustrated in FIG. 88. In alternative arrangements, for example, the anvil inserts may not be of a stepped configuration and may essentially contain lines of like staple forming pockets of the various types disclosed herein that are the same distance from the corresponding portions of the cartridge deck. In such arrangements, the cartridge deck may not be stepped and may or may not contain deck features of the types disclosed herein. In at least one variation, the lines of inner staples may have shorter unformed lengths than the staples in the outer lines (farthest from the slot that accommodates the cutting member) and visa versa. The staples in the inner and outer lines may be of the gullwing configurations disclosed herein or they may be of standard U-shape design. The staples in each line may have the same wire diameter which may differ from or be the same as the wire diameter of the staples in an adjacent line.

FIGS. 89 and 90 illustrate various portions of another stapling instrument 5300 in accordance with at least one embodiment configured to capture, incise, and staple tissue. Referring first to FIG. 89, the stapling instrument 5300 comprises a frame assembly 5310, a staple cartridge 5320, and an anvil 5360 that is configured to be supported in confronting relationship relative to the deck 5322 of the staple cartridge 5320. The staple cartridge 5320 and anvil 5360 may be curved or they may be straight. The stapling instrument 5300 further comprises a knife assembly comprising a cutting member 5312 that is configured to incise the tissue captured between the staple cartridge 5320 and the anvil 5360. The staple cartridge 5320 comprises a deck 5322 that includes a centrally disposed cutting slot 5328 that is configured to receive the cutting member 5312. An inner row of spaced inner staple cavities 5330A is provided on each side of the cutting slot 5228. An outer row of space outer staple cavities 5330B is provided adjacent to each of the inner rows of inner staple cavities 5330A. As can be seen in FIG. 89, deck features 5331 of the various configurations disclosed herein may be associated with each of the inner and outer staple cavities 5330A, 5330B. In other embodiments, every other one of the inner and/or outer staple cavities 5330A, 5330B in each respective row has a deck feature 5331 associated therewith. In still other arrangements, no deck features may be employed in connection with any of the inner and outer staple cavities 5330A, 5330B.

In at least one arrangement, each inner staple cavity 5330A removably stores an inner staple 5340 therein and each outer staple cavity 5330B removably stores an outer staple 5350 therein. Each inner staple 5340 is supported on a corresponding driver 5314 and each outer staple 5350 is supported on a corresponding driver 5316. The drivers 5314, 5316 form a portion of a movable driver assembly 5318 that is operably supported in the stapling instrument 5300. It will be understood that the application of an actuation motion to the driver assembly 5318 will result in the advancement of each staple 5340, 5350 into forming contact with the anvil 5260. In the illustrated arrangement, the inner staples 5340 may comprise legs of the gullwing design and have an unformed height $L_1$. The outer staples 5350 may also have legs of the gullwing design and have an unformed height $L_2$. In the illustrated arrangement, $L_1 > L_2$ However, other staple configurations disclosed herein may also be employed.

The stapling instrument 5300 may employ an anvil 5360 as shown in FIG. 89. As can be seen in FIG. 89, the anvil 5360 may include two inserts 5364 that are supported in the anvil body 5362 such that one insert 5364 corresponds to the staples located on one side of the cutting slot 5328 and the other insert 5364 corresponds to the staple located on the other side of the cutting slot 5328. As can be seen in FIG. 89, when the anvil 5360 is closed, the inserts 5364 are located a uniform distance $G_1$ from the cartridge deck 5322. Each insert 5364 comprises an inner row of inner staple forming pockets 5368A and an outer row of outer staple forming pockets 5368B. The staple forming pockets 5368A, 5368B may be provided in any of the various staple forming pocket configurations disclosed herein. When the device 5300 is fired, the formed height $F_2$ of each outer staple 5350 is greater than the formed height $F_1$ of each inner staple 5240 as illustrated in FIG. 90.

Figure 91:
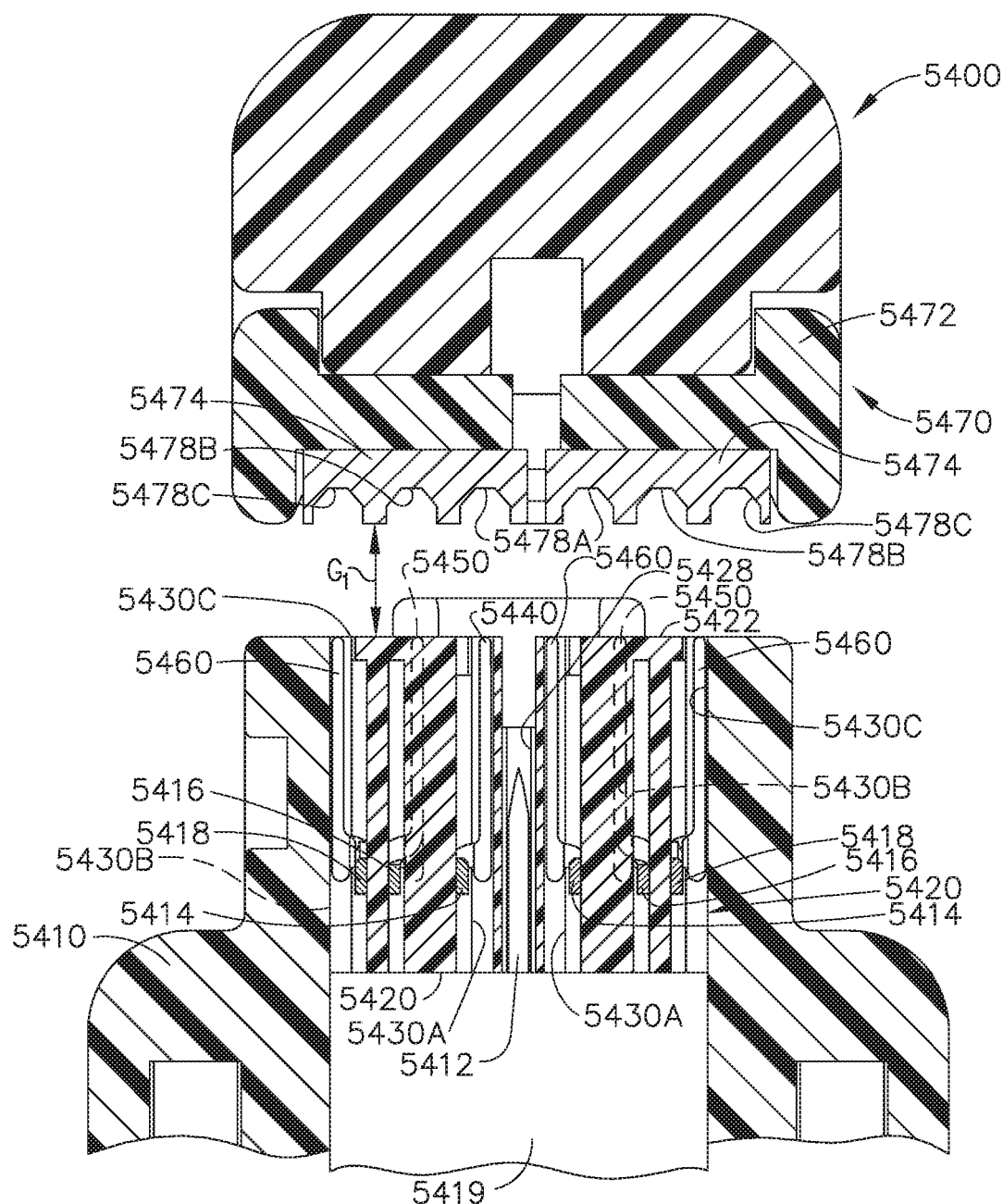
FIG. 91 is a side elevational cross-sectional view of a portion of a surgical stapling device according to at least one embodiment.
Figure 84:
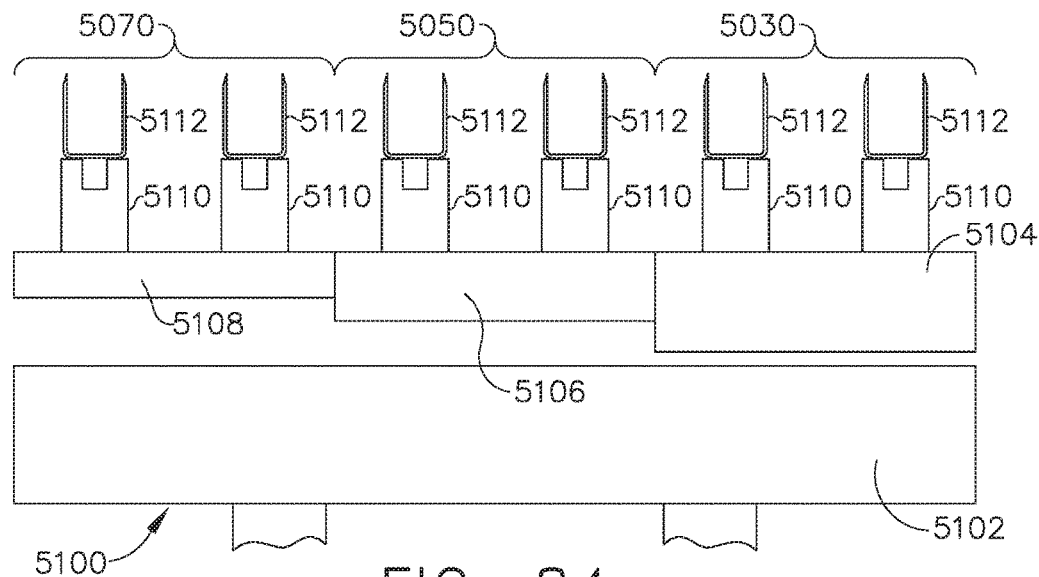
FIG. 84 is a side elevational view of a staple driver assembly according to at least one embodiment.

FIG. 91 illustrates various portions of another stapling instrument 5400 in accordance with at least one embodiment configured to capture, incise, and staple tissue. The stapling instrument 5400 comprises a frame assembly 5410, a staple cartridge 5420, and an anvil 5470 that is configured to be supported in confronting relationship relative to the deck 5422 of the staple cartridge 5420. The staple cartridge 5420 and anvil 5470 may be curved or they may be straight. The stapling instrument 5400 further comprises a knife assembly comprising a cutting member 5412 that is configured to incise the tissue captured between the staple cartridge 5420 and the anvil 5470. The staple cartridge 5420 comprises a deck 5422 that includes a centrally disposed cutting slot 5428 that is configured to receive the cutting member 5412. An inner row of spaced inner staple cavities 5430A is provided on each side of the cutting slot 5428. A middle row of spaced middle staple cavities 5430B is provided adjacent each inner row of spaced inner staple cavities 5430A on each side of the cutting slot 5428. An outer row of spaced outer staple cavities 5430C are provided adjacent to each of the spaced middle rows of middle staple cavities 5430B. No deck features are illustrated in connection with this embodiment. However, other embodiments employ deck features of the various configurations disclosed herein in connection with some or all of the inner staple cavities and/or in connection with some or all of the middle staple cavities and/or in connection with some or all of the outer staple cavities.

In at least one arrangement, each inner staple cavity 5430A removably stores an inner staple 5440 therein. Each middle staple cavity 5430B removably stores a middle staple 5450 therein. Each outer staple cavity 5430C removably stores an outer staple 5460 therein. Each inner staple 5440 is supported on a corresponding driver 5414. Each middle staple 5450 is supported on a corresponding middle staple driver 5416. Each outer staple 5460 is supported on a corresponding outer driver 5418. The drivers 5414, 5416, 5418 form a portion of a movable driver assembly 5419 that is operably supported in the stapling instrument 5400. It will be understood that the application of an actuation motion to the driver assembly 5419 will result in the advancement of each staple 5440, 5450, 5460 into forming contact with the anvil 5470. In the illustrated arrangement, the inner, middle and outer staples, 5440, 5450, 5460 may be of identical construction and have the same unformed heights.

The stapling instrument 5400 may employ an anvil 5470 as shown in FIG. 91. As can be seen in FIG. 91, the anvil 5470 may include two inserts 5474 that are supported in the anvil body 5472 such that one insert 5474 corresponds to the staples located on one side of the cutting slot 5428 and the other insert 5474 corresponds to the staples located on the other side of the cutting slot 5428. As can be seen in FIG. 89, when the anvil 5470 is closed, the inserts 5474 are located a uniform distance $G_1$ from the cartridge deck 5422. Each insert 5474 comprises an inner row of inner staple forming cavities 5478A, a middle row of middle staple forming cavities 5478B and an outer row of outer staple forming cavities 5478C. The staple forming cavities 5478A, 5478B, and 5478C may comprise any of the various staple forming pocket configurations disclosed herein. When the device 5400 is fired, each of the staples 5440, 5450, 5460 has the same formed height and configuration. However, other staple configurations and staple forming pocket configurations disclosed herein may also be employed so as to create staples with different formed heights and configurations.

Figure 92:
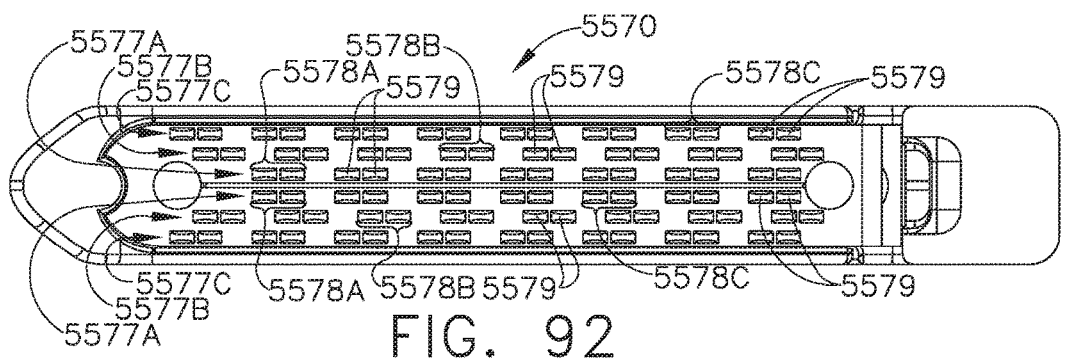
FIG. 92 is a top view of a portion of a surgical stapling device according to at least one embodiment.

FIG. 92 illustrates another stapling instrument 5500 in accordance with at least one embodiment configured to capture, incise, and staple tissue. The stapling instrument 5500 comprises a frame assembly 5510, a staple cartridge 5520, and an anvil 5570 (FIG. 93) that is configured to be supported in confronting relationship relative to the deck 5522 of the staple cartridge 5520. The stapling instrument 5500 further comprises a knife assembly comprising a cutting member 5512 that is configured to incise the tissue captured between the staple cartridge 5520 and the anvil 5570. The staple cartridge 5520 comprises a deck 5522 that includes a centrally disposed cutting slot 5528 that is configured to receive the cutting member 5512. An inner row of space inner staple cavities 5530A is provided on each side of the cutting slot 5528. A middle row of spaced middle staple cavities 5530B is provided adjacent each inner row of space inner staple cavities 5530A on each side of the cutting slot 5528. An outer row of spaced outer staple cavities 5530C are provided adjacent to each of the middle rows of middle staple cavities 5530B. No deck features are illustrated in connection with this embodiment. However, other embodiments employ deck features of the various configurations disclosed herein in connection with some or all of the inner staple cavities and/or in connection with some or all of the middle staple cavities and/or in connection with some or all of the outer staple cavities. In still other arrangements, the staple cavities located in every other row may have deck features associated therewith.

Figure 95:
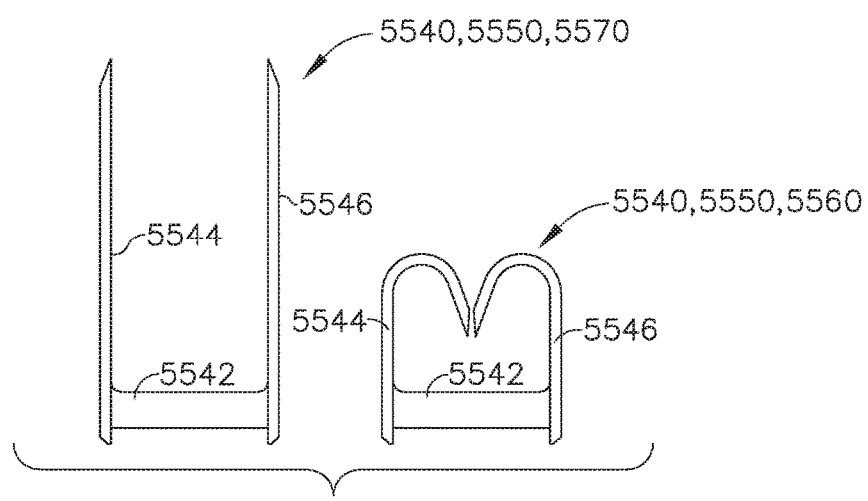
FIG. 95 depicts unformed staples according to at least one embodiment.

In at least one arrangement, each inner staple cavity 5530A removably stores an inner staple 5540 therein. Each middle staple cavity 5530B removably stores a middle staple 5550 therein. Each outer staple cavity 5530C removably stores an outer staple 5560 therein. Each staple 5540, 5550, 5560 is supported on a corresponding driver that forms a portion of a movable driver assembly that is operably supported in the stapling instrument 5500. It will be understood that the application of an actuation motion to the driver assembly will result in the advancement of each staple 5540, 5550, 5560 into forming contact with the anvil 5570. In the illustrated arrangement, the inner, middle and outer staples, 5440, 5450, 5460 may be of identical construction and have the same unformed heights as shown in FIG. 95. In one arrangement, for example, the staples 5540, 5550, and 5560 may be of the type and configurations disclosed in U.S. patent application Ser. No. 14/836,110, filed Aug. 26, 2015, entitled SURGICAL STAPLING CONFIGURATIONS FOR CURVED AND CIRCULAR STAPLING INSTRUMENTS, the entire disclosure of which is hereby incorporated by reference herein.

Figure 94:
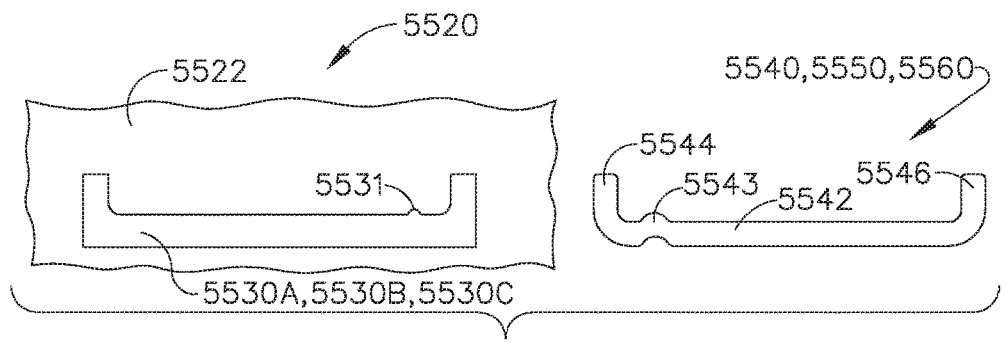
FIG. 94 is a top view of a staple cavity according to at least one embodiment and a corresponding staple.

Further to the above, the staples of the staple cartridges disclosed herein can include one or more features configured to hold the staples in the staple cavities of the staple cartridge. Turning now to FIGS. 94 and 95, a staple 5540, 5550, 5560 each includes a base 5542 and staple legs 5544, 5546 that extend from the base 5542. The base 5542 comprises a protrusion 5543 extending therefrom which is engaged with a corresponding detent or groove 5531 in the sidewall of the corresponding staple cavity 5530A, 5530B, and 5530C. The interaction between the protrusions 5543 and the detent or groove 5531 in the staple cavity sidewall keeps the staple 5540, 5550, 5560 from falling out of the bottom of the cartridge 5520. The interaction between the protrusion 5543 and the staple cavity sidewall comprises an interference fit; however, such an interference fit does not prevent the staples 5540, 5550, 5560 from being ejected from the respective cavities 5530A, 5530B, and 5530C. The protrusion 5543 can be formed in the base 5542 during a stamping process, for example. The stamping process can form the protrusion 5543 by creating a dent in the opposite side of the base 5542. Alternative embodiments are envisioned which do not comprise the groove or detent 5531.

Figure 93:
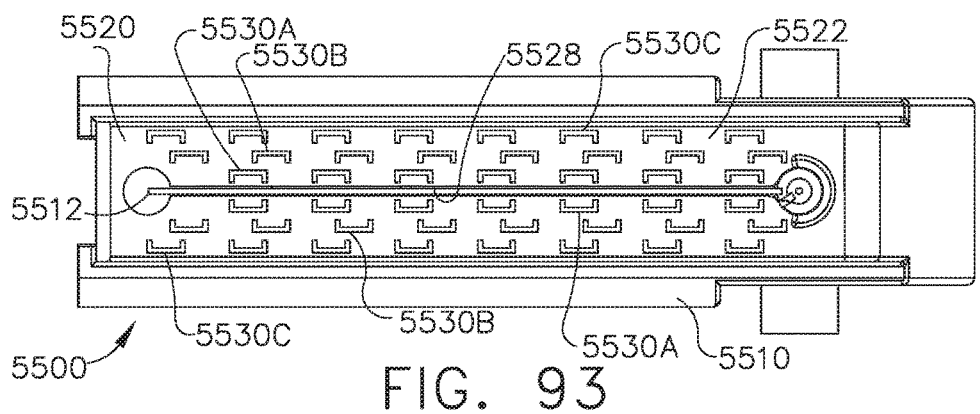
FIG. 93 is a bottom view of an anvil in accordance with at least one embodiment that may be used in connection with the surgical stapling device of FIG. 92.

The stapling instrument 5500 may employ an anvil 5570 as shown in FIG. 93. As can be seen in FIG. 93, the anvil 5570 may include two inner rows of pairs 5578A of inner staple forming pockets 5579, two middle rows 5577B of pairs 5578B of middle staple forming pockets 5579 and two outer rows 5577C of pairs 5578C of outer staple forming pockets 5579. The staple forming pockets 5579 in a single pair 5578A, 5578B, and 5578C are spaced from each other and are configured to receive and form a corresponding leg 5544, 5546 of a particular staple 5540, 5550, and 5560. However, the staple forming pockets 5579 may be provided in any of the various staple forming pocket configurations disclosed herein.

Figure 96:
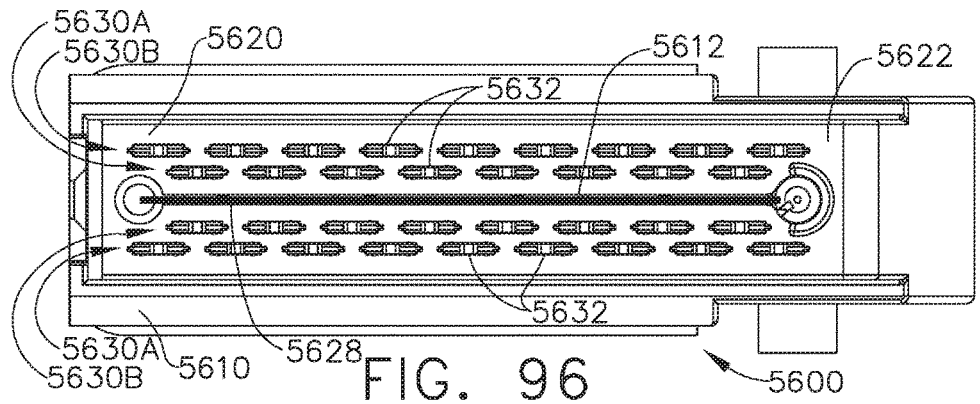
FIG. 96 is a top view of a surgical stapling device according to at least one embodiment.

FIG. 96 illustrates another stapling instrument 5600 in accordance with at least one embodiment configured to capture, incise, and staple tissue. The stapling instrument 5600 comprises a frame assembly 5610, a staple cartridge 5620, and an anvil 5670 (FIG. 97) that is configured to be supported in confronting relationship relative to the deck 5622 of the staple cartridge 5620. The stapling instrument 5600 further comprises a knife assembly comprising a cutting member 5612 that is configured to incise the tissue captured between the staple cartridge 5620 and the anvil 5670. The staple cartridge 5620 comprises a deck 5622 that includes a centrally disposed cutting slot 5628 that is configured to receive the cutting member 5612. An inner row 5630A of spaced staple cavities 5632 is provided on each side of the cutting slot 5528. An outer row 5630B of spaced staple cavities 5632 is provided adjacent to each of the inner rows 5630A of staple cavities 5632. No deck features are illustrated in connection with this embodiment. However, other embodiments employ deck features of the various configurations disclosed herein in connection with some or all of the inner staple cavities and/or in connection with some or all of the outer staple cavities.

Figure 97:
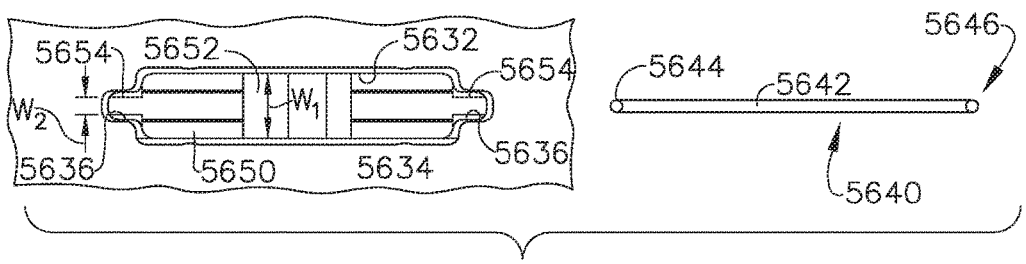
FIG. 97 is a top view of a staple cavity according to at least one embodiment and a corresponding staple.

In at least one arrangement, each staple cavity 5632 removably stores a staple 5640 therein. Each staple 5640 is supported on a corresponding driver 5650 that forms a portion of a movable driver assembly that is operably supported in the stapling instrument 5600. It will be understood that the application of an actuation motion to the driver assembly will result in the advancement of each staple 5640 into forming contact with the anvil 5670. In the illustrated arrangement, each staple 5640 comprises a crown 5642 and two spaced legs 5644, 5646. As discussed herein, the legs 5644, 5646 may be perpendicular to the crown 5642 or they may not be perpendicular to the crown 5642. As can be seen in FIG. 97, each staple driver 5650 comprises a central portion 5652 that has a first width $W_1$ and two end portions 5644 that each has a narrower width $W_2$. The end portions 5654 support each end of the corresponding staple 5642. Each cavity 5632 is similarly shaped with a central portion 5634 and two end portions 5636. The narrow end portions 5636 provide lateral support to the staple legs 5644, 5646 as the staple 5642 is ejected out of the cavity 5632.

Figure 98:
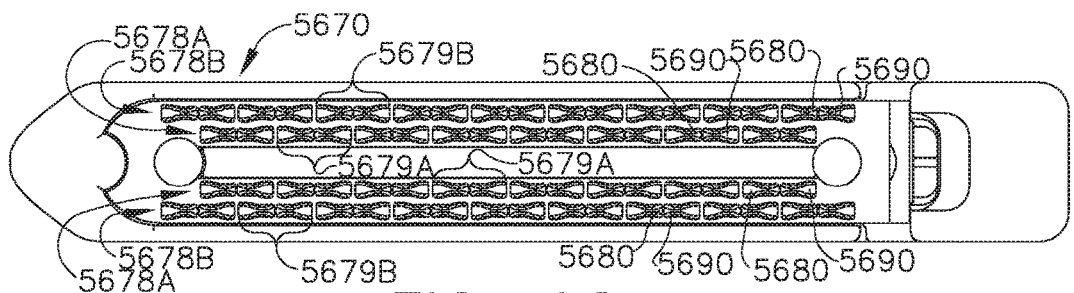
FIG. 98 is a bottom view of an anvil according to at least one embodiment that may be employed in connection with the surgical stapling device of FIG. 96.
Figure 99:
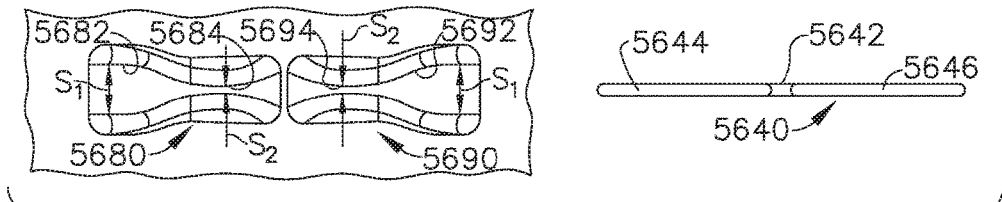
FIG. 99 is an enlarged view of staple forming pockets of the anvil of FIG. 98 with a corresponding formed staple.

The stapling instrument 5600 may employ an anvil 5670 as shown in FIG. 98. As can be seen in that Figure, the anvil 5670 includes two inner rows 5678A of pairs 5679A of staple forming pockets 5680, 5690 and two outer rows 5678B of pairs 5679B of staple forming pockets 5680, 5690. The staple forming pockets 5680, 5690 in a single pair 5679A, 5679B are spaced from each other and are configured to receive and form a corresponding leg 5544, 5546 of a particular staple 5640. As can be see in FIG. 99, each staple pocket 5680 includes an outer pocket portion 5682 that is configured to initially be contacted by the end of a corresponding leg 5644 and an inner pocket portion 5684 to capture the leg 5644 as it is formed inward to complete the forming process. Similarly, each staple pocket 5690 includes an outer pocket 5692 that is configured to initially be contacted by the end of a corresponding leg 5646 and an inner pocket portion 5694 to capture the leg 5646 as it is formed inward to complete the forming process. The outer pocket portion 5682 has a width $S_1$ and the inner pocket portion 5684 has a width $S_2$ In the illustrated embodiment, $S_1 > S_2$ Such an arrangement serves to provide a wider initial contact area for the legs and serves to retain the legs in planar alignment with the staple crown during the forming process to provide the staple 5640 with the formed shape illustrated in FIG. 99.

Figure 100:
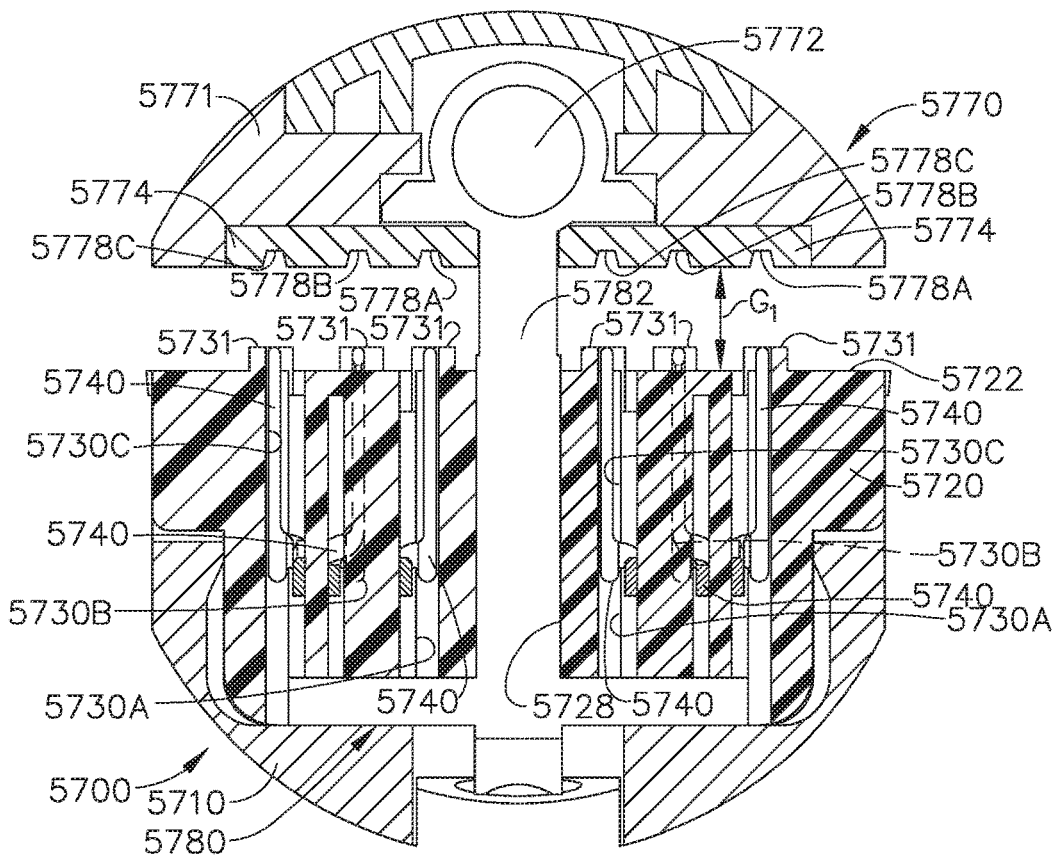
FIG. 100 is a partial cross-sectional view of a surgical stapling device according to at least one embodiment.

FIG. 100 illustrates a portion of another stapling instrument 5700 in accordance with at least one embodiment configured to capture, incise, and staple tissue. The stapling instrument 5700 comprises an elongate channel 5710, a staple cartridge 5720, and an anvil 5770 that is configured to be supported in confronting relationship relative to the deck 5722 of the staple cartridge 5720. The stapling instrument 5700 further comprises a knife assembly 5780 comprising a cutting member 5782 that is configured to incise the tissue that is captured between the staple cartridge 5720 and the anvil 5770. In the illustrated arrangement, the knife assembly 5780 is suspended from a rotary drive shaft 5772 that is operably supported in the anvil 5770. Rotation of the rotary drive shaft 5772 in a first rotary direction will drive the knife assembly 5780 distally through the staple cartridge 5720. Rotation of the drive shaft 5772 in a second opposite direction will cause the knife assembly 5780 to be retracted in a proximal direction. The knife assembly 5780 serves to drive a wedge sled (not shown) distally which interfaces with the staple drivers to sequentially eject the staples from the staple cartridge 5720.

The staple cartridge 5720 comprises a deck 5722 that includes a centrally disposed cutting slot 5728 that is configured to receive the cutting member 5782. An inner row of spaced inner staple cavities 5730A is provided on each side of the cutting slot 5728. A middle row of spaced middle staple cavities 5730B is provided adjacent each inner row of spaced inner staple cavities 5730A on each side of the cutting slot 5728. An outer row of spaced outer staple cavities 5730C are provided adjacent to each of the middle rows of middle staple cavities 5730B. As can be seen in FIG. 100, a deck feature 5731 of the various configurations disclosed herein may be associated with each of the staple cavities 5730A, 5730B, 5730C. In other embodiments, every other one of the inner staple cavities 5730A and/or every other one of the middle staple cavities 5730B and/or every other one of the outer staple cavities 5730C has a deck feature 5731 associated therewith. In still other arrangements, no deck features may be employed in connection with any of the staple cavities 5730A, 5730B, and 5730C.

As can be seen in FIG. 100, the anvil 5770 may include two inserts 5774 that are supported in the anvil body 5771 such that one insert 5774 corresponds to the staples located on one side of the cutting slot 5728 and the other insert 5774 corresponds to the staples located on the other side of the cutting slot 5728. As can be seen in FIG. 100, when the anvil 5770 is closed, the inserts 5774 are located a uniform distance $G_1$ from the cartridge deck 5722. Each insert 5774 comprises an inner row of inner staple forming cavities 5778A, a middle row of middle staple forming cavities 5778B and an outer row of outer staple forming cavities 5778C. The staple forming cavities 5778A, 5778B, and 5778C may comprise any of the various staple forming pocket configurations disclosed herein. When the device 5700 is fired, each of the staples 5740 attains the same formed height and configuration. However, other staple configurations and staple forming pocket configurations disclosed herein may also be employed so as to create staples with different formed heights and configurations.

Figure 101:
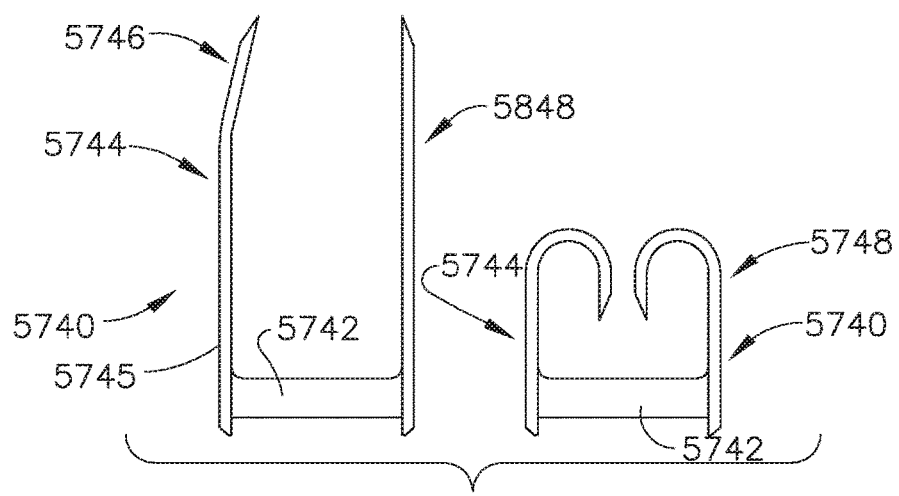
FIG. 101 depicts unformed staples according to at least one embodiment.

Referring now to FIG. 101, a staple 5740 comprises a base 5742 and staple legs 5744, 5548 that extend from the base 5542. In the illustrated arrangement, the leg 5744 may have a gullwing configuration. That is, the leg 5744 has a vertically extending portion 5745 and an inwardly angled end portion 5746. Other embodiments may employ the type and staple configurations disclosed in U.S. patent application Ser. No. 14/836,110, filed Aug. 26, 2015, entitled SURGICAL STAPLING CONFIGURATIONS FOR CURVED AND CIRCULAR STAPLING INSTRUMENTS, which is hereby incorporated by reference herein in its entirety.

Figure 102:
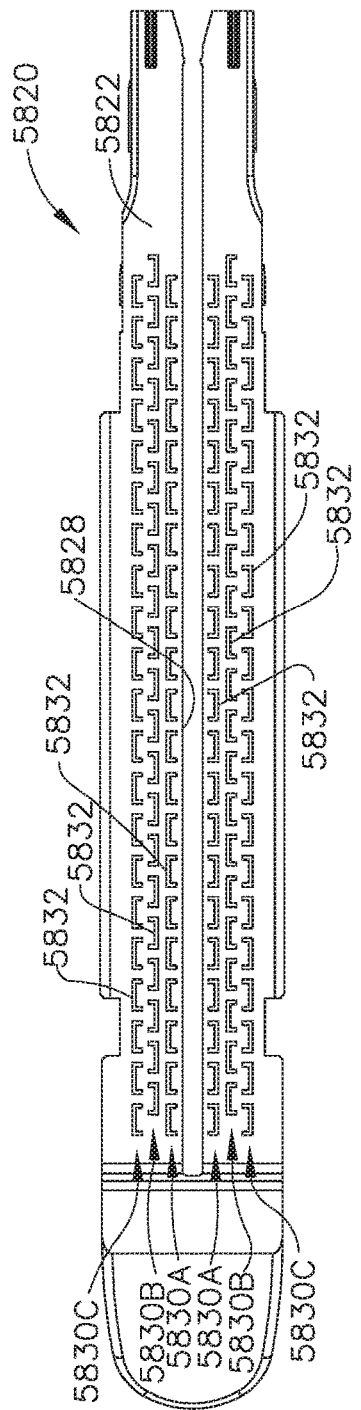
FIG. 102 is a top plan view of a staple cartridge according to at least one embodiment.

FIG. 102 illustrates a surgical staple cartridge 5820, which may be used, for example, in connection with the stapling device 5700 described above or one of the similar stapling device arrangements disclosed in the various references incorporated by reference herein. The staple cartridge 5820 comprises a deck 5822 that includes a centrally disposed cutting slot 5828 that is configured to receive the cutting member therethrough. An inner row 5830A of spaced staple cavities 5832 is provided on each side of the cutting slot 5828. A middle row 5830B of spaced staple cavities 5832 is provided adjacent each inner row 5830A on each side of the cutting slot 5828. An outer row 5832C of spaced cavities 5832 is provided adjacent to each of the middle rows 5830B of staple cavities 5832. No deck features are illustrated in connection with this embodiment. However, other embodiments employ deck features of the various configurations disclosed herein in connection with some or all of the inner staple cavities and/or in connection with some or all of the middle staple cavities and/or in connection with some or all of the outer staple cavities.

Figure 103:
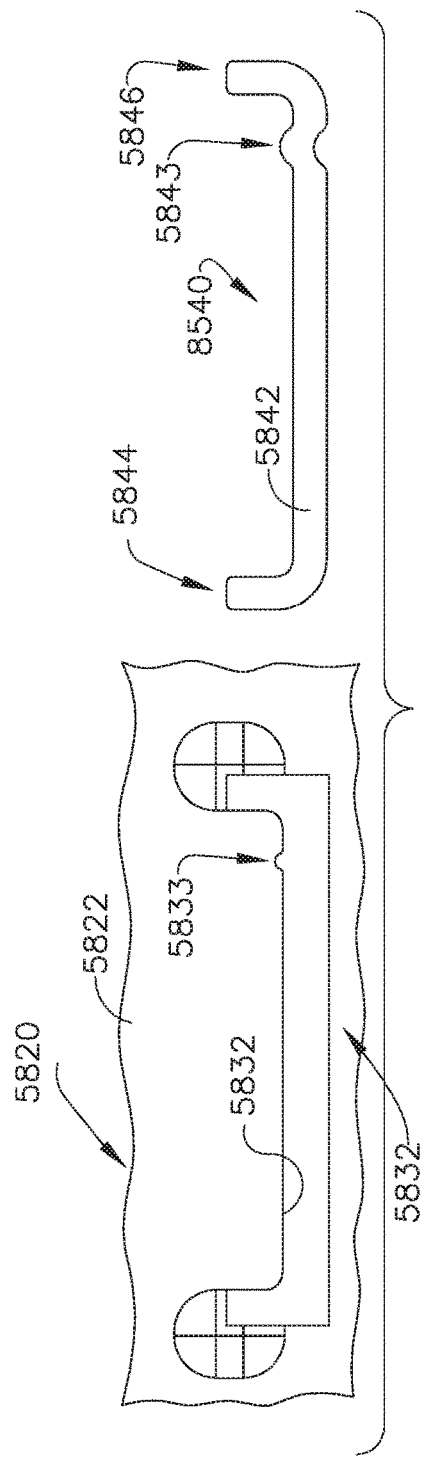
FIG. 103 is a top view of a staple cavity according to at least one embodiment and a corresponding staple.

In at least one arrangement, each staple cavity 5832 removably stores a staple 5840 therein. In one arrangement, for example, the staples 5840 may be of the type and configurations disclosed in U.S. patent application Ser. No. 14/836,110, filed Aug. 26, 2015, and entitled SURGICAL STAPLING CONFIGURATIONS FOR CURVED AND CIRCULAR STAPLING INSTRUMENTS, which is hereby incorporated by reference herein in its entirety. Further to the above, the staples of the staple cartridges disclosed herein can include one or more features configured to hold the staples in the staple cavities of the staple cartridge. Turning now to FIG. 103, a staple 5840 includes a base 5842 and staple legs 5844, 5846 that extend from the base 5842. The base 5842 comprises a protrusion 5843 extending therefrom which is engaged with a corresponding detent or groove 5833 in the sidewall of the corresponding staple cavity 5832. The interaction between the protrusion 5843 and the detent or groove 5833 in the staple cavity sidewall keeps the staple 5840 from falling out of the bottom of the cartridge 5820. The interaction between the protrusion 5843 and the staple cavity sidewall comprises an interference fit; however, such an interference fit does not prevent the staples 5840 from being ejected from the respective cavities 5832. The protrusion 5843 can be formed in the base 5842 during a stamping process, for example. The stamping process can form the protrusion 5843 by creating a dent in the opposite side of the base 5842. Alternative embodiments are envisioned which do not comprise the groove or detent 5833.

Figure 104:
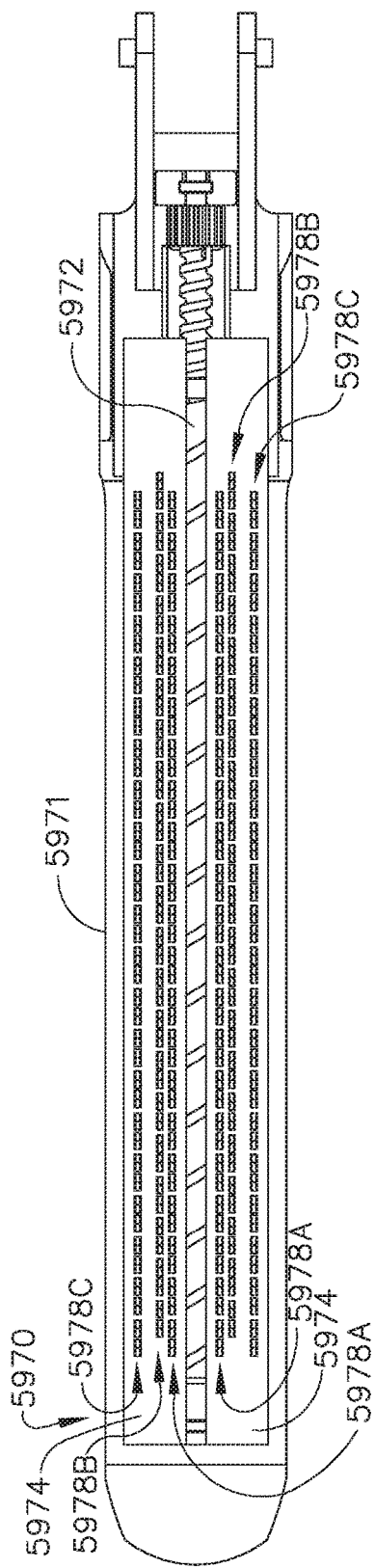
FIG. 104 is a bottom view of a surgical stapling device anvil according to at least one embodiment.
Figure 105:
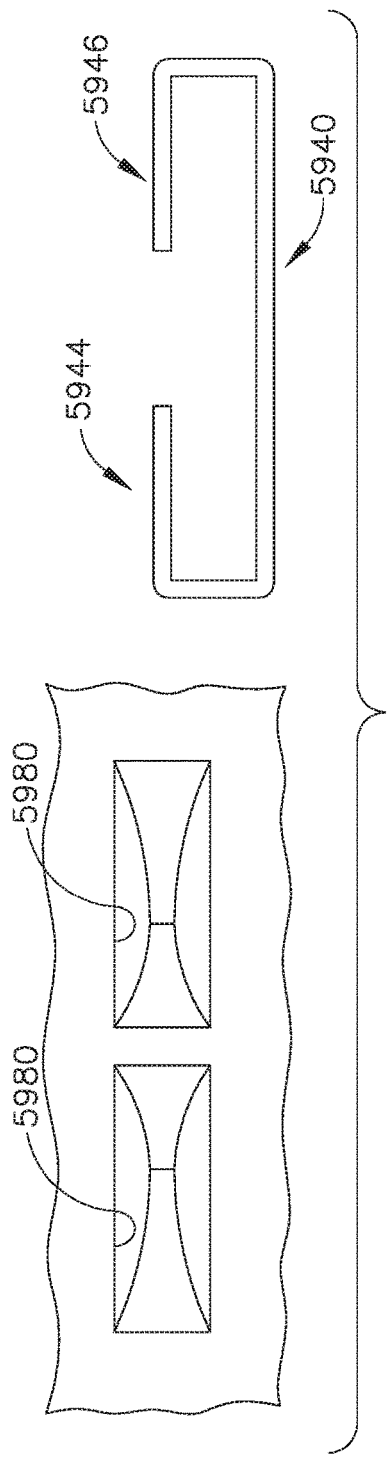
FIG. 105 is a top view of a pair of staple cavities according to at least one embodiment and a corresponding staple.

FIG. 104 illustrates an anvil 5970 that includes a rotary drive shaft 5972 for driving a knife assembly in the above described manner. The anvil 5970 may include two inserts 5974 that are supported in the anvil body 5971 such that one insert 5974 corresponds to the staples located on one side of the cutting slot in a corresponding staple cartridge (not shown) and the other insert 5974 corresponds to the staples located on the other side of the cutting slot. Each insert 5974 comprises an inner row 5978A of pairs 5979A of staple forming cavities 5980, a middle row 5978B of pairs 5979B of staple forming cavities 5980 and an outer row 5978C of pairs 5979C of staple forming cavities 5980. The staple forming pockets 5980 in a single pair 5979A, 5979B, 5979C are spaced from each other and are configured to receive and form a corresponding leg 5944, 5946 of a corresponding staple 5940.

The various staple cartridge and staple configurations disclosed herein may be employed in connection with various drug eluting arrangements. Each of the following references is hereby incorporated by reference herein in its respective entirety: U.S. patent application Ser. No. 14/840,613, filed Aug. 31, 2015, entitled DRUG ELUTING ADJUNCTS AND METHODS OF USING DRUG ELUTING ADJUNCTS; U.S. patent application Ser. No. 14/667,874, filed Mar. 25, 2015, entitled MALLEABLE BIOABSORBABLE POLYMER ADHESIVE FOR RELEASABLY ATTACHING A STAPLE BUTTRESS TO A SURGICAL STAPLER; U.S. patent application Ser. No. 13/531,619, filed Jun. 25, 2012, entitled TISSUE STAPLER HAVING A THICKNESS COMPENSATOR COMPRISING INCORPORATING A HEMOSTATIC AGENT, U.S. Patent Application Publication No. 2012/0318842; U.S. patent application Ser. No. 13/531,623, filed Jun. 25, 2012, entitled TISSUE STAPLER HAVING A THICKNESS COMPENSATOR INCORPORATING AN OXYGEN GENERATING AGENT, U.S. Patent Application Publication No. 2012/0318843; U.S. patent application Ser. No. 13/531,627, filed Jun. 25, 2012, entitled TISSUE STAPLER HAVING A THICKNESS COMPENSATOR INCORPORATING AN ANTI-MICROBIAL AGENT, U.S. Patent Application Publication No. 2012/0312860; U.S. patent application Ser. No. 13/531,630, filed Jun. 25, 2012, entitled TISSUE STAPLER HAVING A THICKNESS COMPENSATOR INCORPORATING AN ANTI-INFLAMMATORY AGENT, U.S. Patent Application Publication No. 2012/0318844; U.S. patent application Ser. No. 13/763,161, filed Feb. 8, 2013, entitled RELEASABLE LAYER OF MATERIAL AND SURGICAL END EFFECTOR HAVING THE SAME, U.S. Patent Application Publication No. 2013/0153641; U.S. patent application Ser. No. 13/763,177, filed Feb. 8, 2013, entitled ACTUATOR FOR RELEASING A LAYER OF MATERIAL FROM A SURGICAL END EFFECTOR, U.S. Patent Application Publication No. 2013/0146641; U.S. patent application Ser. No. 13/763,192, filed Feb. 8, 2013, entitled MULTIPLE THICKNESS IMPLANTABLE LAYERS FOR SURGICAL STAPLING DEVICES, U.S. Patent Application Publication No. 2013/0146642; U.S. patent application Ser. No. 13/763,028, filed Feb. 8, 2013, entitled ADHESIVE FILM LAMINATE, U.S. Patent Application Publication No. 2013/0146643; U.S. patent application Ser. No. 13/763,035, filed Feb. 8, 2013 entitled, ACTUATOR FOR RELEASING A TISSUE THICKNESS COMPENSATOR FROM A FASTENER CARTRIDGE, U.S. Patent Application Publication No. 2013/0214030; U.S. patent application Ser. No. 13/763,042, filed Feb. 8, 2013, entitled RELEASABLE TISSUE THICKNESS COMPENSATOR AND FASTENER CARTRIDGE HAVING THE SAME, U.S. Patent Application Publication No. 2013/0221063; U.S. patent application Ser. No. 13/763,048, filed Feb. 8, 2013, entitled FASTENER CARTRIDGE COMPRISING A RELEASABLE TISSUE THICKNESS COMPENSATOR, U.S. Patent Application Publication No. 2013/0221064; U.S. patent application Ser. No. 13/763,054, filed Feb. 8, 2013, entitled FASTENER CARTRIDGE COMPRISING A CUTTING MEMBER FOR RELEASING A TISSUE THICKNESS COMPENSATOR, U.S. Patent Application Publication No. 2014/0097227; U.S. patent application Ser. No. 13/763,065, filed Feb. 8, 2013, entitled FASTENER CARTRIDGE COMPRISING A RELEASABLY ATTACHED TISSUE THICKNESS COMPENSATOR, U.S. Patent Application Publication No. 2013/0221065; U.S. patent application Ser. No. 13/763,078, filed Feb. 8, 2013, entitled ANVIL LAYER ATTACHED TO A PROXIMAL END OF AN END EFFECTOR, U.S. Patent Application Publication No. 2013/0256383; U.S. patent application Ser. No. 13/763,094, filed Feb. 8, 2013, entitled LAYER COMPRISING DEPLOYABLE ATTACHMENT MEMBERS, U.S. Patent Application Publication No. 2013/0256377; U.S. patent application Ser. No. 13/763,106, filed Feb. 8, 2013, entitled END EFFECTOR COMPRISING A DISTAL TISSUE ABUTMENT MEMBER, U.S. Patent Application Publication No. 2013/0256378; U.S. patent application Ser. No. 13/532,825, filed Jun. 26, 2012, entitled TISSUE THICKNESS COMPENSATOR HAVING IMPROVED VISIBILITY, U.S. Patent Application Publication No. 2013/0256376; U.S. patent application Ser. No. 14/300,954, filed Jun. 10, 2014, entitled ADJUNCT MATERIALS AND METHODS OF USING SAME IN SURGICAL METHODS FOR TISSUE SEALING, U.S. Patent Application Publication No. 2015/0351758; U.S. patent application Ser. No. 14/926,027, filed Oct. 29, 2015, entitled SURGICAL STAPLER BUTTRESS ASSEMBLY WITH GEL ADHESIVE RETAINER; U.S. patent application Ser. No. 14/926,029, filed Oct. 29, 2015, entitled FLUID PENETRABLE BUTTRESS ASSEMBLY FOR A SURGICAL STAPLER; U.S. patent application Ser. No. 14/926,072, filed Oct. 29, 2015, entitled SURGICAL STAPLER BUTTRESS ASSEMBLY WITH FEATURES TO INTERACT WITH MOVABLE END EFFECTOR COMPONENTS; U.S. patent application Ser. No. 14/926,090, filed Oct. 29, 2015, entitled EXTENSIBLE BUTTRESS ASSEMBLY FOR SURGICAL STAPLER; and U.S. patent application Ser. No. 14/926,160, filed Oct. 29, 2015, entitled MULTI-LAYER SURGICAL STAPLER BUTTRESS ASSEMBLY.

The various anvil arrangements disclosed herein may employ relatively planar forming inserts that include staple forming pockets that are formed therein or they may have "stepped" forming surfaces that have corresponding staple forming pockets formed therein. The various staple cartridge arrangements herein may have planar deck surfaces or the deck surfaces may be stepped (include deck surface portions that are on different planes). In some embodiments, deck features may be associated with all of the staple cavities in the staple cartridge. In other arrangements, deck features are employed in connection with all of the staple cavities in every other row of staple cavities. Still other embodiments are envisioned wherein the deck features are associated with every other staple cavity in a particular row, with every other row of cavities being so constructed. Still other embodiments are contemplated wherein no deck features are employed.

The various embodiments disclosed herein may employ staples that have a "U"-shaped unformed configuration or the staples may be of different unformed shapes wherein, for example, the base or crown has a rectangular cross-sectional shape. The various staples may be formed from wire that has a round cross-sectional shape, a squared cross-sectional shape, combinations of round and squared cross-sectional shapes, etc. The staples may be provided with one or more legs that have a gullwing or tapered configuration. The staples may have different wire diameters and different maximum cross-sectional dimensions. The staple legs may be symmetric or they may be asymmetric (with and without bent tips). The legs of a particular staple may be parallel to each other or they may not be parallel to each other. Staples in a particular cartridge may have identical unformed heights or they may have different unformed heights. The staples in a particular cartridge or region may have identical crown widths or they may have different crown widths. The staples and their corresponding staple pockets may be configured such that when the staple is formed, the legs lie in the same plane as the staple crown or base or they may be configured such that when the staple is formed, the legs do not lie in the same plane with the crown or the base. All of the aforementioned staple features can vary from staple to staple, between regions of staples and between cartridge selections.

In circular staple anvil arrangements, the staple forming pockets may be tangent to the circumference of the anvil. In other arrangements or in addition to the tangentially arranged staple forming pockets, other staple forming pockets may be provided at angles to the tangential direction. Such variations in staple forming pocket orientations may be provided within a particular row of staple forming pockets or in different rows of staple forming pockets. A variety of different staple forming pocket geometries may also be employed. Conventional symmetrical staple forming pocket geometries may be employed. In addition to or in the alternative, asymmetrical staple forming pocket geometries may be employed. Other staple forming pockets may have a bowtie shape with there is a large landing zone for each staple leg to funnel the corresponding leg to a narrower exit pocket portion. All of the aforementioned staple forming pocket features can vary from pocket to pocket, between regions or lines of pockets and between particular anvil selections.

The various stapling devices disclosed herein may also be configured to provide different amounts of driver travel that is tailored to achieve desired formed staple heights relative to corresponding gaps provided between the anvil and the cartridge. For example, in some arrangements, a staple driver may be driven just past the cartridge deck or well past the cartridge deck to control the formed staple height. By matching an amount of driver travel to a particular staple having a desired unformed length or height, staples with desired formed heights can be obtained.

As described in various embodiments of the present disclosure, a surgical stapling and cutting instrument includes an anvil and a cartridge channel configured to receive a staple cartridge. One or both of the anvil and the staple cartridge is movable relative to the other between an open configuration and a closed configuration to capture tissue therebetween. Staples are deployed from staple cavities in the staple cartridge into the captured tissue. The staples are formed against forming pockets in the anvil. After the staples are deployed, the staple cartridge can be replaced.

To properly form the staples, the staple cavities and the forming pockets need to be closely aligned in the closed configuration. A limitation arises in that one type of anvil is only useable with one type of staple cartridge. Different staple cartridges that have staple cavities that are arranged differently cannot be used with the same anvil because the staple cavities cannot be properly aligned with the forming pockets of the anvil. The present disclosure comprises various embodiments that modify an anvil to be useable with different staple cartridges. Another limitation arises when an anvil includes one or more components that are configured to be changed or spent during staple deployment. The present disclosure comprises various embodiments that modify an anvil to replenish components or features that are changed or spent during staple deployment and/or to present new features and/or components.

Figure 106:
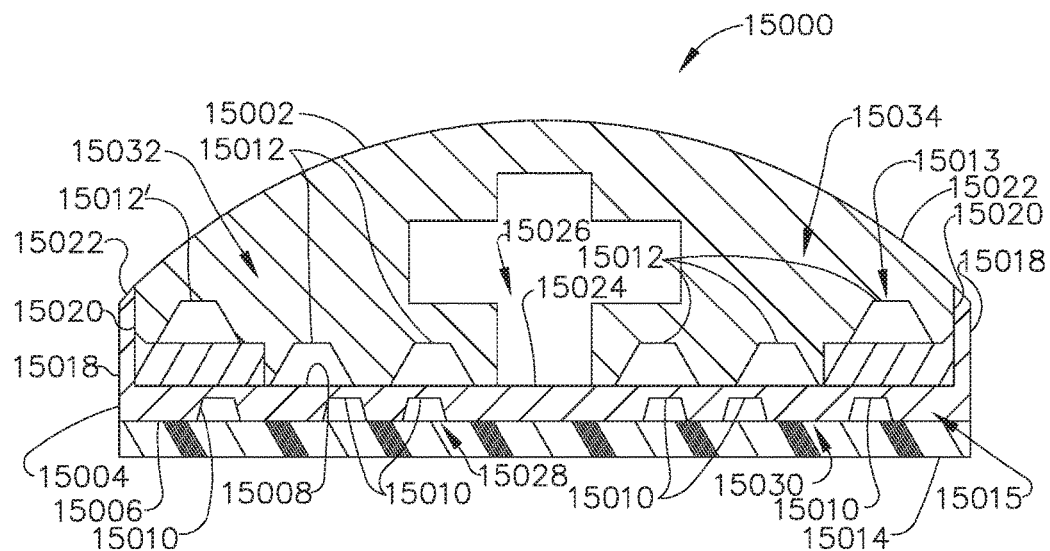
FIG. 106 is a cross-sectional view of an anvil assembly of a surgical stapler in accordance with at least one embodiment.

Referring to FIG. 106, an anvil assembly 15000 includes an anvil modification member 15004 that is attached to an anvil 15002. The anvil modification member 15004 includes a tissue-contacting surface 15006 and an anvil-contacting surface 15008. The tissue-contacting surface 15006 comprises pockets 15010 that are different from forming pockets 15012 of the anvil 15002. When the anvil modification member 15004 is not attached to the anvil 15002, the forming pockets 15012 are alignable with the staple cavities of a first staple cartridge. When the anvil modification member 15004 is attached to the anvil 15002, however, the forming pockets 15010 are alignable with the staple cavities of a second staple cartridge while are different from the staple cavities of the first staple cartridge.

As illustrated in FIG. 106, an anvil 15002 comprises a stepped deck 15013 while the anvil modification member 15004 comprises a non-stepped deck 15015. Alternatively, an anvil may comprise a non-stepped deck, which can be modified by an anvil modification member that comprises a stepped deck. The stepped deck 15013 includes outer rows of forming pockets 15012' that are stepped up from inner rows of forming pockets 15012. The non-stepped deck 15015 includes forming pockets 15010 that are defined in a planar tissue-contacting surface 15006. In at least one instance, an anvil modification member can include one or more rows of forming pockets 15010 that are stepped up from other rows of forming pockets 15010.

In at least one instance, an anvil modification member 15004 can be used when one or more components or features of an anvil have been changed or spent during a previous use of the anvil. In such instances, the anvil modification member replaces a spent or changed tissue-contacting surface of the anvil with a new tissue-contacting surface with new components or features. For example, the forming pockets 15012 of the anvil 15002 may include circuit elements that are severable during staple deployment. Instead of repairing the severed circuit elements every time the anvil is used, an anvil modification member can be employed to present a replacement tissue-contacting surface including anvil pockets with intact circuit elements. In another example, an anvil may include an implantable layer positioned against a tissue-contacting surface of the anvil. Instead of attaching a new implantable layer to the anvil every time the anvil is used, an anvil modification member can be employed to present a replacement tissue-contacting surface with an implantable layer that is attached to the replacement tissue-contacting surface.

Figure 107:
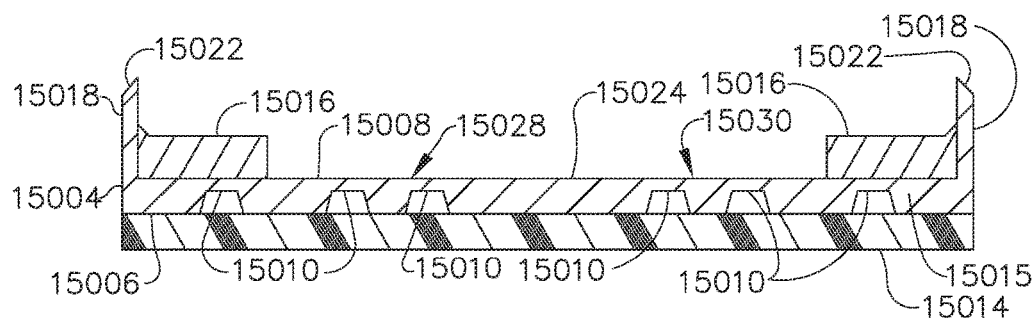
FIG. 107 is a cross-sectional view of an anvil modification member of the anvil assembly of FIG. 106.

In at least one instance, an anvil modification member 15004 can be used to introduce one or more new components or features in an anvil. As illustrated in FIG. 107, the anvil modification member 15004 comprises an implantable layer 15014. Although the anvil 15002 may not originally include an implantable layer, an implantable layer can be added to the anvil 15002 by attaching the anvil modification member 15004 to the anvil 15002, as illustrated in FIG. 106. The implantable layer 15014 can be attached to the anvil modification member 15004 using various attachment means such as, for example, biocompatible glue and/or straps. The implantable layer 15014 is released from the anvil modification member 15004 during deployment of the staples. In certain instances, a formed staple defines an entrapment area that may include tissue and a portion of the implantable layer 15014. In such instances, the entrapped portion of implantable layer 15014 can function as a tissue thickness compensator. The implantable layer 15014 may comprise a polymeric composition. The polymeric composition may comprise one or more synthetic polymer and/or one or more non-synthetic polymer. The synthetic polymer may comprise a synthetic absorbable polymer and/or a synthetic non-absorbable polymer.

During the staple formation process, an anvil is subjected to significant forces. Gaps between an anvil and an anvil modification member can lead to reduction in stability and/or an increased risk of collapse during the staple formation process. As illustrated in FIGS. 106 and 107, an anvil modification member 15004 includes gap fillers 15016 that extend from the anvil-contacting surface 15008 of the anvil modification member 15004. The gap fillers 15016 are configured to provide additional support between an anvil 15002 and an anvil modification member 15004, and are especially useful in situations where the anvil includes a stepped deck.

As illustrated in FIG. 106, the stepped deck 15013 of the anvil 15002 has one or more gaps between the anvil 15002 and the anvil modification member 15004. The gap fillers 15016 are strategically positioned against the outer rows of forming pockets 15012' of the stepped deck 15013 to minimize the gaps between the anvil modification member 15004 and the anvil 15002 when the anvil modification member 15004 is attached to the anvil 15002. In at least one instance, an anvil-contacting surface 15008 of anvil modification member 15004 includes protrusions configured to fill, or at least substantially fill, corresponding anvil pockets of an anvil attached to the anvil modification member 15004.

The anvil modification member 15004 includes one or more attachment features 15018. In at least one instance, the attachment features 15018 are configured to releasably attach the anvil modification member 15004 to the anvil 15002. As illustrated in FIGS. 106 and 107, the attachment features 15018 of the anvil modification member 15004 are comprised of side walls that are sufficiently spaced apart from one another to snuggly grip the outer walls 15020 of the anvil 15002. The attachment features 15018 include beveled, curved, radiused, and/or shaved edges 15022 that are configured to form continuous or flush surfaces with the anvil 15002 when the anvil modification member 15004 is attached to the anvil 15002. The resulting flush surfaces are intended to reduce or prevent trauma to tissue.

In at least one instance, an anvil modification member can be designed for snapping engagement with an anvil. For example, an anvil can include one or more slits that are configured to frictionally receive one or more upstanding tabs that extend from an anvil-contacting surface of an anvil modification member. Other attachment means can be utilized to position an anvil modification member against an anvil such as, for example, biocompatible glue and/or screws.

Referring again to FIGS. 106 and 107, an anvil modification member 15004 includes a transectable portion 15024 extending longitudinally between two sides 15028 and 15030 of the anvil modification member 15004. When the anvil modification member 15004 is attached to the anvil 15002, as illustrated in FIG. 106, the transectable portion 15024 is aligned with a longitudinal slot 15026 extending between two sides 15032 and 15034 of the stepped deck 15013 of the anvil 15002. The transectable portion 15024 is severed by a cutting member traveling distally along the longitudinal slot 15026. The transectable portion 15024 stabilizes the anvil modification member 15004 when the anvil modification member 15004 is attached to the anvil 15002. In at least one instance, the sides 15028 and 15030 of the anvil modification member 15004 are completely severed, and separated, by the cutting member as the cutting member is advanced distally along the longitudinal slot 15026. In other instances, the sides 15028 and 15030 of the anvil modification member 15004 are only partially severed by the cutting member as the cutting member is advanced distally along the longitudinal slot 15026.

Figure 108:
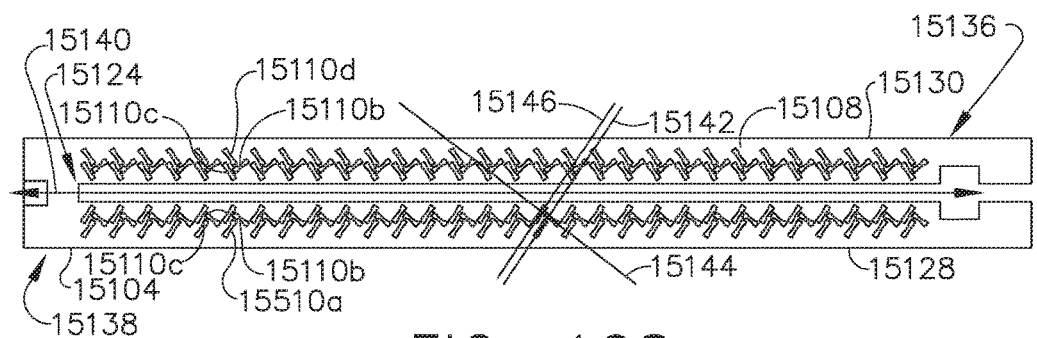
FIG. 108 is a top view of an anvil modification member of the anvil assembly of FIG. 106.

Referring to FIG. 108, an anvil modification member 15104 is depicted. The anvil modification member 15104 is similar in many respects to the anvil modification member 15004. For example, the anvil modification member 15104 is releasably attached to an anvil 15002. Unlike the anvil modification member 15004, the anvil modification member 15104 lacks a transectable portion. Instead, the anvil modification member 15104 includes an elongate slot 15124 extending between two sides 15128 and 15130 of the anvil modification member 15104. In other instances, however, the anvil modification member 15104 may be equipped with a transectable portion in place of the elongate slot 15124.

The anvil modification member 15104 includes a proximal end 15136 and a distal end 15138. The elongate slot 15124 can be defined through the proximal end 15136 and/or the distal end 15138. Furthermore, the elongate slot 15124 defines a longitudinal axis 15140 extending between the two sides 15128 and 15130. As illustrated in FIG. 109, the elongate slot 15124 is aligned with an elongate slot 15026 of an anvil 15002 when the anvil modification member 15104 is attached to the anvil 15002. While in alignment, the elongate slots 15124 and 15026 are configured to receive a cutting member adapted to sever soft tissue, for example.

The anvil modification member 15104 includes three rows of forming pockets 15110*a*, 15110*b*, and 15110*c* on each of the sides 15128 and 15130. As illustrated in FIG. 109, a plurality of first forming pocket 15110*a* can be parallel, or at least substantially parallel, to one another. Likewise, a plurality of second forming pockets 15110*b* can be parallel, or at least substantially parallel, to one another and/or a plurality of third forming pockets 15110*c* can be parallel, or at least substantially parallel, to one another. In at least one instance, "substantially parallel", for purposes herein, can mean being within about 15 degrees of parallel in either direction.

In certain instances, at least one first forming pocket 15110*a*, at least one second forming pocket 15110*b*, and at least one third forming pocket 15110*c* are defined in a tissue-contacting surface 15108 of the anvil modification member 15004. The first forming pocket 15110*a*, the second forming pocket 15110*b*, and the third forming pocket 15110*c* can be situated on the side 15128 and/or the side 15130. As illustrated in FIG. 109, the first forming pocket 15110*a* defines a first axis 15142 extending through a proximal end and a distal end of the first forming pocket 15110*a*. Likewise, the second forming pocket 15110*b* defines a second axis 15144 extending through a proximal end and a distal end of the second forming pocket 15110*b*. Also, the third forming pocket 15110*c* defines a third axis 15146 extending through a proximal end and a distal end of the third forming pocket 15110*c*. The second axis 15144 is transverse to the first axis 15142 such that the axes 15144 and 15142 create an acute or obtuse angle therebetween. In addition, the second axis 15144 is transverse to the third axis 15146 such as the axes 15144 and 15146 create an acute or obtuse angle therebetween.

As illustrated in FIG. 109, the first axis 15142 is parallel, or at least substantially parallel, to the third axis 15146, while the second axis 15144 is perpendicular, or at least substantially perpendicular, to the first axis 15142 and/or the third axis 15146. In at least one instance, "substantially perpendicular", for purposes herein, can mean being within about 15 degrees of perpendicular in either direction.

Referring to FIGS. 109-112, the first forming pockets 15110*a*, second forming pockets 15110*b*, and third forming pockets 15110*c* of the anvil modification member 15104 are configured to form or bend staples deployable from first staple cavities 15210*a*, second staple cavities 15210*b*, and third staple cavities 15210*c*, respectively, of a staple cartridge 15200. For example, a first forming pocket 15110*a* includes two forming pockets 15152 that are configured to receive and form staple legs 15254 of a staple 15256 as the staple 15256 is deployed from a first staple cavity 15210*a*.

In a closed configuration, the anvil 15002 is aligned, or at least substantially aligned, with the staple cartridge 15200 such that tissue is captured between a tissue-contacting surface 15108 of the anvil modification member 15104 and a tissue-contacting surface 15208 of the staple cartridge 15200. In addition, the first forming pockets 15110*a*, second forming pockets 15110*b*, and third forming pockets 15110*c* of the anvil modification member 15104 are aligned, or at least substantially aligned, with the first staple cavities 15210*a*, second staple cavities 15210*b*, and third staple cavities 15210*c*, respectively, to capture and form the staple legs 15254 of the deployed staples 15256.

The staple cartridge 15200 includes a first side 15228 and a second side 15230. An elongate slot 15224 extends between the first side 15228 and the second side 15230. The elongate slot 15224 can extend between and/or through a proximal end 15236 and a distal end 15238 of the staple cartridge 15200. The staple cartridge 15200 includes three rows of staple cavities 15210*a*, 15210*b*, and 15210*c* on each of the sides 15228 and 15230. In the closed configuration, the elongate slot 15224 is aligned, or at least substantially aligned, with the elongate slot 15026 of an anvil 15002 and the elongate slot 15124 of the anvil modification member 15104. While in alignment, the elongate slots 15224, 15124 and 15026 are configured to receive a cutting member adapted to sever soft tissue, for example.

As illustrated in FIG. 110, a plurality of first staple cavities 15210*a* are parallel, or at least substantially parallel, to one another. Likewise, a plurality of second staple cavities 15210*b* are parallel, or at least substantially parallel, to one another and/or a plurality of third staple cavities 15210*c* are parallel, or at least substantially parallel, to one another.

In certain instances, at least one first staple cavity 15210*a*, at least one second staple cavity 15210*b*, and at least one third staple cavity 15210*c* are defined in a tissue-contacting surface 15208 of the staple cartridge 15200. The first staple cavity 15210*a*, the second staple cavity 15210*b*, and the third staple cavity 15210*c* can be situated on the side 15228 and/or the side 15230. As illustrated in FIG. 110, the first staple cavity 15210*a* defines a first axis 15242 extending through a proximal end and a distal end of the first staple cavity 15210*a*. Likewise, the second staple cavity 15210*b* defines a second axis 15244 extending through a proximal end and a distal end of the second staple cavity 15210*b*. Also, the third staple cavity 15210*c* defines a third axis 15246 extending through a proximal end and a distal end of the third staple cavity 15210*c*. The second axis 15244 is transverse to the first axis 15242 such that the axes 15244 and 15242 create an acute or obtuse angle therebetween. In addition, the second axis 15244 is transverse to the third axis 15246 such as the axes 15244 and 15246 create an acute or obtuse angle therebetween. As illustrated in FIG. 110, the first axis 15242 is parallel, or at least substantially parallel, to the second axis 15246, while the second axis 15244 is perpendicular, or at least substantially perpendicular, to the first axis 15242 and/or the second axis 15246, for example.

In various instances, further to the above, an anvil can comprise rows of staple forming pockets aligned along a first set of longitudinal axes. An anvil modification member which is attachable to the anvil can comprise rows of staple forming pockets aligned along a second set of longitudinal axes which are not aligned with the first set of longitudinal axes. As a result, the staple forming pockets on the anvil modification member are not longitudinally aligned with the staple forming pockets on the anvil. In some instances, some longitudinal rows of forming pockets on the anvil modification member are aligned with the longitudinal rows of forming pockets on the anvil while other longitudinal rows of forming pockets on the anvil modification member are not aligned with the longitudinal rows of forming pockets on the anvil.

Figure 113:
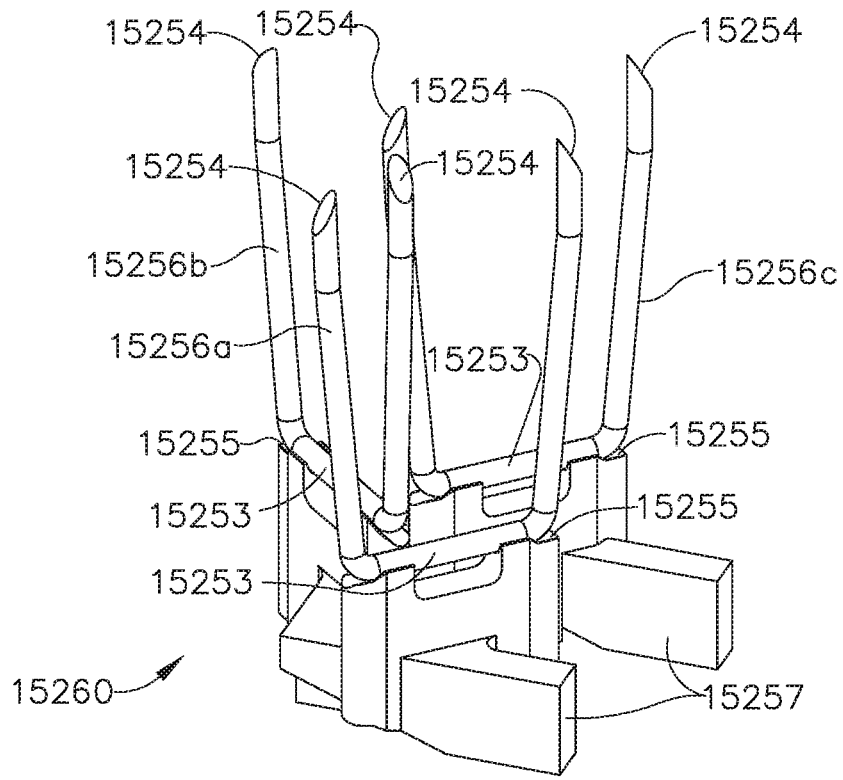
Figure 114:
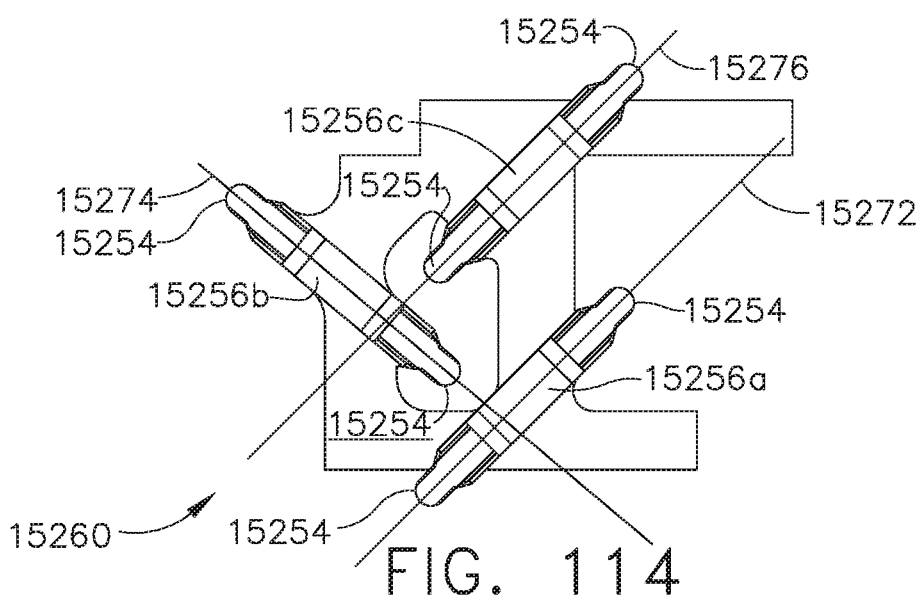

Referring to FIGS. 113 and 114, at least one first staple 15256*a* from at least one first staple cavity 15210*a*, at least one second staple 15256*b* from at least one second staple cavity 15210*b*, and at least one third staple 15256*c* from at least one third staple cavity 15210*c* are simultaneously deployable into tissue captured between the anvil modification member 15104 and the staple cartridge 15200. A triple staple driver 15260 can be configured to cooperate with a cam sled of the staple cartridge 15200 to simultaneously deploy three staples 15256*a*, 15256*b*, and 15256*c* from their respective staple cavities 15210*a*, 15210*b*, and 15210*c*. Staple drivers 15260 can be lifted, or slid, upwardly within staple cavities 15210*a*, 15210*b*, and 15210*c* by the cam sled such that the upward movement of staple drivers 15260 can eject, or deploy, staples 15256*a*, 15256*b*, and 15256*c*.

As illustrated FIGS. 113 and 114, each of the three staples 15256*a*, 15256*b*, and 15256*c* includes a base 15253 situated against a cradle 15255 of the staple driver 15260. The staple driver 15260 comprises two ramps 15257 that are configured to cooperate with a cam sled of the staple cartridge 15200 to simultaneously deploy three staples 15256*a*, 15256*b*, and 15256*c* from their respective staple cavities 15210*a*, 15210*b*, and 15210*c*.

The three staples 15256*a*, 15256*b*, and 15256*c* define common planes 15272, 15274, and 15276, respectively. The three staples 15256*a*, 15256*b*, and 15256*c* are oriented with respect to the staple driver 15260 such that, the second common plane 15274 is transverse to the first common plane 15272 such that the common planes 15274 and 15272 create an acute or obtuse angle therebetween. In addition, the second common plane 15274 is transverse to the third common plane 15276 such that the common planes 15274 and 15276 create an acute or obtuse angle therebetween. As illustrated in FIG. 114, the first common plane 15272 is parallel, or at least substantially parallel, to the third common plane 15276, while the second common plane 15274 is perpendicular, or at least substantially perpendicular, to the first common plane 15272 and the second common plane 15276.

Figure 115:
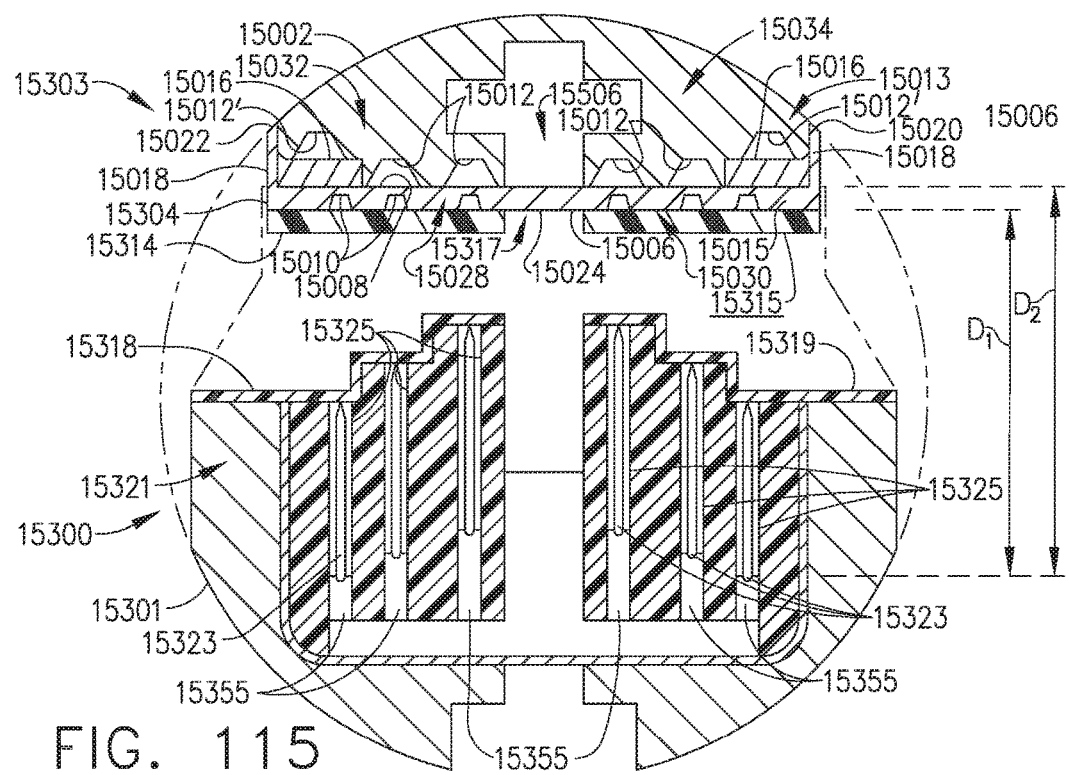

Referring to FIG. 115, an end effector 15300 includes a staple cartridge 15301 illustrated in a closed configuration with an anvil assembly 15303 that includes an anvil modification member 15304 attached to an anvil 15002. The anvil modification member 15304 is similar in many respects to the anvil modification member 15004. For example, the anvil modification member 15304 includes a transectable portion 15024 and forming pockets 15010 disposed on two sides 15028 and 15030 of the anvil modification member 15304. An implantable layer 15314 is disposed against the forming pockets 15010 of the side 15028, and an implantable layer 15315 is disposed against the forming pockets 15010 of the side 15030. The implantable layers 15314 and 15315 are spaced apart defining a gap 15317 therebetween. The gap 15317 extends longitudinally in parallel, or at least substantially in parallel, with the transectable portion 15024. Implantable layers 15318 and 15319 are disposed against a stepped deck 15321 of the staple cartridge 15301. Staples 15323 are supported by cradles 15355 within staple cavities 15325 of the staple cartridge 15301. The staples 15323 are configured to be formed against the forming pockets 15010 when the anvil modification member 15304 is attached to the anvil 15002, as illustrated in FIG. 114. Alternatively, when the anvil modification member 15304 is not attached to the anvil 15002, the staples 15323 are configured to be formed against the forming pockets 15012 and 15012' of the anvil 15002.

Figure 116:
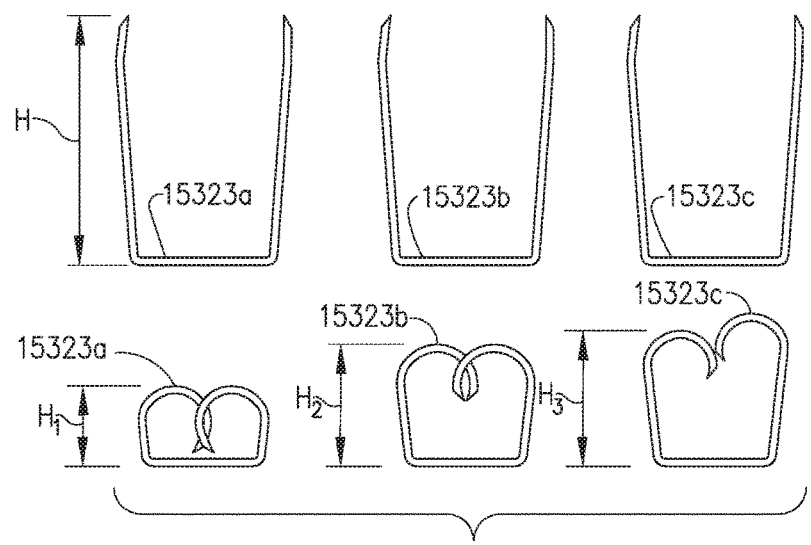

FIG. 116 illustrates three unformed staples 15323a, 15323b, and 15323c that are similar to one another, and are similarly situated within a staple cavity 15325 of a staple cartridge 15301. The staples 15323a, 15323b, and 15323c comprise the same, or at least substantially the same, unformed height H of about 0.150". In various instances, the unformed height H can be selected from a range of about 0.100" to about 0.200", for example. As illustrated in FIG. 116, the staples 15323a, 15323b, and 15323c comprise different formed heights H1, H2, and H3, respectively. The staples 15323a, 15323b, and 15323c were formed in an inner row, intermediate row, and outer row of the staple cartridge 15301, respectively. A formed height of a staple depends on a forming distance defined between a forming pocket and a corresponding cradle that supports the staple in a corresponding staple cavity. The forming distance can be changed by positioning a forming pocket closer or further away from a corresponding cradle. An anvil modification member can be employed to change a forming distance. For example, as illustrated in FIG. 115, a first forming distance D1 is defined between a forming pocket 15010 of the anvil modification member 15304 and a forming cradle 15355, while a second forming distance D2, greater than the first forming distance D1, is defined between a forming pocket 15012' of the anvil 15002 and the same cradle 15355.

Referring to FIG. 116, the staple 15323b comprises a formed height H2 greater than the formed height H1 of the staple 15323a because the second forming distance D2 is greater than the first forming distance D1. Said another way, the staple 15323b was formed against a forming pocket 15012' of the anvil 15002 while the staple 15323a was formed against a forming pocket 15010 of the anvil modification member 15304. As illustrated in FIG. 116, the formed height H3 of the staple 15323c of the outer row of staples of the staple cartridge 15301 is a formed height of a first staple leg of the staple 15323c which is less than a formed height of a second staple leg of the staple 15323c. A staple such as the staple 15323c can comprise staple legs that are formed to different staple heights, as illustrated in FIG. 116.

In various instances, an anvil modification member may include a stepped tissue-contacting surface, wherein at least one row of forming pockets is stepped up or down with respect to the other rows of forming pockets, for example. In certain instances, an anvil modification member may be positioned against a particular portion of an anvil to modify that portion. For example, an anvil modification member can be positioned against a proximal portion of an anvil to modify the proximal portion while the distal and central portions remain unchanged. In another example, an anvil modification member can be positioned against a central portion of an anvil to modify the central portion while the distal and proximal portions remain unchanged. In yet another example, an anvil modification member can be positioned against a distal portion of an anvil to modify the distal portion while the proximal and central portions remain unchanged.

In various instances, an anvil modification member can be configured to modify a subset of forming pockets of an anvil. For example, an anvil modification member can be positioned against one or more rows of forming pockets of an anvil to modify the one or more rows of forming pockets while the remaining rows of forming pockets of the anvil remain unchanged. In at least one instance, an anvil modification member such as, for example, the anvil modification member 15304 can modify or change a compression exerted onto tissue captured between a staple cartridge such as, for example, the staple cartridge 15301 and an anvil such as, for example, the anvil 15002. The anvil modification member 15304 can increase the compression exerted onto the captured tissue by reducing the tissue compression gap between the staple cartridge 15301 and the anvil 15002. By positioning the anvil modification member 15304 against the anvil 15002, the size of the tissue compression gap is effectively reduced by the size of the anvil modification member 15304 which increases the compression applied to the captured tissue. The tissue compression gap comprises a height of about 0.045". In various instances, the tissue compression gap may comprise a height selected from a range of about 0.03" to about 0.10" for example. Other values for the height of the tissue compression gap are contemplated by the present disclosure.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

European Patent Application No. EP 795298, entitled LINEAR STAPLER WITH IMPROVED FIRING STROKE, which was filed on Mar. 12, 1997;

U.S. Pat. No. 5,605,272, entitled TRIGGER MECHANISM FOR SURGICAL INSTRUMENTS, which issued on Feb. 25, 1997;

U.S. Pat. No. 5,697,543, entitled LINEAR STAPLER WITH IMPROVED FIRING STROKE, which issued on Dec. 16, 1997;

U.S. Patent Application Publication No. 2005/0246881, entitled METHOD FOR MAKING A SURGICAL STAPLER, which published on Nov. 10, 2005;

U.S. Patent Application Publication No. 2007/0208359, entitled METHOD FOR STAPLING TISSUE, which published on Sep. 6, 2007;

U.S. Pat. No. 4,527,724, entitled DISPOSABLE LINEAR SURGICAL STAPLING INSTRUMENT, which issued on Jul. 9, 1985;

U.S. Pat. No. 5,137,198, entitled FAST CLOSURE DEVICE FOR LINEAR SURGICAL STAPLING INSTRUMENT, which issued on Aug. 11, 1992;

U.S. Pat. No. 5,405,073, entitled FLEXIBLE SUPPORT SHAFT ASSEMBLY, which issued on Apr. 11, 1995;

U.S. Pat. No. 8,360,297, entitled SURGICAL CUTTING AND STAPLING INSTRUMENT WITH SELF ADJUSTING ANVIL, which issued on Jan. 29, 2013;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, which was filed on Jul. 30, 2015;

U.S. patent application Ser. No. 14/813,259, entitled SURGICAL INSTRUMENT COMPRISING SEPARATE TISSUE SECURING AND TISSUE CUTTING SYSTEMS, which was filed on Jul. 30, 2015;

U.S. patent application Ser. No. 14/813,266, entitled SURGICAL INSTRUMENT COMPRISING SYSTEMS FOR PERMITTING THE OPTIONAL TRANSECTION OF TISSUE, which was filed on Jul. 30, 2015;

U.S. patent application Ser. No. 14/813,274, entitled SURGICAL INSTRUMENT COMPRISING A SYSTEM FOR BYPASSING AN OPERATIONAL STEP OF THE SURGICAL INSTRUMENT; which was filed on Jul. 30, 2015;

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE, DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapling instrument, comprising:
   a shaft;
   an articulation joint; and
   an end effector assembly, comprising:
      a first jaw;
      a second jaw movable relative to said first jaw;
      an anvil configured to deform staples;
      a drive system, comprising:
         a rotary input;
         a closure drive configured to move said second jaw;
         a firing drive configured to fire staples from a staple cartridge; and
         a first lockout comprising an unlocked configuration when a staple cartridge is installed within said end effector assembly and a locked configuration where a staple cartridge is not installed within said end effector assembly, wherein, when in said unlocked configuration, said first lockout is configured to permit actuation of said closure drive and said firing drive, and wherein, when in said locked configuration, said first lockout is configured to prevent said closure drive and said firing drive from being actuated; and
      a second lockout comprising an unlocked configuration where an unfired staple cartridge is installed within said end effector assembly and a locked configuration, wherein, when said second lockout is in said unlocked configuration, said second lockout is configured to permit actuation of said closure drive and said firing drive, and wherein, when said second lockout is in said locked configuration, said second lockout is configured to prevent actuation of said closure drive and said firing drive.

2. The surgical stapling instrument of claim 1, wherein said first lockout further comprises a lockout shaft operably engaged with said rotary input such that when said first lockout is in said locked configuration, said first lockout prevents said rotary input from rotating.

3. The surgical stapling instrument of claim 2, wherein said lockout shaft comprises a spring-loaded interference gear configured to engage said second jaw when said first lockout is in said locked configuration.

4. The surgical stapling instrument of claim 1, further comprising a cartridge driver, wherein said second lockout further comprises a cartridge driver engagement arm configured to move said second lockout from said locked configuration to said unlocked configuration when said cartridge driver engagement arm is engaged by a staple driver of a staple cartridge.

5. The surgical stapling instrument of claim 4, wherein said second lockout is configured to prevent retraction of the staple driver when said cartridge driver is retracted from a fired position.

6. The surgical stapling instrument of claim 1, wherein said closure drive and said firing drive share a common drive axis.

7. The surgical stapling instrument of claim 1, further comprising a staple cartridge.

8. The surgical stapling instrument of claim 7, wherein said staple cartridge comprises a status indicator configured to illustrate firing status during a surgical stapling operation.

9. The surgical stapling instrument of claim 8, wherein said staple cartridge comprises a window, and wherein said status indicator comprises visual indicia visible within said window.

10. The surgical stapling instrument of claim 7, wherein said end effector assembly further comprises a tissue-retention pin mechanism configured to automatically deploy and retract a tissue-retention pin of said staple cartridge during actuation of said closure drive.

11. The surgical stapling instrument of claim 10, wherein said tissue-retention pin mechanism comprises a manual override system configured to provide a user with the ability to retract said tissue-retention pin manually.

12. The surgical stapling instrument of claim 11, wherein said tissue-retention pin mechanism comprises a pair of lever arms each comprising an actuation projection interfacing with said second jaw, and wherein said manual override system is configured to disengage each said actuation projection from said second jaw.

13. The surgical stapling instrument of claim 12, wherein said second jaw comprises a closure frame comprising corresponding slots engaged with said actuation projections to automatically control said tissue-retention pin mechanism during actuation of said closure drive.

14. A surgical stapling instrument, comprising:
a shaft;
an articulation joint; and
an end effector assembly, comprising:
 a first jaw;
 a second jaw movable relative to the said first jaw;
 an anvil configured to deform staples;
 a drive system, comprising:
  a rotary input;
  a main drive comprising a first input gear configured to be driven by said rotary input, wherein said main drive is configured to move said second jaw and fire a plurality of staples from a staple cartridge; and
  a lockout drive, comprising:
   a second input gear configured to be driven by said rotary input;
   an unlocked configuration when a staple cartridge is installed within said end effector assembly, wherein said lockout drive is configured to permit said main drive to be driven when said lockout drive is in said unlocked configuration; and
   a locked configuration when a staple cartridge is not installed within said end effector assembly and said lockout drive prevents said main drive from being driven; and
 a lockout comprising an unlocked configuration when an unfired staple cartridge is installed within said end effector assembly and a locked configuration, wherein, when said lockout is in said unlocked configuration, said lockout is configured to permit actuation of said main drive, and wherein, when said lockout is in said locked configuration, said lockout is configured to prevent actuation of said main drive.

15. The surgical stapling instrument of claim 14, further comprising said staple cartridge.

16. The surgical stapling instrument of claim 14, wherein said lockout drive comprises an interference gear configured to be locked by said second jaw.

17. The surgical stapling instrument of claim 14, wherein said main drive and said lockout drive comprise a common drive input.

18. A surgical stapling attachment configured to be attached to a surgical instrument handle, said surgical stapling attachment comprising:
 an attachment portion;
 a shaft; and
 an end effector assembly, comprising:
  an unclamped configuration and a clamped configuration;
  a replaceable staple cartridge comprising a cartridge body and a plurality of staples removably stored within said cartridge body, wherein said replaceable staple cartridge is configured to be installed into said end effector assembly;
  an anvil configured to deform said staples;
  a drive system, comprising:
   a rotary input;
   a main drive in driving engagement with said rotary input, wherein said main drive is configured to approximate said cartridge body and said anvil and fire said staples; and
   a lockout drive in driving engagement with said rotary input, wherein said lockout drive is configured to prevent said main drive from being driven when said end effector assembly is in said unclamped configuration and said replaceable staple cartridge is not installed within said end effector assembly; and
  a lockout member configured to prevent actuation of said main drive when said end effector assembly is in said unclamped configuration and said replaceable staple cartridge has been fired.

19. The surgical stapling attachment of claim 18, further comprising a closure frame, wherein said lockout drive comprises an interference gear, and wherein said closure frame is configured prevent said interference gear from rotating when said staple cartridge is not installed within said end effector assembly.

20. The surgical stapling attachment of claim 18, wherein said main drive comprise a first axis and said lockout drive comprises a second axis, and wherein said first axis and said second axis are parallel.

* * * * *